US010184133B2

(12) United States Patent
Spangenberg et al.

(10) Patent No.: US 10,184,133 B2
(45) Date of Patent: Jan. 22, 2019

(54) **ICE RECRYSTALLISATION INHIBITION PROTEIN OR ANTIFREEZE PROTEINS FROM *DESCHAMPSIA* SPECIES OF GRASS**

(71) Applicant: Agriculture Victoria Services Pty Ltd, Attwood (AU)

(72) Inventors: German Spangenberg, Bundoora (AU); Peter John Ulrik, Westgarth (AU); Renata Martina Polotonianka, Collingwood (AU)

(73) Assignee: AGRICULTURE VICTORIA SERVICES PTY. LTD., Attwood, Victoria (AU)

( * ) Notice: Subject to any disclaimer, the term of this patent is extended or adjusted under 35 U.S.C. 154(b) by 0 days.

(21) Appl. No.: 14/873,090

(22) Filed: Oct. 1, 2015

(65) Prior Publication Data

US 2016/0251674 A1    Sep. 1, 2016

Related U.S. Application Data

(63) Continuation of application No. 13/975,378, filed on Aug. 26, 2013, now abandoned, which is a continuation of application No. 13/104,869, filed on May 10, 2011, now abandoned, which is a continuation of application No. 10/580,868, filed as application No. PCT/AU2004/001633 on Nov. 24, 2004, now abandoned.

(30) Foreign Application Priority Data

Nov. 24, 2003    (AU) ............................... 2003906477

(51) Int. Cl.
*A01H 1/00*      (2006.01)
*C12N 15/82*      (2006.01)
*C07K 14/415*      (2006.01)
*A01H 5/12*      (2018.01)

(52) U.S. Cl.
CPC ........ *C12N 15/8273* (2013.01); *C07K 14/415* (2013.01); *Y10T 436/13* (2015.01)

(58) Field of Classification Search
None
See application file for complete search history.

(56) References Cited

U.S. PATENT DOCUMENTS

| | | | |
|---|---|---|---|
| 6,852,841 | B1 | 2/2005 | Jarman |
| 7,132,263 | B2 | 11/2006 | Demmer |
| 2004/0146884 | A1 | 7/2004 | Demmer |
| 2007/0250964 | A1 | 10/2007 | Spangenberg |

FOREIGN PATENT DOCUMENTS

| | | |
|---|---|---|
| WO | 1990013571 | 11/1990 |
| WO | 1999037782 | 7/1999 |
| WO | 2004022700 | 3/2004 |

OTHER PUBLICATIONS

McKersie et al. Acta Physiologiae Plantarum, 1997, vol. 19, No. 4, pp. 485-495, Abstract only.*
Wallis et al. Plant Molecular Biology, 1997, vol. 35, No. 3, pp. 323-330, Abstract only.*
Fan et al. Plant Cell Reports, Nov. 2002, vol. 21, No. 4, pp. 296-301, Abstract only.*
Huang et al. Plant Molecular Biology, Oct. 2002, vol. 50, No. 3, Abstract only, pp. 333-344.*
Y: Tomczak et al. (Biophysical Journal, Feb. 2002, vol. 82, No. 2, pp. 874-881, Abstract only.*
Agriculture Victoria Services Pty Ltd., International Search Report, International Application No. PCT/AU2004/001633, 399., dated Sep. 2, 2008.
Atici et al., "Antifreeze proteins in higher plants," Phytochemistry, 64:1187-1196 (2003).
Gidekel et al., "Identification and Characterization of three novel cold acclimation-responsive genes from the extremophile hair grass Deschampsia Antarctica Desv.," Extremophiles 7:459-469 (2003).
Kuiper et al., "A theoretical Model of a Plant Antifreeze Protein from Lolium perenne," Biophysical Journal, 81:3560-3565 (Dec. 2001).
Pudney et al., The physico-chemical characterization of a boiling stable antifreeze protein from a perennial grass (Lolium perenne), Archives of Biochemistry and Biophysics,410:238-245 (2003).
CoreNucleotide. NCBI [online]. 2007, [retrieved on May 31, 2007]. Retrieved from the Internet: <URL: http://www.ncbi.him.nih.gov/entrez/viewer. fcgi?db=nuccore&id=7573547>, 2pp.
Agriculture Victoria Services Pty Ltd., Supplemental European Search Report for EP Application No. 04797081.9 dated Sep. 2, 2008.
Database EMBL [Online] Jan. 12, 2002 (Jan. 12, 2002), "*Hordeum vulgare* subsp. Vulgare cv.Akashinriki cDNA clone:baak11i18, 3'mRNA sequence." XP002470735, Retrieved from EBI accession No. EMBL:AV910970, Abstract.
Database EMBL [Online] Jan. 4, 2006 (Jan. 4, 2006 ), "EST26793 Larval Stage 1 Aedes aegypti cDNA clone AEMR-LS1-076-006-U.AB1 5', mRNA sequence." XP002470736, Retrieved from EBI accession No. EMBL: DW210529, Abstract.
Harrison et al., "Acclimation to freezing temperatures in perennial ryegrass (Lolium perenne)", Steel in Translation, Abstract, 1 page (1998).
Lee et al., "Molecular cloning of abscisic acid-responsive mRNAs expressed during the induction of freezing tolerance in bromegrass (Bromus inermis Leyss) suspension culture", Plant Physiology, American Society of Plant Physiologists Rockville, MD, US, vol. 101 (1993), pp. 1089-1096.
Sidebottom, C. et al., "Heat-stable antifreeze proteins from grass", Nature, vol. 406, Jul. 2000, p. 256.
Tase et al., "Analysis of hardening related proteins in *Lolium temulentum* L.", Dialog Med line, Abstract, 2 pages (1996).

* cited by examiner

*Primary Examiner* — Phuong T Bui
(74) *Attorney, Agent, or Firm* — McDermott Will & Emery LLP

(57) ABSTRACT

The present invention relates to nucleic acids or nucleic acid fragments encoding amino acid sequences for polypeptides involved in tolerance to freezing and/or low temperature stress in plants. More particularly, the present invention relates to nucleic acids or nucleic acid fragments encoding amino acid sequences for ice recrystallization inhibition proteins (IRIPs) in plants, and the use thereof for the modification of plant response to freezing and/or low temperature stress. Even more particularly, the present invention relates to polypeptides involved in tolerance to freezing and/or low temperature stress in *Deschampsia* and *Festuca* species.

3 Claims, 108 Drawing Sheets

Figure 1:
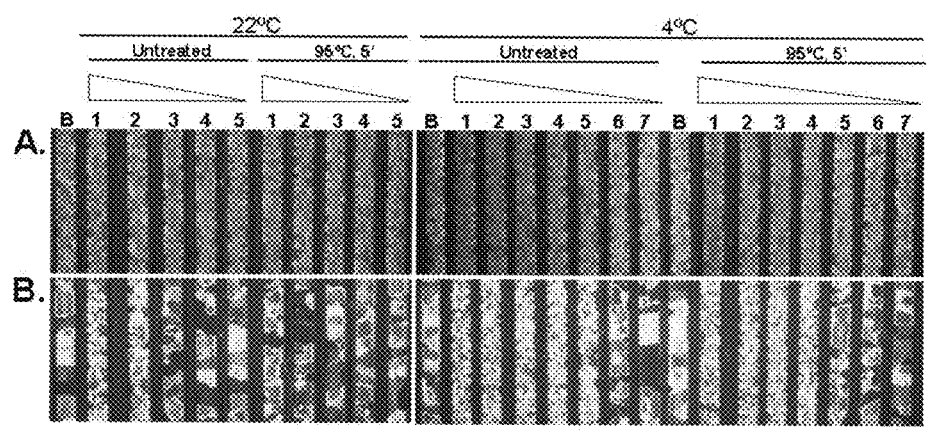

Specification includes a Sequence Listing.

*Da*IRIPd

```
MAPKCWLLLLFSAFLLSAAGATSCHPDDLRALQSFAGNLGSPGGVLPRAAWSGASCCDWEGVSCDGASGRVTALRLPTRGL-----GASLAGLTR---
HVKGNRRTLAVQPNT-ITG                                                                 LxLxxNxLTGxIPx-xLGxLxxLxx
           TNNNVRSG                                                                        S
           SNN-VVSG
           NDNTVISG
           NRN-IVSG
           SYNTVVTG
           SDNT-ITG
           SNH-VVSG
           KNH-IVTD
           NNN-AVTG
           HDH-NVSG
           SFHT-VSG
           NHNT-VSG
           SNNT-VSG
           SNH-VVSG
           SNK-VVTGG*
           SNNTVVSG
```

FIGURE 2A-2

FIG. 2B-1

FIG. 2B-3

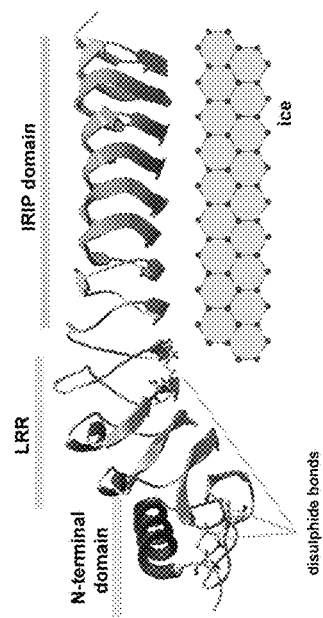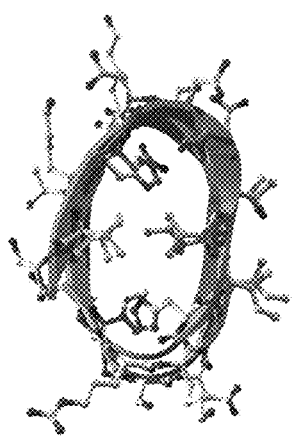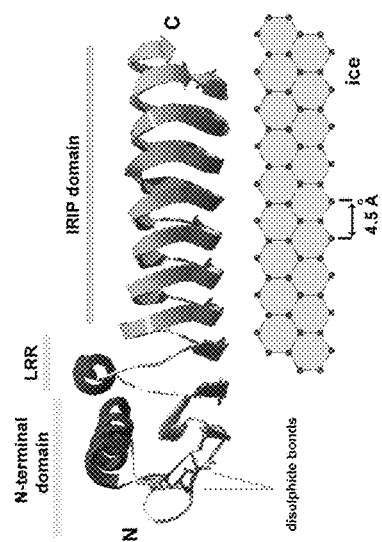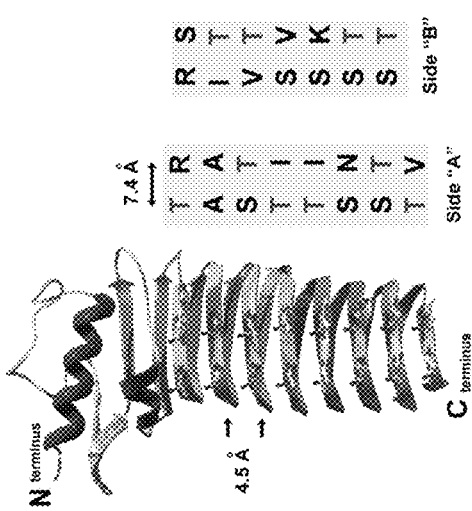
FIG. 3

```
              *        20         *        40         *        60
DaIRIPa : GATTACTATAGGGCACGCGTGGTCGACGGCCCGGGCTGGTATCGTCCTTGCATTAGGCCG :  60

*        80         *       100         *       120
DaIRIPa : GTCACGATGTGTGGTCTAGCCATTCCATGTCATCCACATCATATAGTTGGTGACGTTTA : 120

*       140         *       160         *       180
DaIRIPa : TTTTGAAGTCTGCGTAATAAAATCTTCCTAGGATATTTGCATGGTATCACTCAATTATTA : 180

*       200         *       220         *       240
DaIRIPa : CTCTGAGTAGGCATGGTGACAAGTACCTCTCCAGCCAGCTCCAATCCTACATGTGGTA : 240

*       260         *       280         *       300
DaIRIPa : GCTAACAACAAGCAGCTTGAGTGCTTGCCACCCACGAATTCCAGTCGACAGAAAACACCA : 300

*       320         *       340         *       360
DaIRIPa : AAAACCAAGTTTGAATTGGGAGGCAGTTTGTGACCTTGTGGTCACGGACTAGTATTAGA : 360

*       380         *       400         *       420
DaIRIPa : CCACTTGCAATGCATGCTTACAAACATACACGCACACTATAAGTAAGATGTACCACCCA : 420

*       440         *       460         *       480
DaIRIPa : GCAGTTTTTAACAACACACTTGTGAATCACTTCCATTCCAAAAAGGTTTCTTGCCGAAT : 480

*       500         *       520         *       540
DaIRIPa : CCATATATAGCATACCACGGCTGAATCCATGCGGCTGAAATGCGGGTTGTTGCTGCTCTT : 540

*       560         *       580         *       600
DaIRIPa : CTCAGCATTCCTCTTGCCGGCAGCGACGCGCTACGGCGTGGCACTCCGGTGACCTCCGCGC : 600

*       620         *       640         *       660
DaIRIPa : GCTGCAGGCTTCGCTAGGAACCTGGCGGCGTCGGGGCGTCCTCCTCCGTGCCGCGTG : 660

*       680         *       700         *       720
DaIRIPa : GTCCGGTGACGGGTGCTGCGACTGGGAAGGTGTGGGCTGCGACGGTGCAAGCGGCCGCGT : 720

*       740         *       760         *       780
DaIRIPa : CACTACGTTGCAGCTACCCACGCGTGGCCTGGCGGGCCCATCCCCGGAGCATCCTTGGC : 780

*       800         *       820         *       840
DaIRIPa : GGGCCTCGTGCAGCATGTGAAGGGTAACAGGAGAACACTTGCCGAACAACCGAATAGAAT : 840
```

FIG. 9A

```
             *         860         *         880         *         900
DaIRIPa : ATXGGGACCAACAACAGTGTGAGGTTTGGGAGAAACAATGCTCTTGCCXGAATGACAA : 900

*         920         *         940         *         960
DaIRIPa : CACCGTCATATCTGGGAATAACAACACTGTGTCTGXGAGCTTCAACACXGTCXTAANTGS : 960

*         980         *        1000         *        1020
DaIRIPa : GAGTGACAATATCATAACCXXTAGCAAGCATGTXTATCTXGAGCAAACATATCGTAAC : 1020

*        1040         *        1060         *        1080
DaIRIPa : TGATAACAACAACAAAGTATXCXGGAATGACAATAATGTATCCGGGAGCTTCCACACCGT : 1080

*        1100         *        1120         *        1140
DaIRIPa : ATCCGGAGCCACAACACCGTATCCXGGAGCAACAATACCGTTTCCGGGAGCAACCATGT : 1140

*        1160         *        1180         *        1200
DaIRIPa : CGTGTCTGGGAGCAACAAAGTCCTGACAGGAGGTTAATTATGTGTCAGTGTAGGATTGTC : 1200

*        1220         *        1240         *        1260
DaIRIPa : TCCACCTGAGCTCACCCCTTGTCCAAATTGAGTCTAGCTCACAATCAGTTGGTGGGCCA : 1260

*        1280         *        1300         *        1320
DaIRIPa : ATXGCXGCATGTAACTTCATGGATGGATATAGCATCATTTTCCCACTTTAAATAAAATTT : 1320

*        1340         *        1360
DaIRIPa : GCCTCGTGGATGTCTAAAAAAAAAGAAAAAAAAAAAAAAAAAAAA : 1365
```

FIG. 9B

```
              *        20         *        40         *        60
DaIRIPa : MALKCDLLLLPSAFLLPAASATACHSRDLNALQGFARRLGGVGSVLKAANDGDGCCDWE :  60

*        80         *       100         *       120
DaIRIPa : GVGCDGASCRVTTLQLPTRGLAGFIPGASLAGLVQHVKGNRRTLAEQPNRISGTNNSVRF : 120

*       140         *       160         *       180
DaIRIPa : GRNNALAGNENTVISGNNNTVSGSFNTVVIGSDNILTGSKNVVSGRKHIVTGNNNKVSGN : 180

*       200         *       220
DaIRIPa : DNNVSGSFNTVSGSRNTVSGSNNTVSGSNHVVSGSNKVVTGG : 222
```

FIG. 10

```
                      *         20         *         40         *         60
DaIRIPb.1  :  AACAGCAACGTTGTGACTGGAAACCACAACACACTATTACGTGGGAGTGACGACAATGCC  :   60
DaIRIPb.2  :  AACAGCAACGTTGTGACTGGAAACCACAACACACTATTACGTGGGAGTGACGACAATGCC  :   60
DaIRIPb.3  :  AACAGCAACGTTGTGACTGGAAACCACAACACACTATTACGTGGGAGTGACGACAATGCC  :   60
                      *         80         *        100         *        120
DaIRIPb.1  :  GTAAGTGGTAGCAAGCATGTCGTATCTGGGACCCACCATGTCGTAACTGGCGACAACAAT  :  120
DaIRIPb.2  :  GTAAGTGGTAGCAAGCATGTCGTATCTGGGACCCACCATGTCGTAACTGGCGACAACAAT  :  120
DaIRIPb.3  :  GTAAGTGGTAGCAAGCATGTCGTATCTGGGACCCACCATGTCGTAACTGGCGACAACAAT  :  120
                      *        140         *        160         *        180
DaIRIPb.1  :  GCCGTAACAAGGAACCACAATACCGTATCCGGGAGCCATAATACCGTACCTGGGAGCCAT  :  180
DaIRIPb.2  :  GCCGTAACAAGGAACCACAATACCGTATCCGGGAGCCATAATACCGTACCTGGGAGCCAT  :  180
DaIRIPb.3  :  GCCGTAACAAGGAACCACAATACCGTATCCGGGAGCCATAATACCGTACCTGGGAGCCAT  :  180
                      *        200         *        220         *        240
DaIRIPb.1  :  AATACCGTATCTGGGAGCCACAATACCGTATCTGGGAGCCACAATACCGTATCTGGAAGC  :  240
DaIRIPb.2  :  AATACCGTATCTGGGAGCCACAATACCGTATCTGGGAGCCACAATACCGTATCTGGAAGC  :  240
DaIRIPb.3  :  AATACCGTATCTGGGAGCCACAATACCGTATCTGGGAGCCACAATACCGTATCTGGAAGC  :  240
                      *        260         *        280         *        300
DaIRIPb.1  :  AACCACATCGTATCTGGGAACAACAAAGTCGTGACATGAGGTTAATGATCTTTAGTGGAT  :  300
DaIRIPb.2  :  AACCACATCGTATCTGGGAACAACAAAGTCGTGACATGAGGTTAATGATCTTTAGTGGAT  :  300
DaIRIPb.3  :  AACCACATCGTATCTGGGAACAACAAAGTCGTGACATGAGGTTAATGATCTTTAGTGGAT  :  300
                      *        320         *        340         *        360
DaIRIPb.1  :  TGTTTCCATCTTCCCTAACGAAGCTCATGTTCATGTCCAAGCTAATAAGTGTACCTCACA  :  360
DaIRIPb.2  :  TGTTTCCATCTTCCCTAACGAAGCTCATGTTCATGTCCAAGCTAATAAGTGTACCTCACA  :  360
DaIRIPb.3  :  TGTTTCCATCTTCCCTAACGAAGCTCATGTTCATGTCCAAGCTAATAAGTGTACCTCACA  :  360
                      *        380         *        400         *        420
DaIRIPb.1  :  GTCACTTGGTGGGGCCAATCGCGTTATGTAACTTGATGGATATAGCATCATTTTCGTACT  :  420
DaIRIPb.2  :  GTCACTTGGTGGGGCCAATCGCGTTATGTAACTTGATGGATATAGCATCATTTTCGTACT  :  420
DaIRIPb.3  :  GTCACTTGGTGGGGCCAATCGCGTTATGTAACTTGATGGATATAGCATCATTTTCGTACT  :  420
                      *        440
DaIRIPb.1  :  TTAAATAAAACTCCCTTAAAAAACAAAAA  :  449
DaIRIPb.2  :  TTAAATAAAACTCCCTTAAAAAACAAAAA  :  449
DaIRIPb.3  :  TTAAATAAAACTCCCTTAAAAAACAAAAA  :  449
```

FIG. 11

```
              *        20         *        40         *        60
DaIRIPb : AACAGCAACGTTGTGACTGGAAACCACAACACACTATTACGTGGAGTGACGACAATGCC :  60

*        80         *       100         *       120
DaIRIPb : GTAAGTGGTAGCAAGCATGTCGTATGTGGGACCCACCATGTCGTAACTGCGACAACAAT : 120

*       140         *       160         *       180
DaIRIPb : GCCGTAACAAGGAACCACAATACCGTATCGGGAGCCATAATACGGTACTTGGGAGCCAT : 180

*       200         *       220         *       240
DaIRIPb : AATACCGTATCTGGGAGCCACAATACCGTATCTGGGAGCCACAATACCGTATCTGGAAGC : 240

*       260         *       280         *       300
DaIRIPb : AACCACATCGTATGTGGAACAACAAAGTCGTAACATGAGGTTAATGATCTTAGTGGAT : 300

*       320         *       340         *       360
DaIRIPb : TGTTTCCATCTTCCCTAACGAAGCTCATGTTCATGTCCAAGCTAATAAGTGTACCTCACA : 360

*       380         *       400         *       420
DaIRIPb : GTCACTTGTTGGGGCCAATCGCGTTATGTAACTTGATGGATATAGCATCATTTTCGTACT : 420

*       440
DaIRIPb : TTAAATAAAACTCCCTTAAAAACAAAAA : 448
```

FIG. 12

```
                  *         20         *         40         *         60
DaIRIPb : NSNVVTSNHNTLLRGSDDNAVSGSKHVVSHTHKVVTGDNNAVTRNHNTVSGSHNTVPGSH : 60

*         80         *
DaIRIPb : NTVSGSHNTVSGSHNTVSGSNHIVSQNHKVVT : 92
```

FIG. 13

```
                         *        20         *        40         *        60
DaIRIPd.1  :  CTGGTATTTTGTTTCTCTGCGTGCACTGGAACTGTAGGCGCACGGTATCACTCACTTATT  :   60
DaIRIPd.2  :  ------------------------------------------------------------  :    -
DaIRIPd.3  :  ------------------------------------------------------------  :    -
DaIRIPd.4  :  ------------------------------------------------------------  :    -
DaIRIPd.5  :  ------------------------------------------------------------  :    -
DaIRIPd.6  :  ------------------------------------------------------------  :    -
DaIRIPd.7  :  ------------------------------------------------------------  :    -
                         *        80         *       100         *       120
DaIRIPd.1  :  ACTCTGCCAAGGCATGGGTGACAAGTACCTCTCCAGCTCAGTTCCAACCCTATATGCGGT  :  120
DaIRIPd.2  :  ------------------------------------------------------------  :    -
DaIRIPd.3  :  ------------------------------------------------------------  :    -
DaIRIPd.4  :  ------------------------------------------------------------  :    -
DaIRIPd.5  :  ------------------------------------------------------------  :    -
DaIRIPd.6  :  ------------------------------------------------------------  :    -
DaIRIPd.7  :  ------------------------------------------------------------  :    -
                         *       140         *       160         *       180
DaIRIPd.1  :  AGCTGACGAAGGGCAGCTTGAGTCCATGCCACCCACGAATTTCAGTCGACAGACAACACC  :  180
DaIRIPd.2  :  ------------------------------------------------------------  :    -
DaIRIPd.3  :  ------------------------------------------------------------  :    -
DaIRIPd.4  :  ------------------------------------------------------------  :    -
DaIRIPd.5  :  ------------------------------------------------------------  :    -
DaIRIPd.6  :  ------------------------------------------------------------  :    -
DaIRIPd.7  :  ------------------------------------------------------------  :    -
                         *       200         *       220         *       240
DaIRIPd.1  :  AAAAACAAAGTTTGAACTGGGAGGCACTTGTGGGCCTTGTGGTCACGGACTAGCTAGTAC  :  240
DaIRIPd.2  :  ------------------------------------------------------------  :    -
DaIRIPd.3  :  ------------------------------------------------------------  :    -
DaIRIPd.4  :  ------------------------------------------------------------  :    -
DaIRIPd.5  :  ------------------------------------------------------------  :    -
DaIRIPd.6  :  ------------------------------------------------------------  :    -
DaIRIPd.7  :  ------------------------------------------------------------  :    -
                         *       260         *       280         *       300
DaIRIPa.1  :  TGAACCACTTGCAACACATGCTTACACACACTATAAGTAGCATGTACCACCCAAGTAG   :  300
DaIRIPd.2  :  ------------------------------------------------------------  :    -
DaIRIPd.3  :  ------------------------------------------------------------  :    -
DaIRIPd.4  :  ------------------------------------------------------------  :    -
DaIRIPd.5  :  ------------------------------------------------------------  :    -
DaIRIPd.6  :  ------------------------------------------------------------  :    -
DaIRIPd.7  :  ------------------------------------------------------------  :    -
                         *       320         *       340         *       360
DaIRIPa.1  :  TTTTTAACAACAACACTTGCGAATCACTTGCATTCCAAAAAAGTCCATTCCTGAGTTGCA  :  360
DaIRIPd.2  :  ---------------------------------------------------GAGTTGCA  :    8
DaIRIPd.3  :  ------------------------------------------------------------  :    -
DaIRIPd.4  :  ------------------------------------------------------------  :    -
DaIRIPd.5  :  ------------------------------------------------------------  :    -
DaIRIPd.6  :  ------------------------------------------------------------  :    -
DaIRIPd.7  :  ------------------------------------------------------------  :    -
```

FIG. 14A

```
                          *         380         *         400         *         420
DaIRIPd.1  :  TACCACAGCTGAATCCATGGCGCCGAAATGCTGGCTGCTACTGCTCTTCTCGGCGTTCCT  :  420
DaIRIPd.2  :  TACCACAGCTGAATCCATGGCGCCGAAATGCTGGCTGCTACTGCTCTTCTCGGCGTTCCT  :   68
DaIRIPd.3  :  ------------------------------------------------------------  :    -
DaIRIPd.4  :  ------------------------------------------------------------  :    -
DaIRIPd.5  :  ------------------------------------------------------------  :    -
DaIRIPd.6  :  ------------------------------------------------------------  :    -
DaIRIPd.7  :  ------------------------------------------------------------  :    -

*         440         *         460         *         480
DaIRIPd.1  :  CTTGTCGGCGGCAGGCGCAACATCGTGCCACCCCGATGACCTCCGCGCGCTGCAAAGCTT  :  480
DaIRIPd.2  :  CTTGTCGGCGGCAGGCGCAACATCGTGCCACCCCGATGACCTCCGCGCGCTGCAAAGCTT  :  128
DaIRIPd.3  :  ------------------------------------------------------------  :    -
DaIRIPd.4  :  ------------------------------------------------------------  :    -
DaIRIPd.5  :  ------------------------------------------------------------  :    -
DaIRIPd.6  :  ------------------------------------------------------------  :    -
DaIRIPd.7  :  ------------------------------------------------------------  :    -

*         500         *         520         *         540
DaIRIPd.1  :  CGCCGGGAACCTCGGCAGCCCAGGGGGGGTCCTCCCCCGCGCCGCGTGGTCCGGCGCCTC  :  540
DaIRIPd.2  :  CGCCGGGAACCTCGGCAGCCCAGGGGGGGTCCTCCCCCGCGCCGCGTGGTCCGGCGCCTC  :  188
DaIRIPd.3  :  ------------------------------------------------------------  :    -
DaIRIPd.4  :  ------------------------------------------------------------  :    -
DaIRIPd.5  :  ------------------------------------------------------------  :    -
DaIRIPd.6  :  ------------------------------------------------------------  :    -
DaIRIPd.7  :  ------------------------------------------------------------  :    -

*         560         *         580         *         600
DaIRIPd.1  :  ATGCTGCGACTGGGAAGGCGTGAGCTGCGACGGTGCAAGCGGCCGCGTCACTGCGTTGCG  :  600
DaIRIPd.2  :  ATGCTGCGACTGGGAAGGCGTGAGCTGCGACGGTGCAAGCGGCCGCGTCACTGCGTTGCG  :  248
DaIRIPd.3  :  ------------------------------------------------------------  :    -
DaIRIPd.4  :  ------------------------------------------------------------  :    -
DaIRIPd.5  :  ------------------------------------------------------------  :    -
DaIRIPd.6  :  ------------------------------------------------------------  :    -
DaIRIPd.7  :  ------------------------------------------------------------  :    -

*         620         *         640         *         660
DaIRIPa.1  :  GCTCCCTACGCGCGGCCTTGGAGCATCCTTGGCGGGCCTCACGCGGCATGTGAAAGGTAA  :  660
DaIRIPd.2  :  GCTCCCTACGCGCGGCCTTGGAGCATCCTTGGCGGGCCTCACGCGGCATGTGAAAGGTAA  :  308
DaIRIPd.3  :  ------------------------------------------------------------  :    -
DaIRIPd.4  :  ------------------------------------------------------------  :    -
DaIRIPd.5  :  ------------------------------------------------------------  :    -
DaIRIPd.6  :  ----------------------GCATCCTTGGCGGGCCTCACGCGGCATGTGAAAGGTAA  :   38
DaIRIPd.7  :  ----------------------GCATCCTTGGCGGGCCTCACGCGGCATGTGAAAGGTAA  :   38

*         680         *         700         *         720
DaIRIPa.1  :  CAGGAGAACACTTGCCGTACAACCGAATACAATTACTGGGACCAACAACAACGTCAGGTC  :  720
DaIRIPd.2  :  CAGGAGAACACTTGCCGTACAACCGAATACAATTACTGGGACCAACAACAACGTCAGGTC  :  368
DaIRIPd.3  :  ------------------------------------------------------------  :    -
DaIRIPd.4  :  ------------------------------------------------------------  :    -
DaIRIPd.5  :  ------------------------------------------------------------  :    -
DaIRIPd.6  :  CAGGAGAACACTTGCCGTACAACCGAATACAATTACTGGGACCAACAACAACGTCAGGTC  :   98
DaIRIPd.7  :  CAGGAGAACACTTGCCGTACAACCGAATACAATTACTGGGACCAACAACAACGTCAGGTC  :   98
```

FIG. 14B

```
                            *         740         *         760         *         780
DaIRIPd.1  : TGGAAGCA-----------------------------------------------------  :  728
DaIRIPd.2  : TGGAAGCAACAATGTTGTTTCCGGGAACGACAACACCGTCATATCTGGGAACAGGAACAT  :  428
DaIRIPd.3  : ---GAGCAACAATGTTGTTTCCGGGAACGACAACACCGTCATATCTGGGAACAGGAACAT  :   57
DaIRIPd.4  : ----AGCAACAATGTTGTTTCCGGGAACGACAACACCGTCATATCTGGGAACAGGAACAT  :   56
DaIRIPd.5  : ----AGCAACAATGTTGTTTCCGGGAACGACAACACCGTCATATCTGGGAACAGGAACAT  :   56
DaIRIPd.6  : TGGGAGCAACAATGTTGTTTCCGGGAACGACAACACCGTCATATCTGGGAACAGGAACAT  :  158
DaIRIPd.7  : TGGGAGCAACAATGTTGTTTCCGGGAACGACAACACCGTCATATCTGGGAACAGGAACAT  :  158
                            *         800         *         820         *         840
DaIRIPd.1  : ------------------------------------------------------------  :    -
DaIRIPd.2  : TGTGTCTGGGAGCTACAACACCGTCGTAACTGGGAGTGATAATACCACAACCGGTAGCAA  :  488
DaIRIPd.3  : TGTGTCTGGGAGCTACAACACCGTCGTAACTGGGAGTGATAATACCATAACCGGTAGCAA  :  117
DaIRIPd.4  : TGTGTCTGGGAGCTACAACACCGTCGTAACTGGGAGTGATAATACCATAACCGGTAGCAA  :  116
DaIRIPd.5  : TGTGTCTGGGAGCTACAACACCGTCGTAACTGGGAGTGATAATACCATAACCGGTAGCAA  :  116
DaIRIPd.6  : TGTGTCTGGGAGCTACAACACCGTCGTAACTGGGAGTGATAATACCATAACCGGTAGCAA  :  218
DaIRIPd.7  : TGTGTCTGGGAGCTACAACACCGTCGTAACTGGGAGTGATAATACCATAACCGGTAGCAA  :  218
                            *         860         *         880         *         900
DaIRIPd.1  : ------------------------------------------------------------  :    -
DaIRIPd.2  : CCATGTCGTGTCTGGGAAGAACCATATCGTAACCGACAACAACAACGCCGTAACCGGGCA  :  548
DaIRIPd.3  : CCATGTCGTGTCTGGGAAGAACCATATCGTAACCGACAACAACAACGCCGTAACCGGGCA  :  177
DaIRIPd.4  : CCATGTCGTGTCTGGGAAGAACCATATCGTAACCGACAACAACAACGCCGTAACCGGGCA  :  176
DaIRIPd.5  : CCATGTCGTGTCTGGGAAGAACCATATCGTAACCGACAACAACAACGCCGTAACCGGGCA  :  176
DaIRIPd.6  : CCATGTCGTGTCTGGGAAGAACCATATCGTAACCGACAACAACAACGCCGTAACCGGGCA  :  278
DaIRIPd.7  : CCATGTCGTGTCTGGGAAGAACCATATCGTAACCGACAACAACAACGCCGTAACCGGGCA  :  278
                            *         920         *         940         *         960
DaIRIPd.1  : ------------------------------------------------------------  :    -
DaIRIPd.2  : CGACAATAATGTATCCGGGAGCTTCCATACCGTATCCGGGAACCACAACACAGTATCTGG  :  608
DaIRIPd.3  : CGACAATAATGTATCCGGGAGCTTCCATACCGTATCCGGGAACCACAACACAGTATCTGG  :  237
DaIRIPd.4  : CGACAATAATGTATCCGGGAGCTTCCATACCGTATCCGGGAACCACAACACAGTATCTGG  :  236
DaIRIPd.5  : CGACAATAATGTATCCGGGAGCTTCCATACCGTATCCGGGAACCACAACACAGTATCTGG  :  236
DaIRIPd.6  : CGACAATAATGTATCCGGGAGCTTCCATACCGTATCCGGGAACCACAACACAGTATCTGG  :  338
DaIRIPd.7  : CGACAATAATGTATCCGGGAGCTTCCATACCGTATCCGGGAACCACAACACAGTATCTGG  :  338
                            *         980         *         100         *        1020
DaIRIPa.1  : ------------------------------------------------------------  :    -
DaIRIPd.2  : GAGCAATAATACTGTATCAGGGAGCAACCGTGTCGTGTCCGGGAGCAACAAAGTCGTGAC  :  668
DaIRIPd.3  : GAGCAATAATACTGTATCAGGGAGCAACCATGTCGTGTCCGGGAGCAACAAAGTCGTGAC  :  297
DaIRIPd.4  : GAGCAATAATACTGTATCAGGGAGCAACCGTGTCGTGTCCGGGAGCAACAAAGTCGTGAC  :  296
DaIRIPd.5  : GAGCAATAATACTGTATCAGGGAGCAACCATGTCGTGTCCGGGAGCAACAAAGTCGTGAC  :  296
DaIRIPd.6  : GAGCAATAATACTGTATCAGGGAGCAACCATGTCGTGTCCGGGAGCAACAAAGTCGTGAC  :  398
DaIRIPd.7  : GAGCAATAATACTGTATCAGGGAGCAACCATGTCGTGTCCGGGAGCAACAAAGTCGTGAC  :  398
                            *        1040         *        1060         *        1080
DaIRIPa.1  : ------------------------------------------------------------  :    -
DaIRIPd.2  : AGGAGGTTAATGATATGTCCGTGCAGGATGCTTC---------------------------  :  702
DaIRIPd.3  : AGGAGGTTAATGATATGTCCGTGCAGGATGCTTCCATGTTCCCTAAAGGAGATCGCGGCA  :  357
DaIRIPd.4  : AGGAGGTTAATGATATGTCCGTGCAGGATGCTTCCATGTTCCCTAAAGGAGATCGCGGCA  :  356
DaIRIPd.5  : AGGAGGTTAATGATATGTCCGTGCAGGATGCTTCCATGTTCCCTAAAGGAGATCGCGGCA  :  356
DaIRIPd.6  : AGGAGGTTAATGATATGTCCGTGCAGGATGCTTCCATGTTCCCTAAAGGAGATCGCGGCA  :  458
DaIRIPd.7  : AGGAGGTTAATGATATGTCCGTGCAGGATGCTTCCATGTTCCCTAAAGGAGATCGCGGCA  :  458
```

FIG. 14C

```
                       *         1100         *         1120         *         1140
DaIRIPd.1 : ------------------------------------------------------------ : -
DaIRIPd.2 : ------------------------------------------------------------ : -
DaIRIPd.3 : TTGTACAAGTTTTGTGTAGCTCACAATCACTTGGTGGGACCAATCGCGATGTCATGTAAC : 417
DaIRIPd.4 : TTGTACAAGTTTTGTGTAGCTCACAATCACTTGGTGGGACCAATCGCGATGTCATGTAAC : 416
DaIRIPd.5 : TTGTACAAGTTTTGTGTAGCTCACAATCACTTGGTGGGACCAATCGCGATGTCATGTAAC : 416
DaIRIPd.6 : TTGTACAAGTTTTGTGTAGCTCACAATCACTTGGTGGGACCAATCGCGATGTCATGTAAC : 518
DaIRIPd.7 : TTGTACAAGTTTTGTGTAGCTCACAATCACTTGGTGGGACCAATCGCGATGTCATGTAAC : 518
                       *         1160         *         1180         *         1200
DaIRIPa.1 : ------------------------------------------------------------ : -
DaIRIPd.2 : ------------------------------------------------------------ : -
DaIRIPd.3 : TTCATGGATATAGCATCCTTTTCCTAATTTAAATAAAGTTTGCCTTGTGGAAAAAAAAAA : 477
DaIRIPd.4 : TTCATGGATATAGCATCCTTTTCCTAATTTAAATAAAGTTTGCCTTGTGGAAAAAAAAAA : 476
DaIRIPd.5 : TTCATGGATATAGCATCCTTTTCCTAATTTAAATAAAGTTTGCCTTGTGGAAAAAAAAAA : 476
DaIRIPd.6 : TTCATGGATATAGCATCCTTTTCCTAATTTAAATAAAGTTTGCCTTGTGTAAAAAAAAAA : 578
DaIRIPd.7 : TTCATGGATATAGCATCCTTTTCCTAATTTAAATAAAGTTTGCCTTGTGTAAAAAAAAAA : 578

*         1220
DaIRIPa.1 : ------------------------ : -
DaIRIPd.2 : ------------------------ : -
DaIRIPd.3 : AAAAAAAAAAAAAAAAAAAAAAAA : 498
DaIRIPd.4 : AAAAAAAAAAAAAAAAAAAAAAA  : 497
DaIRIPd.5 : AAAAAAAAAAAAAAAAAAAAAAA  : 497
DaIRIPd.6 : AAAAAAAAAAAAAAAAAAAAAAA  : 599
DaIRIPd.7 : AAAAAAAAAAAAAAAAAAAAAAA  : 599
```

FIG. 14D

```
                    *        20         *        40         *        60
DaIRIPd : CTGGTATTTGTTTCTCTGCGTGCACTGGAACTGTAGGCGCACGGTATCACTCACTTATT :  60

*        80         *       100         *       120
DaIRIPd : ACTCTGCCAAGGCATGGGTGACAAGTACCTCTCCAGCTCAGTTGCAACCCTATATGCGGT : 120

*       140         *       160         *       180
DaIRIPd : AGCTGACGAAGGGCAGCTTGAGTCCATGCCACCCACGAATTTCAGTCGACAGACAACACC : 180

*       200         *       220         *       240
DaIRIPd : AAAAACAAAGTTTGAACTGGGAGGCACTTGTGGGCCTTGTGGTCACGGACTAGCTAGTAC : 240

*       260         *       280         *       300
DaIRIPd : TGAACCACTTGCAACACATGCTTACACACACTATAAGTAGCATGTACCACCCAAGTAG   : 300

*       320         *       340         *       360
DaIRIPd : TTTTAACAACAACACTTGCGAATCACTTGCATTCCAAAAAGTCCATTCCTGAGTTGCA   : 360

*       380         *       400         *       420
DaIRIPd : TACCACAGCTGAATCCATGGCGCCGAAATGCTGGCTGCTACTGCTCTTCTCGGCGTTCCT : 420

*       440         *       460         *       480
DaIRIPd : CTTGTCGGCGGCAGGCGCAACATCGTGCCACCCCGATGACCTCCGGCGCTGCAAAGCTT  : 480

*       500         *       520         *       540
DaIRIPd : CGCCGGAACCTCGCAGCCAGGGGGGTCCTCCCGGCGCCGGTGGTCCGGCGCCTC       : 540

*       560         *       580         *       600
DaIRIPd : ATGCTGCGACTGGAAGGCGTGAGCTGCGACGGTGCAAGCGGCCGGTCACTGCGTTGCG   : 600

*       620         *       640         *       660
DaIRIPd : GCTCCCTACGCGCGGGCCTTGGAGCATCCTTGGCGGGCCTCACGCGGCATGTAAAGGTAA : 660

*       680         *       700         *       720
DaIRIPd : CAGGAGAACACTTGCCGTACAACGGAATACAATTACTGGGACCAACAACAACGTCAGGTC : 720

*       740         *       760         *       780
DaIRIPd : TGGGAGCAACAATGTTGTTTCCGGGAACGACAACACCGTCATATCTGGGAACAGGAACAT : 780

*       800         *       820         *       840
DaIRIPd : TGTGTCTGGCAGCTACAACACCGTCGTAACTGGGAGTGATAATACCATAACCGCTAGCAA : 840
```

FIG. 15A

```
                   *         960         *         980         *        900
DaIRIPd : CCATGTGTGTCTGGGAAGAACCATATCGTAACCGACAACAACAACGCCGTAACCGGGCA :  900

*         920         *         940         *        960
DaIRIPd : CGACAATAATGTATCCGGGAGCTTCCATACCGTATCCGGGAACCACAACACAGTATCTGG :  960

*         980         *        1000         *       1020
DaIRIPd : GAGCAATAATACTGTATCAGGGAGCAACCATGTCGTGTCCGGGAGCAACAAAGTGGTGAC : 1020

*        1040         *        1060         *       1080
DaIRIPd : AGGAGGTTAATGATATGTCCGTGCAGGATGCTTCCATGTTCCCTAAAGGAGATCGCGGCA : 1080

*        1100         *        1120         *       1140
DaIRIPd : TTGTACAAGTTTGTGTAGCTTCACAATCACTTGGTGGGACCAATCGCGATGTCATGTRAC : 1140

*        1160         *        1180         *       1200
DaIRIPd : TTCATGGATATAGCATCTTTTTCCTAATTTAAATAAAGTTTGCCTTGTGGAAAAAAAAA  : 1200

*        1220
DaIRIPd : AAAAAAAAAAAAAAAAAAAAA : 1221
```

FIG. 15B

```
                  *        20         *        40         *        60
DaIRIPd : MAPKCWLILLPSAFLLSAAGATSCHPDDLRALQSPAGNLGSPQGVLPRAANSGASCCDWE :  60

*        80         *       100         *       120
DaIRIPd : GVSCDGASGRVTALRLPTRGLGASLAGLTRHVKENRRTLAVQPNTITGTNNEVRSGSNEV : 120

*       140         *       160         *       180
DaIRIPd : VSGNDNTVISGNRNIVSGSYNTVVTGSDNTITGSNHVVSGKNHIVTDNNEAVTGNDNNVS : 180

*       200         *
DaIRIPd : GSPHTVSGNENTVSGSNFTVSGSNHVVSGSNKVVTGG : 217
```

FIG. 16

|              |   | *          20          *          40          *          60          |   |     |
|---|---|---|---|---|
| DaIRIPe.7.1 | : | GCCACGGAAGACAAGCAGTACTGAACCACTTGCAACGCATACTTACACACACACGCACAC | : | 60  |
| DaIRIPe.7.2 | : | GCCACGGAAGACAAGCAGTACTGAACCACTTGCAACGCATACTTACACACACACGCACAC | : | 60  |
| DaIRIPe.7.3 | : | ------------------------------------------------------------ | : | -   |
| DaIRIPe.7.4 | : | ------------------------------------------------------------ | : | -   |
| DaIRIPe.7.5 | : | ------------------------------------------------------------ | : | -   |
|              |   | *          80          *          100         *          120         |   |     |
| DaIRIPe.7.1 | : | ACTATAAGATAGGATGCACCACCCAAGCAGTTTTAGCCAAGGAACACTTGCGAATCACTT | : | 120 |
| DaIRIPe.7.2 | : | ACTATAAGATAGGATGCACCACCCAAGCAGTTTTAGCCAAGGAACACTTGCGAATCACTT | : | 120 |
| DaIRIPe.7.3 | : | ------------------------------------------------------------ | : | -   |
| DaIRIPe.7.4 | : | ------------------------------------------------------------ | : | -   |
| DaIRIPe.7.5 | : | ------------------------------------------------------------ | : | -   |
|              |   | *          140         *          160         *          180         |   |     |
| DaIRIPe.7.1 | : | GCATTCCAAAGAAGGTTTCCTACTCAGTTGTTGCGTCTGTGTATACATAGCGTAACACAG | : | 180 |
| DaIRIPe.7.2 | : | GCATTCCAAAGAAGGTTTCCTACTCAGTTGTTGCGTCTGTGTATACATAGCGTAACACAG | : | 180 |
| DaIRIPe.7.3 | : | ------------------------------------------------------------ | : | -   |
| DaIRIPe.7.4 | : | ------------------------------------------------------------ | : | -   |
| DaIRIPe.7.5 | : | ------------------------------------------------------------ | : | -   |
|              |   | *          200         *          220         *          240         |   |     |
| DaIRIPe.7.1 | : | CTTGAGTCCATGGCGAACTGCTGTCTGCTACTCCTCTTCTTGGCGTTACCCTTGCCTGCG | : | 240 |
| DaIRIPe.7.2 | : | CTTGAGTCCATGGCGAACTGCTGTCTGCTACTCCTCTTCTTGGCGTTACCCTTGCCTGCG | : | 240 |
| DaIRIPe.7.3 | : | ------------------------------------------------------------ | : | -   |
| DaIRIPe.7.4 | : | ------------------------------------------------------------ | : | -   |
| DaIRIPe.7.5 | : | ------------------------------------------------------------ | : | -   |
|              |   | *          260         *          280         *          300         |   |     |
| DaIRIPe.7.1 | : | GCGAGCGCAACATCGTGCCGCCCCGATGACCTCCACGCGCTACGGGGCTTCGCCGGAAAC | : | 300 |
| DaIRIPe.7.2 | : | GCGAGCGCAACATCGTGCCGCCCCGATGACCTCCACGCGCTACGGGGCTTCGCCGGAAAC | : | 300 |
| DaIRIPe.7.3 | : | ------------------------------------------------------------ | : | -   |
| DaIRIPe.7.4 | : | ------------------------------------------------------------ | : | -   |
| DaIRIPe.7.5 | : | ------------------------------------------------------------ | : | -   |
|              |   | *          320         *          340         *          360         |   |     |
| DaIRIPe.7.1 | : | CTGAGCGGCGGGGGTGTCCTCCTCCGCTCCGTGTGGTCCGGCGACTCGTGCTGCGGCTGG | : | 360 |
| DaIRIPe.7.2 | : | CTGAGCGGCGGGGGTGTCCTCCTCCGCTCCGTGTGGTCCGGCGACTCGTGCTGCGGCTGG | : | 360 |
| DaIRIPe.7.3 | : | ----------------------------------------------------GCGGCTGG | : | 8   |
| DaIRIPe.7.4 | : | ----------------------------------------------------GCGGCTGG | : | 8   |
| DaIRIPe.7.5 | : | ----------------------------------------------------GCGGCTGG | : | 8   |
|              |   | *          380         *          400         *          420         |   |     |
| DaIRIPe.7.1 | : | GAAGGCGTGGGCTGCGACAGCGCAAGCGGCCGCGTCACGGCGATGTTGCTCCCCAGGCGC | : | 420 |
| DaIRIPe.7.2 | : | GAAGGCGTGGGCTGCGACAGCGCAAGCGGCCGCGTCACGGCGATGTTGCTCCCCAGGCGC | : | 420 |
| DaIRIPe.7.3 | : | GAAGGCGTGGGCTGCGACAGCGCAAGCGGCCGCGTCACGGCGATGTTGCTCCCCAGGCAC | : | 68  |
| DaIRIPe.7.4 | : | GAAGGCGTGGGCTGCGACAGCGCAAGCGGCCGCGTCACGGCGATGTTGCTCCCCAGGCAC | : | 68  |
| DaIRIPe.7.5 | : | GAAGGCGTGGGCTGCGACAGCGCAAGCGGCCGCGTCACGGCGATGTTGCTCCCCAGGCAC | : | 68  |

FIG. 17A

```
                         *        440         *        460         *        480
DaIRIPe.7.1 : GGCCTCGCGAAGCCCGTCCCAGGAGCATCCTTGGCGAGCCTCGCACGGCTAGAGGAGCTC : 480
DaIRIPe.7.2 : GGCCTCGCGAAGCCCGTCCCAGGAGCATCCTTGGCGAGCCTCGCACGGCTAGAGGAGCTC : 480
DaIRIPe.7.3 : GGCCTCGCGAAGCCCGTCCCAGGAGCATCCTTGGCGAGCCTCGCACGGCTAGAGGAGCTC : 128
DaIRIPe.7.4 : GGCCTCGCGAAGCCCGTCCCAGGAGCATCCTTGGCGAGCCTCGCACGGCTAGAGGAGCTC : 128
DaIRIPe.7.5 : GGCCTCGCGAAGCCCGTCCCAGGAGCATCCTTGGCGAGCCTCGCACGGCTAGAGGAGCTC :  18
                         *        500         *        520         *        540
DaIRIPe.7.1 : TTCAAGCGTAACAGAAGAACACTGGAGGAACAGCCAAATACAATTCAAGGGACCAACAAC : 540
DaIRIPe.7.2 : TTCAAGCGTAACAGAAGAACACTGGAGGAACAGCCAAATACAATTCAAGGGACCAACAAC : 540
DaIRIPe.7.3 : TTCAAGCGTAACAGAAGAACACTGGAGGAACAGCCAAATACAATTCAAGGGACCAACAAC : 188
DaIRIPe.7.4 : TTCAAGCGTAACAGAAGAACACTGGAGGAACAGCCAAATACAATTCAAGGGACCAACAAC : 188
DaIRIPe.7.5 : TTCAAGCGTAACAGAAGAACACTGGAGGAACAGCCAAATACAATTCAAGGGACCAACAAC : 188
                         *        560         *        580         *        600
DaIRIPe.7.1 : AATGTCAGAGATGGGTGCTACAATGCTCTTTCTGGAAATGACAACACTGTCATATCCGGA : 600
DaIRIPe.7.2 : AATGTCAGAGATGGGTGCTACAATGCTCTTTCTGGAAATGACAACACTGTCATATCCGGA : 600
DaIRIPe.7.3 : AATGTCAGAGATGGGTGCTACAATGCTCTTTCTGGAAATGACAACACTGTCATATCCGGA : 248
DaIRIPe.7.4 : AATGTCAGAGATGGGTGCTACAATGCTCTTTCTGGAAATGACAACACTGTCATATCCGGA : 248
DaIRIPe.7.5 : AATGTCAGAGATGGGTGCTACAATGCTCTTTCTGGAAATGACAACACTGTCATATCCGGA : 248
                         *        620         *        640         *        660
DaIRIPe.7.1 : AACAACAACACTGTGTCTGGGAGCTTTAACACTATCGTAACTGGGTGTCACAACACTGTG : 660
DaIRIPe.7.2 : AACAACAACACTGTGTCTGGGAGCTTTAACACTATCGTAACTGGGTGTCACAACACTGTG : 660
DaIRIPe.7.3 : AACAACAACACTGTGTCTGGGAGCTTTAACACTATCGTAACTGGGTGTCACAACACTGTG : 308
DaIRIPe.7.4 : AACAACAACACTGTGTCTGGGAGCTTTAACACTATCGTAACTGGGTGTCACAACACTGTG : 308
DaIRIPe.7.5 : AACAACAACACTGTGTCTGGGAGCTTTAACACTATCGTAACTGGGTGTCACAACACTGTG : 308
                         *        680         *        700         *        720
DaIRIPe.7.1 : TCTGGTAGCAACCAGGTTGTGTCCGGGCTCAACCATATCGTAACTGACGACAACAATGAC : 720
DaIRIPe.7.2 : TCTGGTAGCAACCAGGTTGTGTCCGGGCTCAACCATATCGTAACTGACGACAACAATGAC : 720
DaIRIPe.7.3 : TCTGGTAGCAACCAGGTTGTGTCCGGGCTCAACCATATCGTAACTGACGACAACAATGAC : 368
DaIRIPe.7.4 : TCTGGTAGCAACCAGGTTGTGTCCGGGCTCAACCATATCGTAACTGACGACAACAATGAC : 368
DaIRIPe.7.5 : TCTGGTAGCAACCAGGTTGTGTCCGGGCTCAACCATATCGTAACTGACGACAACAATGAC : 368
                         *        740         *        760         *        780
DaIRIPe.7.1 : GTATCAGGTAACGATAATAATGTATCCGGTAGCTTTCATACCGTATCTGGGAGCCACAAT : 780
DaIRIPe.7.2 : GTATCAGGTAACGATAATAATGTATCCGGTAGCTTTCATACCGTATCTGGGAGCCACAAT : 780
DaIRIPe.7.3 : GTATCAGGTAACGATAATAATGTATCCGGTAGCTTTCATACCGTATCTGGGAGCCACAAT : 428
DaIRIPe.7.4 : GTATCAGGTAACGATAATAATGTATCCGGTAGCTTTCATACCGTATCTGGGAGCCACAAT : 428
DaIRIPe.7.5 : GTATCAGGTAACGATAATAATGTATCCGGTAGCTTTCATACCGTATCTGGGAGCCACAAT : 428
                         *        800         *        820         *        840
DaIRIPe.7.1 : ACCGTATCTGGGAGCAACAATACCGTATCTGGGAGAAACCATGTCGTAACTGGGAGTAAC : 840
DaIRIPe.7.2 : ACCGTATCTGGGAGCAACAATACCGTATCTGGGAGAAACCATGTCGTAACTGGGAGTAAC : 840
DaIRIPe.7.3 : ACCGTATCTGGGAGCAACAATACCGTATCTGGGAGAAACCATGTCGTAACTGGGAGTAAC : 488
DaIRIPe.7.4 : ACCGTATCTGGGAGCAACAATACCGTATCTGGGAGAAACCATGTCGTAACTGGGAGTAAC : 488
DaIRIPe.7.5 : ACCGTATCTGGGAGCAACAATACCGTATCTGGGAGAAACCATGTCGTAACTGGGAGTAAC : 488
```

FIG. 17B

```
                          *         860         *         880         *         900
DaIRIPe.7.1 : ------------------------------------------------------------ :   -
DaIRIPe.7.2 : AAAGTCGTGACGGGTGGTTAATGATCAGTGAGTGGATT---------------------- : 878
DaIRIPe.7.3 : AAAGTCGTGACAGGAGGTTAATGATCAGTGAGTGGATTGTTTCCATCTTCACTAACGAAG : 548
DaIRIPe.7.4 : AAAGTCGTGACAGGAGGTTAATGATCAGTGAGTGGATTGTTTCCATCTTCACTAACGAAG : 548
DaIRIPe.7.5 : AAAGTCGTGACAGGAGGTTAATGATCAGTGAGTGGATTGTTTCCATCTTCACTAACGAAG : 548

*         920         *         940         *         960
DaIRIPe.7.1 : ------------------------------------------------------------ :   -
DaIRIPe.7.2 : ------------------------------------------------------------ :   -
DaIRIPe.7.3 : CTTACGACCTTGTCCAAGTTCAACCTAGAGCTCACAATATCTTGGTGGGGCCAATCGTCT : 608
DaIRIPe.7.4 : CTTACGACCTTGTCCAAGTTCAACCTAGAGCTCACAATATCTTGGTGGGGCCAATCGTCTC: 608
DaIRIPe.7.5 : CTTACGACCTTGTCCAAGTTCAACCTAGAGCTCACAATATCTTGGTGGGGCCAATCGTCT : 608

*         980         *        1000         *        1020
DaIRIPe.7.1 : ------------------------------------------------------------ :   -
DaIRIPe.7.2 : ------------------------------------------------------------ :   -
DaIRIPe.7.3 : TATGTAACTTCATGGATGTATCCTCCTTTTCCTACTTTAAATAAATTTCCTTAAAATGTC : 668
DaIRIPe.7.4 : TATGTAACTTCATGGATGTATCCTCCTTTTCCTACTTTAAATAAATTTCCTTAAAATGTC : 668
DaIRIPe.7.5 : TATGTAACTTCATGGATGTATCCTCCTTTTCCTACTTTAAATAAATTTCCTTAAAATGTC : 668

*
DaIRIPe.7.1 : -------------------- :   -
DaIRIPe.7.2 : -------------------- :   -
DaIRIPe.7.3 : TTACAAAAAAAAAAAAAAA  : 687
DaIRIPe.7.4 : TTACAAAAAAAAAAAAAAA  : 687
DaIRIPe.7.5 : TTACAAAAAAAAAAAAAAA  : 687
```

FIG. 17C

```
                  *        20         *        40         *        60
DaIRIPe.7 : GCCACGGAAGACAAGCAGTACTGAACCACTTGCAAGGCATACTACACACACGCACAC :  60

*        80         *       100         *       120
DaIRIPe.7 : ACTATAAGATAGGATGCACCACCCAAGCAGTTTTAGCCAAGGAACACTTGCGAATCACTT : 120

*       140         *       160         *       180
DaIRIPe.7 : GCATTCCAAAGAAGGTTTCCTACTCAGTTGTTGCGTCTGTGTATACATAGCGTAACACAG : 180

*       200         *       220         *       240
DaIRIPe.7 : CTTGAGTCCATGGCGAACTGCTGTCTGCTACTCCTCTGCTTGGCGTTACCCTTGCTGCG : 240

*       260         *       280         *       300
DaIRIPe.7 : GCGAGCGGCAACATCGTGCCGCCCCGATGACCTCCACGCGCTACGGGGCTTCGCCGGAAAC : 300

*       320         *       340         *       360
DaIRIPe.7 : CTGAGCGGCGGGGTGTCCTCCTCCGCTCCGTGTGGTCCGGCGACTCGTGCTGCGGCTGG : 360

*       380         *       400         *       420
DaIRIPe.7 : GAAGGCGTGGCTGCGACAGCGCAAGCGGCCGGCGTCACGGCGATGTTGCTCCCCAGGCAC : 420

*       440         *       460         *       480
DaIRIPe.7 : GGCTGGCGAAGCCGTCCGAGGAGTATCTTGGCGAGCCTGGACGGCTAGAGGAGCTC : 480

*       500         *       520         *       540
DaIRIPe.7 : TTCAAGCGTAACAGAAGAACACTGGAGGAACAGCCAAATGCAATTCAAGGGACCAACAAC : 540

*       560         *       580         *       600
DaIRIPe.7 : AAGGTCAGAGATGGTTGCTACAATGCTCTTTCTGGAAATGACAACACTGTCATATCCGGA : 600

*       620         *       640         *       660
DaIRIPe.7 : AACAACAACACTGTGTCTGGGAGCTTTAACACTATCGTAACTGGTGTCACAACACTGTG : 660

*       680         *       700         *       720
DaIRIPe.7 : TCTGGTAGCAACCAGTTGTGTCCGGGCTCAACCATATCGTAACTGACGACAACAATGAC : 720

*       740         *       760         *       780
DaIRIPe.7 : GTATCAGGTAACGATAATGATGTATCCGGTAGCTTTCATACCGTATCTGGAGCCACAAT : 780

*       800         *       820         *       840
DaIRIPe.7 : ACCGTATCTGGGAGCAACAATACCGTATCTGGAGAAACCATGTCGTAACTGGGAGTAAC : 840
```

FIG. 18A

```
                    *         860         *         880         *         900
DaIRIPe.7 : AAAGTCGTRACAGRARGTTAATGATCAGTGAGTGGATTGTTTCCATCTTCACTAACGAAG : 900

*         920         *         940         *         960
DaIRIPe.7 : CTTACGACCTTGTCCAAGTTCAACCTAGAGCTCACAATATCTTGGTGGGCCAATCGTCT : 960

*         980         *         1000        *         1020
DaIRIPe.7 : TATGTAACTTCATGGATGTATCCTCCTTTTCCTACTTTAATAAATTTCCTAAAATGTC : 1020

*
DaIRIPe.7 : TTACAAAAAAAAAAAAAAA : 1039
```

FIG. 18B

```
                  *        20         *        40         *        60
DaIRIPe.7 : MANCCLLLLPLALPLPAASATSCRPDDLSALRQFAGHLSSGSVLLRSVWSGDSCCSWEGV :  60

*        80         *       100         *       120
DaIRIPe.7 : GCDSASGRVTAMLLPRSGLAKPVPGASLASLARLESLFKSSRTLESQPWTIQSTESWVR : 120

*       140         *       160         *       180
DaIRIPe.7 : DWCYNALSGNDNTVISGNDNTVSGSFNTIVTGSNTVSGSNQVVSGLSHIVTDDNNDVGS : 160

*       200         *       220
DaIRIPe.7 : NDNNVSGSFNTVSGSRNTVSGSNTVSGRNRVVTGSNKVVTGS : 223
```

FIG. 19

```
                         *        20         *        40         *        60
DaIRIPe.8.1  :  ACACACACGCACACACTATAAGATAGGATGCACCACCCAAGCAGTTTTAGCCAAGGAACA  :   60
DaIRIPe.8.2  :  ACACACACGCACACACTATAAGATAGGATGCACCACCCAAGCAGTTTTAGCCAAGGAACA  :   60
DaIRIPe.8.3  :  ------------------------------------------------------------  :    -
DaIRIPe.8.4  :  ------------------------------------------------------------  :    -
DaIRIPe.8.5  :  ------------------------------------------------------------  :    -
DaIRIPe.8.6  :  ------------------------------------------------------------  :    -
                         *        80         *       100         *       120
DaIRIPe.8.1  :  CTTGCGAATCACTTGCATTCCAAAGAAGGTTTCTTACTCAGTTGTTGCGTCTGTGTATAC  :  120
DaIRIPe.8.2  :  CTTGCGAATCACTTGCATTCCAAAGAAGGTTTCTTACTCAGTTGTTGCGTCTGTGTATAC  :  120
DaIRIPe.8.3  :  ------------------------------------------------------------  :    -
DaIRIPe.8.4  :  ------------------------------------------------------------  :    -
DaIRIPe.8.5  :  ------------------------------------------------------------  :    -
DaIRIPe.8.6  :  ------------------------------------------------------------  :    -
                         *       140         *       160         *       180
DaIRIPe.8.1  :  ATAGCGTAACACAGCTTGAGTCCATGGCGAACTGCTGTCTGCTACTCCTCTTCTTGGCGT  :  180
DaIRIPe.8.2  :  ATAGCGTAACACAGCTTGAGTCCATGGCGAACTGCTGTCTGCTACTCCTCTTCTTGGCGT  :  180
DaIRIPe.8.3  :  ----CGTAACACAGCTTGAGTCCATGGCGAACTGCTGTCTGCTACTCCTCTTCTTGGCGT  :   56
DaIRIPe.8.4  :  ----CGTAACACAGCTTGAGTCCATGGCGAACTGCTGTCTGCTACTCCTCTTCTTGGCGT  :   56
DaIRIPe.8.5  :  ----CGTAACACAGCTTGAGTCCATGGCGAACTGCTGTCTGCTACTCCTCTTCTTGGCGT  :   56
DaIRIPe.8.6  :  ----CGTAACACAGCTTGAGTCCATGGCGAACTGCTGTCTGCTACTCCTCTTCTTGGCGT  :   56
                         *       200         *       220         *       240
DaIRIPe.8.1  :  TACTCTTGCCTGCGGCGTGCGCAACATCGTGCCACCCCGATGACCTCCACGCGCTACGGG  :  240
DaIRIPe.8.2  :  TACTCTTGCCTGCGGCGTGCGCAACATCGTGCCACCCCGATGACCTCCACGCGCTACGGG  :  240
DaIRIPe.8.3  :  TACTCTTGCCTGCGGCGAGCGCAACATCGTGCCACCCCGATGACCTCCACGCGCTACGGG  :  116
DaIRIPe.8.4  :  TACTCTTGCCTGCGGCGAGCGCAACATCGTGCCACCCCGATGACCTCCACGCGCTACGGG  :  116
DaIRIPe.8.5  :  TACTCTTGCCTGCGGCGTGCGCAACATCGTGCCACCCCGATGACCTCCACGCGCTACGGG  :  116
DaIRIPe.8.6  :  TACTCTTGCCTGCGGCGTGCGCAACATCGTGCCACCCCGATGACCTCCACGCGCTACGGG  :  116
                         *       260         *       280         *       300
DaIRIPe.8.1  :  GCTTCGCCGGAAACCTGAGCGGCGGGGGTGTCCTCCCCCGCTCCGTGTGGTCCGGTGACT  :  300
DaIRIPe.8.2  :  GCTTCGCCGGAAACCTGAGCGGCGGGGGTGTCCTCCCCCGCTCCGTGTGGTCCGGTGACT  :  300
DaIRIPe.8.3  :  GCTTCGCCGGAAACCTGAGCGGCGGGGGTGTCCTCCTCCGCTCCGTGTGGTCCGGCGACT  :  176
DaIRIPe.8.4  :  GCTTCGCCGGAAACCTGAGCGGCGGGGGTGTCCTCCTCCGCTCCGTGTGGTCCGGCGACT  :  176
DaIRIPe.8.5  :  GCTTCGCCGGAAACCTGAGCGGCGGGGGTGTCCTCCCCCGCTCCGTGTGGTCCGGTGACT  :  176
DaIRIPe.8.6  :  GCTTCGCCGGAAACCTGAGCGGCGGGGGTGTCCTCCCCCGCTCCGTGTGGTCCGGTGACT  :  176
                         *       320         *       340         *       360
DaIRIPe.8.1  :  CGTGCTGCGGCTGGGAAGGTGTGGGCTGCGACGACGCAAGCGGCCGGGTCACGACGATGT  :  360
DaIRIPe.8.2  :  CGTGCTGCGGCTGGGAAGGTGTGGGCTGCGACGACGCAAGCGGCCGGGTCACGACGATGT  :  360
DaIRIPe.8.3  :  CGTGCTGCGGCT:GGAAGGTGTGGGCTGCGACGACGCAAGCGGCCGGGTCACGACGATGT  :  235
DaIRIPe.8.4  :  CGTGCTGCGGCT:GGAAGGTGTGGGCTGCGACGACGCAAGCGGCCGGGTCACGACGATGT  :  235
DaIRIPe.8.5  :  CGTGCTGCGGCTGGGAAGGTGTGGGCTGCGACGACGCAAGCGGCCGGGTCACGACGATGT  :  236
DaIRIPe.8.6  :  CGTGCTGCGGCTGGGAAGGTGTGGGCTGCGACGACGCAAGCGGCCGGGTCACGACGATGT  :  236
```

FIG. 20A

|  |  | * | 380 | * | 400 | * | 420 |  |  |
|---|---|---|---|---|---|---|---|---|---|
| DaIRIPe.8.1 | : | GGCTCCCCAGGCGCGGCCTCGTGAAGCCCGTCCCCGGAGCATCCTTGGCGGGCGTCACGG | : | 420 |
| DaIRIPe.8.2 | : | GGCTCCCCAGGCGCGGCCTCGTGAAGCCCGTCCCCGGAGCATCCTTGGCGGGCGTCACGG | : | 420 |
| DaIRIPe.8.3 | : | GGCTCCCCAGGCGCGGCCTCGTGAAGCCCGTCCCCGGAGCATCCTTGGCGGGCGTCACGG | : | 295 |
| DaIRIPe.8.4 | : | GGCTCCCCAGGCGCGGCCTCGTGAAGCCCGTCCCCGGAGCATCCTTGGCGGGCGTCACGG | : | 295 |
| DaIRIPe.8.5 | : | GGCTCCCCAGGCGCGGCCTCGTGAAGCCCGTCCCCGGAGCATCCTTGGCGGGCGTCACGG | : | 296 |
| DaIRIPe.8.6 | : | GGCTCCCCAGGCGCGGCCTCGTGAAGCCCGTCCCCGGAGCATCCTTGGCGGGCGTCACGG | : | 296 |
|  |  | * | 440 | * | 460 | * | 480 |  |  |
| DaIRIPe.8.1 | : | AGCTGGAGGAGCTCATCACGCGTAACAGAAGAGCACTGGAGGAACAACCAAATACAATTC | : | 480 |
| DaIRIPe.8.2 | : | AGCTGGAGGAGCTCATCACGCGTAACAGAAGAGCACTGGAGGAACAACCAAATACAATTC | : | 480 |
| DaIRIPe.8.3 | : | AGCTGGAGGAGCTCATCACGCGTAACAGAAGAGCACTGGAGGAACAACCAAATACAATTC | : | 355 |
| DaIRIPe.8.4 | : | AGCTGGAGGAGCTCATCACGCGTAACAGAAGAGCACTGGAGGAACAACCAAATACAATTC | : | 355 |
| DaIRIPe.8.5 | : | AGCTGGAGGAGCTCATCACGCGTAACAGAAGAGCACTGGAGGAACAACCAAATACAATTC | : | 356 |
| DaIRIPe.8.6 | : | AGCTGGAGGAGCTCATCACGCGTAACAGAAGAGCACTGGAGGAACAACCAAATACAATTC | : | 356 |
|  |  | * | 500 | * | 520 | * | 540 |  |  |
| DaIRIPe.8.1 | : | AAGGGACCAACAACAATGTCAGAGATGGGTGCTACAATGCTCTTTCTGGGAATGACAACA | : | 540 |
| DaIRIPe.8.2 | : | AAGGGACCAACAACAATGTCAGAGATGGGTGCTACAATGCTCTTTCTGGGAATGACAACA | : | 540 |
| DaIRIPe.8.3 | : | AAGGGACCAACAACAATGTCAGAGATGGGTGCTACAATGCTCTTTCTGGGAATGGCAACA | : | 415 |
| DaIRIPe.8.4 | : | AAGGGACCAACAACAATGTCAGAGATGGGTGCTACAATGCTCTTTCTGGGAATGGCAACA | : | 415 |
| DaIRIPe.8.5 | : | AAGGGACCAACAACAATGTCAGAGATGGGTGCTACAATGCTCTTTCTGGGAATGACAACA | : | 416 |
| DaIRIPe.8.6 | : | AAGGGACCAACAACAATGTCAGAGATGGGTGCTACAATGCTCTTTCTGGGAATGACAACA | : | 416 |
|  |  | * | 560 | * | 580 | * | 600 |  |  |
| DaIRIPe.8.1 | : | CTGTCATATCCGGAAACAACAACACTGTGTCTGGGAGCTTTAACACTATCGTAACTGGGT | : | 600 |
| DaIRIPe.8.2 | : | CTGTCATATCCGGAAACAACAACACTGTGTCTGGGAGCTTTAACACTATCGTAACTGGGT | : | 600 |
| DaIRIPe.8.3 | : | CTGTCATATCCGGAAACAACAACACTGTGTCTGGGAGCTTTAACACTATCGTAACTGGGT | : | 475 |
| DaIRIPe.8.4 | : | CTGTCATATCCGGAAACAACAACACTGTGTCTGGGAGCTTTAACACTATCGTAACTGGGT | : | 475 |
| DaIRIPe.8.5 | : | CTGTCATATCCGGAAACAACAACACTGTGTCTGGGAGCTTTAACACTATCGTAACTGGGT | : | 476 |
| DaIRIPe.8.6 | : | CTGTCATATCCGGAAACAACAACACTGTGTCTGGGAGCTTTAACACTATCGTAACTGGGT | : | 476 |
|  |  | * | 620 | * | 640 | * | 660 |  |  |
| DaIRIPe.8.1 | : | GTCACAACACTGTGTCTGGTAGCAACCAGGTTGTATCTGGGCTCAACCATATCGTAACTG | : | 660 |
| DaIRIPe.8.2 | : | GTCACAACACTGTGTCTGGTAGCAACCAGGTTGTATCTGGGCTCAACCATATCGTAACTG | : | 660 |
| DaIRIPe.8.3 | : | GTCACAACACTGTGTCTGGTAGCAACCAGGTTGTATCTGGGCTCAACCATATCGTAACTG | : | 535 |
| DaIRIPe.8.4 | : | GTCACAACACTGTGTCTGGTAGCAACCAGGTTGTATCTGGGCTCAACCATATCGTAACTG | : | 535 |
| DaIRIPe.8.5 | : | GTCACAACACTGTGTCTGGTAGCAACCAGGTTGTATCTGGGCTCAACCATATCGTAACTG | : | 536 |
| DaIRIPe.8.6 | : | GTCACAACACTGTGTCTGGTAGCAACCAGGTTGTATCTGGGCTCAACCATATCGTAACTG | : | 536 |
|  |  | * | 680 | * | 700 | * | 720 |  |  |
| DaIRIPe.8.1 | : | ACGACAACAATGACGTATCAGGTAACGATAATAATGTATCTGGTAGCTTTCATACCGTAT | : | 720 |
| DaIRIPe.8.2 | : | ACGACAACAATGACGTATCAGGTAACGATAATAATGTATCTGGTAGCTTTCATACCGTAT | : | 720 |
| DaIRIPe.8.3 | : | ACGACAACAATGACGTATCAGGTAACGATAATAATGTATCTGGTAGCTTTCATACCGTAT | : | 595 |
| DaIRIPe.8.4 | : | ACGACAACAATGACGTATCAGGTAACGATAATAATGTATCTGGTAGCTTTCATACCGTAT | : | 595 |
| DaIRIPe.8.5 | : | ACGACAACAATGACGTATCAGGTAACGATAATAATGTATCTGGTAGCTTTCATACCGTAT | : | 596 |
| DaIRIPe.8.6 | : | ACGACAACAATGACGTATCAGGTAACGATAATAATGTATCTGGTAGCTTTCATACCGTAT | : | 596 |

FIG. 20B

```
                          *        740         *        760         *        780
DaIRIPe.8.1 :  CTGGGAGCCACAATACCGTATCTGGGAGCAA------------------------------  :  751
DaIRIPe.8.2 :  CTGGGAGCCACAATACCGTATCTGGGAGCAACAATACCGTATCTGGGAGAAACCATGTCG  :  780
DaIRIPe.8.3 :  CTGGGAGCCACAATACCGTATCTGGGAGCAACAATACCGTATCTGGGAGAAACCATGTCG  :  655
DaIRIPe.8.4 :  CTGGGAGCCACAATACCGTATCTGGGAGCAACAATACCGTATCTGGGAGAAACCATGTCG  :  655
DaIRIPe.8.5 :  CTGGGAGCCACAATACCGTATCTGGGAGCAACAATACCGTATCTGGGAGAAACCATGTCG  :  656
DaIRIPe.8.6 :  CTGGGAGCCACAATACCGTATCTGGGAGCAACAATACCGTATCTGGGAGAAACCATGTCG  :  656

*        800         *        820         *
DaIRIPe.8.1 :  ------------------------------------------------------  :   -
DaIRIPe.8.2 :  TAACTGGGAGTAACAAAGTCGTGACAGGTGGTTAATGATCAGTGAGTGGATT  :  832
DaIRIPe.8.3 :  TAACTGGGAGTAACAAAGTCGTGACAGGAGGTTAATGATCAGTGAGTGGATT  :  707
DaIRIPe.8.4 :  TAACTGGGAGTAACAAAGTCGTGACAGGAGGTTAATGATCAGTGAGTGGATT  :  707
DaIRIPe.8.5 :  TAACTGGGAGTAACAAAGTCGTGACAGGTGGTTAATGATCAGTGAGTGGATT  :  708
DaIRIPe.8.6 :  TAACTGGGAGTAACAAAGTCGTGACAGGTGGTTAATGATCAGTGAGTGGATT  :  708
```

FIG. 20C

```
                    *         20         *         40         *         60
DaIRIPe.8 : ACACACACGCACACACTATAAGATAGHATGCACCACCCAAGCAGTTTTGGCCAAGCAACA :  60

*         80         *        100         *        120
DaIRIPe.8 : CTTGCGAATCACTTGCATTCCAAAGAAGGTTTCTTACTCAGTTGTTGCGTCTGTGTATAC : 120

*        140         *        160         *        180
DaIRIPe.8 : ATAGCGTAACACAGCTTGAGTCCATGGCGAACTGCTGTCTGCTACTCCTCTTCTTGGCGT : 180

*        200         *        220         *        240
DaIRIPe.8 : TACTCTTGCCTGCGGCGTGCGCAACATGGTGCCACTCGATGACCTCGACGCGCTACGGG : 240

*        260         *        280         *        300
DaIRIPe.8 : GCTTCGCCGGAAACCTGAGCGGCGGGGGTGTCCTCCCCGGTCCGTGTGTCCGGTGACT : 300

*        320         *        340         *        360
DaIRIPe.8 : CGTGCTGCGGCTGGGAAGGTGTGGGCTGCGACGACGCAAGCGGCCGGGTCACGACGATGT : 360

*        380         *        400         *        420
DaIRIPe.8 : GGCTCCGCCAGGCGGGGCCTCGGTGAAGCCCGTCCCCGGAGCATCCTTGGCGGGCGTCACGGG : 420

*        440         *        460         *        480
DaIRIPe.8 : AGGTGGAGGAGGTCATCACGCGTAACAAAGAGCACTGGAGGAACAACCAAATACAATTC : 480

*        500         *        520         *        540
DaIRIPe.8 : AAGGGACCAACAACAATGTCAGAGATGGTGCTACAATGCTCTTTCTGGGAATGACAACA : 540

*        560         *        580         *        600
DaIRIPe.8 : CTGTCATATCGGAAACAGCAACACTGTGTCTGGGAGCTTTAACACTATCGTAACTGGT : 600

*        620         *        640         *        660
DaIRIPe.8 : GTCACAACACTGTGTCTGGTAGCAACCAGGTTGTATCTGGGCTCAACCATATCGTAACTG : 660

*        680         *        700         *        720
DaIRIPe.8 : ACGACAACAATGACGTATCGGTAGCGATAATAATGTATCTGGTAGCTTTCATACGGTAT : 720

*        740         *        760         *        780
DaIRIPe.8 : CTGGGAGCCACAATACCGTATCTGGGAGCAACAATACCGTATCTGGGAGAAACCATGTCG : 780

*        800         *        820         *
DaIRIPe.8 : TAACTGGGAGTAACAAAGTCGTGACAGGTGGTTAATGATCAGTGAGTCGATT : 832
```

FIG. 21

```
              *        20         *        40         *        60
DaIRIPe.8 : MANCCLLLLPLALLLFAACATSCPDDLNALRGFACNLSGGGVLPREVWSGDSCCGWEGV :  60

*        80         *       100         *       120
DaIRIPe.8 : GCDDASGRVTYNWLPRRGLVKPVPGASLAGVTELEELITRNRRALEEQPNTIQGTRNNRVR : 120

*       140         *       160         *       180
DaIRIPe.8 : DGCYNALSENDRTVISGNRNTVSGSFNTIVTSCKNFVSGSNQVVSGLRHIVTDDNNDVSG : 180

*       200         *       220
DaIRIPe.8 : NDNRVSGSFNTVSGSHNTVSGSNNTVSGRNHVVTGSNKVVTGG : 223
```

FIG. 22

```
                         *        20         *        40         *        60
DaIRIPf.1  :  CTCCCCAGGCGCGGCCTCGCGGGCCCCATCACAGGAGCAACCTTGGCCGGCCTGACACGG  :   60
DaIRIPf.2  :  CTCCCCAGGCGCGGCCTCGCGGGCCCCATCACAGGAGCAACCTTGGCCGGCCTGACACGG  :   60
DaIRIPf.3  :  CTCCCCAGGCGCGGCCTCGCGGGCCCCATCACAGGAGCAACCTTGGCCGGCCTGACACGG  :   60
DaIRIPf.4  :  CTCCCCAGGCGCGGCCTCGCGGGCCCCATCACAGGAGCAACCTTGGCCGGCCTGACACGG  :   60
DaIRIPf.5  :  CTCCCCAGGCGCGGCCTCGCGGGCCCCATCACAGGAGCAACCTTGGCCGGCCTGACACGG  :   60
DaIRIPf.6  :  CTCCCCAGGCGCGGCCTCGCGGGCCCCATCACAGGAGCAACCTTGGCCGGCCTGACACGG  :   60
                         *        80         *       100         *       120
DaIRIPf.1  :  CTTGAGTCGCTCAACCTTGCCAACAACAGTCTGGTAGGCACCATCCCATCATGGATCGGT  :  120
DaIRIPf.2  :  CTTGAGTCGCTCAACCTTGCCAACAACAGTCTGGTAGGCACCATCCCATCATGGATCGGT  :  120
DaIRIPf.3  :  CTTGAGTCGCTCAACCTTGCCAACAACAGTCTGGTAGGCACCATCCCATCATGGATCGGT  :  120
DaIRIPf.4  :  CTTGAGTCGCTCAACCTTGCCAACAACAGTCTGGTAGGCACCATCCCATCATGGATCGGT  :  120
DaIRIPf.5  :  CTTGAGTCGCTCAACCTTGCCAACAACAGTCTGGTAGGCACCATCCCATCATGGATCGGT  :  120
DaIRIPf.6  :  CTTGAGTCGCTCAACCTTGCCAACAACAGTCTGGTAGGCACCATCCCATCATGGATCGGT  :  120
                         *       140         *       160         *       180
DaIRIPf.1  :  GAGCTTGACCACCTTTGCTACATGGATCTCTCACACAATTCACTAGATGGCGAGGTACCC  :  180
DaIRIPf.2  :  GAGCTTGACCACCTTTGCTACATGGATCTCTCACACAATTCACTAGATGGCGAGGTACCC  :  180
DaIRIPf.3  :  GAGCTTGACCACCTTTGCTACATGGATCTCTCACACAATTCACTAGATGGCGAGGTACCC  :  180
DaIRIPf.4  :  GAGCTTGACCACCTTTGCTACATGGATCTCTCACACAATTCACTAGATGGCGAGGTACCC  :  180
DaIRIPf.5  :  GAGCTTGACCACCTTTGCTACATGGATCTCTCACACAATTCACTAGATGGCGAGGTACCC  :  180
DaIRIPf.6  :  GAGCTTGACCACCTTTGCTACATGGATCTCTCACACAATTCACTAGATGGCGAGGTACCC  :  180
                         *       200         *       220         *       240
DaIRIPf.1  :  AAGAGTTTGCAGATACGGCTCAGGGCCCTCACTACGACCGGTCGTTCACTGGGCATGGTT  :  240
DaIRIPf.2  :  AAGAGTTTGCAGATACGGCTCAGGGCCCTCACTACGACCGGTCGTTCACTGGGCATGGTT  :  240
DaIRIPf.3  :  AAGAGTTTGCAGATACGGCTCAGGGCCCTCACTACGACCGGTCGTTCACTGGGCATGGTT  :  240
DaIRIPf.4  :  AAGAGTTTGCAGATACGGCTCAGGGCCCTCACTACGACCGGTCGTTCACTGGGCATGGTT  :  240
DaIRIPf.5  :  AAGAGTTTGCAGATACGGCTCAGGGCCCTCACTACGACCGGTCGTTCACTGGGCATGGTT  :  240
DaIRIPf.6  :  AAGAGTTTGCAGATACGGCTCAGGGCCCTCACTACGACCGGTCGTTCACTGGGCATGGTT  :  240
                         *       260         *       280         *       300
DaIRIPf.1  :  TTCATTAACATGCCGTTGCATATGAAGCGTAGCCGAAGAACACTCCAAGAACAACCAAAT  :  300
DaIRIPf.2  :  TTCATTAACATGCCGTTGCATATGAAGCGTAGCCGAAGAACACTCCAAGAACAACCAAAT  :  300
DaIRIPf.3  :  TTCATTAACATGCCGTTGCATATGAAGCGTAGCCGAAGAACACTCCAAGAACAACCAAAT  :  300
DaIRIPf.4  :  TTCATTAACATGCCGTTGCATATGAAGCGTAGCCGAAGAACACTCCAAGAACAACCAAAT  :  300
DaIRIPf.5  :  TTCATTAACATGCCGTTGCATATGAAGCGTAGCCGAAGAACACTCCAAGAACAACCAAAT  :  300
DaIRIPf.6  :  TTCATTAACATGCCGTTGCATATGAAGCGTAGCCGAAGAACACTCCAAGAACAACCAAAT  :  300
                         *       320         *       340         *       360
DaIRIPf.1  :  GTAATAACTGGGACCAACAACAGTGTCAGATCTGGGAGAAACAATGTTGTTTCCGGGAAC  :  360
DaIRIPf.2  :  GTAATAACTGGGACCAACAACAGTGTCAGATCTGGGAGAAACAATGTTGTTTCCGGGAAC  :  360
DaIRIPf.3  :  GTAATAACTGGGACCAACAACAGTGTCAGATCTGGGAGAAACAATGTTGTTTCCGGGAAC  :  360
DaIRIPf.4  :  GTAATAACTGGGACCAACAACAGTGTCAGATCTGGGAGAAACAATGTTGTTTCCGGGAAC  :  360
DaIRIPf.5  :  GTAATAACTGGGACCAACAACAGTGTCAGATCTGGGAGAAACAATGTTGTTTCCGGGAAC  :  360
DaIRIPf.6  :  GTAATAACTGGGACCAACAACAGTGTCAGATCTGGGAGAAACAATGTTGTTTCCGGGAAC  :  360
```

FIG. 23A

```
            *         380         *         400         *         420
DaIRIPf.1 : GACAATACTGTCATATCTGGGAACAACAATGTTGTGTCTGGGAGCCACAACACTGTCGTA :  420
DaIRIPf.2 : GACAATACTGTCATATCTGGGAACAACAATGTTGTGTCTGGGAGCCACAACACTGTCGTA :  420
DaIRIPf.3 : GACAATACTGTCATATCTGGGAACAACAATGTTGTGTCTGGGAGCCACAACACTGTCGTA :  420
DaIRIPf.4 : GACAATACTGTCATATCTGGGAACAACAATGTTGTGTCTGGGAGCCACAACACTGTCGTA :  420
DaIRIPf.5 : GACAATACTGTCATATCTGGGAACAACAATGTTGTGTCTGGGAGCCACAACACTGTCGTA :  420
DaIRIPf.6 : GACAATACTGTCATATCTGGGAACAACAATGTTGTGTCTGGGAGCCACAACACTGTCGTA :  420
            *         440         *         460         *         480
DaIRIPf.1 : ACGGGGAGTGACAATGTCGTAAGTGGTAGTAACCATGTCGTATCTAGGACCAACCATGTC :  480
DaIRIPf.2 : ACGGGGAGTGACAATGTCGTAAGTGGTAGTAACCATGTCGTATCTAGGACCAACCATGTC :  480
DaIRIPf.3 : ACGGGGAGTGACAATGTCGTAAGTGGTAGTAACCATGTCGTATCTAGGACCAACCATGTC :  480
DaIRIPf.4 : ACGGGGAGTGACAATGTCGTAAGTGGTAGTAACCATGTCGTATCTAGGACCAACCATGTC :  480
DaIRIPf.5 : ACGGGGAGTGACAATGTCGTAAGTGGTAGTAACCATGTCGTATCTAGGACCAACCATGTC :  480
DaIRIPf.6 : ACGGGGAGTGACAATGTCGTAAGTGGTAGTAACCATGTCGTATCTAGGACCAACCATGTC :  480
            *         500         *         520         *         540
DaIRIPf.1 : GTAACTGATAACAACAATGCCGTAACCGGGAACCACAACACTGTATCCGGGAGCCACAAC :  540
DaIRIPf.2 : GTAACTGATAACAACAATGCCGTAACCGGGAACCACAACACTGTATCCGGGAGCCACAAC :  540
DaIRIPf.3 : GTAACTGATAACAACAATGCCGTAACCGGGAACCACAACACTGTATCCGGGAGCCACAAC :  540
DaIRIPf.4 : GTAACTGATAACAACAATGCCGTAACCGGGAACCACAACACTGTATCCGGGAGCCACAAC :  540
DaIRIPf.5 : GTAACTGATAACAACAATGCCGTAACCGGGAACCACAACACTGTATCCGGGAGCCACAAC :  540
DaIRIPf.6 : GTAACTGATAACAACAATGCCGTAACCGGGAACCACAACACTGTATCCGGGAGCCACAAC :  540
            *         560         *         580         *         600
DaIRIPf.1 : ACTGTATCCGGGAGCAACAATGTCGTATCCGGGAGCAACCATGTTGTATCAGGGAGCAAC :  600
DaIRIPf.2 : ACTGTATCCGGGAGCAACAATGTCGTATCCGGGAGCAACCATGTTGTATCAGGGAGCAAC :  600
DaIRIPf.3 : ACTGTATCCGGGAGCAACAATGTCGTATCCGGGAGCAACCATGTTGTATCAGGGAGCAAC :  600
DaIRIPf.4 : ACTGTATCCGGGAGCAACAATGTCGTATCCGGGAGCAACCATGTTGTATCAGGGAGCAAC :  600
DaIRIPf.5 : ACTGTATCCGGGAGCAACAATGTCGTATCCGGGAGCAACCATGTTGTATCAGGGAGCAAC :  600
DaIRIPf.6 : ACTGTATCCGGGAGCAACAATGTCGTATCCGGGAGCAACCATGTTGTATCAGGGAGCAAC :  600
            *         620         *         640         *         660
DaIRIPf.1 : AAAGTCGTGACGGGAGGTTAATTAATGATCTATCAGTGGATTGTCTCCATCGTCCCTGAC :  660
DaIRIPf.2 : AAAGTCGTGACGGGAGGTTAATTAATGATCTATCAGTGGATTGTCTCCATCGTCCCTGAC :  660
DaIRIPf.3 : AAAGTCGTGACGGGAGGTTAATTAATGATCTATCAGTGGATTGTCTCCATCGTCCCTGAC :  660
DaIRIPf.4 : AAAGTCGTGACGGGAGGTTAATTAATGATCTATCAGTGGATTGTCTCCATCGTCCCTGAC :  660
DaIRIPf.5 : AAAGTCGTGACGGGAGGTTAATTAATGATCTATCAGTGGATTGTCTCCATCGTCCCTGAC :  660
DaIRIPf.6 : AAAGTCGTGACGGGAGGTTAATTAATGATCTATCAGTGGATTGTCTCCATCGTCCCTGAC :  660
            *         680         *         700         *         720
DaIRIPf.1 : GGAGTTCACGTCCTTGTCCAAGTTCAGTGTAGCTTACAATCACATGGTAGGGCCAATCGC :  720
DaIRIPf.2 : GGAGTTCACGTCCTTGTCCAAGTTCAGTGTAGCTTACAATCACATGGTAGGGCCAATCGC :  720
DaIRIPf.3 : GGAGTTCACGTCCTTGTCCAAGTTCAGTGTAGCTTACAATCACATGGTAGGGCCAATCGC :  720
DaIRIPf.4 : GGAGTTCACGTCCTTGTCCAAGTTCAGTGTAGCTTACAATCACATGGTAGGGCCAATCGC :  720
DaIRIPf.5 : GGAGTTCACGTCCTTGTCCAAGTTCAGTGTAGCTTACAATCACATGGTAGGGCCAATCGC :  720
DaIRIPf.6 : GGAGTTCACGTCCTTGTCCAAGTTCAGTGTAGCTTACAATCACATGGTAGGGCCAATCGC :  720
```

FIG. 23B

```
                        *         740         *         760         *         780
DaIRIPf.1   :   ATTATGTAACTTCATGGATATAGCATCCTTTTTCTGTTTTAAATAAAAACCCCTAAACTA   :   780
DaIRIPf.2   :   ATTATGTAACTTCATGGATATAGCATCCTTTTTCTGTTTTAAATAAAAACCCCTAAACTA   :   780
DaIRIPf.3   :   ATTATGTAACTTCATGGATATAGCATCCTTTTTCTGTTTTAAATAAAAACCCCTAAACTA   :   780
DaIRIPf.4   :   ATTATGTAACTTCATGGATATAGCATCCTTTTTCTGTTTTAAATAAAAACCCCTAAACTA   :   780
DaIRIPf.5   :   ATTATGTAACTTCATGGATATAGCATCCTTTTTCTGTTTTAAATAAAAACCCCTAAACTA   :   780
DaIRIPf.6   :   ATTATGTAACTTCATGGATATAGCATCCTTTTTCTGTTTTAAATAAAAACCCCTAAACTA   :   780

*         800         *
DaIRIPf.1   :   TCTTACAAAAAAAAAAAAAAAAAAAAAAAA   :   810
DaIRIPf.2   :   TCTTACAAAAAAAAAAAAAAAAAAAAAAAA   :   810
DaIRIPf.3   :   TCTTACAAAAAAAAAAAAAAAAAAAAAAAA   :   810
DaIRIPf.4   :   TCTTACAAAAAAAAAAAAAAAAAAAAAAAA   :   810
DaIRIPf.5   :   TCTTACAAAAAAAAAAAAAAAAAAAAAAAA   :   810
DaIRIPf.6   :   TCTTACAAAAAAAAAAAAAAAAAAAAAAAA   :   810
```

FIG. 23C

```
                    *         20         *         40         *         60
DaIRIP6 : CTCCCCAGGCGCGGCTGGCGGCCCCATCACAGGAGCAACTTTGGCGGCCTGACACGG :  60

*         80         *        100         *        120
DaIRIP6 : CTTGAGTCGCTCAACCTTGCCAACAACAGTCTGGTAGGCACCATCCCATCATGGATCGT : 120

*        140         *        160         *        180
DaIRIP6 : GAGCTTGACCACCTTTGCTACATGGATCTCTCACACAATTCACTAGATGCCGAGGTACCC : 180

*        200         *        220         *        240
DaIRIP6 : AAGAGTTTNCAGATACGGCTCAGGGCCCTCACTACGACCGGTGTTCACTGGGCATGGTT : 240

*        260         *        280         *        300
DaIRIP6 : TTCATTAACATGCCGTTGCATATGAAGCGTAGCCGAAGAACACTCCAAGAACAACCAAAT : 300

*        320         *        340         *        360
DaIRIP6 : GTAATAACTGGGACCAACAACAGTGTCAGNTCTGGGAGAACAATGTTGTTTCCGGGAC : 360

*        380         *        400         *        420
DaIRIP6 : GACAATACTGTCATATCTGGGAACAACAATGTTGTGTCTGGAGCCACAACACTGTCGTA : 420

*        440         *        460         *        480
DaIRIP6 : ACGGGGAGTGCAATGTCGTAAGTGGTAGTAACCATGTCGTATCTAGGACCAACCATGTC : 480

*        500         *        520         *        540
DaIRIP6 : GTAACTGATAACAACAATGCGGTAACCGGAACCACAACACTGTATCCGGAGCCACAAC : 540

*        560         *        580         *        600
DaIRIP6 : ACTGTATCCGGGAGCAACAATGTCGTATCCGGGAGCAACCATGTTGTATCAGGGAGCAAC : 600

*        620         *        640         *        660
DaIRIP6 : AAAGTCGTGACGGGAGGTTAATTAATGATCTATCAGTGGATTGTCTCCATCGTCCTGAC : 660

*        680         *        700         *        720
DaIRIP6 : GGAGTTCACGTCCTTGTCCAAGTTCAGTGTAGCTTACAATCACATGGTAGGGCCAATCGC : 720

*        740         *        760         *        780
DaIRIP6 : ATTATGTAACTTCATNGATATAGCATCCTTTTTCTNTTTAAATAAAAACCCCTAAACTA : 780

*        800         *
DaIRIP6 : TCTTACAAAAAAAAAAAAAAAAAAAAAAAA : 810
```

FIG. 24

```
                  *         20         *         40         *         60
DaIRIP5 : LPERGLAGFITGATLAGLTRLESLRLASNSLVGTIPSSIGRLDHLCYMDLSHNSLDGSVP :  60

*         80         *        100         *        120
DaIRIP5 : KSLQIRLRALTTTGRSLGRVFINMPLHMKRSPRTLQKQPRVITGTNRSVRSGRNVVSGN  : 120

*        140         *        160         *        180
DaIRIP5 : DNTVISGNRNVVSGSHNTVVTGSDVVSGSNBVVSRTNRVVTDNRNAVTGNRNTVSGSRN : 180

*        200
DaIRIP5 : TVSGSNRVVSGSNBVVSGSNKVVTGS : 206
```

FIG. 25

```
                           *        20         *        40         *        60
LpIRIPa.1   : CCCGGGCTGGTAAAAGGTTTACGAAATAGTTGTTATTAAACTATATATGTTCATGTAACT :  60
LpIRIPa.2   : CCCGGGCTGGTAAAAGGTTTACGAAATAGTTGTTATTAAACTATATATGTTCATGTAACT :  60
LpIRIPa.3   : ------------------------------------------------------------ :   -
LpIRIPa.4   : ------------------------------------------------------------ :   -
LpIRIPa.5   : ------------------------------------------------------------ :   -
LpIRIPa.6   : ------------------------------------------------------------ :   -
LpIRIPa.7   : ------------------------------------------------------------ :   -
LpIRIPa.8   : ------------------------------------------------------------ :   -
LpIRIPa.9   : ------------------------------------------------------------ :   -
LpIRIPa.10  : ------------------------------------------------------------ :   -
LpIRIPa.11  : ------------------------------------------------------------ :   -
LpIRIPa.12  : ------------------------------------------------------------ :   -
LpIRIPa.13  : ------------------------------------------------------------ :   -
LpIRIPa.14  : ------------------------------------------------------------ :   -
LpIRIPa.15  : ------------------------------------------------------------ :   -
LpIRIPa.16  : ------------------------------------------------------------ :   -
LpIRIPa.17  : ------------------------------------------------------------ :   -
LpIRIPa.18  : ------------------------------------------------------------ :   -
LpIRIPa.19  : ------------------------------------------------------------ :   -
LpIRIPa.20  : ------------------------------------------------------------ :   -
LpIRIPa.21  : ------------------------------------------------------------ :   -
LpIRIPa.22  : ------------------------------------------------------------ :   -
LpIRIPa.23  : ------------------------------------------------------------ :   -
LpIRIPa.24  : ------------------------------------------------------------ :   -
LpIRIPa.25  : ------------------------------------------------------------ :   -
LpIRIPa.26  : ------------------------------------------------------------ :   -
LpIRIPa.27  : ------------------------------------------------------------ :   -
LpIRIPa.28  : ------------------------------------------------------------ :   -
LpIRIPa.29  : ------------------------------------------------------------ :   -
LpIRIPa.30  : ------------------------------------------------------------ :   -
LpIRIPa.31  : ------------------------------------------------------------ :   -
LpIRIPa.32  : ------------------------------------------------------------ :   -
LpIRIPa.33  : ------------------------------------------------------------ :   -
LpIRIPa.34  : ------------------------------------------------------------ :   -
LpIRIPa.35  : ------------------------------------------------------------ :   -
LpIRIPa.36  : ------------------------------------------------------------ :   -
LpIRIPa.37  : ------------------------------------------------------------ :   -
LpIRIPa.38  : ------------------------------------------------------------ :   -
LpIRIPa.39  : ------------------------------------------------------------ :   -
LpIRIPa.40  : ------------------------------------------------------------ :   -
LpIRIPa.41  : ------------------------------------------------------------ :   -
LpIRIPa.42  : ------------------------------------------------------------ :   -
LpIRIPa.43  : ------------------------------------------------------------ :   -
LpIRIPa.44  : ------------------------------------------------------------ :   -
LpIRIPa.45  : ------------------------------------------------------------ :   -
LpIRIPa.46  : ------------------------------------------------------------ :   -
```

FIG. 26A

```
                         *         80         *        100         *        120
LpIRIPa.1   : ATATTTCAATATAATTATTTGTATTACAGCAGAAAATCATTATTTCTATTACTTTGTATT :  120
LpIRIPa.2   : ATATTTCAATATAATTATTTGTATTACAGCAGAAAATCATTATTTCTATTACTTTGTATT :  120
LpIRIPa.3   : ------------------------------------------------------------ :    -
LpIRIPa.4   : ------------------------------------------------------------ :    -
LpIRIPa.5   : ------------------------------------------------------------ :    -
LpIRIPa.6   : ------------------------------------------------------------ :    -
LpIRIPa.7   : ------------------------------------------------------------ :    -
LpIRIPa.8   : ------------------------------------------------------------ :    -
LpIRIPa.9   : ------------------------------------------------------------ :    -
LpIRIPa.10  : ------------------------------------------------------------ :    -
LpIRIPa.11  : ------------------------------------------------------------ :    -
LpIRIPa.12  : ------------------------------------------------------------ :    -
LpIRIPa.13  : ------------------------------------------------------------ :    -
LpIRIPa.14  : ------------------------------------------------------------ :    -
LpIRIPa.15  : ------------------------------------------------------------ :    -
LpIRIPa.16  : ------------------------------------------------------------ :    -
LpIRIPa.17  : ------------------------------------------------------------ :    -
LpIRIPa.18  : ------------------------------------------------------------ :    -
LpIRIPa.19  : ------------------------------------------------------------ :    -
LpIRIPa.20  : ------------------------------------------------------------ :    -
LpIRIPa.21  : ------------------------------------------------------------ :    -
LpIRIPa.22  : ------------------------------------------------------------ :    -
LpIRIPa.23  : ------------------------------------------------------------ :    -
LpIRIPa.24  : ------------------------------------------------------------ :    -
LpIRIPa.25  : ------------------------------------------------------------ :    -
LpIRIPa.26  : ------------------------------------------------------------ :    -
LpIRIPa.27  : ------------------------------------------------------------ :    -
LpIRIPa.28  : ------------------------------------------------------------ :    -
LpIRIPa.29  : ------------------------------------------------------------ :    -
LpIRIPa.30  : ------------------------------------------------------------ :    -
LpIRIPa.31  : ------------------------------------------------------------ :    -
LpIRIPa.32  : ------------------------------------------------------------ :    -
LpIRIPa.33  : ------------------------------------------------------------ :    -
LpIRIPa.34  : ------------------------------------------------------------ :    -
LpIRIPa.35  : ------------------------------------------------------------ :    -
LpIRIPa.36  : ------------------------------------------------------------ :    -
LpIRIPa.37  : ------------------------------------------------------------ :    -
LpIRIPa.38  : ------------------------------------------------------------ :    -
LpIRIPa.39  : ------------------------------------------------------------ :    -
LpIRIPa.40  : ------------------------------------------------------------ :    -
LpIRIPa.41  : ------------------------------------------------------------ :    -
LpIRIPa.42  : ------------------------------------------------------------ :    -
LpIRIPa.43  : ------------------------------------------------------------ :    -
LpIRIPa.44  : ------------------------------------------------------------ :    -
LpIRIPa.45  : ------------------------------------------------------------ :    -
LpIRIPa.46  : ------------------------------------------------------------ :    -
```

FIG. 26B

|            |   |                                                                              |   |     |
|------------|---|------------------------------------------------------------------------------|---|-----|
|            |   | *         140         *         160         *         180                    |   |     |
| LpIRIPa.1  | : | ATTATTTTGTTTTGAGTGTTGTAAAATTGGGAATTACAACTATACTATTTTCGTATGGGA                 | : | 180 |
| LpIRIPa.2  | : | ATTATTTTGTTTTGAGTGTTGTAAAATTGGGAATTACAACTATACTATTTTCGTATGGGA                 | : | 180 |
| LpIRIPa.3  | : | ------------------------------------------------------------                 | : | -   |
| LpIRIPa.4  | : | ------------------------------------------------------------                 | : | -   |
| LpIRIPa.5  | : | ------------------------------------------------------------                 | : | -   |
| LpIRIPa.6  | : | ------------------------------------------------------------                 | : | -   |
| LpIRIPa.7  | : | ------------------------------------------------------------                 | : | -   |
| LpIRIPa.8  | : | ------------------------------------------------------------                 | : | -   |
| LpIRIPa.9  | : | ------------------------------------------------------------                 | : | -   |
| LpIRIPa.10 | : | ------------------------------------------------------------                 | : | -   |
| LpIRIPa.11 | : | ------------------------------------------------------------                 | : | -   |
| LpIRIPa.12 | : | ------------------------------------------------------------                 | : | -   |
| LpIRIPa.13 | : | ------------------------------------------------------------                 | : | -   |
| LpIRIPa.14 | : | ------------------------------------------------------------                 | : | -   |
| LpIRIPa.15 | : | ------------------------------------------------------------                 | : | -   |
| LpIRIPa.16 | : | ------------------------------------------------------------                 | : | -   |
| LpIRIPa.17 | : | ------------------------------------------------------------                 | : | -   |
| LpIRIPa.18 | : | ------------------------------------------------------------                 | : | -   |
| LpIRIPa.19 | : | ------------------------------------------------------------                 | : | -   |
| LpIRIPa.20 | : | ------------------------------------------------------------                 | : | -   |
| LpIRIPa.21 | : | ------------------------------------------------------------                 | : | -   |
| LpIRIPa.22 | : | ------------------------------------------------------------                 | : | -   |
| LpIRIPa.23 | : | ------------------------------------------------------------                 | : | -   |
| LpIRIPa.24 | : | ------------------------------------------------------------                 | : | -   |
| LpIRIPa.25 | : | ------------------------------------------------------------                 | : | -   |
| LpIRIPa.26 | : | ------------------------------------------------------------                 | : | -   |
| LpIRIPa.27 | : | ------------------------------------------------------------                 | : | -   |
| LpIRIPa.28 | : | ------------------------------------------------------------                 | : | -   |
| LpIRIPa.29 | : | ------------------------------------------------------------                 | : | -   |
| LpIRIPa.30 | : | ------------------------------------------------------------                 | : | -   |
| LpIRIPa.31 | : | ------------------------------------------------------------                 | : | -   |
| LpIRIPa.32 | : | ------------------------------------------------------------                 | : | -   |
| LpIRIPa.33 | : | ------------------------------------------------------------                 | : | -   |
| LpIRIPa.34 | : | ------------------------------------------------------------                 | : | -   |
| LpIRIPa.35 | : | ------------------------------------------------------------                 | : | -   |
| LpIRIPa.36 | : | ------------------------------------------------------------                 | : | -   |
| LpIRIPa.37 | : | ------------------------------------------------------------                 | : | -   |
| LpIRIPa.38 | : | ------------------------------------------------------------                 | : | -   |
| LpIRIPa.39 | : | ------------------------------------------------------------                 | : | -   |
| LpIRIPa.40 | : | ------------------------------------------------------------                 | : | -   |
| LpIRIPa.41 | : | ------------------------------------------------------------                 | : | -   |
| LpIRIPa.42 | : | ------------------------------------------------------------                 | : | -   |
| LpIRIPa.43 | : | ------------------------------------------------------------                 | : | -   |
| LpIRIPa.44 | : | ------------------------------------------------------------                 | : | -   |
| LpIRIPa.45 | : | ------------------------------------------------------------                 | : | -   |
| LpIRIPa.46 | : | ------------------------------------------------------------                 | : | -   |

FIG. 26C

```
                     *       200        *       220        *       240
LpIRIPa.1   : ACAATTTGTTAATTTTTGTGTCTCTCTTTCTCTTCATAGCTAGCTGACAGCGAGAACAAA :  240
LpIRIPa.2   : ACAATTTGTTAATTTTTGTGTCTCTCTTTCTCTTCATAGCTAGCTGACAGCGAGAACAAA :  240
LpIRIPa.3   : ------------------------------------------------------------ :   -
LpIRIPa.4   : ------------------------------------------------------------ :   -
LpIRIPa.5   : ------------------------------------------------------------ :   -
LpIRIPa.6   : ------------------------------------------------------------ :   -
LpIRIPa.7   : ------------------------------------------------------------ :   -
LpIRIPa.8   : ------------------------------------------------------------ :   -
LpIRIPa.9   : ------------------------------------------------------------ :   -
LpIRIPa.10  : ------------------------------------------------------------ :   -
LpIRIPa.11  : ------------------------------------------------------------ :   -
LpIRIPa.12  : ------------------------------------------------------------ :   -
LpIRIPa.13  : ------------------------------------------------------------ :   -
LpIRIPa.14  : ------------------------------------------------------------ :   -
LpIRIPa.15  : ------------------------------------------------------------ :   -
LpIRIPa.16  : ------------------------------------------------------------ :   -
LpIRIPa.17  : ------------------------------------------------------------ :   -
LpIRIPa.18  : ------------------------------------------------------------ :   -
LpIRIPa.19  : ------------------------------------------------------------ :   -
LpIRIPa.20  : ------------------------------------------------------------ :   -
LpIRIPa.21  : ------------------------------------------------------------ :   -
LpIRIPa.22  : ------------------------------------------------------------ :   -
LpIRIPa.23  : ------------------------------------------------------------ :   -
LpIRIPa.24  : ------------------------------------------------------------ :   -
LpIRIPa.25  : ------------------------------------------------------------ :   -
LpIRIPa.26  : ------------------------------------------------------------ :   -
LpIRIPa.27  : ------------------------------------------------------------ :   -
LpIRIPa.28  : ------------------------------------------------------------ :   -
LpIRIPa.29  : ------------------------------------------------------------ :   -
LpIRIPa.30  : ------------------------------------------------------------ :   -
LpIRIPa.31  : ------------------------------------------------------------ :   -
LpIRIPa.32  : ------------------------------------------------------------ :   -
LpIRIPa.33  : ------------------------------------------------------------ :   -
LpIRIPa.34  : ------------------------------------------------------------ :   -
LpIRIPa.35  : ------------------------------------------------------------ :   -
LpIRIPa.36  : ------------------------------------------------------------ :   -
LpIRIPa.37  : ------------------------------------------------------------ :   -
LpIRIPa.38  : ------------------------------------------------------------ :   -
LpIRIPa.39  : ------------------------------------------------------------ :   -
LpIRIPa.40  : ------------------------------------------------------------ :   -
LpIRIPa.41  : ------------------------------------------------------------ :   -
LpIRIPa.42  : ------------------------------------------------------------ :   -
LpIRIPa.43  : ------------------------------------------------------------ :   -
LpIRIPa.44  : ------------------------------------------------------------ :   -
LpIRIPa.45  : ------------------------------------------------------------ :   -
LpIRIPa.46  : ------------------------------------------------------------ :   -
```

FIG. 26D

```
                  *       260       *       280       *       300
LpIRIPa.1    : AACCAAGATCTAATTGTGGAAGTAGACTAGTAGTCGACCACCCATGCATGCTTACATAAG : 300
LpIRIPa.2    : AACCAAGATCTAATTGTGGAAGTAGACTAGTAGTCGACCACCCATGCATGCTTACATAAG : 300
LpIRIPa.3    : ------------------------------------------------------------ : -
LpIRIPa.4    : ------------------------------------------------------------ : -
LpIRIPa.5    : ------------------------------------------------------------ : -
LpIRIPa.6    : ------------------------------------------------------------ : -
LpIRIPa.7    : ------------------------------------------------------------ : -
LpIRIPa.8    : ------------------------------------------------------------ : -
LpIRIPa.9    : ------------------------------------------------------------ : -
LpIRIPa.10   : ------------------------------------------------------------ : -
LpIRIPa.11   : ------------------------------------------------------------ : -
LpIRIPa.12   : ------------------------------------------------------------ : -
LpIRIPa.13   : ------------------------------------------------------------ : -
LpIRIPa.14   : ------------------------------------------------------------ : -
LpIRIPa.15   : ------------------------------------------------------------ : -
LpIRIPa.16   : ------------------------------------------------------------ : -
LpIRIPa.17   : ------------------------------------------------------------ : -
LpIRIPa.18   : ------------------------------------------------------------ : -
LpIRIPa.19   : ------------------------------------------------------------ : -
LpIRIPa.20   : ------------------------------------------------------------ : -
LpIRIPa.21   : ------------------------------------------------------------ : -
LpIRIPa.22   : ------------------------------------------------------------ : -
LpIRIPa.23   : ------------------------------------------------------------ : -
LpIRIPa.24   : ------------------------------------------------------------ : -
LpIRIPa.25   : ------------------------------------------------------------ : -
LpIRIPa.26   : ------------------------------------------------------------ : -
LpIRIPa.27   : ------------------------------------------------------------ : -
LpIRIPa.28   : ------------------------------------------------------------ : -
LpIRIPa.29   : ------------------------------------------------------------ : -
LpIRIPa.30   : ------------------------------------------------------------ : -
LpIRIPa.31   : ------------------------------------------------------------ : -
LpIRIPa.32   : ------------------------------------------------------------ : -
LpIRIPa.33   : ------------------------------------------------------------ : -
LpIRIPa.34   : ------------------------------------------------------------ : -
LpIRIPa.35   : ------------------------------------------------------------ : -
LpIRIPa.36   : ------------------------------------------------------------ : -
LpIRIPa.37   : ------------------------------------------------------------ : -
LpIRIPa.38   : ------------------------------------------------------------ : -
LpIRIPa.39   : ------------------------------------------------------------ : -
LpIRIPa.40   : ------------------------------------------------------------ : -
LpIRIPa.41   : ------------------------------------------------------------ : -
LpIRIPa.42   : ------------------------------------------------------------ : -
LpIRIPa.43   : ------------------------------------------------------------ : -
LpIRIPa.44   : ------------------------------------------------------------ : -
LpIRIPa.45   : ------------------------------------------------------------ : -
LpIRIPa.46   : ------------------------------------------------------------ : -
```

FIG. 26E

```
                          *         320         *         340         *         360
LpIRIPa.1    : AAAACACACGCACTATAAGATTGGATGCACCACCCAAGCACTATAAAAAGGATGCACCAC :  360
LpIRIPa.2    : AAAACACACGCACTATAAGATTGGATGCACCACCCAAGCACTATAAAAAGGATGCACCAC :  360
LpIRIPa.3    : ------------------------------------------------------------ :   -
LpIRIPa.4    : ------------------------------------------------------------ :   -
LpIRIPa.5    : ------------------------------------------------------------ :   -
LpIRIPa.6    : ------------------------------------------------------------ :   -
LpIRIPa.7    : ------------------------------------------------------------ :   -
LpIRIPa.8    : ------------------------------------------------------------ :   -
LpIRIPa.9    : ------------------------------------------------------------ :   -
LpIRIPa.10   : ------------------------------------------------------------ :   -
LpIRIPa.11   : ------------------------------------------------------------ :   -
LpIRIPa.12   : ------------------------------------------------------------ :   -
LpIRIPa.13   : ------------------------------------------------------------ :   -
LpIRIPa.14   : ------------------------------------------------------------ :   -
LpIRIPa.15   : ------------------------------------------------------------ :   -
LpIRIPa.16   : ------------------------------------------------------------ :   -
LpIRIPa.17   : ------------------------------------------------------------ :   -
LpIRIPa.18   : ------------------------------------------------------------ :   -
LpIRIPa.19   : ------------------------------------------------------------ :   -
LpIRIPa.20   : ------------------------------------------------------------ :   -
LpIRIPa.21   : ------------------------------------------------------------ :   -
LpIRIPa.22   : ------------------------------------------------------------ :   -
LpIRIPa.23   : ------------------------------------------------------------ :   -
LpIRIPa.24   : ------------------------------------------------------------ :   -
LpIRIPa.25   : ------------------------------------------------------------ :   -
LpIRIPa.26   : ------------------------------------------------------------ :   -
LpIRIPa.27   : ------------------------------------------------------------ :   -
LpIRIPa.28   : ------------------------------------------------------------ :   -
LpIRIPa.29   : ------------------------------------------------------------ :   -
LpIRIPa.30   : ------------------------------------------------------------ :   -
LpIRIPa.31   : ------------------------------------------------------------ :   -
LpIRIPa.32   : ------------------------------------------------------------ :   -
LpIRIPa.33   : ------------------------------------------------------------ :   -
LpIRIPa.34   : ------------------------------------------------------------ :   -
LpIRIPa.35   : ------------------------------------------------------------ :   -
LpIRIPa.36   : ------------------------------------------------------------ :   -
LpIRIPa.37   : ------------------------------------------------------------ :   -
LpIRIPa.38   : ------------------------------------------------------------ :   -
LpIRIPa.39   : ------------------------------------------------------------ :   -
LpIRIPa.40   : ------------------------------------------------------------ :   -
LpIRIPa.41   : ------------------------------------------------------------ :   -
LpIRIPa.42   : ------------------------------------------------------------ :   -
LpIRIPa.43   : ------------------------------------------------------------ :   -
LpIRIPa.44   : ------------------------------------------------------------ :   -
LpIRIPa.45   : ------------------------------------------------------------ :   -
LpIRIPa.46   : ------------------------------------------------------------ :   -
```

FIG. 26F

```
                      *        380         *        400         *        420
LpIRIPa.1  : CTAAGCAATTTTTGCCAACAGCGCGCACTTGTTTGCATTCAAAAAGAAAATCTTACATAG :  420
LpIRIPa.2  : CTAAGCAATTTTTGCCAACAGCGCGCACTTGTTTGCATTCAAAAAGAAAATCTTACATAG :  420
LpIRIPa.3  : ------------------------------------------------------CTTACATAG :    9
LpIRIPa.4  : ------------------------------------------------------CTTACATAG :    9
LpIRIPa.5  : ------------------------------------------------------CTTACATAG :    9
LpIRIPa.6  : ------------------------------------------------------CTTACATAG :    9
LpIRIPa.7  : ------------------------------------------------------CTTACATAG :    9
LpIRIPa.8  : ------------------------------------------------------CTTACATAG :    9
LpIRIPa.9  : ------------------------------------------------------CTTACATAG :    9
LpIRIPa.10 : ------------------------------------------------------CTTACATAG :    9
LpIRIPa.11 : ------------------------------------------------------CTTACATAG :    9
LpIRIPa.12 : ------------------------------------------------------CTTACATAG :    9
LpIRIPa.13 : ------------------------------------------------------CTTACATAG :    9
LpIRIPa.14 : ------------------------------------------------------CTTACATAG :    9
LpIRIPa.15 : ------------------------------------------------------CTTACATAG :    9
LpIRIPa.16 : ------------------------------------------------------------ :    -
LpIRIPa.17 : ------------------------------------------------------------ :    -
LpIRIPa.18 : ------------------------------------------------------------ :    -
LpIRIPa.19 : ------------------------------------------------------------ :    -
LpIRIPa.20 : ------------------------------------------------------------ :    -
LpIRIPa.21 : ------------------------------------------------------------ :    -
LpIRIPa.22 : ------------------------------------------------------------ :    -
LpIRIPa.23 : ------------------------------------------------------------ :    -
LpIRIPa.24 : ------------------------------------------------------------ :    -
LpIRIPa.25 : ------------------------------------------------------------ :    -
LpIRIPa.26 : ------------------------------------------------------------ :    -
LpIRIPa.27 : ------------------------------------------------------------ :    -
LpIRIPa.28 : ------------------------------------------------------------ :    -
LpIRIPa.29 : ------------------------------------------------------------ :    -
LpIRIPa.30 : ------------------------------------------------------------ :    -
LpIRIPa.31 : ------------------------------------------------------------ :    -
LpIRIPa.32 : ------------------------------------------------------------ :    -
LpIRIPa.33 : ------------------------------------------------------------ :    -
LpIRIPa.34 : ------------------------------------------------------------ :    -
LpIRIPa.35 : ------------------------------------------------------------ :    -
LpIRIPa.36 : ------------------------------------------------------------ :    -
LpIRIPa.37 : ------------------------------------------------------------ :    -
LpIRIPa.38 : ------------------------------------------------------------ :    -
LpIRIPa.39 : ------------------------------------------------------------ :    -
LpIRIPa.40 : ------------------------------------------------------------ :    -
LpIRIPa.41 : ------------------------------------------------------------ :    -
LpIRIPa.42 : ------------------------------------------------------------ :    -
LpIRIPa.43 : ------------------------------------------------------------ :    -
LpIRIPa.44 : ------------------------------------------------------------ :    -
LpIRIPa.45 : ------------------------------------------------------------ :    -
LpIRIPa.46 : ------------------------------------------------------------ :    -
```

FIG. 26G

```
                          *         440         *         460         *         480
LpIRIPa.1    :  CTGAACCAATGGAGAAAAGTTGGTTCTTGCTCCTTTTCTTGGCGTTCCTCCTGCCGGCGG  :  480
LpIRIPa.2    :  CTGAACCAATGGAGAAAAGTTGGTTCTTGCTCCTTTTCTTGGCGTTCCTCCTGCCGGCGG  :  480
LpIRIPa.3    :  CTGAACCAATGGAGAAAAGTTGGTTCTTGCTCCTTTTCTTGGCGTTCCTCCTGCCGGCGG  :   69
LpIRIPa.4    :  CTGAACCAATGGAGAAAAGTTGGTTCTTGCTCCTTTTCTTGGCGTTCCTCCTGCCGGCGG  :   69
LpIRIPa.5    :  CTGAACCAATGGAGAAAAGTTGGTTCTTGCTCCTTTTCTTGGCGTTCCTCCTGCCGGCGG  :   69
LpIRIPa.6    :  CTGAACCAATGGAGAAAAGTTGGTTCTTGCTCCTTTTCTTGGCGTTCCTCCTGCCGGCGG  :   69
LpIRIPa.7    :  CTGAACCAATGGAGAAAAGTTGGTTCTTGCTCCTTTTCTTGGCGTTCCTCCTGCCGGCGG  :   69
LpIRIPa.8    :  CTGAACCAATGGAGAAAAGTTGGTTCTTGCTCCTTTTCTTGGCGTTCCTCCTGCCGGCGG  :   69
LpIRIPa.9    :  CTGAACCAATGGAGAAAAGTTGGTTCTTGCTCCTTTTCTTGGCGTTCCTCCTGCCGGCGG  :   69
LpIRIPa.10   :  CTGAACCAATGGAGAAAAGTTGGTTCTTGCTCCTTTTCTTGGCGTTCCTCCTGCCGGCGG  :   69
LpIRIPa.11   :  CTGAACCAATGGAGAAAAGTTGGTTCTTGCTCCTTTTCTTGGCGTTCCTCCTGCCGGCGG  :   69
LpIRIPa.12   :  CTGAACCAATGGAGAAAAGTTGGTTCTTGCTCCTTTTCTTGGCGTTCCTCCTGCCGGCGG  :   69
LpIRIPa.13   :  CTGAACCAATGGAGAAAAGTTGGTTCTTGCTCCTTTTCTTGGCGTTCCTCCTGCCGGCGG  :   69
LpIRIPa.14   :  CTGAACCAATGGAGAAAAGTTGGTTCTTGCTCCTTTTCTTGGCGTTCCTCCTGCCGGCGG  :   69
LpIRIPa.15   :  CTGAACCAATGGAGAAAAGTTGGTTCTTGCTCCTTTTCTTGGCGTTCCTCCTGCCGGCGG  :   69
LpIRIPa.16   :  ------------------------------------------------------------  :    -
LpIRIPa.17   :  ------------------------------------------------------------  :    -
LpIRIPa.18   :  ------------------------------------------------------------  :    -
LpIRIPa.19   :  ------------------------------------------------------------  :    -
LpIRIPa.20   :  ------------------------------------------------------------  :    -
LpIRIPa.21   :  ------------------------------------------------------------  :    -
LpIRIPa.22   :  ------------------------------------------------------------  :    -
LpIRIPa.23   :  ------------------------------------------------------------  :    -
LpIRIPa.24   :  ------------------------------------------------------------  :    -
LpIRIPa.25   :  ------------------------------------------------------------  :    -
LpIRIPa.26   :  ------------------------------------------------------------  :    -
LpIRIPa.27   :  ------------------------------------------------------------  :    -
LpIRIPa.28   :  ------------------------------------------------------------  :    -
LpIRIPa.29   :  ------------------------------------------------------------  :    -
LpIRIPa.30   :  ------------------------------------------------------------  :    -
LpIRIPa.31   :  ------------------------------------------------------------  :    -
LpIRIPa.32   :  ------------------------------------------------------------  :    -
LpIRIPa.33   :  ------------------------------------------------------------  :    -
LpIRIPa.34   :  ------------------------------------------------------------  :    -
LpIRIPa.35   :  ------------------------------------------------------------  :    -
LpIRIPa.36   :  ------------------------------------------------------------  :    -
LpIRIPa.37   :  ------------------------------------------------------------  :    -
LpIRIPa.38   :  ------------------------------------------------------------  :    -
LpIRIPa.39   :  ------------------------------------------------------------  :    -
LpIRIPa.40   :  ------------------------------------------------------------  :    -
LpIRIPa.41   :  ------------------------------------------------------------  :    -
LpIRIPa.42   :  ------------------------------------------------------------  :    -
LpIRIPa.43   :  ------------------------------------------------------------  :    -
LpIRIPa.44   :  ------------------------------------------------------------  :    -
LpIRIPa.45   :  ------------------------------------------------------------  :    -
LpIRIPa.46   :  ------------------------------------------------------------  :    -
```

FIG. 26H

```
                       *         500         *         520         *         540
LpIRIPa.1   : CGAGCGTGGCGGTGTCATGCCACCCTGATGACCTCCTTGCACTGCGCGGGTTCGCCGGTA :  540
LpIRIPa.2   : CGAGCGTGGCGGTGTCATGCCACCCTGATGACCTCCTTGCACTGCGCGGGTTCGCCGGTA :  540
LpIRIPa.3   : CGAGCGTGGCGGTGTCATGCCACCCTGATGACCTCCTTGCACTGCGCGGGTTCGCCGGTA :  129
LpIRIPa.4   : CGAGCGTGGCGGTGTCATGCCACCCTGATGACCTCCTTGCACTGCGCGGGTTCGCCGGTA :  129
LpIRIPa.5   : CGAGCGTGGCGGTGTCATGCCACCCTGATGACCTCCTTGCACTGCGCGGGTTCGCCGGTA :  129
LpIRIPa.6   : CGAGCGTGGCGGTGTCATGCCACCCTGATGACCTCCTTGCACTGCGCGGGTTCGCCGGTA :  129
LpIRIPa.7   : CGAGCGTGGCGGTGTCATGCCACCCTGATGACCTCCTTGCACTGCGCGGGTTCGCCGGTA :  129
LpIRIPa.8   : CGAGCGTGGCGGTGTCATGCCACCCTGATGACCTCCTTGCACTGCGCGGGTTCGCCGGTA :  129
LpIRIPa.9   : CGAGCGTGGCGGTGTCATGCCACCCTGATGACCTCCTTGCACTGCGCGGGTTCGCCGGTA :  129
LpIRIPa.10  : CGAGCGTGGCGGTGTCATGCCACCCTGATGACCTCCTTGCACTGCGCGGGTTCGCCGGTA :  129
LpIRIPa.11  : CGAGCGTGGCGGTGTCATGCCACCCTGATGACCTCCTTGCACTGCGCGGGTTCGCCGGTA :  129
LpIRIPa.12  : CGAGCGTGGCGGTGTCATGCCACCCTGATGACCTCCTTGCACTGCGCGGGTTCGCCGGTA :  129
LpIRIPa.13  : CGAGCGTGGCGGTGTCATGCCACCCTGATGACCTCCTTGCACTGCGCGGGTTCGCCGGTA :  129
LpIRIPa.14  : CGAGCGTGGCGGTGTCATGCCACCCTGATGACCTCCTTGCACTGCGCGGGTTCGCCGGTA :  129
LpIRIPa.15  : CGAGCGTGGCGGTGTCATGCCACCCTGATGACCTCCTTGCACTGCGCGGGTTCGCCGGTA :  129
LpIRIPa.16  : ------------------------------------------------------------ :    -
LpIRIPa.17  : ------------------------------------------------------------ :    -
LpIRIPa.18  : ------------------------------------------------------------ :    -
LpIRIPa.19  : ------------------------------------------------------------ :    -
LpIRIPa.20  : ------------------------------------------------------------ :    -
LpIRIPa.21  : ------------------------------------------------------------ :    -
LpIRIPa.22  : ------------------------------------------------------------ :    -
LpIRIPa.23  : ------------------------------------------------------------ :    -
LpIRIPa.24  : ------------------------------------------------------------ :    -
LpIRIPa.25  : ------------------------------------------------------------ :    -
LpIRIPa.26  : ------------------------------------------------------------ :    -
LpIRIPa.27  : ------------------------------------------------------------ :    -
LpIRIPa.28  : ------------------------------------------------------------ :    -
LpIRIPa.29  : ------------------------------------------------------------ :    -
LpIRIPa.30  : ------------------------------------------------------------ :    -
LpIRIPa.31  : ------------------------------------------------------------ :    -
LpIRIPa.32  : ------------------------------------------------------------ :    -
LpIRIPa.33  : ------------------------------------------------------------ :    -
LpIRIPa.34  : ------------------------------------------------------------ :    -
LpIRIPa.35  : ------------------------------------------------------------ :    -
LpIRIPa.36  : ------------------------------------------------------------ :    -
LpIRIPa.37  : ------------------------------------------------------------ :    -
LpIRIPa.38  : ------------------------------------------------------------ :    -
LpIRIPa.39  : ------------------------------------------------------------ :    -
LpIRIPa.40  : ------------------------------------------------------------ :    -
LpIRIPa.41  : ------------------------------------------------------------ :    -
LpIRIPa.42  : ------------------------------------------------------------ :    -
LpIRIPa.43  : ------------------------------------------------------------ :    -
LpIRIPa.44  : ------------------------------------------------------------ :    -
LpIRIPa.45  : ------------------------------------------------------------ :    -
LpIRIPa.46  : ------------------------------------------------------------ :    -
```

FIG. 26I

```
                       *         560         *         580         *         600
LpIRIPa.1   : ATCTCAGCAATGGGGGCGTGCTCCTCCATGCCAAGTGGCCCGACAACCCTTGCTGTAGTT :  600
LpIRIPa.2   : ATCTCAGCAATGGGGGCGTGCTCCTCCATGCCAAGTGGCCCGACAACTCTTGCTGTAGTT :  600
LpIRIPa.3   : ATCTCAGCAATGGGGGCGTGCTCCTCCATGCCAAGTGGCCCGACAACTCTTGCTGTAGTT :  189
LpIRIPa.4   : ATCTCAGCAATGGGGGCGTGCTCCTCCATGCCAAGTGGCCCGACAACTCTTGCTGTAGTT :  189
LpIRIPa.5   : ATCTCAGCAATGGGGGCGTGCTCCTCCATGCCAAGTGGCCCGACAACTCTTGCTGTAGTT :  189
LpIRIPa.6   : ATCTCAGCAATGGGGGCGTGCTCCTCCATGCCAAGTGGCCCGACAACTCTTGCTGTAGTT :  189
LpIRIPa.7   : ATCTCAGCAATGGGGGCGTGCTCCTCCATGCCAAGTGGCCCGACAACTCTTGCTGTAGTT :  189
LpIRIPa.8   : ATCTCAGCAATGGGGGCGTGCTCCTCCATGCCAAGTGGCCCGACAACTCTTGCTGTAGTT :  189
LpIRIPa.9   : ATCTCAGCAATGGGGGCGTGCTCCTCCATGCCAAGTGGCCCGACAACTCTTGCTGTAGTT :  189
LpIRIPa.10  : ATCTCAGCAATGGGGGCGTGCTCCTCCATGCCAAGTGGCCCGACAACTCTTGCTGTAGTT :  189
LpIRIPa.11  : ATCTCAGCAATGGGGGCGTGCTCCTCCATGCCAAGTGGCCCGACAACTCTTGCTGTAGTT :  189
LpIRIPa.12  : ATCTCAGCAATGGGGGCGTGCTCCTCCATGCCAAGTGGCCCGACAACTCTTGCTGTAGTT :  189
LpIRIPa.13  : ATCTCAGCAATGGGGGCGTGCTCCTCCATGCCAAGTGGCCCGACAACTCTTGCTGTAGTT :  189
LpIRIPa.14  : ATCTCAGCAATGGGGGCGTGCTCCTCCATGCCAAGTGGCCCGACAACTCTTGCTGTAGTT :  189
LpIRIPa.15  : ATCTCAGCAATGGGGGCGTGCTCCTCCATGCCAAGTGGTTCGGCAACTCTTGCTGTAGTT :  189
LpIRIPa.16  : ------------------------------------------------------------ :    -
LpIRIPa.17  : ------------------------------------------------------------ :    -
LpIRIPa.18  : ------------------------------------------------------------ :    -
LpIRIPa.19  : ------------------------------------------------------------ :    -
LpIRIPa.20  : ------------------------------------------------------------ :    -
LpIRIPa.21  : ------------------------------------------------------------ :    -
LpIRIPa.22  : ------------------------------------------------------------ :    -
LpIRIPa.23  : ------------------------------------------------------------ :    -
LpIRIPa.24  : ------------------------------------------------------------ :    -
LpIRIPa.25  : ------------------------------------------------------------ :    -
LpIRIPa.26  : ------------------------------------------------------------ :    -
LpIRIPa.27  : ------------------------------------------------------------ :    -
LpIRIPa.28  : ------------------------------------------------------------ :    -
LpIRIPa.29  : ------------------------------------------------------------ :    -
LpIRIPa.30  : ------------------------------------------------------------ :    -
LpIRIPa.31  : ------------------------------------------------------------ :    -
LpIRIPa.32  : ------------------------------------------------------------ :    -
LpIRIPa.33  : ------------------------------------------------------------ :    -
LpIRIPa.34  : ------------------------------------------------------------ :    -
LpIRIPa.35  : ------------------------------------------------------------ :    -
LpIRIPa.36  : ------------------------------------------------------------ :    -
LpIRIPa.37  : ------------------------------------------------------------ :    -
LpIRIPa.38  : ------------------------------------------------------------ :    -
LpIRIPa.39  : ------------------------------------------------------------ :    -
LpIRIPa.40  : ------------------------------------------------------------ :    -
LpIRIPa.41  : ------------------------------------------------------------ :    -
LpIRIPa.42  : ------------------------------------------------------------ :    -
LpIRIPa.43  : ------------------------------------------------------------ :    -
LpIRIPa.44  : ------------------------------------------------------------ :    -
LpIRIPa.45  : ------------------------------------------------------------ :    -
LpIRIPa.46  : ------------------------------------------------------------ :    -
```

FIG. 26J

```
                        *         620         *         640         *         660
LpIRIPa.1   : GGGAAGGTGTGGGATGCGACGGCGGAAGCGGCCGTGTCACTACGTTGTGGCTCCCTGGGC :  660
LpIRIPa.2   : GGGAAGGTGTGGGATGCGTCGGCGGAAGCGGCCGTGTCACTACGTTGTGGCTCCCTGGAC :  660
LpIRIPa.3   : GGGAAGGTGTGGGATGCGACGGCGGAAGCGGCCGTGTCACTACGTTGTGGCTCCCTGGGC :  249
LpIRIPa.4   : GGGAAGGTGTGGGATGCGACGGCGGAAGCGGCTGTGTCACTACGTTGTGGCTCCCTGGGC :  249
LpIRIPa.5   : GGGAAGGTGTGGGATGCGACGGCGGAAGCGGCCGTGTCACTACGTTGTGGCTCCCTGGGC :  249
LpIRIPa.6   : GGGAAGGTGTGGGATGCGACGGCGGAAGCGGCCGTGTCACTACGTTGTGGCTCCCTGGGC :  249
LpIRIPa.7   : GGGAAGGTGTGGGATGCGACGGCGGAAGCGGCCGTGTCACTACGTTGTGGCTCCCTGGGC :  249
LpIRIPa.8   : GGGAAGGTGTGGGATGCGACGGCGGAAGCGGCCGTGTCACTACGTTGTGGCTCCCTGGGC :  249
LpIRIPa.9   : GGGAAGGTGTGGGATGCGACGGCGGAAGCGGCCGTGTCACTACGTTGTGGCTCCCTGGGC :  249
LpIRIPa.10  : GGGAAGGTGTGGGATGCGACGGCGGAAGCGGCCGTGTCACTACGTTGTGGCTCCCTGGGC :  249
LpIRIPa.11  : GGGAAGGTGTGGGATGCGACGGCGGAAGCGGCCGTGTCACTACGTTGTGGCTCCCTGGGC :  249
LpIRIPa.12  : GGGAAGGTGTGGGATGCGACGGCGGAAGCGGCCGTGTCACTACGTTGTGGCTCCCTGGGC :  249
LpIRIPa.13  : GGGAAGGTGTGGGATGCGACGGCGGAAGCGGCCGTGTCACTACGTTGTGGCTCCCTGGGC :  249
LpIRIPa.14  : GGGAAGGTGTGGGATGCGACGGCGGAAGCGGCCGTGTCACTACGTTGTGGCTCCCTGGGC :  249
LpIRIPa.15  : GGGAAGGTGTGGGATGCGACGGCGGAAGCGGCCGTGTCACTACGTTGTGGCTCCCTGGGC :  249
LpIRIPa.16  : ------------------------------------------------------------ :    -
LpIRIPa.17  : ------------------------------------------------------------ :    -
LpIRIPa.18  : ------------------------------------------------------------ :    -
LpIRIPa.19  : ------------------------------------------------------------ :    -
LpIRIPa.20  : ------------------------------------------------------------ :    -
LpIRIPa.21  : ------------------------------------------------------------ :    -
LpIRIPa.22  : ------------------------------------------------------------ :    -
LpIRIPa.23  : ------------------------------------------------------------ :    -
LpIRIPa.24  : ------------------------------------------------------------ :    -
LpIRIPa.25  : ------------------------------------------------------------ :    -
LpIRIPa.26  : ------------------------------------------------------------ :    -
LpIRIPa.27  : ------------------------------------------------------------ :    -
LpIRIPa.28  : ------------------------------------------------------------ :    -
LpIRIPa.29  : ------------------------------------------------------------ :    -
LpIRIPa.30  : ------------------------------------------------------------ :    -
LpIRIPa.31  : ------------------------------------------------------------ :    -
LpIRIPa.32  : ------------------------------------------------------------ :    -
LpIRIPa.33  : ------------------------------------------------------------ :    -
LpIRIPa.34  : ------------------------------------------------------------ :    -
LpIRIPa.35  : ------------------------------------------------------------ :    -
LpIRIPa.36  : ------------------------------------------------------------ :    -
LpIRIPa.37  : ------------------------------------------------------------ :    -
LpIRIPa.38  : ------------------------------------------------------------ :    -
LpIRIPa.39  : ------------------------------------------------------------ :    -
LpIRIPa.40  : ------------------------------------------------------------ :    -
LpIRIPa.41  : ------------------------------------------------------------ :    -
LpIRIPa.42  : ------------------------------------------------------------ :    -
LpIRIPa.43  : ------------------------------------------------------------ :    -
LpIRIPa.44  : ------------------------------------------------------------ :    -
LpIRIPa.45  : ------------------------------------------------------------ :    -
LpIRIPa.46  : ------------------------------------------------------------ :    -
```

FIG. 26K

```
                       *        680        *        700        *        720
LpIRIPa.1   : ATGGACTCGCAGGCCACATCCCAACAGCATCCTTGGCTGGCCTTGCACGGCTGGAGTCGC :  720
LpIRIPa.2   : ATGGACTCGCAGGCCACATCCCAACAGCATCCTTGGCTGGCCTTGCACGGCTGGAGTCGC :  720
LpIRIPa.3   : ATGGACTCGCAGGCCACATCCCAACAGCATCCTTGGCTGGCCTTGCACGGCTGGAGTCGC :  309
LpIRIPa.4   : ATGGACTCGCAGGCCACATCCCAACAGCATCCTTGGCTGGCCTTGCACGGCTGGAGTCGC :  309
LpIRIPa.5   : ATGGACTCGCAGGCCACATCCCAACAGCATCCTTGGCTGGCCTTGCACGGCTGGAGTCGC :  309
LpIRIPa.6   : ATGGACTCGCAGGCCACATCCCAACAGCATCCTTGGCTGGCCTTGCACGGCTGGAGTCGC :  309
LpIRIPa.7   : ATGGACTCGCAGGCCACATCCCAACAGCATCCTTGGCTGGCCTTGCACGGCTGGAGTCGC :  309
LpIRIPa.8   : ATGGACTCGCAGGCCACATCCCAACAGCATCCTTGGCTGGCCTTGCACGGCTGGAGTCGC :  309
LpIRIPa.9   : ATGGACTCGCAGGCCACATCCCAACAGCATCCTTGGCTGGCCTTGCACGGCTGGAGTCGC :  309
LpIRIPa.10  : ATGGACTCGCAGGCCACATCCCAACAGCATCCTTGGCTGGCCTTGCACGGCTGGAGTCGC :  309
LpIRIPa.11  : ATGGACTCGCAGGCCACATCCCAACAGCATCCTTGGCTGGCCTTGCACGGCTGGAGTCGC :  309
LpIRIPa.12  : ATGGACTCGCAGGCCACATCCCAACAGCATCCTTGGCTGGCCTTGCACGGCTGGAGTCGC :  309
LpIRIPa.13  : ATGGACTCGCAGGCCACATCCCAACAGCATCCTTGGCTGGCCTTGCACGGCTGGAGTCGC :  309
LpIRIPa.14  : ATGGACTCGCAGGCCACATCCCAACAGCATCCTTGGCTGGCCTTGCACGGCTGGAGTCGC :  309
LpIRIPa.15  : ATGGACTCGCAGGCCACATCCCAACAGCATCCTTGGCTGGCCTTGCACGGCTGGAGTCGC :  309
LpIRIPa.16  : ------------------------------------------------------------ :    -
LpIRIPa.17  : ------------------------------------------------------------ :    -
LpIRIPa.18  : ------------------------------------------------------------ :    -
LpIRIPa.19  : ------------------------------------------------------------ :    -
LpIRIPa.20  : ------------------------------------------------------------ :    -
LpIRIPa.21  : ------------------------------------------------------------ :    -
LpIRIPa.22  : ------------------------------------------------------------ :    -
LpIRIPa.23  : ------------------------------------------------------------ :    -
LpIRIPa.24  : ------------------------------------------------------------ :    -
LpIRIPa.25  : ------------------------------------------------------------ :    -
LpIRIPa.26  : ------------------------------------------------------------ :    -
LpIRIPa.27  : ------------------------------------------------------------ :    -
LpIRIPa.28  : ------------------------------------------------------------ :    -
LpIRIPa.29  : ------------------------------------------------------------ :    -
LpIRIPa.30  : ------------------------------------------------------------ :    -
LpIRIPa.31  : ------------------------------------------------------------ :    -
LpIRIPa.32  : ------------------------------------------------------------ :    -
LpIRIPa.33  : ------------------------------------------------------------ :    -
LpIRIPa.34  : ------------------------------------------------------------ :    -
LpIRIPa.35  : ------------------------------------------------------------ :    -
LpIRIPa.36  : ------------------------------------------------------------ :    -
LpIRIPa.37  : ------------------------------------------------------------ :    -
LpIRIPa.38  : ------------------------------------------------------------ :    -
LpIRIPa.39  : ------------------------------------------------------------ :    -
LpIRIPa.40  : ------------------------------------------------------------ :    -
LpIRIPa.41  : ------------------------------------------------------------ :    -
LpIRIPa.42  : ------------------------------------------------------------ :    -
LpIRIPa.43  : ------------------------------------------------------------ :    -
LpIRIPa.44  : ------------------------------------------------------------ :    -
LpIRIPa.45  : ------------------------------------------------------------ :    -
LpIRIPa.46  : ------------------------------------------------------------ :    -
```

FIG. 26L

|  |  | * | 740 | * | 760 | * | 780 |  |  |
|---|---|---|---|---|---|---|---|---|---|
| LpIRIPa.1 | : | TCAACCTCGCCAACAACAAACTGGTCGGCACAATCCCATCTTGGATTGGTGTGCTTGACC | : | 780 |
| LpIRIPa.2 | : | TCAACCTCGCCGACAACAAACTGGTCGGCACAATCCCATCTTGGATTGGTGTGCTTGGCC | : | 780 |
| LpIRIPa.3 | : | TCAACCTCGCCAACAACAAACTGGTCGGCACAATCCCATCTTGGATTGGTGTGCTTGACC | : | 369 |
| LpIRIPa.4 | : | TCAACCTCGCCAACAACAAACTGGTCGGCACAATCCCATCTTGGATTGGTGTGCTTGACC | : | 369 |
| LpIRIPa.5 | : | TCAACCTCGCCAACAACAAACTGGTCGGCACAATCCCATCTTGGATTGGTGTGCTTGACC | : | 369 |
| LpIRIPa.6 | : | TCAACCTCGCCAACAACAAACTGGTCGGCACAATCCCATCTTGGATTGGTGTGCTTGACC | : | 369 |
| LpIRIPa.7 | : | TCAACCTCGCCAACAACAAACTGGTCGGCACAATCCCATCTTGGATTGGTGTGCTTGACC | : | 369 |
| LpIRIPa.8 | : | TCAACCTCGCCAACAACAAACTGGTCGGCACAATCCCATCTTGGATTGGTGTGCTTGACC | : | 369 |
| LpIRIPa.9 | : | TCAACCTCGCCAACAACAAACTGGTCGGCACAATCCCATCTTGGATTGGTGTGCTTGACC | : | 369 |
| LpIRIPa.10 | : | TCAACCTCGCCAACAACAAACTGGTCGGCACAATCCCATCTTGGATTGGTGTGCTTGACC | : | 369 |
| LpIRIPa.11 | : | TCAGCCTCGCCAACAACAAACTGGTCGGCACAATCCCATCTTGGATTGGTGTGCTTGACC | : | 369 |
| LpIRIPa.12 | : | TCAACCTCGCCAACAACAAACTGGTCGGCACAATCCCATCTTGGATTGGTGTGCTTGACC | : | 369 |
| LpIRIPa.13 | : | TCAACCTCGCCAACAACAAACTGGTCGGCACAATCCCATCTTGGATTGGTGTGCTTGACC | : | 369 |
| LpIRIPa.14 | : | TCAACCTCGCCAACAACAAACTGGTCGGCACAATCCCATCTTGGATTGGTGTGCTTGACC | : | 369 |
| LpIRIPa.15 | : | TCAACCTCGCCAACAACAAACTGGTCGGCACAATCCCATCTTGGATTGGTGTGCTTGACC | : | 369 |
| LpIRIPa.16 | : | ------------------------------------------------------------ | : | - |
| LpIRIPa.17 | : | ------------------------------------------------------------ | : | - |
| LpIRIPa.18 | : | ------------------------------------------------------------ | : | - |
| LpIRIPa.19 | : | ------------------------------------------------------------ | : | - |
| LpIRIPa.20 | : | ------------------------------------------------------------ | : | - |
| LpIRIPa.21 | : | ------------------------------------------------------------ | : | - |
| LpIRIPa.22 | : | ------------------------------------------------------------ | : | - |
| LpIRIPa.23 | : | ------------------------------------------------------------ | : | - |
| LpIRIPa.24 | : | ------------------------------------------------------------ | : | - |
| LpIRIPa.25 | : | ------------------------------------------------------------ | : | - |
| LpIRIPa.26 | : | ------------------------------------------------------------ | : | - |
| LpIRIPa.27 | : | ------------------------------------------------------------ | : | - |
| LpIRIPa.28 | : | ------------------------------------------------------------ | : | - |
| LpIRIPa.29 | : | ------------------------------------------------------------ | : | - |
| LpIRIPa.30 | : | ------------------------------------------------------------ | : | - |
| LpIRIPa.31 | : | ------------------------------------------------------------ | : | - |
| LpIRIPa.32 | : | ------------------------------------------------------------ | : | - |
| LpIRIPa.33 | : | ------------------------------------------------------------ | : | - |
| LpIRIPa.34 | : | ------------------------------------------------------------ | : | - |
| LpIRIPa.35 | : | ------------------------------------------------------------ | : | - |
| LpIRIPa.36 | : | ------------------------------------------------------------ | : | - |
| LpIRIPa.37 | : | ------------------------------------------------------------ | : | - |
| LpIRIPa.38 | : | ------------------------------------------------------------ | : | - |
| LpIRIPa.39 | : | ------------------------------------------------------------ | : | - |
| LpIRIPa.40 | : | ------------------------------------------------------------ | : | - |
| LpIRIPa.41 | : | ------------------------------------------------------------ | : | - |
| LpIRIPa.42 | : | ------------------------------------------------------------ | : | - |
| LpIRIPa.43 | : | ------------------------------------------------------------ | : | - |
| LpIRIPa.44 | : | ------------------------------------------------------------ | : | - |
| LpIRIPa.45 | : | ------------------------------------------------------------ | : | - |
| LpIRIPa.46 | : | ------------------------------------------------------------ | : | - |

FIG. 26M

|          |   |                                                                          |   |     |
|----------|---|--------------------------------------------------------------------------|---|-----|
|          |   | *        800         *         820         *         840                 |   |     |
| LpIRIPa.1  | : | ACCTTTGCTACTTGGATCTCTCAAATAATTCATTGGTTGGTGAGATACCAAAGAATTTAC | : | 840 |
| LpIRIPa.2  | : | ACCTTTGCTACTTGGATCTCTCAAATAATTCATTGGTTGGTGAGATACCAAAGAATTTAC | : | 840 |
| LpIRIPa.3  | : | ACCTTTGCTACTTGGATCTCTCAAATAATTCATTGGTTGGTGAGATACCAAAGAATTTAC | : | 429 |
| LpIRIPa.4  | : | ACCTTTGCTACTTGGATCTCTCAAATAATTCATTGGTTGGTGAGATACCAAAGAATTTAC | : | 429 |
| LpIRIPa.5  | : | ACCTTTGCTACTTGGATCTCTCAAATAATTCATTGGTTGGTGAGATACCAAAGAATTTAC | : | 429 |
| LpIRIPa.6  | : | ACCTTTGCTACTTGGATCTCTCAAATAATTCATTGGTTGGTGAGATACCAAGGAATTTAC | : | 429 |
| LpIRIPa.7  | : | ACCTTTGCTACTTGGATCTCTCAAATAATTCATTGGTTGGTGAGATACCAAAGAATTTAC | : | 429 |
| LpIRIPa.8  | : | ACCTTTGCTACTTGGATCTCTCAAATAATTCATTGGTTGGTGAGATACCAAAGAATTTAC | : | 429 |
| LpIRIPa.9  | : | ACCTTTGCTACTTGGATCTCTCAAATAATTCATTGGTTGGTGAGATACCAAAGAATTTAC | : | 429 |
| LpIRIPa.10 | : | ACCTTTGCTACTTGGATCTCTCAAATAATTCATTGGTTGGTGAGATACCAAAGAATTTAC | : | 429 |
| LpIRIPa.11 | : | ACCTTTGCTACTTGGATCTCTCAAATAATTCATTGGTTGGTGAGATACCAAAGAATTTAC | : | 429 |
| LpIRIPa.12 | : | ACCTTTGCTACTTGGATCTCTCAAATAATTCATTGGTTGGTGAGATACCAAAGAATTTAC | : | 429 |
| LpIRIPa.13 | : | ACCTTTGCTACTTGGATCTCTCAAATAATTCATTGGTTGGTGAGATACCAAAGAATTTAC | : | 429 |
| LpIRIPa.14 | : | ACCTTTGCTACTTGGATCTCTCAAATAATTCATTGGTTGGTGAGATACCAAAGAATTTAC | : | 429 |
| LpIRIPa.15 | : | ACCTTTGCTACTTGGATCTCTCAAATAATTCATTGGTTGGTGAGATACCAAAGAATTTAC | : | 429 |
| LpIRIPa.16 | : | ------------------------------------------------------------ | : | -   |
| LpIRIPa.17 | : | ------------------------------------------------------------ | : | -   |
| LpIRIPa.18 | : | ------------------------------------------------------------ | : | -   |
| LpIRIPa.19 | : | ------------------------------------------------------------ | : | -   |
| LpIRIPa.20 | : | ------------------------------------------------------------ | : | -   |
| LpIRIPa.21 | : | ------------------------------------------------------------ | : | -   |
| LpIRIPa.22 | : | ------------------------------------------------------------ | : | -   |
| LpIRIPa.23 | : | ------------------------------------------------------------ | : | -   |
| LpIRIPa.24 | : | ------------------------------------------------------------ | : | -   |
| LpIRIPa.25 | : | ------------------------------------------------------------ | : | -   |
| LpIRIPa.26 | : | ------------------------------------------------------------ | : | -   |
| LpIRIPa.27 | : | ------------------------------------------------------------ | : | -   |
| LpIRIPa.28 | : | ------------------------------------------------------------ | : | -   |
| LpIRIPa.29 | : | ------------------------------------------------------------ | : | -   |
| LpIRIPa.30 | : | ------------------------------------------------------------ | : | -   |
| LpIRIPa.31 | : | ------------------------------------------------------------ | : | -   |
| LpIRIPa.32 | : | ------------------------------------------------------------ | : | -   |
| LpIRIPa.33 | : | ------------------------------------------------------------ | : | -   |
| LpIRIPa.34 | : | ------------------------------------------------------------ | : | -   |
| LpIRIPa.35 | : | ------------------------------------------------------------ | : | -   |
| LpIRIPa.36 | : | ------------------------------------------------------------ | : | -   |
| LpIRIPa.37 | : | ------------------------------------------------------------ | : | -   |
| LpIRIPa.38 | : | ------------------------------------------------------------ | : | -   |
| LpIRIPa.39 | : | ------------------------------------------------------------ | : | -   |
| LpIRIPa.40 | : | ------------------------------------------------------------ | : | -   |
| LpIRIPa.41 | : | ------------------------------------------------------------ | : | -   |
| LpIRIPa.42 | : | ------------------------------------------------------------ | : | -   |
| LpIRIPa.43 | : | ------------------------------------------------------------ | : | -   |
| LpIRIPa.44 | : | ------------------------------------------------------------ | : | -   |
| LpIRIPa.45 | : | ------------------------------------------------------------ | : | -   |
| LpIRIPa.46 | : | ------------------------------------------------------------ | : | -   |

FIG. 26N

|  |  | * 860 * 880 * 900 |  |  |
| --- | --- | --- | --- | --- |
| LpIRIPa.1 | : | AAATAAGGCTCAGGTGCCTCAACATCGTTGGTCGTTCACTGGGTATGGCTTCCACTAACA | : | 900 |
| LpIRIPa.2 | : | AAATAAGGCTCAGGTGCCTCAACATCGTTGGTCGTTCACTGGGTATGGCTTCCACTAACA | : | 900 |
| LpIRIPa.3 | : | AAATAAGGCTCAGGTGCCTCAACATCGTTGGTCGTTCACTGGGCATGGCTTCCACTAACA | : | 489 |
| LpIRIPa.4 | : | AAATAAGGCTCAGGTGCCTCAACATCGTTGGTCGTTCACTGGGCATGGCTTCCACTAACA | : | 489 |
| LpIRIPa.5 | : | AAATAAGGCTCAGGTGCCTCAACATCGTTGGTCGTTCACTGGGCATGGCTTCCACTAACA | : | 489 |
| LpIRIPa.6 | : | AAATAAGGCTCAGGTGCCTCAACATCGTTGGTCGTTCACTGGGCATGGCTTCCACTAACA | : | 489 |
| LpIRIPa.7 | : | AAATAAGGCTCAGGTGCCTCAACATCGTTGGTCGTTCACTGGGCATGGCTTCCACTAACA | : | 489 |
| LpIRIPa.8 | : | AAATAAGGCTCAGGTGCCTCAACATCGTTGGTCGTTCACTGGGCATGGCTTCCACTAACA | : | 489 |
| LpIRIPa.9 | : | AAATAAGGCTCAGGTGCCTCAACATCGTTGGTCGTTCACTGGGCATGGCTTCCACTAACA | : | 489 |
| LpIRIPa.10 | : | AAATAAGGCTCAGGTGCCTCAACATCGTTGGTCGTTCACTGGGCATGGCTTCCACTAACA | : | 489 |
| LpIRIPa.11 | : | AAATAAGGCTCAGGTGCCTCAACATCGTTGGTCGTTCACTGGGCATGGCTTCCACTAACA | : | 489 |
| LpIRIPa.12 | : | AAATAAGGCTCAGGTGCCTCAACATCGTTGGTCGTTCACTGGGCATGGCTTCCACTAACA | : | 489 |
| LpIRIPa.13 | : | AAATAAGGCTCAGGTGCCTCAACATCGTTGGTCGTTCACTGGGCATGGCTTCCACTAACA | : | 489 |
| LpIRIPa.14 | : | AAATAAGGCTCAGGTGCCTCAACATCGTTGGTCGTTCACTGGGCATGGCTTCCACTAACA | : | 489 |
| LpIRIPa.15 | : | AAATAAGGCTCAGGTGCCTCAACATCGTTGGTCGTTCACTGGGCATGGCTTCCACTAACA | : | 489 |
| LpIRIPa.16 | : | ------------GGTGCCTCAACATCGTTGGTCGTTCACTGGGCATGGCTTCCACTAACA | : | 48 |
| LpIRIPa.17 | : | ------------GGTGCCTCAACATCGTTGGTCGTTCACTGGGCATGGCTTCCACTAACA | : | 48 |
| LpIRIPa.18 | : | ------------GGTGCCTCAACATCGTTGGTCGTTCACTGGGCATGGCTTCCACTAACA | : | 48 |
| LpIRIPa.19 | : | ------------GGTGCCTCAACATCGTTGGTCGTTCACTGGGCATGGCTTCCACTAACA | : | 48 |
| LpIRIPa.20 | : | ------------GGTGCCTCAACATCGTTGGTCGTTCACTGGGCATGGCTTCCACTAACA | : | 48 |
| LpIRIPa.21 | : | ------------GGTGCCTCAACATCGTTGGTCGTTCACTGGGCATGGCTTCCACTAACA | : | 48 |
| LpIRIPa.22 | : | ------------GGTGCCTCAACATCGTTGGTCGTTCACTGGGCATGGCTTCCACTAACA | : | 48 |
| LpIRIPa.23 | : | ------------GGTGCCTCAACATCGTTGGTCGTTCACTGGGCATGGCTTCCACTAACA | : | 48 |
| LpIRIPa.24 | : | ------------GGTGCCTCAACATCGTTGGTCGTTCACTGGGCATGGCTTCCACTAACA | : | 48 |
| LpIRIPa.25 | : | ------------GGTGCCTCAACATCGTTGGTCGTTCACTGGGCATGGCTTCCACTAACA | : | 48 |
| LpIRIPa.26 | : | ------------GGTGCCTCAACATCGTTGGTCGTTCACTAGGCATGGCTTCCACTAACA | : | 48 |
| LpIRIPa.27 | : | ------------GGTGCCTCAACATCGTTGGTCGTTCACTGGGCATGGCTTCCACTAACA | : | 48 |
| LpIRIPa.28 | : | ------------GGTGCCTCAACATCGTTGGTCGTTCACTGGGCATGGCTTCCACTAACA | : | 48 |
| LpIRIPa.29 | : | ------------GGTGCCTCAACATCGTTGGTCGTTCACTGGGCATGGCTTCCACTAACA | : | 48 |
| LpIRIPa.30 | : | ------------GGTGCCTCAACATCGTTGGTCGTTCACTGGGCATGGCTTCCACTAACA | : | 48 |
| LpIRIPa.31 | : | ------------GGTGCCTCAACATCGTTGGTCGTTCACTGGGCATGGCTTCCACTAACA | : | 48 |
| LpIRIPa.32 | : | ------------GGTGCCTCAACATCGTTGGTCGTTCACTGGGCATGGCTTCCACTAACA | : | 48 |
| LpIRIPa.33 | : | ------------GGTGCCTCAACATCGTTGGTCGTTCACTGGGCATGGCTTCCACTAACA | : | 48 |
| LpIRIPa.34 | : | ------------GGTGCCTCAACATCGTTGGTCGTTCACTGGGCATGGCTTCCACTAACA | : | 48 |
| LpIRIPa.35 | : | ------------GGTGCCTCAACATCGTTGGTCGTTCACTGGGCATGGCTTCCACTAACA | : | 48 |
| LpIRIPa.36 | : | ------------GGTGCCTCAACATCGTTGGTCGTTCACTGGGCATGGCTTCCACTAACA | : | 48 |
| LpIRIPa.37 | : | ------------GGTGCCTCAACATCGTTGGTCGTTCACTGGGCATGGCTTCCACTAACA | : | 48 |
| LpIRIPa.38 | : | ------------GGTGCCTCAACATCGTTGGTCGTTCACTGGGCATGGCTTCCACTAACA | : | 48 |
| LpIRIPa.39 | : | ------------GGTGCCTCAACATCGTTGGTCGTTCACTGGGCATGGCTCCCACTAACA | : | 48 |
| LpIRIPa.40 | : | --------------TGCCTCAACATCGTTGGTCGTTCACTGGGCATGGCTTCCACTAACA | : | 46 |
| LpIRIPa.41 | : | ---------------GCCTCAACATCGTTGGTCGTTCACTGGGCATGGCTTCCACTAACA | : | 45 |
| LpIRIPa.42 | : | -------------------CAACATCGTTGGTCGTTCACTGGGCATGGCTTCCACTAACA | : | 41 |
| LpIRIPa.43 | : | -------------------CAACATCGTTGGTCGTTCACTGGGCATGGCTTCCACTAACA | : | 41 |
| LpIRIPa.44 | : | -------------------CAACATCGTTGGTCGTTCACTGGGCATGGCTTCCACTAACA | : | 41 |
| LpIRIPa.45 | : | -------------------------CGTTGGTCGTTCACTGGGCATGGCTTCCACTAACA | : | 35 |
| LpIRIPa.46 | : | ------------------------------------------------------------ | : | - |

FIG. 26O

|            |   |          *          920          *          940          *          960           |   |     |
|------------|---|-------------------------------------------------------------------------------------|---|-----|
| LpIRIPa.1  | : | TGACATTGCAGGTGAAGCATAACCAAATGGCACTAAGTGGGCAACCAAACACAATAACCG                        | : | 960 |
| LpIRIPa.2  | : | CGACATTGCAGGTGAAGCATAACCAAATAGCACTAAGTGGGCAACCAAACACAATAACCG                        | : | 960 |
| LpIRIPa.3  | : | TGACATTGCAGGTGAAGCATAACCAAATAGCACTAAGTGGGCAACCAAACACAATAACCG                        | : | 549 |
| LpIRIPa.4  | : | TGACATTGCAGGTGAAGCATAACCAAATAGCACTAAGTGGGCAACCAAACACAATAACCG                        | : | 549 |
| LpIRIPa.5  | : | TGACATTGCAGGTGAAGCATAACCAAATAGCACTAAGTGGGCAACCAAACACAATAACCG                        | : | 549 |
| LpIRIPa.6  | : | TGACATTGCAGGTGAAGCATAACCAAATAGCACTAAGTGGGCAACCAAACACAATAACCG                        | : | 549 |
| LpIRIPa.7  | : | TGACATTGCAGGTGAAGCATAACCAAATAGCACTAAGTGGGCAACCAAACACAATAACCG                        | : | 549 |
| LpIRIPa.8  | : | TGACATTGCAGGTGAAGCATAACCAAATAGCACTAAGTGGGCAACCAAACACAATAACCG                        | : | 549 |
| LpIRIPa.9  | : | TGACATTGCAGGTGAAGCATAACCAAATAGCACTAAGTGGGCAACCAAACACAATAACCG                        | : | 549 |
| LpIRIPa.10 | : | TGACATTGCAGGTGAAGCATAACCAAATAGCACTAAGTGGGCAACCAAACACAATAACCG                        | : | 549 |
| LpIRIPa.11 | : | TGACATTGCAGGTGAAGCATAACCAAATAGCACTAAGTGGGCAACCAAACACAATAACCG                        | : | 549 |
| LpIRIPa.12 | : | TGACATTGCAGGTGAAGCATAACCAAATAGCACTAAGTGGGCAACCAAACACAATAACCG                        | : | 549 |
| LpIRIPa.13 | : | TGACATTGCAGGTGAAGCATAACCAAATAGCACTAAGTGGGCAACCAAACACAATAACCG                        | : | 549 |
| LpIRIPa.14 | : | TGACATTGCAGGTGAAGCATAACCAAATAGCACTAAGTGGGCAACCAAACACAATAACCG                        | : | 549 |
| LpIRIPa.15 | : | TGACATTGCAGGTGAAGCATAACCAAATAGCACTAAGTGGGCAACCAAACACAATAACCG                        | : | 549 |
| LpIRIPa.16 | : | TGACATTGCAGGTGAAGCATAACCAAATAGCACTAAGTGGGCAACCAAACACAATAACCG                        | : | 108 |
| LpIRIPa.17 | : | TGACATTGCAGGTGAAGCATAACCAAATAGCACTAAGTGGGCAACCAAACACAATAACCG                        | : | 108 |
| LpIRIPa.18 | : | TGACATTGCAGGTGAAGCATAACCAAATAGCACTAAGTGGGCAACCAAACACAATAACCG                        | : | 108 |
| LpIRIPa.19 | : | TGACATTGCAGGTGAAGCATAACCAAATAGCACTAAGTGGGCAACCAAACACAATAACCG                        | : | 108 |
| LpIRIPa.20 | : | TGACATTGCAGGTGAAGCATAACCAAATAGCACTAAGTGGGCAACCAAACACAATAACCG                        | : | 108 |
| LpIRIPa.21 | : | TGACATTGCAGGTGAAGCATAACCAAATAGCACTAAGTGGGCAACCAAACACAATAACCG                        | : | 108 |
| LpIRIPa.22 | : | TGACATTGCAGGTGAAGCATAACCAAATAGCACTAAGTGGGCAACCAAACACAATAACCG                        | : | 108 |
| LpIRIPa.23 | : | TGACATTGCAGGTGAAGCATAACCAAATAGCACTAAGTGGGCAACCAAACACAATAACCG                        | : | 108 |
| LpIRIPa.24 | : | TGACATTGCAGGTGAAGCATAACCAAATAGCACTAAGTGGGCAACCAAACACAATAACCG                        | : | 108 |
| LpIRIPa.25 | : | TGACATTGCAGGTGAAGCATAACCAAATAGCACTAAGTGGGCAACCAAACACAATAACCG                        | : | 108 |
| LpIRIPa.26 | : | TGACATTGCAGGTGAAGCATAACCAAATAGCACTAAGTGGGCAACCAAACACAATAACCG                        | : | 108 |
| LpIRIPa.27 | : | TGACATTGCAGGTGAAGCATAACCAAATAGCACTAAGTGGGCAACCAAACACAATAACCG                        | : | 108 |
| LpIRIPa.28 | : | TGACATTGCAGGTGAAGCATAACCAAATAGCACTAAGTGGGCAACCAAACACAATAACCG                        | : | 108 |
| LpIRIPa.29 | : | TGACATTGCAGGTGAAGCATAACCAAATAGCACTAAGTGGGCAACCAAACACAATAACCG                        | : | 108 |
| LpIRIPa.30 | : | TGACATTGCAGGTGAAGCATAACCAAATAGCACTAAGTGGGCAACCAAACACAATAACCG                        | : | 108 |
| LpIRIPa.31 | : | TGACATTGCAGGTGAAGCATAACCAAATAGCACTAAGTGGGCAACCAAACACAATAACCG                        | : | 108 |
| LpIRIPa.32 | : | TGACATTGCAGGTGAAGCATAACCAAATAGCACTAAGTGGGCAACCAAACACAATAACCG                        | : | 108 |
| LpIRIPa.33 | : | TGACATTGCAGGTGAAGCATAACCAAATAGCACTAAGTGGGCAACCAAACACAATAACCG                        | : | 108 |
| LpIRIPa.34 | : | TGACATTGCAGGTGAAGCATAACCAAATAGCACTAAGTGGGCAACCAAACACAATAACCG                        | : | 108 |
| LpIRIPa.35 | : | TGACATTGCAGGTGAAGCATAACCAAATAGCACTAAGTGGGCAACCAAACACAATAACCG                        | : | 108 |
| LpIRIPa.36 | : | TGACATTGCAGGTGAAGCATAACCAAATAGCACTAAGTGGGCAACCAAACACAATAACCG                        | : | 108 |
| LpIRIPa.37 | : | TGACATTGCAGGTGAAGCATAACCAAATAGCACTAAGTGGGCAACCAAACACAATAACCG                        | : | 108 |
| LpIRIPa.38 | : | TGACATTGCAGGTGAAGCATAACCAAATAGCACTAAGTGGGCAACCAAACACAATAACCG                        | : | 108 |
| LpIRIPa.39 | : | TGACATTGCAGGTGAAGCATAACCAAATAGCACTAAGTGGGCAACCAAACACAATAACCG                        | : | 108 |
| LpIRIPa.40 | : | TGACATTGCAGGTGAAGCATAACCAAATAGCACTAAGTGGGCAACCAAACACAATAACCG                        | : | 106 |
| LpIRIPa.41 | : | TGACATTGCAGGTGAAGCATAACCAAATAGCACTAAGTGGGCAACCAAACACAATAACCG                        | : | 105 |
| LpIRIPa.42 | : | TGACATTGCAGGTGAAGCATAACCAAATAGCACTAAGTGGGCAACCAAACACAATAACCG                        | : | 101 |
| LpIRIPa.43 | : | TGACATTGCAGGTGAAGCATAACCAAATAGCACTAAGTGGGCAACCAAACACAATAACCG                        | : | 101 |
| LpIRIPa.44 | : | TGACATTGCAGGTGAAGCATAACCAAATAGCACTAAGTGGGCAACCAAACACAATAACCG                        | : | 101 |
| LpIRIPa.45 | : | TGACATTGCAGGTGAAGCATAACCAAATAGCACTAAGTGGGCAACCAAACACAATAACCG                        | : | 95  |
| LpIRIPa.46 | : | ------------------------------------------------------------                        | : | -   |

FIG. 26P

|            |   |                    | 980 |        * |         100 |         * |     1020   |   |      |
|------------|---|--------------------|-----|----------|-------------|-----------|------------|---|------|
| LpIRIPa.1  | : | GGACCAATAACTATGTCAGATCTGGGGTCAACAATGTTGTTTCTGGGAACCACAACACTG | : | 1020 |
| LpIRIPa.2  | : | GGACCAATAACTATGTCAGATCTGGGGTCAACAATGTTGTTTCTGGGAACCACAACACTG | : | 1020 |
| LpIRIPa.3  | : | GGACCAATAACTATGTCAG----------------------------------------- | : | 568  |
| LpIRIPa.4  | : | GGACCAATAACTATGTCAG----------------------------------------- | : | 568  |
| LpIRIPa.5  | : | GGACCAATAACTATGTCAG----------------------------------------- | : | 568  |
| LpIRIPa.6  | : | GGACCAATAACTATGTCAG----------------------------------------- | : | 568  |
| LpIRIPa.7  | : | GGACC------------------------------------------------------- | : | 554  |
| LpIRIPa.8  | : | GGACCAATAACTATGTCAG----------------------------------------- | : | 568  |
| LpIRIPa.9  | : | GGACCAATAACTATGTCAGA---------------------------------------- | : | 569  |
| LpIRIPa.10 | : | GGACCAATAACTATGTCA------------------------------------------ | : | 567  |
| LpIRIPa.11 | : | GGACCAATAACTATGTC------------------------------------------- | : | 566  |
| LpIRIPa.12 | : | GGACCAATAACTATGTCAG----------------------------------------- | : | 568  |
| LpIRIPa.13 | : | GGACCAATAACTATGTCAG----------------------------------------- | : | 568  |
| LpIRIPa.14 | : | GGACCAATAACTATGTCAG----------------------------------------- | : | 568  |
| LpIRIPa.15 | : | GGACCAATAACTATGTC------------------------------------------- | : | 566  |
| LpIRIPa.16 | : | GGACCAATAACTATGTCAGATCTGGGGTCAACAATGTTGTTTCTGGGAACCACAACACTG | : | 168  |
| LpIRIPa.17 | : | GGACCAATAACTATGTCAGATCTGGGGTCAACAATGTTGTTTCTGGGAACCACAACACTG | : | 168  |
| LpIRIPa.18 | : | GGACCAATAACTATGTCAGATCTGGGGTCAACAATGTTGTTTCTGGGAACCACAACACTG | : | 168  |
| LpIRIPa.19 | : | GGACCAATAACTATGTCAGATCTGGGGTCAACAATGTTGTTTCTGGGAACCACAACACTG | : | 168  |
| LpIRIPa.20 | : | GGACCAATAACTATGTCAGATCTGGGGTCAACAATGTTGTTTCTGGGAACCACAACACTG | : | 168  |
| LpIRIPa.21 | : | GGACCAATAACTATGTCAGATCTGGGGTCAACAATGTTGTTTCTGGGAACCACAACACTG | : | 168  |
| LpIRIPa.22 | : | GGACCAATAACTATGTCAGATCTGGGGTCAACAATGTTGTTTCTGGGAACCACAACACTG | : | 168  |
| LpIRIPa.23 | : | GGACCAATAACTATGTCAGATCTGGGGTCAACAATGTTGTTTCTGGGAACCACAACACTG | : | 168  |
| LpIRIPa.24 | : | GGACCAATAACTATGTCAGATCTGGGGTCAACAATGTTGTTTCTGGGAACCACAACACTG | : | 168  |
| LpIRIPa.25 | : | GGACCAATAACTATGTCAGATCTGGGGTCAACAATGTTGTTTCTGGGAACCACAACACTG | : | 168  |
| LpIRIPa.26 | : | GGACCAATAACTATGTCAGATCTGGGGTCAACAATGTTGTTTCTGGGAACCACAACACTG | : | 168  |
| LpIRIPa.27 | : | GGACCAATAACTATGTCAGATCTGGGGTCAACAATGTTGTTTCTGGGAACCACAACACTG | : | 168  |
| LpIRIPa.28 | : | GGACCAATAACTATGTCAGATCTGGGGTCAACAATGTTGTTTCTGGGAACCACAACACTG | : | 168  |
| LpIRIPa.29 | : | GGACCAATAACTATGTCAGATCTGGGGTCAACAATGTTGTTTCTGGGAACCACAACACTG | : | 168  |
| LpIRIPa.30 | : | GGACCAATAACTATGTCAGATCTGGGGTCAACAATGTTGTTTCTGGGAACCACAACACTG | : | 168  |
| LpIRIPa.31 | : | GGACCAATAACTATGTCAGATCTGGGGTCAACAATGTTGTTTCTGGGAACCACAACACTG | : | 168  |
| LpIRIPa.32 | : | GGACCAATAACTATGTCAGATCTGGGGTCAACAATGTTGTTTCTGGGAACCACAACACTG | : | 168  |
| LpIRIPa.33 | : | GGACCAATAACTATGTCAGATCTGGGGTCAACAATGTTGTTTCTGGGAACCACAACACTG | : | 168  |
| LpIRIPa.34 | : | GGACCAATAACTATGTCAGATCTGGGGTCAACAATGTTGTTTCTGGGAACCACAACACTG | : | 168  |
| LpIRIPa.35 | : | GGACCAATAACTATGTCAGATCTGGGGTCAACAATGTTGTTTCTGGGAACCACAACACTG | : | 168  |
| LpIRIPa.36 | : | GGACCAATAACTATGTCAGATCTGGGGTCAACAATGTTGTTTCTGGGAACCACAACACTG | : | 168  |
| LpIRIPa.37 | : | GGACCAATAACTATGTCAGATCTGGGGTCAACAATGTTGTTTCTGGGAACCACAACACTG | : | 168  |
| LpIRIPa.38 | : | GGACCAATAACTATGTCAGATCTGGGGTCAACAATGTTGTTTCTGGGAACCACAACACTG | : | 168  |
| LpIRIPa.39 | : | GGACCAATAACTATGTCAGATCTGGGGTCAACAATGTTGTTTCTGGGAACCACAACACTG | : | 168  |
| LpIRIPa.40 | : | GGACCAATAACTATGTCAGATCTGGGGTCAACAATGTTGTTTCTGGGAACCACAACACTG | : | 166  |
| LpIRIPa.41 | : | GGACCAATAACTATGTCAGATCTGGGGTCAACAATGTTGTTTCTGGGAACCACAACACTG | : | 165  |
| LpIRIPa.42 | : | GGACCAATAACTATGTCAGATCTGGGGTCAACAATGTTGTTTCTGGGAACCACAACACTG | : | 161  |
| LpIRIPa.43 | : | GGACCAATAACTATGTCAGATCTGGGGTCAACAATGTTGTTTCTGGGAACCACAACACTG | : | 161  |
| LpIRIPa.44 | : | GGACCAATAACTATGTCAGATCTGGGGTCAACAATGTTGTTTCTGGGAACCACAACACTG | : | 161  |
| LpIRIPa.45 | : | GGACCAATAACTATGTCAGATCTGGGGTCAACAATGTTGTTTCTGGGAACCACAACACTG | : | 155  |
| LpIRIPa.46 | : | --------------------------------AATGTTGTTTCTGGGAACCACAACACTG | : | 28   |

FIG. 26Q

```
                        *         1040         *         1060         *         1080
LpIRIPa.1   : TCACATCCGGGAACAACGATGTTGTGTCTGGAAACCACAACACTGTGTCTGGGACCAACC :   1080
LpIRIPa.2   : TCACATCCGGGAACAACAATGTTGTGTCTGGAAACCACAACACTGTGTCTGGGACCAACC :   1080
LpIRIPa.3   : ------------------------------------------------------------ :      -
LpIRIPa.4   : ------------------------------------------------------------ :      -
LpIRIPa.5   : ------------------------------------------------------------ :      -
LpIRIPa.6   : ------------------------------------------------------------ :      -
LpIRIPa.7   : ------------------------------------------------------------ :      -
LpIRIPa.8   : ------------------------------------------------------------ :      -
LpIRIPa.9   : ------------------------------------------------------------ :      -
LpIRIPa.10  : ------------------------------------------------------------ :      -
LpIRIPa.11  : ------------------------------------------------------------ :      -
LpIRIPa.12  : ------------------------------------------------------------ :      -
LpIRIPa.13  : ------------------------------------------------------------ :      -
LpIRIPa.14  : ------------------------------------------------------------ :      -
LpIRIPa.15  : ------------------------------------------------------------ :      -
LpIRIPa.16  : TCACATCCGGGAACAACAATGTTGTGTCTGGAAACCACAACACCGTGTCTGGGACCAACC :    228
LpIRIPa.17  : TCACATCCGGGAACAACAATGTTGTGTCTGGAAACCACAACACCGTGTCTGGGACCAACC :    228
LpIRIPa.18  : TCACATCCGGGAACAACAATGTTGTGTCTGGAAACCACAACACCGTGTCTGGGACCAACC :    228
LpIRIPa.19  : TCACATCCGGGAACAACAATGTTGTGTCTGGAAACCACAACACCGTGTCTGGGACCAACC :    228
LpIRIPa.20  : TCACATCCGGGAACAACAATGTTGTGTCTGGAAACCACAACACCGTGTCTGGGACCAACC :    228
LpIRIPa.21  : TCACATCCGGGAACAACAATGTTGTGTCTGGAAACCACAACACCGTGTCTGGGACCAACC :    228
LpIRIPa.22  : TCACATCCGGGAACAACAATGTTGTGTCTGGAAACCACAACACCGTGTCTGGGACCAACC :    228
LpIRIPa.23  : TCACATCCGGGAACAACAATGTTGTGTCTGGAAACCACAACACCGTGTCTGGGACCAACC :    228
LpIRIPa.24  : TCACATCCGGGAACAACAATGTTGTGTCTGGAAACCACAACACCGTGTCTGGGACCAACC :    228
LpIRIPa.25  : TCACATCCGGGAACAACAATGTTGTGTCTGGAAACCACAACACCGTGTCTGGGACCAACC :    228
LpIRIPa.26  : TCACATCCGGGAACAACAATGTTGTGTCTGGAAACCACAACACCGTGTCTGGGACCAACC :    228
LpIRIPa.27  : TCACATCCGGGAACAACAATGTTGTGTCTGGAAACCACAACACCGTGTCT---------- :    218
LpIRIPa.28  : TCACATCCGGGAACAACAATGTTGTGTCTGGAAACCACAACACCGTGTCTGGGACCAACC :    228
LpIRIPa.29  : TCACATCCGGGAACAACAATGTTGTGTCTGGAAACCACAACACCGTGTCTGGGACCAACC :    228
LpIRIPa.30  : TCACATCCGGGAACAACAATGTTGTGTCTGGAAACCACAACACCGTGTCTGGGACCAACC :    228
LpIRIPa.31  : TCACATCCGGGAACAACAATGTTGTGTCTGGAAACCACAACACCGTGTCTGGGACCAACC :    228
LpIRIPa.32  : TCACATCCGGGAACAACAATGTTGTGTCTGGAAACCACAACACCGTGTCTGGGACCAACC :    228
LpIRIPa.33  : TCACATCCGGGAACAACAATGTTGTGTCTGGAAACCACAACACCGTGTCTGGGACCAACC :    228
LpIRIPa.34  : TCACATCCGGGAACAACAATGTTGTGTCTGGAAACCACAACACCGTGTCTGGGACCAACC :    228
LpIRIPa.35  : TCACATCCGGGAACAACAATGTTGTGTCTGGAAACCACAACACCGTGTCTGGGACCAACC :    228
LpIRIPa.36  : TCACATCCGGGAACAACAATGTTGTGTCTGGAAACCACAACACCGTGTCTGGGACCAACC :    228
LpIRIPa.37  : TCACATCCGGGAACAACAATGTTGTGTCTGGAAACCACAACACCGTGTCTGGGACCAACC :    228
LpIRIPa.38  : TCACATCCGGGAACAACAATGTTGTGTCTGGAAACCACAACACCGTGTCTGGGACCAACC :    228
LpIRIPa.39  : TCACATCCGGGAACAACAATGTTGTGTCTGGAAACCACAACACCGTGTCTGGGACCAACC :    228
LpIRIPa.40  : TCACATCCGGGAACAACAATGTTGTGTCTGGAAACCACAACACCGTGTCTGGGACCAACC :    226
LpIRIPa.41  : TCACATCCGGGAACAACAATGTTGTGTCTGGAAACCACAACACCGTGTCTGGGACCAACC :    225
LpIRIPa.42  : TCACATCCGGGAACAACAATGTTGTGTCTGGAAACCACAACACCGTGTCTGGGACCAACC :    221
LpIRIPa.43  : TCACATCCGGGAACAACAATGTTGTGTCTGGAAACCACAACACCGTGTCTGGGACCAACC :    221
LpIRIPa.44  : TCACATCCGGGAACAACAATGTTGTGTCTGGAAACCACAACACCGTGTCTGGGACCAACC :    221
LpIRIPa.45  : TCACATCCGGGAACAACAATGTTGTGTCTGGAAACCACAACACCGTGTCTGGGACCAACC :    215
LpIRIPa.46  : TCACATCCGGGAACAACAATGTTGTGTCTGGAAACCACAACACCGTGTCTGGGACCAACC :     88
```

FIG. 26R

```
                          *         1100         *        1120         *        1140
LpIRIPa.1   : ATGTTGTAACTGGTAACAACCATGTCGTAACAAGGAACCAGAATACTGTATCTGGGCGCC :  1140
LpIRIPa.2   : ATGTTGTAACTGGTAACAACCATGTCGTAACAAGGAACCAGAATACTGTATCTGGGAGCC :  1140
LpIRIPa.3   : ------------------------------------------------------------ :     -
LpIRIPa.4   : ------------------------------------------------------------ :     -
LpIRIPa.5   : ------------------------------------------------------------ :     -
LpIRIPa.6   : ------------------------------------------------------------ :     -
LpIRIPa.7   : ------------------------------------------------------------ :     -
LpIRIPa.8   : ------------------------------------------------------------ :     -
LpIRIPa.9   : ------------------------------------------------------------ :     -
LpIRIPa.10  : ------------------------------------------------------------ :     -
LpIRIPa.11  : ------------------------------------------------------------ :     -
LpIRIPa.12  : ------------------------------------------------------------ :     -
LpIRIPa.13  : ------------------------------------------------------------ :     -
LpIRIPa.14  : ------------------------------------------------------------ :     -
LpIRIPa.15  : ------------------------------------------------------------ :     -
LpIRIPa.16  : ATGTTGTAACTGGTAACAACCATGTCGTAACAAGGAACCAGAATACTGTATCTGGGAGCC :   288
LpIRIPa.17  : ATGTTGTAACTGGTAACAACCATGTCGTAACAAGGAACCAGAATACTGTATCTGGGAGCC :   288
LpIRIPa.18  : ATGTTGTAACTGGTAACAACCATGTCGTAACAAGGAACCAGAATACTGTATCTGGGAGCC :   288
LpIRIPa.19  : ATGTTGTAACTGGTAACAACCATGTCGTAACAAGGAACCAGAATACTGTATCTGGGAGCC :   288
LpIRIPa.20  : ATGTTGTAACTGGTAACAACCATGTCGTAACAAGGAACCAGAATACTGTATCTGGGAGCC :   288
LpIRIPa.21  : ATGTTGTAACTGGTAACAACCATGTCGTAACAAGGAACCAGAATACTGTATCTGGGAGCC :   288
LpIRIPa.22  : ATGTTGTAACTGGTAACAACCATGTCGTAACAAGGAACCAGAATACTGTATCTGGGAGCC :   288
LpIRIPa.23  : ATGTTGTAACTGGTAACAACCATGTCGTAACAAGGAACCAGAATACTGTATCTGGGAGCC :   288
LpIRIPa.24  : ATGTTGTAACTGGTAACAACCATGTCGTAACAAGGAACCAGAATACTGTATCTGGGAGCC :   288
LpIRIPa.25  : ATGTTGTAACTGGTAACAACCATGTCGTAACAAGGAACCAGAATACTGTATCTGGGAGCC :   288
LpIRIPa.26  : ATGTTGTAACTGGTAACAACCATGTCGTAACAAGGAACCAGAATACTGTATCTGGGAGCC :   288
LpIRIPa.27  : ------------------------------------------------------------ :     -
LpIRIPa.28  : ATGTTGTAACTGGTAACAACCATGTCGTAACAAGGAACCAGAATACTGTATCTGGGAGCC :   288
LpIRIPa.29  : ATGTTGTAACTGGTAACAACCATGTCGTAACAAGGAACCAGAATACTGTATCTGGGAGCC :   288
LpIRIPa.30  : ATGTTGTAACTGGTAACAACCATGTCGTAACAAGGAACCAGAATACTGTATCTGGGAGCC :   288
LpIRIPa.31  : ATGTTGTAACTGGTAACAACCATGTCGTAACAAGGAACCAGAATACTGTATCTGGGAGCC :   288
LpIRIPa.32  : ATGTTGTAACTGGTAACAACCATGTCGTAACAAGGAACCAGAATACTGTATCTGGGAGCC :   288
LpIRIPa.33  : ATGTTGTAACTGGTAACAACCATGTCGTAACAAGGAACCAGAATACTGTATCTGGGAGCC :   288
LpIRIPa.34  : ATGTTGTAACTGGTAACAACCATGTCGTAACAAGGAACCAGAATACTGTATCTGGGAGCC :   288
LpIRIPa.35  : ATGTTGTAACTGGTAACAACCATGTCGTAACAAGGAACCAGAATACTGTATCTGGGAGCC :   288
LpIRIPa.36  : ATGTTGTAACTGGTAACAACCATGTCGTAACAAGGAACCAGAATACTGTATCTGGGAGCC :   288
LpIRIPa.37  : ATGTTGTAACTGGTAACAACCATGTCGTAACAAGGAACCAGAATACTGTATCTGGGAGCC :   288
LpIRIPa.38  : ATGTTGTAACTGGTAACAACCATGTCGTAACAAGGAACCAGAATACTGTATCTGGGAGCC :   288
LpIRIPa.39  : ATGTTGTAACTGGTAACAACCATGTCGTAACAAGGAACCAGAATACTGTATCTGGGAGCC :   288
LpIRIPa.40  : ATGTTGTAACTGGTAACAACCATGTCGTAACAAGGAACCAGAATACTGTATCTGGGAGCC :   286
LpIRIPa.41  : ATGTTGTAACTGGTAACAACCATGTCGTAACAAGGAACCAGAATACTGTATCTGGGAGCC :   285
LpIRIPa.42  : ATGTTGTAACTGGTAACAACCATGTCGTAACAAGGAACCAGAATACTGTATCTGGGAGCC :   281
LpIRIPa.43  : ATGTTGTAACTGGTAACAACCATGTCGTAACAAGGAACCAGAATACTGTATCTGGGAGCC :   281
LpIRIPa.44  : ATGTTGTAACTGGTAACAACCATGTCGTAACAAGGAACCAGAATACTGTATCTGGGAGCC :   281
LpIRIPa.45  : ATGTTGTAACTGGTAACAACCATGTCGTAACAAGGAACCAGAATACTGTATCTGGGAGCC :   275
LpIRIPa.46  : ATGTTGTAACTGGTAACAACCATGTCGTAACAAGGAACCAGAATACTGTATCTGGGAGCC :   148
```

FIG. 26S

```
                       *       1160       *       1180       *       1200
LpIRIPa.1   : ATCATAAAGTATCTGGAGGCCACAATACTGTATCTGGGAGCCACAATACCGTATCTGGAA :   1200
LpIRIPa.2   : ATCATAAAGTATCTGGAGGCCACAATACTGTATCTGGGAGCCACAATACCGTATCTGGAA :   1200
LpIRIPa.3   : ------------------------------------------------------------ :     -
LpIRIPa.4   : ------------------------------------------------------------ :     -
LpIRIPa.5   : ------------------------------------------------------------ :     -
LpIRIPa.6   : ------------------------------------------------------------ :     -
LpIRIPa.7   : ------------------------------------------------------------ :     -
LpIRIPa.8   : ------------------------------------------------------------ :     -
LpIRIPa.9   : ------------------------------------------------------------ :     -
LpIRIPa.10  : ------------------------------------------------------------ :     -
LpIRIPa.11  : ------------------------------------------------------------ :     -
LpIRIPa.12  : ------------------------------------------------------------ :     -
LpIRIPa.13  : ------------------------------------------------------------ :     -
LpIRIPa.14  : ------------------------------------------------------------ :     -
LpIRIPa.15  : ------------------------------------------------------------ :     -
LpIRIPa.16  : ATCATAAAGTATCTGGAGGCCACAATACTGTATCTGGGAGCCACAATACCGTATCTGGAA :    348
LpIRIPa.17  : ATCATAAAGTATCTGGAGGCCACAATACTGTATCTGGGAGCCACAATACCGTATCTGGAA :    348
LpIRIPa.18  : ATCATAAAGTATCTGGAGGCCACAATACTGTATCTGGGAGCCACAATACCGTATCTGGAA :    348
LpIRIPa.19  : ATCATAAAGTATCTGGAGGCCACAATACTGTATCTGGGAGCCACAATACCGTATCTGGAA :    348
LpIRIPa.20  : ATCATAAAGTATCTGGAGGCCACAATACTGTATCTGGGAGCCACAATACCGTATCTGGAA :    348
LpIRIPa.21  : ATCATAAAGTATCTGGAGGCCACAATACTGTATCT------------------------- :    323
LpIRIPa.22  : ATCATAAAGTATCTGGAGGCCACAATACTGTATCTGGGAGCCACAATACCGTATCTGGAA :    348
LpIRIPa.23  : ATCATAAAGTATCTGGAGGCCACAATACTGTATCTGGGAGCCACAATACCGTATCTGGAA :    348
LpIRIPa.24  : ATCATAAAGTATCTGGAGGCCACAATACTGTATCTGGGAGCCACAATACCGTATCTGGAA :    348
LpIRIPa.25  : ATCATAAAGTATCTGGAGGCCACAATACTGTATCTGGGAGCCACAATACCGTATCTGGAA :    348
LpIRIPa.26  : ATCATAAAGTATCTGGAGGCCACAATACTGTATCTGGGAGCCACAATACCGTATCTGGAA :    348
LpIRIPa.27  : ------------------------------------------------------------ :     -
LpIRIPa.28  : ATCATAAAGTATCTGGAGGCCACAATACTGTATCTGGGAGCCACAATACCGTATCTGGAA :    348
LpIRIPa.29  : ATCATAAAGTATCTGGAGGCCACAATACTGTATCTGGGAGCCACAATACCGTATCTGGAA :    348
LpIRIPa.30  : ATCATAAAGTATCTGGAGGCCACAATACTGTATCTGGGAGCCACAATACCGTATCTGGAA :    348
LpIRIPa.31  : ATCATAAAGTATCTGGAGGCCACAATACTGTATCTGGGAGCCACAATACCGTATCTGGAA :    348
LpIRIPa.32  : ATCATAAAGTATCTGGAGGCCACAATACTGTATCTGGGAGCCACAATACCGTATCTGGAA :    348
LpIRIPa.33  : ATCATAAAGTATCTGGAGGCCACAATACTGTATCTGGGAGCCACAATACCGTATCTGGAA :    348
LpIRIPa.34  : ATCATAAAGTATCTGGAGGCCACAATACTGTATCTGGGAGCCACAATACCGTATCTGGAA :    348
LpIRIPa.35  : ATCATAAAGTATCTGGAGGCCACAATACTGTATCTGGGAGCCACAATACCGTATCTGGAA :    348
LpIRIPa.36  : ATCATAAAGTATCTGGAGGCCACAATACTGTATCTGGGAGCCACAATACCGTATCTGGAA :    348
LpIRIPa.37  : ATCATAAAGTATCTGGAGGCCACAATACTGTATCTGGGAGCCACAATACCGTATCTGGAA :    348
LpIRIPa.38  : ATCATAAAGTATCTGGAGGCCACAATACTGTATCTGGGAGCCACAATACCGTATCTGGAA :    348
LpIRIPa.39  : ATCATAAAGTATCTGGAGGCCACAATACTGTATCTGGGAGCCACAATACCGTATCTGGAA :    348
LpIRIPa.40  : ATCATAAAGTATCTGGAGGCCACAATACTGTATCTGGGAGCCACAATACCGTATCTGGAA :    346
LpIRIPa.41  : ATCATAAAGTATCTGGAGGCCACAATACTGTATCTGGGAGCCACAATACCGTATCTGGAA :    345
LpIRIPa.42  : ATCATAAAGTATCTGGAGGCCACAATACTGTATCTGGGAGCCACAATACCGTATCTGGAA :    341
LpIRIPa.43  : ATCATAAAGTATCTGGAGGCCACAATACTGTATCTGGGAGCCACAATACCGTATCTGGAA :    341
LpIRIPa.44  : ATCATAAAGTATCTGGAGGCCACAATACTGTATCTGGGAGCCACAATACCGTATCTGGAA :    341
LpIRIPa.45  : ATCATAAAGTATCTGGAGGCCACAATACTGTATCTGGGAGCCACAATACCGTATCTGGAA :    335
LpIRIPa.46  : ATCATAAAGTATCTGGAGGCCACAATACTGTATCTGGGAGCCACAATACCGTATCTGGAA :    208
```

FIG. 26T

|  |  | * | 1220 | * | 1240 | * | 1260 |  |  |
|---|---|---|---|---|---|---|---|---|---|
| LpIRIPa.1 | : | GCCACAACACAGTATCTGGGAGCAACTGCATCGTACATGGGAACAACAAAGTCGTGACAG | : | 1260 |
| LpIRIPa.2 | : | GCCACAACACAGTATCTGGGAGCAACCACATCGTACATGGGAACAACAAAGTCGTGACAG | : | 1260 |
| LpIRIPa.3 | : | ------------------------------------------------------------ | : | - |
| LpIRIPa.4 | : | ------------------------------------------------------------ | : | - |
| LpIRIPa.5 | : | ------------------------------------------------------------ | : | - |
| LpIRIPa.6 | : | ------------------------------------------------------------ | : | - |
| LpIRIPa.7 | : | ------------------------------------------------------------ | : | - |
| LpIRIPa.8 | : | ------------------------------------------------------------ | : | - |
| LpIRIPa.9 | : | ------------------------------------------------------------ | : | - |
| LpIRIPa.10 | : | ------------------------------------------------------------ | : | - |
| LpIRIPa.11 | : | ------------------------------------------------------------ | : | - |
| LpIRIPa.12 | : | ------------------------------------------------------------ | : | - |
| LpIRIPa.13 | : | ------------------------------------------------------------ | : | - |
| LpIRIPa.14 | : | ------------------------------------------------------------ | : | - |
| LpIRIPa.15 | : | ------------------------------------------------------------ | : | - |
| LpIRIPa.16 | : | GCCACAACACAGTATCTGGGAGCAACCACATCGTACATGGGAACAACAAAGTCGTGACAG | : | 408 |
| LpIRIPa.17 | : | GCCACAACACAGTATCTGGGAGCAACCACATCGTACATGGGAACAACAAAGTCGTGACAG | : | 408 |
| LpIRIPa.18 | : | GCCACAACACAGTATCTGGGAGCAACCACATCGTACATGGGAACAACAAAGTCGTGACAG | : | 408 |
| LpIRIPa.19 | : | GCCACAACACAGTATCTGGGAGCAACCACATCGTACATGGGAACAACAAAGTCGTGACAG | : | 408 |
| LpIRIPa.20 | : | GCCACAACACAGTATCTGGGAGCAACCACATCGTACATGGGAACAACAAAGTCGTGACAG | : | 408 |
| LpIRIPa.21 | : | ------------------------------------------------------------ | : | - |
| LpIRIPa.22 | : | GCCACAACACAGTATCTGGGAGCAACCACATCGTACATGGGAACAACAAAGTCGTGACAG | : | 408 |
| LpIRIPa.23 | : | GCCACAACACAGTATCTGGGAGCAACCACATCGTACATGGGAACAACAAAGTCGTGACAG | : | 408 |
| LpIRIPa.24 | : | GCCACAACACAGTATCTGGGAGCAACCACATCGTACATGGGAACAACAAAGTCGTGACAG | : | 408 |
| LpIRIPa.25 | : | GCCACAACACAGTATCTGGGAGCAACCACATCGTACATGGGAACAACAAAGTCGTGACAG | : | 408 |
| LpIRIPa.26 | : | GCCACAACACAGTATCTGGGAGCAACCACATCGTACATGGGAACAACAAAGTCGTGACAG | : | 408 |
| LpIRIPa.27 | : | ------------------------------------------------------------ | : | - |
| LpIRIPa.28 | : | GCCACAACACAGTATCTGGGAGCAACCACATCGTACATGGGAACAACAAAGTCGTGACAG | : | 408 |
| LpIRIPa.29 | : | GCCACAACACAGTATCTGGGAGCAACCACATCGTACATGGGAACAACAAAGTCGTGACAG | : | 408 |
| LpIRIPa.30 | : | GCCACAACACAGTATCTGGGAGCAACCACATCGTACATGGGAACAACAAAGTCGTGACAG | : | 408 |
| LpIRIPa.31 | : | GCCACAACACAGTATCTGGGAGCAACCACATCGTACATGGGAACAACAAAGTCGTGACAG | : | 408 |
| LpIRIPa.32 | : | GCCACAACACAGTATCTGGGAGCAACCACATCGTACATGGGAACAACAAAGTCGTGACAG | : | 408 |
| LpIRIPa.33 | : | GCCACAACACAGTATCTGGGAGCAACCACATCGTACATGGGAACAACAAAGTCGTGACAG | : | 408 |
| LpIRIPa.34 | : | GCCACAACACAGTATCTGGGAGCAACCACATCGTACATGGGAACAACAAAGTCGTGACAG | : | 408 |
| LpIRIPa.35 | : | GCCACAACACAGTATCTGGGAGCAACCACATCGTACATGGGAACAACAAAGTCGTGACAG | : | 408 |
| LpIRIPa.36 | : | GCCACAACACAGTATCTGGGAGCAACCACATCGTACATGGGAACAACAAAGTCGTGACAG | : | 408 |
| LpIRIPa.37 | : | GCCACAACACAGTATCTGGGAGCAACCACATCGTACATGGGAACAACAAAGTCGTGACAG | : | 408 |
| LpIRIPa.38 | : | GCCACAACACAGTATCTGGGAGCAACCACATCGTACATGGGAACAACAAAGTCGTGACAG | : | 408 |
| LpIRIPa.39 | : | GCCACAACACAGTATCTGGGAGCAACCACATCGTACATGGGAACAACAAAGTCGTGACAG | : | 408 |
| LpIRIPa.40 | : | GCCACAACACAGTATCTGGGAGCAACCACATCGTACATGGGAACAACAAAGTCGTGACAG | : | 406 |
| LpIRIPa.41 | : | GCCACAACACAGTATCTGGGAGCAACCACATCGTACATGGGAACAACAAAGTCGTGACAG | : | 405 |
| LpIRIPa.42 | : | GCCACAACACAGTATCTGGGAGCAACCACATCGTACATGGGAACAACAAAGTCGTGACAG | : | 401 |
| LpIRIPa.43 | : | GCCACAACACAGTATCTGGGAGCAACCACATCGTACATGGGAACAACAAAGTCGTGACAG | : | 401 |
| LpIRIPa.44 | : | GCCACAACACAGTATCTGGGAGCAACCACATCGTACATGGGAACAACAAAGTCGTGACAG | : | 401 |
| LpIRIPa.45 | : | GCCACAACACAGTATCTGGGAGCAACCACATCGTACATGGGAACAACAAAGTCGTGACAG | : | 395 |
| LpIRIPa.46 | : | GCCACAACACAGTATCTGGGAGCAACCACATCGTACATGGGAACAACAAAGTCGTGACAG | : | 236 |

FIG. 26U

```
                             *         1280          *          1300         *          1320
LpIRIPa.1    :   GAGGTTAACAATCTATAGAGAATTGTTTCCATATTCCC---------------------   :   1298
LpIRIPa.2    :   GAGGTTAACAATCTATAGAGAATTGTTTCCATATTCCC---------------------   :   1298
LpIRIPa.3    :   ------------------------------------------------------------   :      -
LpIRIPa.4    :   ------------------------------------------------------------   :      -
LpIRIPa.5    :   ------------------------------------------------------------   :      -
LpIRIPa.6    :   ------------------------------------------------------------   :      -
LpIRIPa.7    :   ------------------------------------------------------------   :      -
LpIRIPa.8    :   ------------------------------------------------------------   :      -
LpIRIPa.9    :   ------------------------------------------------------------   :      -
LpIRIPa.10   :   ------------------------------------------------------------   :      -
LpIRIPa.11   :   ------------------------------------------------------------   :      -
LpIRIPa.12   :   ------------------------------------------------------------   :      -
LpIRIPa.13   :   ------------------------------------------------------------   :      -
LpIRIPa.14   :   ------------------------------------------------------------   :      -
LpIRIPa.15   :   ------------------------------------------------------------   :      -
LpIRIPa.16   :   GAGGTTAACAATCTATAGAGAATTGTTTCCATATTCCCTAACGGAGTTCACGTCCTTGTC   :    468
LpIRIPa.17   :   GAGGTTAACAATCTATAGAGAATTGTTTCCATATTCCCTAACGGAGTTCACGTCCTTGTC   :    468
LpIRIPa.18   :   GAGGTTAACAATCTATAGAGAATTGTTTCCATATTCCCTAACGGAGTTCACGTCCTTGTC   :    468
LpIRIPa.19   :   GAGGTTAACAATCTATAGAGAATTGTTTCCATATTCCCTAACGGAGTTCACGTCCTTGTC   :    468
LpIRIPa.20   :   GAGGTTAACAATCTATAGAGAATTGTTTCCATATTCCCTAACGGAGTTCACGTCCTTGTC   :    468
LpIRIPa.21   :   ------------------------------------------------------------   :      -
LpIRIPa.22   :   GAGGTTAACAATCTATAGAGAATTGTTTCCATATTCCCTAACGGAGTTCACGTCCTTGTC   :    468
LpIRIPa.23   :   GAGGTTAACAATCTATAGAGAATTGTTTCCATATTCCCTAACGGAGTTCACGTCCTTGTC   :    468
LpIRIPa.24   :   GAGGTTAACAATCTATAGAGAATTGTTTCCATATTCCCTAACGGAGTTCACGTCCTTGTC   :    468
LpIRIPa.25   :   GAGGTTAACAATCTATAGAGAATTGTTTCCATATTCCCTAACGGAGTTCACGTCCTTGTC   :    468
LpIRIPa.26   :   GAGGTTAACAATCTATAGAGAATTGTTACCATATTCCCTAACGGAGTTCACGTCCTTGTC   :    468
LpIRIPa.27   :   ------------------------------------------------------------   :      -
LpIRIPa.28   :   GAGGTTAACAATCTATAGAGAATTGTTTCCATATTCCCTAACGGAGTTCACGTCCTTGTC   :    468
LpIRIPa.29   :   GAGGTTAACAATCTATAGAGAATTGTTTCCATATTCCCTAACGGAGTTCACGTCCTTGTC   :    468
LpIRIPa.30   :   GAGGTTAACAATCTATAGAGAATTGTTTCCATATTCCCTAACGGAGTTCACGTCCTTGTC   :    468
LpIRIPa.31   :   GAGGTTAACAATCTATAGAGAATTGTTTCCATATTCCCTAACGGAGTTCACGTCCTTGTC   :    468
LpIRIPa.32   :   GAGGTTAACAATCTATAGAGAATTGTTTCCATATTCCCTAACGGAGTTCACGTCCTTGTC   :    468
LpIRIPa.33   :   GAGGTTAACAATCTATAGAGAATTGTTTCCATATTCCCTAACGGAGTTCACGTCCTTGTC   :    468
LpIRIPa.34   :   GAGGTTAACAATCTATAGAGAATTGTTTCCATATTCCCTAACGGAGTTCACGTCCTTGTC   :    468
LpIRIPa.35   :   GAGGTTAACAATCTATAGAGAATTGTTTCCATATTCCCTAACGGAGTTCACGTCCTTGTC   :    468
LpIRIPa.36   :   GAGGTTAACAATCTATAGAGAATTGTTTCCATATTCCCTAACGGAGTTCACGTCCTTGTC   :    468
LpIRIPa.37   :   GAGGTTAACAATCTATAGAGAATTGTTTCCATATTCCCTAACGGAGTTCACGTCCTTGTC   :    468
LpIRIPa.38   :   GAGGTTAACAATCTATAGAGAATTGTTTCCATATTCCCTAACGGAGTTCACGTCCTTGTC   :    468
LpIRIPa.39   :   GAGGTTAACAATCTATAGAGAATTGTTTCCATATTCCCTAACGGAGTTCACGTCCTTGTC   :    468
LpIRIPa.40   :   GAGGTTAACAATCTATAGAGAATTGTTTCCATATTCCCTAACGGAGTTCACGTCCTTGTC   :    466
LpIRIPa.41   :   GAGGTTAACAATCTATAGAGAATTGTTTCCATATTCCCTAACGGAGTTCACGTCCTTGTC   :    465
LpIRIPa.42   :   GAGGTTAACAATCTATAGAGAATTGTTTCCATATTCCCTAACGGAGTTCACGTCCTTGTC   :    461
LpIRIPa.43   :   GAGGTTAACAATCTATAGAGAATTGTTTCCATATTCCCTAACGGAGTTCACGTCCTTGTC   :    461
LpIRIPa.44   :   GAGGTTAACAATCTATAGAGAATTGTTTCCATATTCCCTAACGGAGTTCACGTCCTTGTC   :    461
LpIRIPa.45   :   GAGGTTAACAATCTATAGAGAATTGTTTCCATATTCCCTAACGGAGTTCACGTCCTTGTC   :    455
LpIRIPa.46   :   GAGGTTAACAATCTATAGAGAATTGTTTCCATATTCCCTAACGGAGTTCACGTCCTTGTC   :    328
```

FIG. 26V

```
                    *       1340      *      1360       *      1380
LpIRIPa.1   : ------------------------------------------------------------ :   -
LpIRIPa.2   : ------------------------------------------------------------ :   -
LpIRIPa.3   : ------------------------------------------------------------ :   -
LpIRIPa.4   : ------------------------------------------------------------ :   -
LpIRIPa.5   : ------------------------------------------------------------ :   -
LpIRIPa.6   : ------------------------------------------------------------ :   -
LpIRIPa.7   : ------------------------------------------------------------ :   -
LpIRIPa.8   : ------------------------------------------------------------ :   -
LpIRIPa.9   : ------------------------------------------------------------ :   -
LpIRIPa.10  : ------------------------------------------------------------ :   -
LpIRIPa.11  : ------------------------------------------------------------ :   -
LpIRIPa.12  : ------------------------------------------------------------ :   -
LpIRIPa.13  : ------------------------------------------------------------ :   -
LpIRIPa.14  : ------------------------------------------------------------ :   -
LpIRIPa.15  : ------------------------------------------------------------ :   -
LpIRIPa.16  : CAAGCTGGGTGTAGCTAAATATCACTTGGTGGGGCCAATGGCGTTATGTAACTTCGTGGA : 528
LpIRIPa.17  : CAAGCTGGGTGTAGCTAAATATCACTTGGTGGGGCCAATGGCGTTATGTAACTTCGTGGA : 528
LpIRIPa.18  : CAAGCTGGGTGTAGCTAAATATCACTTGGTGGGGCCAATGGCGTTATGTAACTTCGTGGA : 528
LpIRIPa.19  : CAAGCTGGGTGTAGCTAAATATCACTTGGTGGGGCCAATGGCGTTATGTAACTTCGTGGA : 528
LpIRIPa.20  : CAAGCTGGGTGTAGCTAAATATCACTTGGTGGGGCCAATGGCGTTATGTAACTTCGTGGA : 528
LpIRIPa.21  : ------------------------------------------------------------ :   -
LpIRIPa.22  : CAAGCTGGGTGTAGCTAAATATCACTTGGTGGGGCCAATGGCGTTATGTAACTTCGTGGA : 528
LpIRIPa.23  : CAAGCTGGGTGTAGCTAAATATCACTTGGTGGGGCCAATGGCGTTATGTAACTTCGTGGA : 528
LpIRIPa.24  : CAAGCTGGGTGTAG---------------------------------------------- : 482
LpIRIPa.25  : CAAGCTGGGTGTAGCTAAATATCACTTGGTGGGGCCAATGGCGTTATGTAACTTCGTGGA : 528
LpIRIPa.26  : CAAGCTGGGTGTAGCTAAATATCACTTGGTGGGGCCAATGGCGTTATGTAACTTCGTGGA : 528
LpIRIPa.27  : ------------------------------------------------------------ :   -
LpIRIPa.28  : CAAGCTGGGTGTAGCTAAATATCACTTGGTGGGGCCAATGGCGTTATGTAACTTCGTGGA : 528
LpIRIPa.29  : CAAGCTGGGTGTAGCTAAATATCACTTGGTGGGGCCAATGGCGTTATGTAACTTCGTGGA : 528
LpIRIPa.30  : CAAGCTGGGTGTAGCTAAATATCACTTGGTGGGGCCAATGGCGTTATGTAACTTCGTGGA : 528
LpIRIPa.31  : CAAGCTGGGTGTAGCTAAATATCACTTGGTGGGGCCAATGGCGTTATGTAACTTCGTGGA : 528
LpIRIPa.32  : CAAGCTGGGTGTAGCTAAATATCACTTGGTGGGGCCAATGGCGTTATGTAACTTCG---- : 524
LpIRIPa.33  : CAAGCTGGGTGTAGCTAAATATCACTTGGTGGGGCCAATGGCGTTATGTAACTTCGTGGA : 528
LpIRIPa.34  : CAAGCTGGGTGTAGCTAAATATCACTTGGTGGGGCCAATGGCGTTATGTAACTTCGTGGA : 528
LpIRIPa.35  : CAAGCTGGGTGTAGCTAAATATCACTTGGTGGGGCCAATGGCGTTATGTAACTTCGTGGA : 528
LpIRIPa.36  : CAAGCTGGGTGTAGCTAAATATCACTTGGTGGGGCCAATGGCGTTATGTAACTTCGTGGA : 528
LpIRIPa.37  : CAAGCTGGGTGTAGCTAAATATCACTTGGTGGGGCCAATGGCGTTATGTAACTTCGTGGA : 528
LpIRIPa.38  : CAAGCTGGGTGTAGCTAAATATCACTTGGTGGGGCCAATGGCGTTATGTAACTTCGTGGA : 528
LpIRIPa.39  : CAAGCTGGGTGTAGCTAAATATCACTTGGTGGGGCCAATGGCGTTATGTAACTTCGTGGA : 528
LpIRIPa.40  : CAAGCTGGGTGTAGCTAAATATCACTTGGTGGGGCCAATGGCGTTATGTAACTTCGTGGA : 526
LpIRIPa.41  : CAAGCTGGGTGTAGCTAAATATCACTTGGTGGGGCCAATGGCGTTATGTAACTTCGTGGA : 525
LpIRIPa.42  : CAAGCTGGGTGTAGCTAAATATCACTTGGTGGGGCCAATGGCGTTATGTAACTTCGTGGA : 521
LpIRIPa.43  : CAAGCTGGGTGTAGCTAAATATCACTTGGTGGGGCCAATGGCGTTATGTAACTTCGTGGA : 521
LpIRIPa.44  : CAAGCTGGGTGTAGCTAAATATCACTTGGTGGGGCCAATGGCGTTATGTAACTTCGTGGA : 521
LpIRIPa.45  : CAAGCTGGGTGTAGCTAAATATCACTTGGTGGGGCCAATGGCGTTATGTAACTTCGTGGA : 515
LpIRIPa.46  : CAAGCTGGGTGTAGCTAAATATCACTTGGTGGGGCCAATGGCGTTATGTAACTTCGTGGA : 388
```

FIG. 26W

```
                         *
LpIRIPa.1   : ----------  :  -
LpIRIPa.2   : ----------  :  -
LpIRIPa.3   : ----------  :  -
LpIRIPa.4   : ----------  :  -
LpIRIPa.5   : ----------  :  -
LpIRIPa.6   : ----------  :  -
LpIRIPa.7   : ----------  :  -
LpIRIPa.8   : ----------  :  -
LpIRIPa.9   : ----------  :  -
LpIRIPa.10  : ----------  :  -
LpIRIPa.11  : ----------  :  -
LpIRIPa.12  : ----------  :  -
LpIRIPa.13  : ----------  :  -
LpIRIPa.14  : ----------  :  -
LpIRIPa.15  : ----------  :  -
LpIRIPa.16  : TATAGCATCAC :  539
LpIRIPa.17  : TATAGCATCAC :  539
LpIRIPa.18  : TATAGCATCAC :  539
LpIRIPa.19  : TATAGCATCAC :  539
LpIRIPa.20  : TATAGCATCAC :  539
LpIRIPa.21  : ----------  :  -
LpIRIPa.22  : TATAGCATCAC :  539
LpIRIPa.23  : TATAGCATCAC :  539
LpIRIPa.24  : ----------  :  -
LpIRIPa.25  : TATAGCATCAC :  539
LpIRIPa.26  : TATAGCATCAC :  539
LpIRIPa.27  : ----------  :  -
LpIRIPa.28  : TATAGCATCAC :  539
LpIRIPa.29  : TATAGCATCAC :  539
LpIRIPa.30  : TATAGCATCAC :  539
LpIRIPa.31  : TATAGCATCAC :  539
LpIRIPa.32  : ----------  :
LpIRIPa.33  : TATAGCATCAC :  539
LpIRIPa.34  : TATAGCATCAC :  539
LpIRIPa.35  : TATAGCATCAC :  539
LpIRIPa.36  : TATAGCATCAC :  539
LpIRIPa.37  : TATAGCATCAC :  539
LpIRIPa.38  : TATAGCATCAC :  539
LpIRIPa.39  : TATAGCATCAC :  539
LpIRIPa.40  : TATAGCATCAC :  537
LpIRIPa.41  : TATAGCATCAC :  536
LpIRIPa.42  : TATAGCATCAC :  532
LpIRIPa.43  : TATAGCATCAC :  532
LpIRIPa.44  : TATAGCATCAC :  532
LpIRIPa.45  : TATAGCATCAC :  526
LpIRIPa.46  : TATAGCATCAC :  399
```

FIG. 26X

```
             *        20         *        40         *        60
LpIRIPa : CCCGGGCTGGTAAAAGGTTTACGAAATAGTTGTTATTAAACTATATATGTTCATGTAACT :  60

*        80         *       100         *       120
LpIRIPa : ATATTTCAATATAATTATTTGTATTACAGCAGAAAATCATTATTTCTATTACTTTGTATT : 120

*       140         *       160         *       180
LpIRIPa : ATTATTTTGTTTTGAGTGTTGTAAAATTGGGAATTACAACTATACTATTTTCGTATGGGA : 180

*       200         *       220         *       240
LpIRIPa : ACAATTTGTTAATTTTTGTGTCTCTCTTTCTCTTCATAGCTAGCTGACAGCGAGAACAAA : 240

*       260         *       280         *       300
LpIRIPa : AACCAAGATCTAATTGTGGAAGTAGACTAGTAGTCGACCACCCATGCATGCTTACATAAG : 300

*       320         *       340         *       360
LpIRIPa : AAAACACACGCACTATAAGATTGGATGCACCACCCAAGCACTATAAAAAGGATGCACCAC : 360

*       380         *       400         *       420
LpIRIPa : CTAAGCAATTTTTGCCAACAGCGCGCACTTGTTTGCATTCAAAAAGAAAATCTTACATAG : 420

*       440         *       460         *       480
LpIRIPa : CTGAACCAATGGAGAAAAGTTGGTTCTTGCTCCTTTTCTTGGCGTTCCTCCTGCCGGCGG : 480

*       500         *       520         *       540
LpIRIPa : CGAGCGTGGCGGTGTCATGCCACCCTGATGACCTCCTTGCACTGCGCGGGTTCGCCGGTA : 540

*       560         *       580         *       600
LpIRIPa : ATCTCAGCAATGGGGCGTGCTCCTCCATGCCAAGTGGCCCGACAACTCTTGCTGTAGTT : 600

*       620         *       640         *       660
LpIRIPa : GGGAAGGTGTGGGATGCGACGGCGGAAGCGGCCGTGTCACTACGTTGTGGCTCCCTGGGC : 660

*       680         *       700         *       720
LpIRIPa : ATGGACTCGCAGGCCACATCCCAACAGCATCCTTGGCTGGCCTTGCACGGCTGGAGTCGC : 720

*       740         *       760         *       780
LpIRIPa : TCAACCTCGCCAACAACAAACTGGTCGGCACAATCCCATCTTGGATTGGTGTGCTTGACC : 780

*       800         *       820         *       840
LpIRIPa : ACCTTTGCTACTTGGATCTCTCAAATAATTCATTGGTTGGTGAGATACCAAAGAATTTAC : 840

*       860         *       880         *       900
LpIRIPa : AAATAAGGCTCAGGTGCCTCAACATCGTTGGTCGTTCACTGGGCATGGCTTCCACTAACA : 900
```

FIG. 27A

```
                      *         920         *         940         *         960
LpIRIPa : TGACATTGCAGGTGAAGCATAACCAAATAGCACTAAGTGGCAACCAAACACAATAACCG : 960

*         980         *         1000        *         1020
LpIRIPa : GGACCAATAACTATGTCAGATCTGGGTCAACAATGTTGTTTCTGGAACCACAACGCTG : 1020

*         1040        *         1060        *         1080
LpIRIPa : TCACTCTGGGAACAACAATGTTGTGTCTGAAACCACAACGCCGTGTCTGGGACCAAC : 1080

*         1100        *         1120        *         1140
LpIRIPa : ATGTTGTAACTGGTAACAACCATGTGTAACAAGGAACCAGAATACTGTATCTGGGAGCC : 1140

*         1160        *         1180        *         1200
LpIRIPa : ATCATAAAGTATCTGGAGGCCACAATACTGTATCTGGGAGCCACAATACCGTATCTGGAA : 1200

*         1220        *         1240        *         1260
LpIRIPa : GCCACAACACAGTATCTGGGAGCAACCACATCGTACATGGGAACAACAAAGTCGTGACAG : 1260

*         1280        *         1300        *         1320
LpIRIPa : GAGGTTAACAATCTATAGAGAATTGTTTCCATATTCCCTGACGAGTTCACGTCCTTGTC : 1320

*         1340        *         1360        *         1380
LpIRIPa : CAAGCTGGGTGTAGCTAAATATCACTTGGTGGGCCAATGGGTTATGTAACTTCGTGGA : 1380

*
LpIRIPa : TATAGCATCAC : 1391
```

FIG. 27B

```
                  *         20         *         40         *         60
LpIRIPa : MKKSWPLLLFLAPLLPAASVAVSCHPDDLLALRGPAGNLSNGGVLLHAKWPDNSCCSWDG : 60

*         80         *        100         *        120
LpIRIPa : VGCDQGSGRVTTLWLPGRGLAGHIPTASLAGLARLESLNLANNKLVGTIPSWIGVLQHLC : 120

*        140         *        160         *        180
LpIRIPa : YLDLSNNSLVGSIPKNLQIRLRCLNIVGRSLGMASTNNTLQVKNNQIALSGQPNTINPTN : 180

*        200         *        220         *        240
LpIRIPa : NYVRSGVNNVVSGNKNTVTSGNKNVVSGNRNTVSGTNRVVTGNNKVVTRNQNTVSGSRNK : 240

*        260         *
LpIRIPa : VSGGRNTVSGSRNTVSGSRNTVSGSNRIVNGNNKVVTGG : 279
```

FIG. 28

```
              *         20         *         40         *         60
LpIRIPb.1   : CTTACATAGCTGAACCAATGGAGAAAAGTTGGTTCTTGCTCCTTTTCTTGACGTTCCTCC :  60
LpIRIPb.2   : CTTACATAGCTGAACCAATGGAGAAAAGTTGGTTCTTGCTCCTTTTCTTGACGTTCCTCC :  60
LpIRIPb.3   : CTTACATAGCTGAACCAATGGAGAAAAGTTGGTTCTTGCTCCTTTTCTTGACGTTCCTCC :  60
LpIRIPb.4   : CTTACATAGCTGAACCAATGGAGGAAAGTTGGTTCTTGCTCCTTTTCTTGGCGTTCCTCC :  60
LpIRIPb.5   : CTTACATAGCTGAACCAATGGAGAAAAGTTGGTTCTTGCTCCTTTTCTTGGCGTTCCTCC :  60
LpIRIPb.6   : CTTACATAGCTGAACCAATGGAGAAAAGTTGGTTCTTGCTCCTTTTCTTGGCGTTCCTCC :  60
LpIRIPb.7   : CTTACATAGCTGAACCAATGGAGAAAAGTTGGTTCTTGCTCCTTTTCTTGGCGTTCCTCC :  60
LpIRIPb.8   : CTTACATAGCTGAACCAATGGAGAAAAGTTGGTTCTTGCTCCTTTTCTTGGCGTTCCTCC :  60
LpIRIPb.9   : CTTACATAGCTGAACCAATGGAGAAAAGTTGGTTCTTGCTCCTTTTCTTGACGTTCCTCC :  60
LpIRIPb.10  : CTTACATAGCTGAACCAATGGAGAAAAGTTGGTTCTTGCTCCTTTTCTTGACGTTCCTCC :  60
LpIRIPb.11  : CTTACATAGCTGAACCAATGGAGAAAAGTTGGTTCTTGCTCCTTTTCTTGACGTTCCTCC :  60
LpIRIPb.12  : ----------------AATGGAGGAAAGTTGGTTCTTGCTCCTTTTCTTGGCGTTCCTCC :  44
LpIRIPb.13  : --------------------------------TTCTTGCTCCTTTTCTTGACGTTCCTCC :  28
LpIRIPb.14  : ----------------------------------------------------------CC :   2
LpIRIPb.15  : ------------------------------------------------------------ :   -
LpIRIPb.16  : ------------------------------------------------------------ :   -
              *         80         *        100         *        120
LpIRIPb.1   : TGCCGGCGGCGAGCGTGGCGGTGTCGTGCCACCCTGATGACCTCCTTGCACTGCGCGGGT : 120
LpIRIPb.2   : TGCCGGCGGCGAGCGTGGCGGTGTCGTGCCACCCTGATGACCTCCTTGCACTGCGCGGGT : 120
LpIRIPb.3   : TGCCGGCGGCGAGCGTGGCGGTGTCGTGCCACCCTGATGACCTCCTTGCACTGCGCGGGT : 120
LpIRIPb.4   : TGCCGGCGGCGAGCGTGGCGGTGGCGTGCCACCCTGATGACCTCCTTGCACTGCGCGGGT : 120
LpIRIPb.5   : TGCCGGCGGCGAGCGTGGCGGTGTCGTGCCACCCTGATGACCTCCTTGCACTGCGCGGGT : 120
LpIRIPb.6   : TGCCGGCGGCGAGCGTGGCGGTGTCGTGCCACCCTGATGACCTCCTTGCACTGCGCGGGT : 120
LpIRIPb.7   : TGCCGGCGGCGAGCGTGGCGGTGTCGTGCCACCCTGATGACCTCCTTGCACTGCGCGGGT : 120
LpIRIPb.8   : TGCCGGCGGCGAGCGTGGCGGTGTCGTGCCACCCTGATGACCTCCTTGCACTGCGCGGGT : 120
LpIRIPb.9   : TGCCGGCGGCGAGCGTGGCGGTGTCGTGCCACCCTGATGACCTCCTTGCACTGCGCGGGT : 120
LpIRIPb.10  : TGCCGGCGGCGAGCGTGGCGGTGTCGTGCCACCCTGATGACCTCCTTGCACTGCGCGGGT : 120
LpIRIPb.11  : TGCCGGCGGCGAGCGTGGCGGTGTCGTGCCACCCTGATGACCTCCTTGCACTGCGCGGGT : 120
LpIRIPb.12  : TGCCGGCGGCGAGCGTGGCGGTGGCGTGCCACCCTGATGACCTCCTTGCACTGCGCGGGT : 104
LpIRIPb.13  : TGCCGGCGGCGAGCGTGGCGGTGTCGTGCCACCCTGATGACCTCCTTGCACTGCGCGGGT :  88
LpIRIPb.14  : TGCCGGCGGCGAGCGTGGCGGTGTCGTGCCACCCTGATGACCTCCTTGCACTGCGCGGGT :  62
LpIRIPb.15  : --------------GTGGCGGTGTCGTGCCACCCTGATGACCTCCTTGCACTGCGCGGGT :  46
LpIRIPb.16  : ------------------------------------------------------------ :   -
              *        140         *        160         *        180
LpIRIPb.1   : TCGCCGGTAATCTCAGCAATGGGGGCGTCCTCCTCCATGCCAAGTGGTTCGGCAACTCTT : 180
LpIRIPb.2   : TCGCCGGTAATCTCAGCAATGGGGGCGTCCTCCTCCATGCCAAGTGGTTCGGCAACTCTT : 180
LpIRIPb.3   : TCGCCGGTAATCTCAGCAATGGGGGCGTCCTCCTCCATGCCAAGTGGTTCGGCAACTCTT : 180
LpIRIPb.4   : TCGCCGGTAATCTCAGCAATGGGGGCGTCCTCCTCCATGCCAAGTGGTCCGGCAACTCTT : 180
LpIRIPb.5   : TCGCCGGTAATCTCAGCAATGGGGGCGTCCTCCTCCATGCCAAGTGGTTCGGCAACTCTT : 180
LpIRIPb.6   : TCGCCGGTAATCTCAGCAATGGGGGCGTCCTCCTCCATGCCAAGTGGTTCGGCAACTCTT : 180
LpIRIPb.7   : TCGCCGGTAATCTCAGCAATGGGGGCGTCCTCCTCCATGCCAAGTGGTTCGGCAACTCTT : 180
LpIRIPb.8   : TCGCCGGTAATCTCAGCAATGGGGGCGTCCTCCTCCATGCCAAGTGGTTCGGCAACTCTT : 180
LpIRIPb.9   : TCGCCGGTAATCTCAGCAATGGGGGCGTCCTCCTCCATGCCAAGTGGTTCGGCAACTCTT : 180
LpIRIPb.10  : TCGCCGGTAATCTCAGCAATGGGGGCGTCCTCCTCCATGCCAAGTGGTTCGGCAACTCTT : 180
LpIRIPb.11  : TCGCCGGTAATCTCAGCAATGGGGGCGTCCTCCTCCATGCCAAGTGGTTCGGCAACTCTT : 180
LpIRIPb.12  : TCGCCGGTAATCTCAGCAATGGGGGCGTCCTCCTCCATGCCAAGTGGTCCGGCAACTCTT : 164
LpIRIPb.13  : TCGCCGGTAATCTCAGCAATGGGGGCGTCCTCCTCCATGCCAAGTGGTTCGGCAACTCTT : 148
LpIRIPb.14  : TCGCCGGTAATCTCAGCAATGGGGGCGTCCTCCTCCATGCCAAGTGGTTCGGCAACTCTT : 122
LpIRIPb.15  : TCGCCGGTAATCTCAGCAATGGGGGCGTCCTCCTCCATGCCAAGTGGTTCGGCAACTCTT : 106
LpIRIPb.16  : ------------------------------------------------------------ :   -
```

FIG. 29A

```
                    *        200         *        220         *        240
LpIRIPb.1   : GCTGTAGTTGGGAAGGTGTGGGATGCGACGGCGGAAGCGGCCGTGTCACTACTTTATGGC : 240
LpIRIPb.2   : GCTGTAGTTGGGAAGGTGTGGGATGCGACGGCGGAAGCGGCCGTGTCACTACTTTATGGC : 240
LpIRIPb.3   : GCTGTAGTTGGGAAGGTGTGGGATGCGACGGCGGAAGCGGCCGTGTCACTACTTTATGGC : 240
LpIRIPb.4   : GCTGTAGTTGGGAAGGTGTGGGATGCGACGGCGGAAGCGGCCGTGTCACTACGTTGTGGC : 240
LpIRIPb.5   : GCTGTAGTTGGGAAGGTGTGGGATGCGACGGCGGAAGCGGCCGTGTCACTACTTTATGGC : 240
LpIRIPb.6   : GCTGTAGTTGGGAAGGTGTGGGATGCGACGGCGGAAGCGGCCGTGTCACTACTTTATGGC : 240
LpIRIPb.7   : GCTGTAGTTGGGAAGGTGTGGGATGCGACGGCGGAAGCGGCCGTGTCACTACTTTATGGC : 240
LpIRIPb.8   : GCTGTAGTTGGGAAGGTGTGGGATGCGACGGCGGAAGCGGCCGTGTCACTACTTTATGGC : 240
LpIRIPb.9   : GCTGTAGTTGGGAAGGTGTGGGATGCGACGGCGGAAGCGGCCGTGTCACTACTTTATGGC : 240
LpIRIPb.10  : GCTGTAGTTGGGAAGGTGTGGGATGCGACGGCGGAAGCGGCCGTGTCACTACTTTATGGC : 240
LpIRIPb.11  : GCTGTAGTTGGGAAGGTGTGGGATGCGACGGCGGAAGCGGCCGTGTCACTACTTTATGGC : 240
LpIRIPb.12  : GCTGTAGTTGGGAAGGTGTGGGATGCGACGGCGGAAGCGGCCGTGTCACTACGTTGTGGC : 224
LpIRIPb.13  : GCTGTAGTTGGGAAGGTGTGGGATGCGACGGCGGAAGCGGCCGTGTCACTACTTTATGGC : 208
LpIRIPb.14  : GCTGTAGTTGGGAAGGTGTGGGATGCGACGGCGGAAGCGGCCGTGTCACTACTTTATGGC : 182
LpIRIPb.15  : GCTGTAGTTGGGAAGGTGTGGGATGCGACGGCGGAAGCGGCCGTGTCACTACTTTATGGC : 166
LpIRIPb.16  : ------------------------------------------------------------ :   -

*        260         *        280         *        300
LpIRIPb.1   : TCCGTGGGCATGGACTCGCAGGCCACATCCCAACAGCATCCTTGGCTGGCCTTGCACGGC : 300
LpIRIPb.2   : TCCGTGGGCATGGACTCGCAGGCCACATCCCAACAGCATCCTTGGCTGGCCTTGCACGGC : 300
LpIRIPb.3   : TCCGTGGGCATGGACTCGCAGGCCACATCCCAACAGCATCCTTGGCTGGCCTTGCACGGC : 300
LpIRIPb.4   : TCCCTGGGCATGGACTCGCAGGCCACATCCCAACAGCATCCTTGGCTGGCCTTGCACGGC : 300
LpIRIPb.5   : TTCGTGGGCATGGACTCGCAGGCCACATCCCAACAGCATCCTTGGCTGGCCTTGCACGGC : 300
LpIRIPb.6   : TTCGTGGGCATGGACTCGCAGGCCACATCCCAACAGCATCCTTGGCTGGCCTTGCACGGC : 300
LpIRIPb.7   : TTCGTGGGCATGGACTCGCAGGCCACATCCCAACAGCATCCTTGGCTGGCCTTGCACGGC : 300
LpIRIPb.8   : TTCGTGGGCATGGACTCGCAGGCCACATCCCAACAGCATCCTTGGCTGGCCTTGCACGGC : 300
LpIRIPb.9   : TCCGTGGGCATGGACTCGCAGGCCACATCCCAACAGCATCCTTGGCTGGCCTTGCACGGC : 300
LpIRIPb.10  : TCCGTGGGCATGGACTCGCAGGCCACATCCCAACAGCATCCTTGGCTGGCCTTGCACGGC : 300
LpIRIPb.11  : TCCGTGGGCATGGACTCGCAGGCCACATCCCAACAGCATCCTTGGCTGGCCTTGCACGGC : 300
LpIRIPb.12  : TCCCTGGGCATGGACTCGCAGGCCACATCCCAACAGCATCCTTGGCTGGCCTTGCACGGC : 284
LpIRIPb.13  : TCCGTGGGCATGGACTCGCAGGCCACATCCCAACAGCATCCTTGGCTGGCCTTGCACGGC : 268
LpIRIPb.14  : TTCGTGGGCATGGACTCGCAGGCCACATCCCAACAGCATCCTTGGCTGGCCTTGCACGGC : 242
LpIRIPb.15  : TTCGTGGGCATGGACTCGCAGGCCACATCCCAACAGCATCCTTGGCTGGCCTTGCACGGC : 226
LpIRIPb.16  : ------------------------------------------------------------ :   -

*        320         *        340         *        360
LpIRIPb.1   : TGGAGTCGCTCAACCTCGCCAACAACAAACTGGTCGGCACAATCCCATCATGGATGGGTG : 360
LpIRIPb.2   : TGGAGTCGCTCAACCTCGCCAACAACAAACTGGTCGGCACAATCCCATCATGGATGGGTG : 360
LpIRIPb.3   : TGGAGTCGCTCAACCTCGCCAACAACAAACTGGTCGGCACAATCCCATCATGGATGGGTG : 360
LpIRIPb.4   : TGGAGTCGCTCAACCTCGCCAACAACAAACTGGTCGGCACAATCCCATCATGGATTGGTG : 360
LpIRIPb.5   : TGGAGTCGCTCAACCTCGCCAACAACAAACTGGTCGGCACAATCCCATCATGGATGGGTG : 360
LpIRIPb.6   : TGGAGTCGCTCAACCTCGCCAACAACAAACTGGTCGGCACAATCCCATCATGGATGGGTG : 360
LpIRIPb.7   : TGGAGTCGCTCAACCTCGCCAACAACAAACTGGTCGGCACAATCCCATCATGGATGGGTG : 360
LpIRIPb.8   : TGGAGTCGCTCAACCTCGCCAACAACAAACTGGTCGGCACAATCCCATCATGGATGGGTG : 360
LpIRIPb.9   : TGGAGTCGCTCAACCTCGCCAACAACAAACTGGTCGGCACAATCCCATCATGGATGGGTG : 360
LpIRIPb.10  : TGGAGTCGCTCAACCTCGCCAACAACAAACTGGTCGGCACAATCCCATCATGGATGGGTG : 360
LpIRIPb.11  : TGGAGTCGCTCAACCTCGCCAACAACAAACTGGTCGGCACAATCCCATCATGGATGGGTG : 360
LpIRIPb.12  : TGGAGTCGCTCAACCTCGCCAACAACAAACTGGTCGGCACAATCCCATCTTGGATTGGTG : 344
LpIRIPb.13  : TGGAGTCGCTCAACCTCGCCAACAACAAACTGGTCGGCACAATCCCATCATGGATGGGTG : 328
LpIRIPb.14  : TGGAGTCGCTCAACCTCGCCAACAACAAACTGGTCGGCACAATCCCATCATGGATGGGTG : 302
LpIRIPb.15  : TGGAGTCGCTCAACCTCGCCAACAACAAACTGGTCGGCACAATCCCATCATGGATGGGTG : 286
LpIRIPb.16  : ------------------------------------------------------------ :   -
```

FIG. 29B

```
                           *        380         *        400         *        420
LpIRIPb.1   : TGCTTGACCACCTTTGCTACTTGGATCTCTCAAATAATTCATTGGTTGGTGAGATACCCA :  420
LpIRIPb.2   : TGCTTGACCACCTTTGCTACTTGGATCTCTCAAATAATTCATTGGTTGGTGAGATACCCA :  420
LpIRIPb.3   : TGCTTGACCACCTTTGCTACTTGGATCTCTCAAATAATTCATTGGTTGGTGAGATACCCA :  420
LpIRIPb.4   : TGCTTGACCACCTTTGCTACTTGGATCTCTCAAATAATTCATTGGTTGGTGAGATACCCA :  420
LpIRIPb.5   : TGCTTGACCACCTTTGCTACTTGGATCTCTCAAATAATTCATTGGTTGGTGAGATACCCA :  420
LpIRIPb.6   : TGCTTGACCACCTTTGCTACTTGGATCTCTCAAATAATTCATTGGTTGGTGAGATACCCA :  420
LpIRIPb.7   : TGCTTGACCACCTTTGCTACTTGGATCTCTCAAATAATTCATTGGTTGGTGAGATACCCA :  420
LpIRIPb.8   : TGCTTGACCACCTTTGCTACTTGGATCTCTCAAATAATTCATTGGTTGGTGAGATACCCA :  420
LpIRIPb.9   : TGCTTGACCACCTTTGCTACTTGGATCTCTCAAATAATTCATTGGTTGGTGAGATACCCA :  420
LpIRIPb.10  : TGCTTGACCACCTTTGCTACTTGGATCTCTCAAATAATTCATTGGTTGGTGAGATACCCA :  420
LpIRIPb.11  : TGCTTGACCACCTTTGCTACTTGGATCTCTCAAATAATTCATTGGTTGGTGAGATACCCA :  420
LpIRIPb.12  : TGCTTGACCACCTTTGCTACTTGGATCTCTCAAATAATTCATTGGTTGGTGAGATACCCA :  404
LpIRIPb.13  : TGCTTGACCACCTTTGCTACTTGGATCTCTCAAATAATTCATTGGTTGGTGAGATACCCA :  388
LpIRIPb.14  : TGCTTGACCACCTTTGCTACTTGGATCTCTCAAATAATTCATTGGTTGGTGAGATACCCA :  362
LpIRIPb.15  : TGCTTGACCACCTTTGCTACTTGGATCTCTCAAATAATTCATTGGTTGGTGAGATACCCA :  346
LpIRIPb.16  : ------------------------------------------------------------ :   --

*        440         *        460         *        480
LpIRIPb.1   : AGAATTTACAGAGAAGGCTCAGTCGCCCCAACATTATTGGTCATTCACTGGGTACGGCTT :  480
LpIRIPb.2   : AGAATTTACAGAGAAGGCTCAGTTGCCCCAGCATTATTGGTCATTCACTGGGTACGGCTT :  480
LpIRIPb.3   : AGAATTTACAGAGAAGGCTCAGTTGCCCCAACATTATTGGTCATTCACTGGGTACGGCTT :  480
LpIRIPb.4   : AGAATTTACAGAGAAGGCTCAGTTGCCCCAACATTGTTGGTCATTCACTGGGTACGGCTT :  480
LpIRIPb.5   : AGAATTTACAGAGAAGGCTCAGTTGCCCCAACATTGTTGGTCATTCACTGGGTACGGCTT :  480
LpIRIPb.6   : AGAATTTACAGAGAAGGCTCAGTTGCCCCAACATTGTTGGTCATTCACTGGGTACGGCTT :  480
LpIRIPb.7   : AGAATTTACAGAGAAGGCTCAGTTGCCCCAACATTGTTGGTCATTCACTGGGTACGGCTT :  480
LpIRIPb.8   : AGAATTTACAGAGAAGGCTCAGTTGCCCCAACATTGTTGGTCATTCACTGGGTACGGCTT :  480
LpIRIPb.9   : AGAATTTACAGAGAAGGCTCAGTTGCCCCAACATTATTGGTCATTCACTGGGTACGGCTT :  480
LpIRIPb.10  : AGAATTTACAGAGAAGGCTCAGTTGCCCCAACATTATTGGTCATTCACTGGGTACGGCTT :  480
LpIRIPb.11  : AGAATTTACAGAGAAGGCTCAGTTGCCCCAACATTATTGGTCATTCACTGGGTACGGCTT :  480
LpIRIPb.12  : AGAATTTACAGAGAAGGCTCAGTTGCCCCAACATTGTTGGTCATTCACTGGGTACGGCTT :  464
LpIRIPb.13  : AGAATTTACAGAGAAGGCTCAGTTGCCCCAACATTATTGGTCATTCACTGGGTACGGCTT :  448
LpIRIPb.14  : AGAATTTACAGAGAAGGCTCAGTTGCCCCAACATTGTTGGTCATTCACTGGGTACGGCTT :  422
LpIRIPb.15  : AGAATTTACAGAGAAGGCTCAGTTGCCCCAACATTGTTGGTCATTCACTGGGTACGGCTT :  406
LpIRIPb.16  : --------------------GGTGCCTCAACATCGTTGGTCATTCACTGGGTACGGCTT :   39

*        500         *        520         *        540
LpIRIPb.1   : CCACTAACATGCCATTGCAGGTGAAGCATAACCAAATAGCACTGAGTGGGCAACCAAACA :  540
LpIRIPb.2   : CCACTAACATGCCATTGCAGGTGAAGCATAACCAAATAGCACTGAGTGGGCAACCAAACA :  540
LpIRIPb.3   : CCACTAACATGCCATTGCAGGTGAAGCATAACCAAATAGCACTGAGTGGGCAACCAAACA :  540
LpIRIPb.4   : CCACTAACATGCCATTGCAGGTGAAGCATAACCAAATAGCACTGAGTGGGCAACCAAACA :  540
LpIRIPb.5   : CCACTAACATGCCATTGCAGGTGAAGCATAACCAAATAGCACTGAGTGGGCAACCAAACA :  540
LpIRIPb.6   : CCACTAACATGCCATTGCAGGTGAAGCATAACCAAATAGCACTGAGTGGGCAACCAAACA :  540
LpIRIPb.7   : CCACTAACATGCCATTGCAGGTGAAGCATAACCAAATAGCACTGAGTGGGCAACCAAACA :  540
LpIRIPb.8   : CCACTAACATGCCATTGCAGGTGAAGCATAACCAAATAGCACTGAGTGGGCAACCAAACA :  540
LpIRIPb.9   : CCACTAACATGCCATTGCAGGTGAAGCATAACCAAATAGCACTGAGTGGGCAACCAAACA :  540
LpIRIPb.10  : CCACTAACATGCCATTGCAGGTGAAGCATAACCAAATAGCACTGAGTGGGCAACCAAACA :  540
LpIRIPb.11  : CCACTAACATGCCATTGCAGGTGAAGCATAACCAAATAGCACTGAGTGGGCAACCAAACA :  540
LpIRIPb.12  : CCACTAACATGCCATTGCAGGTGAAGCATAACCAAATAGCACTGAGTGGGCAACCAAACA :  524
LpIRIPb.13  : CCACTAACATGCCATTGCAGGTGAAGCATAACCAAATAGCACTGAGTGGGCAACCAAACA :  508
LpIRIPb.14  : CCACTAACATGCCATTGCAGGTGAAGCATAACCAAATAGCACTGAGTGGGCAACCAAACA :  482
LpIRIPb.15  : CCACTAACATGCCATTGCAGGTGAAGCATAACCAAATAGCACTGAGTGGGCAACCAAACA :  466
LpIRIPb.16  : CCACTAACATGCCATTGCAGGTGAAGCATAACCAAATAGCACTGAGTGGGCAACCAAACA :   99
```

FIG. 29C

```
                        *         560         *         580         *         600
LpIRIPb.1   : CAATAACCGGGACCAATAACTATGTCAG--------------------------------  :  568
LpIRIPb.2   : CAATAACCGGGACCAATAACTATGTCAG--------------------------------  :  568
LpIRIPb.3   : CAATAACCGGGACCAATAACTATGTCAG--------------------------------  :  568
LpIRIPb.4   : CAATAACCGGGACCAATAACTATGTCAG--------------------------------  :  568
LpIRIPb.5   : CAATAACCGGGACCAATAACTATGTCAG--------------------------------  :  568
LpIRIPb.6   : CAATAACCGGGACCAATAACTATGTCAG--------------------------------  :  568
LpIRIPb.7   : CAATAACCGGGACCAATAACTATGTCAG--------------------------------  :  568
LpIRIPb.8   : CAATAACCGGGACCAATAACTATGTCAG--------------------------------  :  568
LpIRIPb.9   : CAATAACCGGGACCAATAACTATGTCAGAT------------------------------  :  570
LpIRIPb.10  : CAATAACCGGGACCAATAACTATGTCAG--------------------------------  :  568
LpIRIPb.11  : CAATAACCGGGACCAATAACTATGTCAGA-------------------------------  :  569
LpIRIPb.12  : CAATAACCGGGACCAATAACTATGTCAGA-------------------------------  :  552
LpIRIPb.13  : CAATAACCGGGACCAATAACTATGTCAG--------------------------------  :  536
LpIRIPb.14  : CAATAA------------------------------------------------------  :  488
LpIRIPb.15  : CAATAACCGGGACCAATAACTATGTCAG--------------------------------  :  494
LpIRIPb.16  : CAATAACCGGGACCAATAACTATGTCAGATCTGGGGTCAACAATGTTGTTTCTGGGAACC  :  159
                        *         620         *         640         *         660
LpIRIPb.1   : ------------------------------------------------------------  :  -
LpIRIPb.2   : ------------------------------------------------------------  :  -
LpIRIPb.3   : ------------------------------------------------------------  :  -
LpIRIPb.4   : ------------------------------------------------------------  :  -
LpIRIPb.5   : ------------------------------------------------------------  :  -
LpIRIPb.6   : ------------------------------------------------------------  :  -
LpIRIPb.7   : ------------------------------------------------------------  :  -
LpIRIPb.8   : ------------------------------------------------------------  :  -
LpIRIPb.9   : ------------------------------------------------------------  :  -
LpIRIPb.10  : ------------------------------------------------------------  :  -
LpIRIPb.11  : ------------------------------------------------------------  :  -
LpIRIPb.12  : ------------------------------------------------------------  :  -
LpIRIPb.13  : ------------------------------------------------------------  :  -
LpIRIPb.14  : ------------------------------------------------------------  :  -
LpIRIPb.15  : ------------------------------------------------------------  :  -
LpIRIPb.16  : ACAACACTGTCACATCCGGGAACAACAATGTTGTGTCTGGGAACCACAACACCGTGTCTG  :  219
                        *         680         *         700         *         720
LpIRIPb.1   : ------------------------------------------------------------  :  -
LpIRIPb.2   : ------------------------------------------------------------  :  -
LpIRIPb.3   : ------------------------------------------------------------  :  -
LpIRIPb.4   : ------------------------------------------------------------  :  -
LpIRIPb.5   : ------------------------------------------------------------  :  -
LpIRIPb.6   : ------------------------------------------------------------  :  -
LpIRIPb.7   : ------------------------------------------------------------  :  -
LpIRIPb.8   : ------------------------------------------------------------  :  -
LpIRIPb.9   : ------------------------------------------------------------  :  -
LpIRIPb.10  : ------------------------------------------------------------  :  -
LpIRIPb.11  : ------------------------------------------------------------  :  -
LpIRIPb.12  : ------------------------------------------------------------  :  -
LpIRIPb.13  : ------------------------------------------------------------  :  -
LpIRIPb.14  : ------------------------------------------------------------  :  -
LpIRIPb.15  : ------------------------------------------------------------  :  -
LpIRIPb.16  : GGACCAACCATGTTGTAACTGGTAACAACCATGTCGTAACAAGGAACCAGAATACCGTAT  :  279
```

FIG. 29D

```
               *         740         *         760         *         780
LpIRIPb.1   : ------------------------------------------------------------ :   -
LpIRIPb.2   : ------------------------------------------------------------ :   -
LpIRIPb.3   : ------------------------------------------------------------ :   -
LpIRIPb.4   : ------------------------------------------------------------ :   -
LpIRIPb.5   : ------------------------------------------------------------ :   -
LpIRIPb.6   : ------------------------------------------------------------ :   -
LpIRIPb.7   : ------------------------------------------------------------ :   -
LpIRIPb.8   : ------------------------------------------------------------ :   -
LpIRIPb.9   : ------------------------------------------------------------ :   -
LpIRIPb.10  : ------------------------------------------------------------ :   -
LpIRIPb.11  : ------------------------------------------------------------ :   -
LpIRIPb.12  : ------------------------------------------------------------ :   -
LpIRIPb.13  : ------------------------------------------------------------ :   -
LpIRIPb.14  : ------------------------------------------------------------ :   -
LpIRIPb.15  : ------------------------------------------------------------ :   -
LpIRIPb.16  : CTGGGAGCCATCATAAAGTATCTGGAGGCCACAATACTGTATCTGGGAGCCACAATACCG :  339
               *         800         *         820         *         840
LpIRIPb.1   : ------------------------------------------------------------ :   -
LpIRIPb.2   : ------------------------------------------------------------ :   -
LpIRIPb.3   : ------------------------------------------------------------ :   -
LpIRIPb.4   : ------------------------------------------------------------ :   -
LpIRIPb.5   : ------------------------------------------------------------ :   -
LpIRIPb.6   : ------------------------------------------------------------ :   -
LpIRIPb.7   : ------------------------------------------------------------ :   -
LpIRIPb.8   : ------------------------------------------------------------ :   -
LpIRIPb.9   : ------------------------------------------------------------ :   -
LpIRIPb.10  : ------------------------------------------------------------ :   -
LpIRIPb.11  : ------------------------------------------------------------ :   -
LpIRIPb.12  : ------------------------------------------------------------ :   -
LpIRIPb.13  : ------------------------------------------------------------ :   -
LpIRIPb.14  : ------------------------------------------------------------ :   -
LpIRIPb.15  : ------------------------------------------------------------ :   -
LpIRIPb.16  : TATCTGGAAGCCACAACACAGTATCTGGGAGCAACCACGTCGTACACGGGAACAACAAAG :  399
               *         860         *         880         *         900
LpIRIPb.1   : ------------------------------------------------------------ :   -
LpIRIPb.2   : ------------------------------------------------------------ :   -
LpIRIPb.3   : ------------------------------------------------------------ :   -
LpIRIPb.4   : ------------------------------------------------------------ :   -
LpIRIPb.5   : ------------------------------------------------------------ :   -
LpIRIPb.6   : ------------------------------------------------------------ :   -
LpIRIPb.7   : ------------------------------------------------------------ :   -
LpIRIPb.8   : ------------------------------------------------------------ :   -
LpIRIPb.9   : ------------------------------------------------------------ :   -
LpIRIPb.10  : ------------------------------------------------------------ :   -
LpIRIPb.11  : ------------------------------------------------------------ :   -
LpIRIPb.12  : ------------------------------------------------------------ :   -
LpIRIPb.13  : ------------------------------------------------------------ :   -
LpIRIPb.14  : ------------------------------------------------------------ :   -
LpIRIPb.15  : ------------------------------------------------------------ :   -
LpIRIPb.16  : TCGTGACAGGAGGTTAACAATCTATAGAGAATTGTTTCCATATTCCCTAACGGAGTTCAC :  459
```

FIG. 29E

```
               *         920         *         940         *         960
LpIRIPb.1   : ------------------------------------------------------------ :   -
LpIRIPb.2   : ------------------------------------------------------------ :   -
LpIRIPb.3   : ------------------------------------------------------------ :   -
LpIRIPb.4   : ------------------------------------------------------------ :   -
LpIRIPb.5   : ------------------------------------------------------------ :   -
LpIRIPb.6   : ------------------------------------------------------------ :   -
LpIRIPb.7   : ------------------------------------------------------------ :   -
LpIRIPb.8   : ------------------------------------------------------------ :   -
LpIRIPb.9   : ------------------------------------------------------------ :   -
LpIRIPb.10  : ------------------------------------------------------------ :   -
LpIRIPb.11  : ------------------------------------------------------------ :   -
LpIRIPb.12  : ------------------------------------------------------------ :   -
LpIRIPb.13  : ------------------------------------------------------------ :   -
LpIRIPb.14  : ------------------------------------------------------------ :   -
LpIRIPb.15  : ------------------------------------------------------------ :   -
LpIRIPb.16  : GTCCTTGTCCAAGCTGGGTGTAGCTAAATATCACTTGGTGGGGCCAATGGCGTTATGTAA :  519

*         980
LpIRIPb.1   : -------------------- :   -
LpIRIPb.2   : -------------------- :   -
LpIRIPb.3   : -------------------- :   -
LpIRIPb.4   : -------------------- :   -
LpIRIPb.5   : -------------------- :   -
LpIRIPb.6   : -------------------- :   -
LpIRIPb.7   : -------------------- :   -
LpIRIPb.8   : -------------------- :   -
LpIRIPb.9   : -------------------- :   -
LpIRIPb.10  : -------------------- :   -
LpIRIPb.11  : -------------------- :   -
LpIRIPb.12  : -------------------- :   -
LpIRIPb.13  : -------------------- :   -
LpIRIPb.14  : -------------------- :   -
LpIRIPb.15  : -------------------- :   -
LpIRIPb.16  : CTTCGTGGATATAGCATCAC :  539
```

FIG. 29F

```
            *         20         *         40         *         60
LpIRIPb : CTTACATAGCTGAACCAATGGAGAAAAGTTGGTTCTTGCTCCTTTTCTTGACGTTCCTCC : 60

*         80         *        100         *        120
LpIRIPb : TGCCGGCGGCGAGCGTGGCGGTGTCGTGCCACCCTGATGACCTCCTTGCACTGCGCGGGT : 120

*        140         *        160         *        180
LpIRIPb : TCGCCGGTAATCTCAGCAATGGGGCGTCCTCCTCCATGCAAGTGGTTCGGCAACTCTT   : 180

*        200         *        220         *        240
LpIRIPb : GCTGTAGTTGGGAAGTGTGGGATGGACGGCGGAAGCGGCGTGTCACTACTTTATGGC    : 240

*        260         *        280         *        300
LpIRIPb : TCCGTGGGCATGGACTCGCAGGCCACATCCCAACAGCATCCTTGGCTGGCCTTGCACGGC : 300

*        320         *        340         *        360
LpIRIPb : TGGAGTCGCTCAAGCTCGCCAACAACAAACTGGTCGGCACAATCCCATCATGATGGGTG  : 360

*        380         *        400         *        420
LpIRIPb : TGCTTGACCACCTTTGCTACTTGGATCTCTCAAATAATTCATTGGTTGGTGAGATACCCA : 420

*        440         *        460         *        480
LpIRIPb : AGAATTTACAGAGAAGGCTCAGTTGCCCCAACATTGTTGGTCATTCACTGGTACGGCTT  : 480

*        500         *        520         *        540
LpIRIPb : GCACTAACATGCCATTGCAGGTGAAGCATAACCAAATAGCACTGAGTGGGCAACCAAACA : 540

*        560         *        580         *        600
LpIRIPb : CAATAACCGGGACCAATAACTATGTCAGATCTGGGTCAACAATGTTGTTTCTGGGAACC  : 600

*        620         *        640         *        660
LpIRIPb : ACAACACTGTCACATCCGGGAACAACAATGTTTTTCTTGGAACCACAACACCGTGTCTG  : 660

*        680         *        700         *        720
LpIRIPb : GGACCAACCATGTTGTAACTGGTAACAACCATGTCGTAACAAGGAACCAGAATACCGTAT : 720

*        740         *        760         *        780
LpIRIPb : CTGGGAGCCATCATAAAGTATCTGGAGGCCACAATACTGTATCTGGGAGCCACAATACCG : 780

*        800         *        820         *        840
LpIRIPb : TATCTGGAAGCCACAACACAGTATCTGGAACCAACCACGTCGTACACGGGAACAACAAAG : 840
```

FIG. 30A

```
                   *         860         *         880         *         900
LpIR1Pb : TCGTGACAGGAGGTTAACAATCTATAGAGAATTGTTTCCATATTCCCTAACGGAGTTCAC : 900

*         920         *         940         *         960
LpIR1Pb : GTCCTTGTCCAAGCTGGGTGTAGCTAAATATCACTTGGTGXGGCCAATGGXGTTATGTAA : 960

*         980
LpIR1Pb : CTTCGTGGATATAGCATCAC : 985
```

FIG. 30B

```
                    *         20         *         40         *         60
LpIRIPb : MEKSWFLLLFLTFLLPAASVAVSCHPDDLLALDGFAGNLSGGVLLSAKNFGNSCCSMDG :  60

*         80         *        100         *        120
LpIRIPb : VGCDEGSGRVTTLMLRSHSLAGHIPTRSLAGLABLSSLRLANNKLVGTIPSWMGVLDHLC : 120

*        140         *        160         *        180
LpIRIPb : YLDLSNNSLVGEIPKSLQERLSCFRIVGRSLGTASTNMPLQVKHNQIALSGQPNTITGTN : 180

*        200         *        220         *        240
LpIRIPb : NYVRSGVNKVVSGNHNTVTSGSNNVVSGNHNTVSGTNRVVTGSNRVVTRNQNTVSGSNHK : 240

*        260         *
LpIRIPb : VSGGHNTVSGSHNTVSGSHNTVSGSNRVVRGSNKVVTNG : 279
```

FIG. 31

AATCGTCCTTGCATTAGGCCGGTCACGATGTGTGGTCTAGCCATTCCATG
TCATCCACATCATATAGGTTGGTGACGTTTATTTTGAAGTCTGCGTAATA
AAATCTTCCTAGGATATTTGCATGGTATCACTCAATTATTACTCTGAGTA
GGCATGGGTGACAAGTACCTCTCCAGCACAGCTCCAATCCTACATGTGGT
AGCTGACAACAAGCAGCTTGAGTGCTTGCCACCCACGAATTCCAGTCGAC
AGAAAACACCAAAAACCAAGCTTGAATTGGGAGGCAGTTTGTGGGCCTTG
TGGTCACGGACTAGTATTAGACCACTTGCAATGCATGCTTACAAACATAC
ACGCACACTATAAGTAAGATGTACCACCCAAGCAGTTTTTAACAACAACG
CTTGTGAATCACTTCCATTCCAAAAAGGTTTCTTGCCGAATCCATATATA
GCATACCACGGCTGAATCCATG

FIG. 32

```
CCTTGTTCGACTCCGTCTCAAGGGCCTTGAACCTCCTCGCAGACTCCTCT
TCGAGGGCCTGGAGTTTTTGCTCTGAGTCCTTGGAGCGGCGCAAAGCGTC
ATCTCTTTCGGCTACAAAATAAAGAATGTTACAAGTGCTTGCAAGGGAAA
TTCATGGAAGGATCTTAAAGATAGTGCTATACCCGGAAGTCGAGCTCGCT
CTACTAGCAGGGAGCCATGATCAGCTTCAACCTTCGCGAATCTACGCGCC
ATGTCCATTAGCTGGCAAGAAAGAGGCTGCACAGAAATAATTATTCTTAG
TATCCCGCGTTGCCAGAATAGGCTCGGGGGCTACATTAGGATAAAAAGA
TAAGGGTGCGGAACTTACGTTTTCTATGCGAGGAGGAGGTGAAGGTCTGG
GAGTCGAAGTTTTCTCCTCCCGCATGATTGTCTTCTCAGGTGAAGACTTC
AAAGCTTCATCATGGTCCACCAACCTCCGCGCTTCATCAGCGGAAGTGGC
TGTCGACTCCATATCCCTTCTCGGGGGTTTAGCTAAGTCATCTTCCCCTT
CGGATCTGTTGTTTATATTTGTATGTGTGGTTTTATTTTTCAAAGCTGAT
ACGATGGTTGCTAAATATAACAGGCTACAAATAGGATATACTTTCCTCTA
CTCTCCCGTCTATTAATCTTCATATGTATGTGTGCATGTATGATGTATCA
AGTAGAGCATGCATAGGGCTTGTGCACCCCTTGGTAGCCTCGATGACCT
TGACCTTGTGTTGTTTGGTAGCATCGAATCGATTGCGAGAAAATAGTAAG
TTTCTCAATCTGATCAGCCAGACACCGAACATATTATTTGGTAAATAATG
ACGGCGATTCACAATTTTTCAATAATCGTGTAGAATTAGTTGGCTTAACA
AAAGTCGGCACATTAGGCCGGTCACGATGTGTCGTCTCATCCGAGAAATT
CCATGTCAACCACATCGTCTAGGTTCGTATCGTTTATTTGACGTCTGCA
TAATAAGATCTTCCTAGGATATTTTGTTCCTCTGCGTGCACTGGAACTGT
AGGCGCGCGGTATCACTCACTTGTTACTCTGCCAAGGCATGGGTGACAAG
TACCTCTCCAGCTCAGTTCCAACCCTATATGCGGTAGCTGACGAAGGGCA
GCTTGAGTCCATGCCACCCACGAATTTCAGTCGACAGACAACACCAAAAA
CCAAGTTTGAATTGGGAGGCACCTGTGGGCCTTGTGGTCACGGACTAGCT
AGTACTGAACCACTTGCGACACATGCTTACACACACACACACACACACTA
TAAGTAGCATGTACCACCCAAGTAGTTTTTAACAACAACACTTGCGAATC
ACTTGCATTCCAAAAAGTTCATTCCTGAGTTGCATACCACAGCTGAATC
CATG
```

FIG. 33

```
AAAAGGTTTACGAAATAGTTGTTATTAAACTATATATGTTCATGTAACTA
TATTTCAATATAATTATTTGTATTACAGCAGAAAATCATTATTTCTATTA
CTTTGTATTATTATTTTGTTTTGAGTGTTGTAAAATTGGGAATTACAACT
ATACTATTTTCGTATGGAACAATTTGTTAATTTTGTGTCTCTCTTTCT
CTTCATAGCTAGCTGACAGCGAGAACAAAACCAAGATCTAATTGTGGAA
GTAGACTAGTAGTCGACCACCCATGCATGCTTACATAAGAAAACACACGC
ACTATAAGATTGGATGCACCACCCAAGCACTATAAAAGGATGCACCACC
TAAGCAATTTTTGCCAACAGCGCGCACTTGTTTGCATTCAAAAAGAAAAT
CTTACATAGCTGAACCAATG
```

FIG. 34

SEQUENCE LISTING

```
<160> NUMBER OF SEQ ID NOS: 145

<210> SEQ ID NO 1
<211> LENGTH: 976
<212> TYPE: DNA
<213> ORGANISM: Deschampsia antarctica
```

<400> SEQUENCE: 1

```
gattactata gggcacgcgt ggtcgacggc ccgggctggt atcgtccttg cattaggccg      60
gtcacgatgt gtggtctagc cattccatgt catccacatc atataggttg gtgacgttta     120
ttttgaagtc tgcgtaataa aatcttccta ggatatttgc atggtatcac tcaattatta    180
ctctgagtag gcatgggtga caagtacctc tccagcgcag ctccaatcct acatgtggta     240
gctgacaaca agcagcttga gtgcttgcca cccacgaatt ccagtcgaca gaaaacacca     300
aaaaccaagt ttgaattggg aggcagtttg tgggccttgt ggtcacggac tagtattaga     360
ccacttgcaa tgcatgctta caaacataca cgcacactat aagtaagatg taccacccaa     420
gcagttttta acaacaacac ttgtgaatca cttccattcc aaaaaggttt cttgccgaat     480
ccatatatag cataccacgg ctgaatccat ggcgctgaaa tgcgggttgt tgctgctctt     540
ctcagcattc ctcttgccgg cagcgagcgc tacggcgtgc cactcccgtg acctccgcgc     600
gctgcagggc ttcgctagga acctcggcgg cgtcggggc gtcctcctcc gtgccgcgtg      660
gtccggtgac gggtgctgcg actgggaagg tgtgggctgc gacggtgcaa gcggccgcgt     720
cactacgttg cagctaccca cgcgtggcct cgcggggccc atccccggag catccttggc     780
gggcctcgtg cagcatgtga agggtaacag gagaacactt gccgaacaac cgaatagaat     840
atcggggacc aacaacagtg tgaggtttgg gagaaacaat gctcttgccg ggaatgacaa     900
caccgtcata tctgggaata acaacactgt gtctgggagc ttcaacactg tcgtaattgg     960
gagtgacaat atcata                                                    976
```

<210> SEQ ID NO 2
<211> LENGTH: 1004
<212> TYPE: DNA
<213> ORGANISM: Deschampsia antarctica

<400> SEQUENCE: 2

```
gattactata gggcacgcgt ggtcgacggc ccgggctggt atcgtccttg cattaggccg      60
gtcacgatgt gtggtctagc cattccatgt catccacatc atataggttg gtgacgttta     120
ttttgaagtc tgcgtaataa aatcttccta ggatatttgc atggtatcac tcaattatta    180
ctctgagtag gcatgggtga caagtacctc tccagcacag ctccaatcct acatgtggta     240
gctgacaaca agcagcttga gtgcttgcca cccacgaatt ccagtcgaca gaaaacacca     300
aaaaccaagc ttgaattggg aggcagtttg tgggccttgt ggtcacggac tagtattaga     360
ccacttgcaa tgcatgctta caaacataca cgcacactat aagtaagatg taccacccaa     420
gcagttttta acaacaacgc ttgtgaatca cttccattcc aaaaaggttt cttgccgaat     480
ccatatatag cataccacgg ctgaatccat ggcgctgaaa tgcgggttgt tgctgctctt     540
ctcagcattc ctcttgccgg cagcgagcgc tacggcgtgc cactcccgtg acctccgcgc     600
gctgcagggc ttcgctagga acctcggtgg cgtcggggc gtcctcctcc gtgccgcgtg      660
gtccggtgac gggtgctgcg actgggaagg tgtggactgc gacggtgcaa gcggccgcgt     720
cactacgttg cagctaccca cgcgtggcct cgcggggccc atccccggag catccttggc     780
gggcctcgtg cagcatgtga agggtaacag gagaacactt gccgaacaac cgaatagaat     840
atcggggacc aacaacagtg tgaggtttgg gagaaacaat gctcttgccg ggaatgacaa     900
caccgtcata tctgggaata acaacactgt gtctgggagc ttcaacactg tcgtaattgg     960
gagtgacaat atcataaccg gtagcaagca tgtcgtatct ggga                     1004
```

```
<210> SEQ ID NO 3
<211> LENGTH: 912
<212> TYPE: DNA
<213> ORGANISM: Deschampsia antarctica

<400> SEQUENCE: 3
cgaattccag tcgacagaaa acaccaaaaa ccaagcttga attgggaggc agtttgtggg      60
ccttgtggtc acggactagt attagaccac ttgcaatgca tgcttacaaa catacacgca     120
cactataagt aagatgtacc acccaagcag ttttttaacaa caacgcttgt gaatcacttc    180
cattccaaaa aggtttcttg ccgaatccat atatagcata ccacggctga atccatggcg     240
ctgaaatgcg ggttgttgct gctcttctca gcattcctct tgccggcagc gagcgctacg     300
gcgtgccact cccgtgacct ccgcgcgctg cagggcttcg ctaggaacct cggtggcgtc     360
gggggcgtcc tcctccgtgc cgcgtggtcc ggtgacgggt gctgcgactg gaaggtgtg     420 gactgcgacg gtgcaagcgg ccgcgtcact acgttgcagc tacccacgcg tggcctcgcg     480
gggcccatcc ccggagcatc cttggcgggc ctcgtgcagc atgtgaaggg taacaggaga    540
acacttgccg aacaaccgaa tagaatatcg gggaccaaca acagtgtgag gtttgggaga    600
aacaatgctc ttgccgggaa tgacaacacc gtcatatctg gaataacaa cactgtgtct    660 gggagcttca acactgtcgt aattgggagt gacaatatca taaccggtag caagcatgtc   720
gtatctggga ggaaacatat cgtaactgat aacaacaaca aagtatccgg gaatgacaat   780
aatgtatccg ggagcttcca caccgtatcc gggagccaca acaccgtatc cgggagcaac   840
aataccgttt ccgggagcaa caaagtcgtg acaggaggtt aattatgtgt cagtgtagga   900
ttgtctccac ct                                                        912

<210> SEQ ID NO 4
<211> LENGTH: 912
<212> TYPE: DNA
<213> ORGANISM: Deschampsia antarctica

<400> SEQUENCE: 4
cgaattccag tcgacagaaa acaccaaaaa ccaagtttga attgggaggc agtttgtggg      60
ccttgtggtc acggactagt attagaccac ttgcaatgca tgcttacaaa catacacgca     120
cactataagt aagatgtacc acccaagcag ttttttaacaa caacacttgt gaatcacttc    180
cattccaaaa aggtttcttg ccgaatccat atatagcata ccacggctga atccatggcg     240
ctgaaatgcg ggttgttgct gctcttctca gcattcctct tgccggcagc gagcgctacg     300
gcgtgccact cccgtgacct ccgcgcgctg cagggcttcg ctaggaacct cggcggcgtc     360
gggggcgtcc tcctccgtgc cgcgtggtcc ggtgacgggt gctgcgactg gaaggtgtg     420 ggctgcgacg gtgcaagcgg ccgcgtcact acgttgcagc tacccacgcg tggcctcgcg     480
gggcccatcc ccggagcatc cttggcgggc ctcgtgcagc atgtgaaggg taacaggaga    540
acacttgccg aacaaccgaa tagaatatcg gggaccaaca acagtgtgag gtttgggaga    600
aacaatgctc ttgccgggaa tgacaacacc gtcatatctg gaataacaa cactgtgtct    660 gggagcttca acactgtcgt aattgggagt gacaatatca taaccggtag caagcatgtc   720
gtatctggga ggaaacatat cgtaactgat aacaacaaca aagtatccgg gaatgacaat   780
aatgtatccg ggagcttcca caccgtatcc gggagccaca acaccgtatc cgggagcaac   840
aataccgttt ccgggagcaa caaagtcgtg acaggaggtt aattatgtgt cagtgtagga   900
ttgtctccac ct                                                        912
```

<210> SEQ ID NO 5
<211> LENGTH: 769
<212> TYPE: DNA
<213> ORGANISM: Deschampsia antarctica

<400> SEQUENCE: 5

| | | | | | | |
|---|---|---|---|---|---|---|
| acttgtgaat | cacttccatt | ccaaaaaggt | ttcttgccga | atccatatat | agcataccac | 60 |
| ggctgaatcc | atggcgctga | aatgcgggtt | gttgctgctc | ttctcagcat | tcctcttgcc | 120 |
| ggcagcgagc | gctacggcgt | gccactcccg | tgacctccgc | gcgctgcagg | gcttcgctag | 180 |
| gaacctcggc | ggcgtcgggg | gcgtcctcct | ccgtgccgcg | tggtccggtg | acgggtgctg | 240 |
| cgactgggaa | ggtgtgggct | gcgacggtgc | aagcggccgc | gtcactacgt | tgcagctacc | 300 |
| cacgcgtggc | ctcgcggggc | ccatccccgg | agcatccttg | gcgggcctcg | tgcagcatgt | 360 |
| gaagggtaac | aggagaacac | ttgccgaaca | accgaataga | atatcgggga | ccaacaacag | 420 |
| tgtgaggttt | gggagaaaca | atgctcttgc | cgggaatgac | aacaccgtca | tatctgggaa | 480 |
| taacaacact | gtgtctggga | gcttcaacac | tgtcgtaatt | gggagtgaca | atatcataac | 540 |
| cggtagcaag | catgtcgtat | ctgggaggaa | gcatatcgta | actgataaca | acaacaaagt | 600 |
| atccggggaat | gacaataatg | tatccgggag | cttccacacc | gtatccggga | gccacaacac | 660 |
| cgtatccggg | agcaacaata | ccgtttccgg | gagcaaccat | gtcgtgtctg | ggagcaacaa | 720 |
| agtcgtgaca | ggaggttaat | tatgtgtcag | tgtaggattg | tctccacct | | 769 |

<210> SEQ ID NO 6
<211> LENGTH: 769
<212> TYPE: DNA
<213> ORGANISM: Deschampsia antarctica

<400> SEQUENCE: 6

| | | | | | | |
|---|---|---|---|---|---|---|
| acttgtgaat | cacttccatt | ccaaaaaggt | ttcttgccga | atccatatat | agcataccac | 60 |
| ggctgaatcc | atggcgctga | aatgcgggtt | gttgctgctc | ttctcagcat | tcctcttgcc | 120 |
| ggcagcgagc | gctacggcgt | gccactcccg | tgacctccgc | gcgctgcagg | gcttcgctag | 180 |
| gaacctcggc | ggcgtcgggg | gcgtcctcct | ccgtgccgcg | tggtccggtg | acgggtgctg | 240 |
| cgactgggaa | ggtgtgggct | gcgacggtgc | aagcggccgc | gtcactacgt | tgcagctacc | 300 |
| cacgcgtggc | ctcgcggggc | ccatccccgg | agcatccttg | gcgggcctcg | tgcagcatgt | 360 |
| gaagggtaac | aggagaacac | ttgccgaaca | accgaataga | atatcgggga | ccaacaacag | 420 |
| tgtgaggttt | gggagaaaca | atgctcttgc | cgggaatgac | aacaccgtca | tatctgggaa | 480 |
| taacaacact | gtgtctggga | gcttcaacac | tgtcgtaatt | gggagtgaca | atatcataac | 540 |
| cggtagcaag | catgtcgtat | ctgggaggaa | gcatatcgta | actgataaca | acaacaaagt | 600 |
| atccggggaat | gacaataatg | tatccgggag | cttccacacc | gtatccggga | gccacaacac | 660 |
| cgtatccggg | agcaacaata | ccgtttccgg | gagcaaccat | gtcgtgtctg | ggagcaacaa | 720 |
| agtcgtgaca | ggaggttaat | tatgtgtcag | tgtaggattg | tctccacct | | 769 |

<210> SEQ ID NO 7
<211> LENGTH: 769
<212> TYPE: DNA
<213> ORGANISM: Deschampsia antarctica

<400> SEQUENCE: 7

| | | | | | | |
|---|---|---|---|---|---|---|
| acttgtgaat | cacttccatt | ccaaaaaggt | ttcttgccga | atccatatat | agcataccac | 60 |
| ggctgaatcc | atggcgctga | aatgcgggtt | gttgctgctc | ttctcagcat | tcctcttgcc | 120 |

```
ggcagcgagc gctacggcgt gccactcccg tggcctccgc gcgctgcagg gcttcgctag        180
gaacctcggc ggcgtcgggg gcgtcctcct ccgcgccgcg tggtccggtg acgggtgctg        240
cgactgggaa ggtgtgggct gcgacggtgc aagcggccgc gtcactacgt tgcagctacc        300
cacgcgtggc ctcgcggggc ccatccccag agcatccttg gcgggcctcg tgcagcatgt        360
gaagggtaac aggagaacac ttgccgaaca accgaataga atatcgggga ccaacaacag        420
tgtgaggttt gggagaaaca atgctcttgc cgggaatgac aacaccgtca tatctgggaa        480
taacaacact gtgtctggga gcttcaacac tgtcgtaatt gggagtgaca atatcataac        540
cggtagcaag catgtcgtat ctgggaggaa acatatcgta actgataaca acaacaaagt        600
atccgggaat gacaataatg tatccgggag cttccacacc gtatccggga ccacaacac         660 cgtatccggg agcaacaata ccgtttccgg gagcaaccat gtcgtgtctg ggagcgacaa        720
agtcgtgaca ggaggttaat tatgtgtcag tgtaggattg tctccacct                    769

<210> SEQ ID NO 8
<211> LENGTH: 769
<212> TYPE: DNA
<213> ORGANISM: Deschampsia antarctica

<400> SEQUENCE: 8
acttgtgaat cacttccatt ccaaaaaggt ttcttgccga atccatatat agcataccac         60
ggctgaatcc atggcgctga aatgcgggtt gttgctgctc ttctcagcat tcctcttgcc        120
ggcagcgagc gctacggcgt gccactcccg tggcctccgc gcgctgcagg gcttcgctag        180
gaacctcggc ggcgtcgggg gcgtcctcct ccgcgccgcg tggtccggtg acgggtgctg        240
cgactgggaa ggtgtgggct gcgacggtgc aagcggccgc gtcactacgt tgcagctacc        300
cacgcgtggc ctcgcggggc ccatccccag agcatccttg gcgggcctcg tgcagcatgt        360
gaagggtaac aggagaacac ttgccgaaca accgaataga atatcgggga ccaacaacag        420
tgtgaggttt gggagaaaca atgctcttgc cgggaatgac aacaccgtca tatctgggaa        480
taacaacact gtgtctggga gcttcaacac tgtcgtaatt gggagtgaca atatcataac        540
cggtagcaag catgtcgtat ctgggaggaa acatatcgta actgataaca acaacaaagt        600
atccgggaat gacaataatg tatccgggag cttccacacc gtatccggga ccacaacac         660 cgtatccggg agcaacaata ccgtttccgg gagcaaccat gtcgtgtctg ggagcgacaa        720
agtcgtgaca ggaggttaat tatgtgtcag tgtaggattg tctccacct                    769

<210> SEQ ID NO 9
<211> LENGTH: 500
<212> TYPE: DNA
<213> ORGANISM: Deschampsia antarctica

<400> SEQUENCE: 9
acttgtgaat cacttccatt ccaaaaaggt ttcttgccga atccatatat agcataccac         60
ggctgaatcc atggcgctga aatgcgggtt gttgctgctc ttctcagcat tcctcttgcc        120
ggcagcgagc gctacggcgt gccactcccg tgacctccgc gcgctgcagg gcttcgctag        180
gaacctcggc ggcgtcgggg gcgtcctcct ccgtgccgcg tggtccggtg acgggtgctg        240
cgactgggaa ggtgtgggct gcgacggtgc aagcggccgc gtcactacgt tgcagctacc        300
cacgcgtggc ctcgcggggc ccatccccgg agcatccttg gcgggcctcg tgcagcatgt        360
gaagggtaac aggagaacac ttgccgaaca accgaataga atatcgggga ccaacaacag        420
```

```
tgtgaggttt gggagaaaca atgctcttgc cgggaatgac aacaccgtca tatctgggaa    480
taacaacact gtgtctggga                                                500

<210> SEQ ID NO 10
<211> LENGTH: 642
<212> TYPE: DNA
<213> ORGANISM: Deschampsia antarctica

<400> SEQUENCE: 10
acttgtgaat cacttccatt ccaaaaaggt ttcttgccga atccatatat agcataccac     60
ggctgaatcc atggcgctga atgcgggtt gttgctgctc ttctcagcat tcctcttgcc    120
ggcagcgagc gctacggcgt gccactcccg tgacctccgc gcgctgcagg gcttcgctag   180
gaacctcggc ggcgtcgggg gcgtcctcct ccgtgccgcg tggtccggtg acgggtgctg   240
cgactgggaa ggtgtgggct gcgacggtgc aagcggccgc gtcactacgt tgcagctacc   300
cacgcgtggc ctcgcgggc ccatcccgg agcatccttg gcgggcctcg tgcagcatgt    360
gaagggtaac aggagaacac ttgccgaaca accgaataga atatcgggga ccaacaacag   420
tgtgaggttt gggagaaaca atgctcttgc cgggaatgac aacaccgtca tatctgggaa   480
taacaacact gtgtctggga gcttcaacac tgtcgtaatt gggagtgaca atatcataac   540
cggtagcaag catgtcgtat ctggaggaa acatatcgta actgataaca acaacaaagt    600
atccgggaat gacaataatg tatccgggag cttccacacc gt                      642

<210> SEQ ID NO 11
<211> LENGTH: 638
<212> TYPE: DNA
<213> ORGANISM: Deschampsia antarctica

<400> SEQUENCE: 11
gcaagcggcc gcgtcactac gttgcagcta cccacgcgtg gcctcgcggg gcccatcccc     60
ggagcatcct tggcgggcct cgtgcagcat gtgaaggggta acaggagaac acttgccgaa   120
caaccgaata gaatatcggg gaccaacaac agtgtgaggt ttgggagaaa caatgctctt   180
gccgggaatg acaacaccgt catatctggg aataacaaca ctgtgtctgg gagcttcaac   240
actgtcgtaa ttgggagtga caatatcata accggtagca agcatgtcgt atctggggagg   300 aaacatatcg taactgataa caacaacaaa gtatccggga atgacaataa tgtatccggg   360
agcttccaca ccgtatccgg gagccacaac accgtatccg ggagcaacaa taccgtttcc   420
gggagcaaca aagtcgtgac aggaggttaa ttatgtgtca gtgtaggatt gtctccacct   480
gagctcaccc cttgtccaaa ttgagtctag ctcacaatca gttggtgggg ccaatcgcgg   540
catgtaactt catggatgga tatagcatca ttttcccact ttaaataaaa tttgcctcgt   600
ggatgtttac agaaaaaaaa aaaaaaaaa aaaaaaaa                            638

<210> SEQ ID NO 12
<211> LENGTH: 578
<212> TYPE: DNA
<213> ORGANISM: Deschampsia antarctica

<400> SEQUENCE: 12
ggagcatcct tggcgggcct cgtgcagcat gtgaaggggta acaggagaac acttgccgaa     60
caaccgaata gaatatcggg gaccaacaac agtgtgaggt ttgggagaaa caatgctctt   120
gccgggaatg acaacaccgt catatctggg aataacaaca ctgtgtctgg gagcttcaac   180
actgtcgtaa ttgggagtga caatatcata accggtagca agcatgtcgt atctggggagg   240
```

| | |
|---|---:|
| aaacatatcg taactgataa caacaacaaa gtatccggga atgacaataa tgtatccggg | 300 |
| agcttccaca ccgtatccgg gagccacaac accgtatccg ggagcaacaa taccgtttcc | 360 |
| gggagcaaca agtcgtgac aggaggttaa ttatgtgtca gtgtaggatt gtctccacct | 420 |
| gagctcaccc cttgtccaaa ttgagtctag ctcacaatca gttggtgggg ccaatcgcgg | 480 |
| catgtaactt catggatgga tatagcatca ttttcccact ttaaataaaa tttgcctcgt | 540 |
| ggatgtttac agaaaaaaaa aaaaaaaaaa aaaaaaaa | 578 |

<210> SEQ ID NO 13
<211> LENGTH: 431
<212> TYPE: DNA
<213> ORGANISM: Deschampsia antarctica

<400> SEQUENCE: 13

| | |
|---|---:|
| gggagcttca acactgtcgt aattgggagt gacaatatca taaccggtag caagcatgtc | 60 |
| gtatctggga ggaaacatat cgtaactgat aacaacaaca agtatccgg gaatgacaat | 120 |
| aatgtatccg ggagcttcca caccgtatcc gggagccaca caccgtatc cgggagcaac | 180 |
| aataccgttt ccgggagcaa ccatgtcgtg tctgggagca caaagtcgt gacaggaggt | 240 |
| taattatgtg tcagtgtagg attgtctcca cctgagctca cccttgtcc aaattgagtc | 300 |
| tagctcacaa tcagttggtg gggccaatcg cggcatgtaa cttcatggat ggatatagca | 360 |
| tcattttccc actttaaata aaatttgcct cgtggatgtc taaaaaaaaa gaaaaaaaaa | 420 |
| aaaaaaaaaa a | 431 |

<210> SEQ ID NO 14
<211> LENGTH: 431
<212> TYPE: DNA
<213> ORGANISM: Deschampsia antarctica

<400> SEQUENCE: 14

| | |
|---|---:|
| gggagcttca acactgtcgt aattgggagt gacaatatca taaccggtag caagcatgtc | 60 |
| gtatctggga ggaaacatat cgtaactgat aacaacaaca agtatccgg gaatgacaat | 120 |
| aatgtatccg ggagcttcca caccgtatcc gggagccaca caccgtatc cgggagcaac | 180 |
| aataccgttt ccgggagcaa ccatgtcgtg tctgggagca caaagtcgt gacaggaggt | 240 |
| taattatgtg tcagtgtagg attgtctcca cctgagctca cccttgtcc aaattgagtc | 300 |
| tagctcacaa tcagttggtg gggccaatcg cggcatgtaa cttcatggat ggatatagca | 360 |
| tcattttccc actttaaata aaatttgcct cgtggatgtc taaaaaaaaa gaaaaaaaaa | 420 |
| aaaaaaaaaa a | 431 |

<210> SEQ ID NO 15
<211> LENGTH: 430
<212> TYPE: DNA
<213> ORGANISM: Deschampsia antarctica

<400> SEQUENCE: 15

| | |
|---|---:|
| ggagcttcaa cactgtcgta attgggagtg acaatatcat aaccggtagc aagcatgtcg | 60 |
| tatctgggag gaaacatatc gtaactgata acaacaacaa gtatccggg aatgacaata | 120 |
| atgtatccgg gagcttccac accgtatccg ggagccacaa caccgtatcc gggagcaaca | 180 |
| ataccgtttc cgggagcaac catgtcgtgt ctgggagcaa caaagtcgtg acaggaggtt | 240 |
| aattatgtgt cagtgtagga ttgtctccac ctgagctcac cccttgtcca aattgagtct | 300 |
| agctcacaat cagttggtgg ggccaatcgc ggcatgtaac ttcatggatg gatatagcat | 360 |

```
cattttccca ctttaaataa aatttgcctc gtggatgtct aaaaaaaaag aaaaaaaaaa    420
aaaaaaaaaa                                                           430
```

<210> SEQ ID NO 16
<211> LENGTH: 1365
<212> TYPE: DNA
<213> ORGANISM: Deschampsia antarctica

<400> SEQUENCE: 16

```
gattactata gggcacgcgt ggtcgacggc ccgggctggt atcgtccttg cattaggccg     60
gtcacgatgt gtggtctagc cattccatgt catccacatc atataggttg gtgacgttta    120
ttttgaagtc tgcgtaataa aatcttccta ggatatttgc atggtatcac tcaattatta    180
ctctgagtag gcatgggtga caagtacctc tccagcrcag ctccaatcct acatgtggta    240
gctgacaaca agcagcttga gtgcttgcca cccacgaatt ccagtcgaca gaaaacacca    300
aaaaccaagy ttgaattggg aggcagtttg tgggccttgt ggtcacggac tagtattaga    360
ccacttgcaa tgcatgctta caaacataca cgcacactat aagtaagatg taccacccaa    420
gcagttttta acaacaacac ttgtgaatca cttccattcc aaaaggtttt cttgccgaat    480
ccatatatag cataccacgg ctgaatccat ggcgctgaaa tgcgggttgt tgctgctctt    540
ctcagcattc ctcttgccgg cagcgagcgc tacggcgtgc cactcccgtg acctccgcgc    600
gctgcagggc ttcgctagga acctcggcgg cgtcggggc gtcctcctcc gtgccgcgtg    660
gtccggtgac gggtgctgcg actgggaagg tgtgggctgc gacggtgcaa gcggccgcgt    720
cactacgttg cagctaccca cgcgtggcct cgcggggccc atccccggag catccttggc    780
gggcctcgtg cagcatgtga agggtaacag gagaacactt gccgaacaac cgaatagaat    840
atcggggacc aacaacagtg tgaggtttgg gagaaacaat gctcttgccg gaatgacaa    900 caccgtcata tctgggaata acaacactgt gtctgggagc ttcaacactg tcgtaattgg    960
gagtgacaat atcataaccg gtagcaagca tgtcgtatct gggaggaaac atatcgtaac   1020
tgataacaac aacaaagtat ccgggaatga caataatgta ccgggagct tccacaccgt   1080 atccggagc cacaacaccg tatccggag caacaatacc gtttccggga gcaaccatgt   1140
cgtgtctggg agcaacaaag tcgtgacagg aggttaatta tgtgtcagtg taggattgtc   1200
tccacctgag ctcaccccctt gtccaaattg agtctagctc acaatcagtt ggtgggcca    1260 atcgcggcat gtaacttcat ggatggatat agcatcattt tcccactta aataaattt    1320 gcctcgtgga tgtctaaaaa aaagaaaa aaaaaaaaa aaaaa              1365
```

<210> SEQ ID NO 17
<211> LENGTH: 222
<212> TYPE: PRT
<213> ORGANISM: Deschampsia antarctica

<400> SEQUENCE: 17

```
Met Ala Leu Lys Cys Gly Leu Leu Leu Phe Ser Ala Phe Leu Leu
1               5                   10                  15

Pro Ala Ala Ser Ala Thr Ala Cys His Ser Arg Asp Leu Arg Ala Leu
            20                  25                  30

Gln Gly Phe Ala Arg Asn Leu Gly Gly Val Gly Gly Val Leu Leu Arg
        35                  40                  45

Ala Ala Trp Ser Gly Asp Gly Cys Cys Asp Trp Glu Gly Val Gly Cys
    50                  55                  60
```

```
Asp Gly Ala Ser Gly Arg Val Thr Thr Leu Gln Leu Pro Thr Arg Gly
 65                  70                  75                  80

Leu Ala Gly Pro Ile Pro Gly Ala Ser Leu Ala Gly Leu Val Gln His
                 85                  90                  95

Val Lys Gly Asn Arg Arg Thr Leu Ala Glu Gln Pro Asn Arg Ile Ser
            100                 105                 110

Gly Thr Asn Asn Ser Val Arg Phe Gly Arg Asn Asn Ala Leu Ala Gly
        115                 120                 125

Asn Asp Asn Thr Val Ile Ser Gly Asn Asn Thr Val Ser Gly Ser
    130                 135                 140

Phe Asn Thr Val Val Ile Gly Ser Asp Asn Ile Ile Thr Gly Ser Lys
145                 150                 155                 160

His Val Val Ser Gly Arg Lys His Ile Val Thr Asp Asn Asn Lys
                165                 170                 175

Val Ser Gly Asn Asp Asn Val Ser Gly Ser Phe His Thr Val Ser
                180                 185                 190

Gly Ser His Asn Thr Val Ser Gly Ser Asn Asn Thr Val Ser Gly Ser
            195                 200                 205

Asn His Val Val Ser Gly Ser Asn Lys Val Val Thr Gly Gly
    210                 215                 220

<210> SEQ ID NO 18
<211> LENGTH: 449
<212> TYPE: DNA
<213> ORGANISM: Deschampsia antarctica

<400> SEQUENCE: 18
aacagcaacg ttgtgactgg aaaccacaac acactattac gtgggagtga cgacaatgcc      60
gtaagtggta gcaagcatgt cgtatctggg acccaccatg tcgtaactgg cgacaacaat     120
gccgtaacaa ggaaccacaa taccgtatcc gggagccata taccgtacc tgggagccat      180 aataccgtat ctgggagcca caataccgta tctgggagcc acaataccgt atctggaagc     240
aaccacatcg tatctgggaa caacaaagtc gtgacatgag gttaatgatc tttagtggat     300
tgtttccatc ttccctaacg aagctcatgt tcatgtccaa gctaataagt gtacctcaca     360
gtcacttggt ggggccaatc gcgttatgta acttgatgga tatagcatca ttttcgtact     420
ttaaataaaa ctccccttaaa aaacaaaaa                                      449

<210> SEQ ID NO 19
<211> LENGTH: 449
<212> TYPE: DNA
<213> ORGANISM: Deschampsia antarctica

<400> SEQUENCE: 19
aacagcaacg ttgtgactgg aaaccacaac acactattac gtgggagtga cgacaatgcc      60
gtaagtggta gcaagcatgt cgtatctggg acccaccatg tcgtaactgg cgacaacaat     120
gccgtaacaa ggaaccacaa taccgtatcc gggagccata taccgtacc tgggagccat      180 aataccgtat ctgggagcca caataccgta tctgggagcc acaataccgt atctggaagc     240
aaccacatcg tatctgggaa caacaaagtc gtgacatgag gttaatgatc tttagtggat     300
tgtttccatc ttccctaacg aagctcatgt tcatgtccaa gctaataagt gtacctcaca     360
gtcacttggt ggggccaatc gcgttatgta acttgatgga tatagcatca ttttcgtact     420
ttaaataaaa ctccccttaaa aaacaaaaa                                      449
```

<210> SEQ ID NO 20
<211> LENGTH: 449
<212> TYPE: DNA
<213> ORGANISM: Deschampsia antarctica

<400> SEQUENCE: 20

```
aacagcaacg ttgtgactgg aaaccacaac acactattac gtgggagtga cgacaatgcc      60
gtaagtggta gcaagcatgt cgtatctggg acccaccatg tcgtaactgg cgacaacaat     120
gccgtaacaa ggaaccacaa taccgtatcc gggagccata ataccgtacc tgggagccat     180
aataccgtat ctgggagcca caataccgta tctgggagcc acaataccgt atctggaagc     240
aaccacatcg tatctgggaa caacaaagtc gtgacatgag gttaatgatc tttagtggat     300
tgtttccatc ttccctaacg aagctcatgt tcatgtccaa gctaataagt gtacctcaca     360
gtcacttggt ggggccaatc gcgttatgta acttgatgga tatagcatca ttttcgtact     420
ttaaataaaa ctcccttaaa aaacaaaaa                                       449
```

<210> SEQ ID NO 21
<211> LENGTH: 449
<212> TYPE: DNA
<213> ORGANISM: Deschampsia antarctica

<400> SEQUENCE: 21

```
aacagcaacg ttgtgactgg aaaccacaac acactattac gtgggagtga cgacaatgcc      60
gtaagtggta gcaagcatgt cgtatctggg acccaccatg tcgtaactgg cgacaacaat     120
gccgtaacaa ggaaccacaa taccgtatcc gggagccata ataccgtacc tgggagccat     180
aataccgtat ctgggagcca caataccgta tctgggagcc acaataccgt atctggaagc     240
aaccacatcg tatctgggaa caacaaagtc gtgacatgag gttaatgatc tttagtggat     300
tgtttccatc ttccctaacg aagctcatgt tcatgtccaa gctaataagt gtacctcaca     360
gtcacttggt ggggccaatc gcgttatgta acttgatgga tatagcatca ttttcgtact     420
ttaaataaaa ctcccttaaa aaacaaaaa                                       449
```

<210> SEQ ID NO 22
<211> LENGTH: 92
<212> TYPE: PRT
<213> ORGANISM: Deschampsia antarctica

<400> SEQUENCE: 22

```
Asn Ser Asn Val Val Thr Gly Asn His Asn Thr Leu Leu Arg Gly Ser
1               5                  10                  15

Asp Asp Asn Ala Val Ser Gly Ser Lys His Val Val Ser Gly Thr His
            20                  25                  30

His Val Val Thr Gly Asp Asn Ala Val Thr Arg Asn His Asn Thr
        35                  40                  45

Val Ser Gly Ser His Asn Thr Val Pro Gly Ser His Asn Thr Val Ser
    50                  55                  60

Gly Ser His Asn Thr Val Ser Gly Ser His Asn Thr Val Ser Gly Ser
65                  70                  75                  80

Asn His Ile Val Ser Gly Asn Asn Lys Val Val Thr
            85                  90
```

<210> SEQ ID NO 23
<211> LENGTH: 728
<212> TYPE: DNA
<213> ORGANISM: Deschampsia antarctica

<400> SEQUENCE: 23

```
ctggtatttt gtttctctgc gtgcactgga actgtaggcg cacggtatca ctcacttatt      60
actctgccaa ggcatgggtg acaagtacct ctccagctca gttccaaccc tatatgcggt     120
agctgacgaa gggcagcttg agtccatgcc acccacgaat tcagtcgac agacaacacc      180
aaaaacaaag tttgaactgg gaggcacttg tgggccttgt ggtcacggac tagctagtac     240
tgaaccactt gcaacacatg cttacacaca cactataagt agcatgtacc acccaagtag     300
tttttaacaa caacacttgc gaatcacttg cattccaaaa aagtccattc ctgagttgca     360
taccacagct gaatccatgg cgccgaaatg ctggctgcta ctgctcttct cggcgttcct     420
cttgtcggcg gcaggcgcaa catcgtgcca ccccgatgac ctccgcgcgc tgcaaagctt     480
cgccgggaac ctcggcagcc caggggggggt cctccccgc gccgcgtggt ccggcgcctc     540
atgctgcgac tgggaaggcg tgagctgcga cggtgcaagc ggccgcgtca ctgcgttgcg     600
gctccctacg cgcggccttg agcatcctt ggcgggcctc acgcggcatg tgaaaggtaa      660
caggagaaca cttgccgtac aaccgaatac aattactggg accaacaaca acgtcaggtc     720
tggaagca                                                              728
```

<210> SEQ ID NO 24
<211> LENGTH: 702
<212> TYPE: DNA
<213> ORGANISM: Deschampsia antarctica

<400> SEQUENCE: 24

```
gagttgcata ccacagctga atccatggcg ccgaaatgct ggctgctact gctcttctcg      60
gcgttcctct tgtcggcggc aggcgcaaca tcgtgccacc ccgatgacct ccgcgcgctg     120
caaagcttcg ccgggaacct cggcagccca ggggggtcc tccccgcgc cgcgtggtcc       180
ggcgcctcat gctgcgactg gaaggcgtg agctgcgacg gtgcaagcgg ccgcgtcact      240
gcgttgcggc tccctacgcg cggccttgga gcatccttgg cgggcctcac gcggcatgtg     300
aaaggtaaca ggagaacact tgccgtacaa ccgaatacaa ttactgggac caacaacaac     360
gtcaggtctg gaagcaacaa tgttgtttcc gggaacgaca caccgtcat atctgggaac     420
aggaacattg tgtctgggag ctacaacacc gtcgtaactg ggagtgataa taccacaacc    480
ggtagcaacc atgtcgtgtc tgggaagaac catatcgtaa ccgacaacaa caacgccgta     540
accgggcacg acaataatgt atccgggagc ttccataccg tatccgggaa ccacaacaca     600
gtatctggga gcaataatac tgtatcaggg agcaaccgtg tcgtgtccgg agcaacaaa      660
gtcgtgacag gaggttaatg atatgtccgt gcaggatgct tc                        702
```

<210> SEQ ID NO 25
<211> LENGTH: 498
<212> TYPE: DNA
<213> ORGANISM: Deschampsia antarctica

<400> SEQUENCE: 25

```
gagcaacaat gttgtttccg ggaacgacaa caccgtcata tctgggaaca ggaacattgt      60
gtctgggagc tacaacaccg tcgtaactgg gagtgataat accataaccg gtagcaacca    120
tgtcgtgtct gggaagaacc atatcgtaac cgacaacaac aacgccgtaa ccgggcacga    180
caataatgta tccgggagct tccataccgt atccgggaac cacaacacag tatctgggag     240
caataatact gtatcaggga gcaaccatgt cgtgtccggg agcaacaaag tcgtgacagg     300
aggttaatga tatgtccgtg caggatgctt ccatgttccc taaaggagat cgcggcattg     360
```

```
tacaagttttt gtgtagctca caatcacttg gtgggaccaa tcgcgatgtc atgtaacttc    420
atggatatag catccttttc ctaatttaaa taaagtttgc cttgtggaaa aaaaaaaaa     480 aaaaaaaaaa aaaaaaa                                                    498
```

<210> SEQ ID NO 26
<211> LENGTH: 497
<212> TYPE: DNA
<213> ORGANISM: Deschampsia antarctica

<400> SEQUENCE: 26

```
agcaacaatg ttgtttccgg gaacgacaac accgtcatat ctgggaacag gaacattgtg    60
tctgggagct acaacaccgt cgtaactggg agtgataata ccataaccgg tagcaaccat   120
gtcgtgtctg ggaagaacca tatcgtaacc gacaacaaca acgccgtaac cgggcacgac   180
aataatgtat ccgggagctt ccataccgta tccgggaacc acaacacagt atctgggagc   240
aataatactg tatcagggag caaccatgtc gtgtccggga gcaacaaagt cgtgacagga   300
ggttaatgat atgtccgtgc aggatgcttc catgttccct aaaggagatc gcggcattgt   360
acaagttttg tgtagctcac aatcacttgg tgggaccaat cgcgatgtca tgtaacttca   420
tggatatagc atccttttcc taatttaaat aaagtttgcc ttgtggaaaa aaaaaaaaa    480 aaaaaaaaaa aaaaaaa                                                  497
```

<210> SEQ ID NO 27
<211> LENGTH: 497
<212> TYPE: DNA
<213> ORGANISM: Deschampsia antarctica

<400> SEQUENCE: 27

```
agcaacaatg ttgtttccgg gaacgacaac accgtcatat ctgggaacag gaacattgtg    60
tctgggagct acaacaccgt cgtaactggg agtgataata ccataaccgg tagcaaccat   120
gtcgtgtctg ggaagaacca tatcgtaacc gacaacaaca acgccgtaac cgggcacgac   180
aataatgtat ccgggagctt ccataccgta tccgggaacc acaacacagt atctgggagc   240
aataatactg tatcagggag caaccatgtc gtgtccggga gcaacaaagt cgtgacagga   300
ggttaatgat atgtccgtgc aggatgcttc catgttccct aaaggagatc gcggcattgt   360
acaagttttg tgtagctcac aatcacttgg tgggaccaat cgcgatgtca tgtaacttca   420
tggatatagc atccttttcc taatttaaat aaagtttgcc ttgtggaaaa aaaaaaaaa    480 aaaaaaaaaa aaaaaaa                                                  497
```

<210> SEQ ID NO 28
<211> LENGTH: 599
<212> TYPE: DNA
<213> ORGANISM: Deschampsia antarctica

<400> SEQUENCE: 28

```
gcatccttgg cgggcctcac gcggcatgtg aaaggtaaca ggagaacact tgccgtacaa    60
ccgaatacaa ttactgggac caacaacaac gtcaggtctg ggagcaacaa tgttgtttcc   120
gggaacgaca acaccgtcat atctgggaac aggaacattg tgtctgggag ctacaacacc   180
gtcgtaactg ggagtgataa taccataacc ggtagcaacc atgtcgtgtc tgggaagaac   240
catatcgtaa ccgacaacaa caacgccgta accgggcacg acaataatgt atccgggagc   300
ttccataccg tatccgggaa ccacaacaca gtatctggga gcaataatac tgtatcaggg   360
agcaaccatg tcgtgtccgg gagcaacaaa gtcgtgacag gaggttaatg atatgtccgt   420
```

```
gcaggatgct tccatgttcc ctaaaggaga tcgcggcatt gtacaagttt tgtgtagctc    480
acaatcactt ggtgggacca atcgcgatgt catgtaactt catggatata gcatccttt    540 cctaatttaa ataaagtttg ccttgtgtaa aaaaaaaaaa aaaaaaaaaa aaaaaaaa     599

<210> SEQ ID NO 29
<211> LENGTH: 599
<212> TYPE: DNA
<213> ORGANISM: Deschampsia antarctica

<400> SEQUENCE: 29
gcatccttgg cgggcctcac gcggcatgtg aaaggtaaca ggagaacact tgccgtacaa     60
ccgaatacaa ttactgggac caacaacaac gtcaggtctg ggagcaacaa tgttgtttcc    120
gggaacgaca acaccgtcat atctgggaac aggaacattg tgtctgggag ctacaacacc    180
gtcgtaactg ggagtgataa taccataacc ggtagcaacc atgtcgtgtc tgggaagaac    240
catatcgtaa ccgacaacaa caacgccgta accgggcacg acaataatgt atccgggagc    300
ttccataccg tatccgggaa ccacaacaca gtatctggga gcaataatac tgtatcaggg    360
agcaaccatg tcgtgtccgg gagcaacaaa gtcgtgacag gaggttaatg atatgtccgt    420
gcaggatgct tccatgttcc ctaaaggaga tcgcggcatt gtacaagttt tgtgtagctc    480
acaatcactt ggtgggacca atcgcgatgt catgtaactt catggatata gcatccttt    540 cctaatttaa ataaagtttg ccttgtgtaa aaaaaaaaaa aaaaaaaaaa aaaaaaaa     599

<210> SEQ ID NO 30
<211> LENGTH: 1221
<212> TYPE: DNA
<213> ORGANISM: Deschampsia antarctica

<400> SEQUENCE: 30
ctggtatttt gtttctctgc gtgcactgga actgtaggcg cacggtatca ctcacttatt     60
actctgccaa ggcatgggtg acaagtacct ctccagctca gttccaaccc tatatgcgt    120 agctgacgaa gggcagcttg agtccatgcc acccacgaat tcagtcgac agacaacacc    180 aaaaacaaag tttgaactgg gaggcacttg tgggccttgt ggtcacggac tagctagtac    240
tgaaccactt gcaacacatg cttacacaca cactataagt agcatgtacc acccaagtag    300
tttttaacaa caacacttgc gaatcacttg cattccaaaa aagtccattc ctgagttgca    360
taccacagct gaatccatgg cgccgaaatg ctggctgcta ctgctcttct cggcgttcct    420
cttgtcggcg gcaggcgcaa catcgtgcca ccccgatgac ctccgcgcgc tgcaaagctt    480
cgccgggaac ctcggcagcc caggggggt cctccccgc gccgcgtggt ccggcgcctc    540
atgctgcgac tggaaggcg tgagctgcga cggtgcaagc ggccgcgtca ctgcgttgcg    600
gctccctacg cgcggccttg agcatccttt ggcgggcctc acgcggcatg tgaaaggtaa    660
caggagaaca cttgccgtac aaccgaatac aattactggg accaacaaca acgtcaggtc    720
tgggagcaac aatgttgttt ccgggaacga caacaccgtc atatctggga acaggaacat    780
tgtgtctggg agctacaaca ccgtcgtaac tgggagtgat aataccataa ccggtagcaa    840
ccatgtcgtg tctgggaaga accatatcgt aaccgacaac aacaacgccg taaccgggca    900
cgacaataat gtatccggga gcttccatac cgtatccggg aaccacaaca cagtatctgg    960
gagcaataat actgtatcag ggagcaacca tgtcgtgtcc gggagcaaca aagtcgtgac    1020
aggaggttaa tgatatgtcc gtgcaggatg cttccatgtt ccctaaagga tcgcggca    1080 ttgtacaagt tttgtgtagc tcacaatcac ttggtgggac caatcgcgat gtcatgtaac    1140
```

```
ttcatggata tagcatcctt ttcctaattt aaataaagtt tgccttgtgg aaaaaaaaaa    1200
aaaaaaaaaa aaaaaaaaaa a                                              1221
```

<210> SEQ ID NO 31
<211> LENGTH: 217
<212> TYPE: PRT
<213> ORGANISM: Deschampsia antarctica

<400> SEQUENCE: 31

```
Met Ala Pro Lys Cys Trp Leu Leu Leu Phe Ser Ala Phe Leu Leu
1               5                   10                  15

Ser Ala Ala Gly Ala Thr Ser Cys His Pro Asp Asp Leu Arg Ala Leu
            20                  25                  30

Gln Ser Phe Ala Gly Asn Leu Gly Ser Pro Gly Gly Val Leu Pro Arg
        35                  40                  45

Ala Ala Trp Ser Gly Ala Ser Cys Cys Asp Trp Glu Gly Val Ser Cys
    50                  55                  60

Asp Gly Ala Ser Gly Arg Val Thr Ala Leu Arg Leu Pro Thr Arg Gly
65                  70                  75                  80

Leu Gly Ala Ser Leu Ala Gly Leu Thr Arg His Val Lys Gly Asn Arg
                85                  90                  95

Arg Thr Leu Ala Val Gln Pro Asn Thr Ile Thr Gly Thr Asn Asn Asn
            100                 105                 110

Val Arg Ser Gly Ser Asn Asn Val Ser Gly Asn Asp Asn Thr Val
        115                 120                 125

Ile Ser Gly Asn Arg Asn Ile Val Ser Gly Ser Tyr Asn Thr Val Val
    130                 135                 140

Thr Gly Ser Asp Asn Thr Ile Thr Gly Ser Asn His Val Val Ser Gly
145                 150                 155                 160

Lys Asn His Ile Val Thr Asp Asn Asn Asn Ala Val Thr Gly His Asp
                165                 170                 175

Asn Asn Val Ser Gly Ser Phe His Thr Val Ser Gly Asn His Asn Thr
            180                 185                 190

Val Ser Gly Ser Asn Asn Thr Val Ser Gly Ser Asn His Val Val Ser
        195                 200                 205

Gly Ser Asn Lys Val Val Thr Gly Gly
    210                 215
```

<210> SEQ ID NO 32
<211> LENGTH: 840
<212> TYPE: DNA
<213> ORGANISM: Deschampsia antarctica

<400> SEQUENCE: 32

```
gccacggaag acaagcagta ctgaaccact tgcaacgcat acttacacac acacgcacac      60
actataagat aggatgcacc acccaagcag ttttagccaa ggaacacttg cgaatcactt     120
gcattccaaa gaaggtttcc tactcagttg ttgcgtctgt gtatacatag cgtaacacag     180
cttgagtcca tggcgaactg ctgtctgcta ctcctcttct tggcgttacc cttgcctgcg     240
gcgagcgcaa catcgtgccg ccccgatgac ctccacgcgc tacggggctt cgccggaaac     300
ctgagcggcg ggggtgtcct cctccgctcc gtgtggtccg gcgactcgtg ctgcggctgg     360
gaaggcgtgg gctgcgacag cgcaagcggc cgcgtcacgg cgatgttgct ccccaggcgc     420
ggcctcgcga agcccgtccc aggagcatcc ttggcgagcc tcgcacggct agaggagctc     480
ttcaagcgta acagaagaac actggaggaa cagccaaata caattcaagg gaccaacaac     540
```

```
aatgtcagag atgggtgcta caatgctctt tctggaaatg acaacactgt catatccgga      600
aacaacaaca ctgtgtctgg gagctttaac actatcgtaa ctgggtgtca caacactgtg      660
tctggtagca accaggttgt gtccgggctc aaccatatcg taactgacga caacaatgac      720
gtatcaggta acgataataa tgtatccggt agctttcata ccgtatctgg agccacaat       780 accgtatctg ggagcaacaa taccgtatct gggagaaacc atgtcgtaac tgggagtaac      840
```

<210> SEQ ID NO 33
<211> LENGTH: 878
<212> TYPE: DNA
<213> ORGANISM: Deschampsia antarctica

<400> SEQUENCE: 33

```
gccacggaag acaagcagta ctgaaccact tgcaacgcat acttacacac acacgcacac       60
actataagat aggatgcacc acccaagcag ttttagccaa ggaacacttg cgaatcactt      120
gcattccaaa gaaggtttcc tactcagttg ttgcgtctgt gtatacatag cgtaacacag      180
cttgagtcca tggcgaactg ctgtctgcta ctcctcttct tggcgttacc cttgcctgcg      240
gcgagcgcaa catcgtgccg ccccgatgac ctccacgcgc tacggggctt cgccggaaac      300
ctgagcggcg gggtgtcct cctccgctcc gtgtggtccg gcgactcgtg ctgcggctgg       360
gaaggcgtgg gctgcgacag cgcaagcggc cgcgtcacgg cgatgttgct ccccaggcgc      420
ggcctcgcga agcccgtccc aggagcatcc ttggcgagcc tcgcacggct agaggagctc      480
ttcaagcgta acagaagaac actggaggaa cagccaaata caattcaagg gaccaacaac      540
aatgtcagag atgggtgcta caatgctctt tctggaaatg acaacactgt catatccgga      600
aacaacaaca ctgtgtctgg gagctttaac actatcgtaa ctgggtgtca caacactgtg      660
tctggtagca accaggttgt gtccgggctc aaccatatcg taactgacga caacaatgac      720
gtatcaggta acgataataa tgtatccggt agctttcata ccgtatctgg agccacaat       780 accgtatctg ggagcaacaa taccgtatct gggagaaacc atgtcgtaac tgggagtaac      840
aaagtcgtga cgggtggtta atgatcagtg agtggatt                              878
```

<210> SEQ ID NO 34
<211> LENGTH: 687
<212> TYPE: DNA
<213> ORGANISM: Deschampsia antarctica

<400> SEQUENCE: 34

```
gcggctggga aggcgtgggc tgcgacagcg caagcggccg cgtcacggcg atgttgctcc       60
ccaggcacgg cctcgcgaag cccgtcccag gagcatcctt ggcgagcctc gcacggctag      120
aggagctctt caagcgtaac agaagaacac tggaggaaca gccaaataca attcaaggga      180
ccaacaacaa tgtcagagat gggtgctaca atgctctttc tggaaatgac aacactgtca      240
tatccggaaa caacaacact gtgtctggga gctttaacac tatcgtaact gggtgtcaca      300
acactgtgtc tggtagcaac caggttgtgt ccgggctcaa ccatatcgta actgacgaca      360
acaatgacgt atcaggtaac gataataatg tatccggtag ctttcatacc gtatctggga      420
gccacaatac cgtatctggg agcaacaata ccgtatctgg agaaaccat gtcgtaactg       480 ggagtaacaa agtcgtgaca ggaggttaat gatcagtgag tggattgttt ccatcttcac      540
taacgaagct tacgaccttg tccaagttca acctagagct cacaatatct tggtggggcc      600
aatcgtctta tgtaacttca tggatgtatc ctccttttcc tactttaaat aaatttcctt      660
aaaatgtctt acaaaaaaaa aaaaaaa                                          687
```

<210> SEQ ID NO 35
<211> LENGTH: 687
<212> TYPE: DNA
<213> ORGANISM: Deschampsia antarctica

<400> SEQUENCE: 35

```
gcggctggga aggcgtgggc tgcgacagcg caagcggccg cgtcacggcg atgttgctcc      60
ccaggcacgg cctcgcgaag cccgtcccag gagcatcctt ggcgagcctc gcacggctag     120
aggagctctt caagcgtaac agaagaacac tggaggaaca gccaaataca attcaaggga     180
ccaacaacaa tgtcagagat gggtgctaca atgctctttc tggaaatgac aacactgtca     240
tatccggaaa caacaacact gtgtctggga gctttaacac tatcgtaact gggtgtcaca     300
acactgtgtc tggtagcaac caggttgtgt ccgggctcaa ccatatcgta actgacgaca     360
acaatgacgt atcaggtaac gataataatg tatccggtag ctttcatacc gtatctggga     420
gccacaatac cgtatctggg agcaacaata ccgtatctgg gagaaaccat gtcgtaactg     480
ggagtaacaa agtcgtgaca ggaggttaat gatcagtgag tggattgttt ccatcttcac     540
taacgaagct tacgaccttg tccaagttca acctagagct cacaatatct tggtggggcc     600
aatcgtctta tgtaacttca tggatgtatc ctccttttcc tactttaaat aaatttcctt     660
aaaatgtctt acaaaaaaaa aaaaaaa                                         687
```

<210> SEQ ID NO 36
<211> LENGTH: 687
<212> TYPE: DNA
<213> ORGANISM: Deschampsia antarctica

<400> SEQUENCE: 36

```
gcggctggga aggcgtgggc tgcgacagcg caagcggccg cgtcacggcg atgttgctcc      60
ccaggcacgg cctcgcgaag cccgtcccag gagcatcctt ggcgagcctc gcacggctag     120
aggagctctt caagcgtaac agaagaacac tggaggaaca gccaaataca attcaaggga     180
ccaacaacaa tgtcagagat gggtgctaca atgctctttc tggaaatgac aacactgtca     240
tatccggaaa caacaacact gtgtctggga gctttaacac tatcgtaact gggtgtcaca     300
acactgtgtc tggtagcaac caggttgtgt ccgggctcaa ccatatcgta actgacgaca     360
acaatgacgt atcaggtaac gataataatg tatccggtag ctttcatacc gtatctggga     420
gccacaatac cgtatctggg agcaacaata ccgtatctgg gagaaaccat gtcgtaactg     480
ggagtaacaa agtcgtgaca ggaggttaat gatcagtgag tggattgttt ccatcttcac     540
taacgaagct tacgaccttg tccaagttca acctagagct cacaatatct tggtggggcc     600
aatcgtctta tgtaacttca tggatgtatc ctccttttcc tactttaaat aaatttcctt     660
aaaatgtctt acaaaaaaaa aaaaaaa                                         687
```

<210> SEQ ID NO 37
<211> LENGTH: 1039
<212> TYPE: DNA
<213> ORGANISM: Deschampsia antarctica

<400> SEQUENCE: 37

```
gccacggaag acaagcagta ctgaaccact tgcaacgcat acttacacac acacgcacac      60
actataagat aggatgcacc acccaagcag ttttagccaa ggaacacttg cgaatcactt     120
gcattccaaa gaaggtttcc tactcagttg ttgcgtctgt gtatacatag cgtaacacag     180
cttgagtcca tggcgaactg ctgtctgcta ctcctcttct tggcgttacc cttgcctgcg     240
```

```
gcgagcgcaa catcgtgccg ccccgatgac ctccacgcgc tacggggctt cgccggaaac    300
ctgagcggcg ggggtgtcct cctccgctcc gtgtggtccg gcgactcgtg ctgcggctgg    360
gaaggcgtgg gctgcgacag cgcaagcggc cgcgtcacgg cgatgttgct ccccaggcac    420
ggcctcgcga agcccgtccc aggagcatcc ttggcgagcc tcgcacggct agaggagctc    480
ttcaagcgta acagaagaac actggaggaa cagccaaata caattcaagg gaccaacaac    540
aatgtcagag atgggtgcta caatgctctt tctggaaatg acaacactgt catatccgga    600
aacaacaaca ctgtgtctgg gagctttaac actatcgtaa ctgggtgtca caacactgtg    660
tctggtagca accaggttgt gtccgggctc aaccatatcg taactgacga caacaatgac    720
gtatcaggta acgataataa tgtatccggt agctttcata ccgtatctgg gagccacaat    780
accgtatctg ggagcaacaa taccgtatct gggagaaacc atgtcgtaac tgggagtaac    840
aaagtcgtga caggaggtta atgatcagtg agtggattgt ttccatcttc actaacgaag    900
cttacgacct tgtccaagtt caacctagag ctcacaatat cttggtgggg ccaatcgtct    960
tatgtaactt catggatgta tcctcctttt cctactttaa ataaatttcc ttaaaatgtc    1020
ttacaaaaaa aaaaaaaaa                                                 1039
```

<210> SEQ ID NO 38
<211> LENGTH: 223
<212> TYPE: PRT
<213> ORGANISM: Deschampsia antarctica

<400> SEQUENCE: 38

```
Met Ala Asn Cys Cys Leu Leu Leu Phe Leu Ala Leu Pro Leu Pro
1               5                   10                  15

Ala Ala Ser Ala Thr Ser Cys Arg Pro Asp Asp Leu His Ala Leu Arg
            20                  25                  30

Gly Phe Ala Gly Asn Leu Ser Gly Gly Gly Val Leu Leu Arg Ser Val
        35                  40                  45

Trp Ser Gly Asp Ser Cys Cys Gly Trp Glu Gly Val Gly Cys Asp Ser
    50                  55                      60

Ala Ser Gly Arg Val Thr Ala Met Leu Leu Pro Arg His Gly Leu Ala
65                  70                  75                  80

Lys Pro Val Pro Gly Ala Ser Leu Ala Ser Leu Ala Arg Leu Glu Glu
                85                  90                  95

Leu Phe Lys Arg Asn Arg Arg Thr Leu Glu Glu Gln Pro Asn Thr Ile
            100                 105                 110

Gln Gly Thr Asn Asn Asn Val Arg Asp Gly Cys Tyr Asn Ala Leu Ser
        115                 120                 125

Gly Asn Asp Asn Thr Val Ile Ser Gly Asn Asn Thr Val Ser Gly
    130                 135                 140

Ser Phe Asn Thr Ile Val Thr Gly Cys His Asn Thr Val Ser Gly Ser
145                 150                 155                 160

Asn Gln Val Val Ser Gly Leu Asn His Ile Val Thr Asp Asp Asn Asn
                165                 170                 175

Asp Val Ser Gly Asn Asp Asn Val Ser Gly Ser Phe His Thr Val
            180                 185                 190

Ser Gly Ser His Asn Thr Val Ser Gly Ser Asn Thr Val Ser Gly
        195                 200                 205

Arg Asn His Val Val Thr Gly Ser Asn Lys Val Val Thr Gly Gly
    210                 215                 220
```

<210> SEQ ID NO 39
<211> LENGTH: 751
<212> TYPE: DNA
<213> ORGANISM: Deschampsia antarctica

<400> SEQUENCE: 39

```
acacacacgc acacactata agataggatg caccacccaa gcagttttag ccaaggaaca      60
cttgcgaatc acttgcattc caaagaaggt ttcttactca gttgttgcgt ctgtgtatac     120
atagcgtaac acagcttgag tccatggcga actgctgtct gctactcctc ttcttggcgt     180
tactcttgcc tgcggcgtgc gcaacatcgt gccaccccga tgacctccac gcgctacggg     240
gcttcgccgg aaacctgagc ggcggggtg tcctcccccg ctccgtgtgg tccggtgact      300
cgtgctgcgg ctgggaaggt gtgggctgcg acgacgcaag cggccgggtc acgacgatgt     360
ggctccccag gcgcggcctc gtgaagcccg tccccggagc atccttggcg ggcgtcacgg     420
agctggagga gctcatcacg cgtaacagaa gagcactgga ggaacaacca aatacaattc     480
aagggaccaa caacaatgtc agagatgggt gctacaatgc tctttctggg aatgacaaca     540
ctgtcatatc cggaaacaac aacactgtgt ctgggagctt aaacactatc gtaactgggt     600
gtcacaacac tgtgtctggt agcaaccagg ttgtatctgg gctcaaccat atcgtaactg     660
acgacaacaa tgacgtatca ggtaacgata ataatgtatc tggtagcttt cataccgtat     720
ctgggagcca caataccgta tctgggagca a                                   751
```

<210> SEQ ID NO 40
<211> LENGTH: 832
<212> TYPE: DNA
<213> ORGANISM: Deschampsia antarctica

<400> SEQUENCE: 40

```
acacacacgc acacactata agataggatg caccacccaa gcagttttag ccaaggaaca      60
cttgcgaatc acttgcattc caaagaaggt ttcttactca gttgttgcgt ctgtgtatac     120
atagcgtaac acagcttgag tccatggcga actgctgtct gctactcctc ttcttggcgt     180
tactcttgcc tgcggcgtgc gcaacatcgt gccaccccga tgacctccac gcgctacggg     240
gcttcgccgg aaacctgagc ggcggggtg tcctcccccg ctccgtgtgg tccggtgact      300
cgtgctgcgg ctgggaaggt gtgggctgcg acgacgcaag cggccgggtc acgacgatgt     360
ggctccccag gcgcggcctc gtgaagcccg tccccggagc atccttggcg ggcgtcacgg     420
agctggagga gctcatcacg cgtaacagaa gagcactgga ggaacaacca aatacaattc     480
aagggaccaa caacaatgtc agagatgggt gctacaatgc tctttctggg aatgacaaca     540
ctgtcatatc cggaaacaac aacactgtgt ctgggagctt aaacactatc gtaactgggt     600
gtcacaacac tgtgtctggt agcaaccagg ttgtatctgg gctcaaccat atcgtaactg     660
acgacaacaa tgacgtatca ggtaacgata ataatgtatc tggtagcttt cataccgtat     720
ctgggagcca caataccgta tctgggagca acaataccgt atctgggaga aaccatgtcg     780
taactgggag taacaaagtc gtgacaggtg gttaatgatc agtgagtgga tt             832
```

<210> SEQ ID NO 41
<211> LENGTH: 707
<212> TYPE: DNA
<213> ORGANISM: Deschampsia antarctica

<400> SEQUENCE: 41

```
cgtaacacag cttgagtcca tggcgaactg ctgtctgcta ctcctcttct tggcgttact    60
cttgcctgcg gcgagcgcaa catcgtgcca ccccgatgac ctccacgcgc tacggggctt   120
cgccggaaac ctgagcggcg ggggtgtcct cctccgctcc gtgtggtccg gcgactcgtg   180
ctgcggctgg aaggtgtggg ctgcgacgac gcaagcggcc gggtcacgac gatgtggctc   240
cccaggcgcg gcctcgtgaa gcccgtcccc ggagcatcct tggcgggcgt cacggagctg   300
gaggagctca tcacgcgtaa cagaagagca ctggaggaac aaccaaatac aattcaaggg   360
accaacaaca atgtcagaga tgggtgctac aatgctcttt ctgggaatgg caacactgtc   420
atatccggaa acaacaacac tgtgtctggg agctttaaca ctatcgtaac tgggtgtcac   480
aacactgtgt ctggtagcaa ccaggttgta tctgggctca accatatcgt aactgacgac   540
aacaatgacg tatcaggtaa cgataataat gtatctggta gctttcatac cgtatctggg   600
agccacaata ccgtatctgg gagcaacaat accgtatctg ggagaaacca tgtcgtaact   660
gggagtaaca aagtcgtgac aggaggttaa tgatcagtga gtggatt              707
```

<210> SEQ ID NO 42
<211> LENGTH: 707
<212> TYPE: DNA
<213> ORGANISM: Deschampsia antarctica

<400> SEQUENCE: 42

```
cgtaacacag cttgagtcca tggcgaactg ctgtctgcta ctcctcttct tggcgttact    60
cttgcctgcg gcgagcgcaa catcgtgcca ccccgatgac ctccacgcgc tacggggctt   120
cgccggaaac ctgagcggcg ggggtgtcct cctccgctcc gtgtggtccg gcgactcgtg   180
ctgcggctgg aaggtgtggg ctgcgacgac gcaagcggcc gggtcacgac gatgtggctc   240
cccaggcgcg gcctcgtgaa gcccgtcccc ggagcatcct tggcgggcgt cacggagctg   300
gaggagctca tcacgcgtaa cagaagagca ctggaggaac aaccaaatac aattcaaggg   360
accaacaaca atgtcagaga tgggtgctac aatgctcttt ctgggaatgg caacactgtc   420
atatccggaa acaacaacac tgtgtctggg agctttaaca ctatcgtaac tgggtgtcac   480
aacactgtgt ctggtagcaa ccaggttgta tctgggctca accatatcgt aactgacgac   540
aacaatgacg tatcaggtaa cgataataat gtatctggta gctttcatac cgtatctggg   600
agccacaata ccgtatctgg gagcaacaat accgtatctg ggagaaacca tgtcgtaact   660
gggagtaaca aagtcgtgac aggaggttaa tgatcagtga gtggatt              707
```

<210> SEQ ID NO 43
<211> LENGTH: 708
<212> TYPE: DNA
<213> ORGANISM: Deschampsia antarctica

<400> SEQUENCE: 43

```
cgtaacacag cttgagtcca tggcgaactg ctgtctgcta ctcctcttct tggcgttact    60
cttgcctgcg gcgtgcgcaa catcgtgcca ccccgatgac ctccacgcgc tacggggctt   120
cgccggaaac ctgagcggcg ggggtgtcct ccccgctcc  gtgtggtccg gtgactcgtg   180
ctgcggctgg gaaggtgtgg gctgcgacga cgcaagcggc cgggtcacga cgatgtggct   240
ccccaggcgc ggcctcgtga agcccgtccc cggagcatcc ttggcgggcg tcacggagct   300
ggaggagctc atcacgcgta acagaagagc actggaggaa caaccaaata caattcaagg   360
gaccaacaac aatgtcagag atgggtgcta caatgctctt tctgggaatg caacactgt    420
```

```
catatccgga acaacaaca ctgtgtctgg gagctttaac actatcgtaa ctgggtgtca    480
caacactgtg tctggtagca accaggttgt atctgggctc aaccatatcg taactgacga    540
caacaatgac gtatcaggta acgataataa tgtatctggt agctttcata ccgtatctgg    600
gagccacaat accgtatctg ggagcaacaa taccgtatct gggagaaacc atgtcgtaac    660
tgggagtaac aaagtcgtga caggtggtta atgatcagtg agtggatt                708
```

<210> SEQ ID NO 44
<211> LENGTH: 708
<212> TYPE: DNA
<213> ORGANISM: Deschampsia antarctica

<400> SEQUENCE: 44

```
cgtaacacag cttgagtcca tggcgaactg ctgtctgcta ctcctcttct tggcgttact     60
cttgcctgcg gcgtgcgcaa catcgtgcca ccccgatgac ctccacgcgc tacggggctt    120
cgccggaaac ctgagcggcg ggggtgtcct cccccgctcc gtgtggtccg gtgactcgtg    180
ctgcggctgg gaaggtgtgg gctgcgacga cgcaagcggc cgggtcacga cgatgtggct    240
ccccaggcgc ggcctcgtga agcccgtccc cggagcatcc ttggcgggcg tcacggagct    300
ggaggagctc atcacgcgta acagaagagc actggaggaa caaccaaata caattcaagg    360
gaccaacaac aatgtcagag atgggtgcta caatgctctt tctgggaatg acaacactgt    420
catatccgga acaacaaca ctgtgtctgg gagctttaac actatcgtaa ctgggtgtca    480
caacactgtg tctggtagca accaggttgt atctgggctc aaccatatcg taactgacga    540
caacaatgac gtatcaggta acgataataa tgtatctggt agctttcata ccgtatctgg    600
gagccacaat accgtatctg ggagcaacaa taccgtatct gggagaaacc atgtcgtaac    660
tgggagtaac aaagtcgtga caggtggtta atgatcagtg agtggatt                708
```

<210> SEQ ID NO 45
<211> LENGTH: 832
<212> TYPE: DNA
<213> ORGANISM: Deschampsia antarctica

<400> SEQUENCE: 45

```
acacacacgc acacactata agataggatg caccacccaa gcagttttag ccaaggaaca     60
cttgcgaatc acttgcattc caaagaaggt ttcttactca gttgttgcgt ctgtgtatac    120
atagcgtaac acagcttgag tccatggcga actgctgtct gctactcctc ttcttggcgt    180
tactcttgcc tgcggcgtgc gcaacatcgt gccaccccga tgacctccac gcgctacggg    240
gcttcgccgg aaacctgagc ggcggggtg tcctccccg ctccgtgtgg tccggtgact    300
cgtgctgcgg ctgggaaggt gtgggctgcg acgacgcaag cggccgggtc acgacgatgt    360
ggctccccag gcgcggcctc gtgaagcccg tccccggagc atccttggcg ggcgtcacgg    420
agctggagga gctcatcacg cgtaacagaa gagcactgga ggaacaacca aatacaattc    480
aagggaccaa caacaatgtc agagatgggt gctacaatgc tctttctggg aatgacaaca    540
ctgtcatatc cggaaacaac aacactgtgt ctggagctt taacactatc gtaactgggt    600
gtcacaacac tgtgtctggt agcaaccagg ttgtatctgg gctcaaccat atcgtaactg    660
acgacaacaa tgacgtatca ggtaacgata ataatgtatc tggtagcttt cataccgtat    720
ctgggagcca ataccgta tctgggagca acaataccgt atctgggaga aaccatgtcg    780
taactgggag taacaaagtc gtgacaggtg gttaatgatc agtgagtgga tt            832
```

<210> SEQ ID NO 46
<211> LENGTH: 223
<212> TYPE: PRT
<213> ORGANISM: Deschampsia antarctica

<400> SEQUENCE: 46

Met Ala Asn Cys Cys Leu Leu Leu Phe Leu Ala Leu Leu Leu Pro
1               5                   10                  15

Ala Ala Cys Ala Thr Ser Cys His Pro Asp Asp Leu His Ala Leu Arg
            20                  25                  30

Gly Phe Ala Gly Asn Leu Ser Gly Gly Val Leu Pro Arg Ser Val
        35                  40                  45

Trp Ser Gly Asp Ser Cys Cys Gly Trp Glu Val Gly Cys Asp Asp
50                  55                  60

Ala Ser Gly Arg Val Thr Thr Met Trp Leu Pro Arg Arg Gly Leu Val
65                  70                  75                  80

Lys Pro Val Pro Gly Ala Ser Leu Ala Gly Val Thr Glu Leu Glu Glu
                85                  90                  95

Leu Ile Thr Arg Asn Arg Arg Ala Leu Glu Glu Gln Pro Asn Thr Ile
            100                 105                 110

Gln Gly Thr Asn Asn Val Arg Asp Gly Cys Tyr Asn Ala Leu Ser
        115                 120                 125

Gly Asn Asp Asn Thr Val Ile Ser Gly Asn Asn Thr Val Ser Gly
130                 135                 140

Ser Phe Asn Thr Ile Val Thr Gly Cys His Asn Thr Val Ser Gly Ser
145                 150                 155                 160

Asn Gln Val Val Ser Gly Leu Asn His Ile Val Thr Asp Asn Asn
                165                 170                 175

Asp Val Ser Gly Asn Asp Asn Val Ser Gly Ser Phe His Thr Val
            180                 185                 190

Ser Gly Ser His Asn Thr Val Ser Gly Ser Asn Asn Thr Val Ser Gly
        195                 200                 205

Arg Asn His Val Val Thr Gly Ser Asn Lys Val Val Thr Gly Gly
210                 215                 220

<210> SEQ ID NO 47
<211> LENGTH: 810
<212> TYPE: DNA
<213> ORGANISM: Deschampsia antarctica

<400> SEQUENCE: 47
ctccccaggc gcggcctcgc gggccccatc acaggagcaa ccttggccgg cctgacacgg     60
cttgagtcgc tcaaccttgc caacaacagt ctggtaggca ccatcccatc atggatcggt    120
gagcttgacc acctttgcta catggatctc tcacacaatt cactagatgg cgaggtaccc    180
aagagtttgc agatacggct cagggccctc actacgaccg tcgttcact gggcatggtt     240 ttcattaaca tgccgttgca tatgaagcgt agccgaagaa cactccaaga caaccaaat     300 gtaataactg gaccaacaa cagtgtcaga tctgggagaa caatgttgt tccgggaac      360 gacaatactg tcatatctgg gaacaacaat gttgtgtctg ggagccacaa cactgtcgta    420
acggggagtg acaatgtcgt aagtggtagt aaccatgtcg tatctaggac caaccatgtc    480
gtaactgata caacaatgc cgtaaccggg aaccacaaca ctgtatccgg gagccacaac    540
actgtatccg ggagcaacaa tgtcgtatcc gggagcaacc atgttgtatc agggagcaac    600
aaagtcgtga cgggaggtta attaatgatc tatcagtgga ttgtctccat cgtccctgac    660

```
ggagttcacg tccttgtcca agttcagtgt agcttacaat cacatggtag ggccaatcgc    720
attatgtaac ttcatggata tagcatcctt tttctgtttt aaataaaaac ccctaaacta    780
tcttacaaaa aaaaaaaaaa aaaaaaaaaa                                     810
```

```
<210> SEQ ID NO 48
<211> LENGTH: 810
<212> TYPE: DNA
<213> ORGANISM: Deschampsia antarctica

<400> SEQUENCE: 48
ctccccaggc gcggcctcgc gggccccatc acaggagcaa ccttggccgg cctgacacgg     60
cttgagtcgc tcaaccttgc caacaacagt ctggtaggca ccatcccatc atggatcggt    120
gagcttgacc acctttgcta catggatctc tcacacaatt cactagatgg cgaggtaccc    180
aagagtttgc agatacggct cagggccctc actacgaccg gtcgttcact gggcatggtt    240
ttcattaaca tgccgttgca tatgaagcgt agccgaagaa cactccaaga caaccaaat     300 gtaataactg ggaccaacaa cagtgtcaga tctgggagaa acaatgttgt tccgggaac    360 gacaatactg tcatatctgg gaacaacaat gttgtgtctg ggagccacaa cactgtcgta    420
acggggagtg acaatgtcgt aagtggtagt aaccatgtcg tatctaggac caaccatgtc    480
gtaactgata caacaatgc cgtaaccggg aaccacaaca ctgtatccgg gagccacaac     540
actgtatccg ggagcaacaa tgtcgtatcc gggagcaacc atgttgtatc agggagcaac    600
aaagtcgtga cgggaggtta attaatgatc tatcagtgga ttgtctccat cgtccctgac    660
ggagttcacg tccttgtcca agttcagtgt agcttacaat cacatggtag ggccaatcgc    720
attatgtaac ttcatggata tagcatcctt tttctgtttt aaataaaaac ccctaaacta    780
tcttacaaaa aaaaaaaaaa aaaaaaaaaa                                     810
```

```
<210> SEQ ID NO 49
<211> LENGTH: 810
<212> TYPE: DNA
<213> ORGANISM: Deschampsia antarctica

<400> SEQUENCE: 49
ctccccaggc gcggcctcgc gggccccatc acaggagcaa ccttggccgg cctgacacgg     60
cttgagtcgc tcaaccttgc caacaacagt ctggtaggca ccatcccatc atggatcggt    120
gagcttgacc acctttgcta catggatctc tcacacaatt cactagatgg cgaggtaccc    180
aagagtttgc agatacggct cagggccctc actacgaccg gtcgttcact gggcatggtt    240
ttcattaaca tgccgttgca tatgaagcgt agccgaagaa cactccaaga caaccaaat     300 gtaataactg ggaccaacaa cagtgtcaga tctgggagaa acaatgttgt tccgggaac    360 gacaatactg tcatatctgg gaacaacaat gttgtgtctg ggagccacaa cactgtcgta    420
acggggagtg acaatgtcgt aagtggtagt aaccatgtcg tatctaggac caaccatgtc    480
gtaactgata caacaatgc cgtaaccggg aaccacaaca ctgtatccgg gagccacaac     540
actgtatccg ggagcaacaa tgtcgtatcc gggagcaacc atgttgtatc agggagcaac    600
aaagtcgtga cgggaggtta attaatgatc tatcagtgga ttgtctccat cgtccctgac    660
ggagttcacg tccttgtcca agttcagtgt agcttacaat cacatggtag ggccaatcgc    720
attatgtaac ttcatggata tagcatcctt tttctgtttt aaataaaaac ccctaaacta    780
tcttacaaaa aaaaaaaaaa aaaaaaaaaa                                     810
```

<210> SEQ ID NO 50
<211> LENGTH: 810
<212> TYPE: DNA
<213> ORGANISM: Deschampsia antarctica

<400> SEQUENCE: 50

```
ctccccaggc gcggcctcgc gggccccatc acaggagcaa ccttggccgg cctgacacgg      60
cttgagtcgc tcaaccttgc caacaacagt ctggtaggca ccatcccatc atggatcggt     120
gagcttgacc acctttgcta catggatctc tcacacaatt cactagatgg cgaggtaccc     180
aagagtttgc agatacggct cagggccctc actacgaccg gtcgttcact gggcatggtt     240
ttcattaaca tgccgttgca tatgaagcgt agccgaagaa cactccaaga caaccaaat     300
gtaataactg ggaccaacaa cagtgtcaga tctgggagaa acaatgttgt ttccgggaac     360
gacaatactg tcatatctgg gaacaacaat gttgtgtctg ggagccacaa cactgtcgta     420
acggggagtg acaatgtcgt aagtggtagt aaccatgtcg tatctaggac caaccatgtc     480
gtaactgata acaacaatgc cgtaaccggg aaccacaaca ctgtatccgg gagccacaac     540
actgtatccg ggagcaacaa tgtcgtatcc gggagcaacc atgttgtatc agggagcaac     600
aaagtcgtga cgggaggtta attaatgatc tatcagtgga ttgtctccat cgtccctgac     660
ggagttcacg tccttgtcca agttcagtgt agcttacaat cacatggtag ggccaatcgc     720
attatgtaac ttcatggata tagcatcctt tttctgtttt aaataaaaac ccctaaacta     780
tcttacaaaa aaaaaaaaaa aaaaaaaaaa                                      810
```

<210> SEQ ID NO 51
<211> LENGTH: 810
<212> TYPE: DNA
<213> ORGANISM: Deschampsia antarctica

<400> SEQUENCE: 51

```
ctccccaggc gcggcctcgc gggccccatc acaggagcaa ccttggccgg cctgacacgg      60
cttgagtcgc tcaaccttgc caacaacagt ctggtaggca ccatcccatc atggatcggt     120
gagcttgacc acctttgcta catggatctc tcacacaatt cactagatgg cgaggtaccc     180
aagagtttgc agatacggct cagggccctc actacgaccg gtcgttcact gggcatggtt     240
ttcattaaca tgccgttgca tatgaagcgt agccgaagaa cactccaaga caaccaaat     300
gtaataactg ggaccaacaa cagtgtcaga tctgggagaa acaatgttgt ttccgggaac     360
gacaatactg tcatatctgg gaacaacaat gttgtgtctg ggagccacaa cactgtcgta     420
acggggagtg acaatgtcgt aagtggtagt aaccatgtcg tatctaggac caaccatgtc     480
gtaactgata acaacaatgc cgtaaccggg aaccacaaca ctgtatccgg gagccacaac     540
actgtatccg ggagcaacaa tgtcgtatcc gggagcaacc atgttgtatc agggagcaac     600
aaagtcgtga cgggaggtta attaatgatc tatcagtgga ttgtctccat cgtccctgac     660
ggagttcacg tccttgtcca agttcagtgt agcttacaat cacatggtag ggccaatcgc     720
attatgtaac ttcatggata tagcatcctt tttctgtttt aaataaaaac ccctaaacta     780
tcttacaaaa aaaaaaaaaa aaaaaaaaaa                                      810
```

<210> SEQ ID NO 52
<211> LENGTH: 810
<212> TYPE: DNA
<213> ORGANISM: Deschampsia antarctica

<400> SEQUENCE: 52

```
ctccccaggc gcggcctcgc gggccccatc acaggagcaa ccttggccgg cctgacacgg        60
cttgagtcgc tcaaccttgc caacaacagt ctggtaggca ccatcccatc atggatcggt       120
gagcttgacc acctttgcta catggatctc tcacacaatt cactagatgg cgaggtaccc       180
aagagtttgc agatacggct cagggccctc actacgaccg gtcgttcact gggcatggtt       240
ttcattaaca tgccgttgca tatgaagcgt agccgaagaa cactccaaga caaccaaat       300
gtaataactg ggaccaacaa cagtgtcaga tctgggagaa acaatgttgt ttccgggaac       360
gacaatactg tcatatctgg gaacaacaat gttgtgtctg ggagccacaa cactgtcgta       420
acggggagtg acaatgtcgt aagtggtagt aaccatgtcg tatctaggac caaccatgtc       480
gtaactgata caacaatgc cgtaaccggg aaccacaaca ctgtatccgg gagccacaac       540
actgtatccg ggagcaacaa tgtcgtatcc gggagcaacc atgttgtatc agggagcaac       600
aaagtcgtga cggaggtta attaatgatc tatcagtgga ttgtctccat cgtccctgac       660
ggagttcacg tccttgtcca agttcagtgt agcttacaat cacatggtag gccaatcgc       720
attatgtaac ttcatggata tagcatcctt tttctgtttt aaataaaaac ccctaaacta       780
tcttacaaaa aaaaaaaaaa aaaaaaaaaa                                        810
```

<210> SEQ ID NO 53
<211> LENGTH: 810
<212> TYPE: DNA
<213> ORGANISM: Deschampsia antarctica

<400> SEQUENCE: 53

```
ctccccaggc gcggcctcgc gggccccatc acaggagcaa ccttggccgg cctgacacgg        60
cttgagtcgc tcaaccttgc caacaacagt ctggtaggca ccatcccatc atggatcggt       120
gagcttgacc acctttgcta catggatctc tcacacaatt cactagatgg cgaggtaccc       180
aagagtttgc agatacggct cagggccctc actacgaccg gtcgttcact gggcatggtt       240
ttcattaaca tgccgttgca tatgaagcgt agccgaagaa cactccaaga caaccaaat       300
gtaataactg ggaccaacaa cagtgtcaga tctgggagaa acaatgttgt ttccgggaac       360
gacaatactg tcatatctgg gaacaacaat gttgtgtctg ggagccacaa cactgtcgta       420
acggggagtg acaatgtcgt aagtggtagt aaccatgtcg tatctaggac caaccatgtc       480
gtaactgata caacaatgc cgtaaccggg aaccacaaca ctgtatccgg gagccacaac       540
actgtatccg ggagcaacaa tgtcgtatcc gggagcaacc atgttgtatc agggagcaac       600
aaagtcgtga cggaggtta attaatgatc tatcagtgga ttgtctccat cgtccctgac       660
ggagttcacg tccttgtcca agttcagtgt agcttacaat cacatggtag gccaatcgc       720
attatgtaac ttcatggata tagcatcctt tttctgtttt aaataaaaac ccctaaacta       780
tcttacaaaa aaaaaaaaaa aaaaaaaaaa                                        810
```

<210> SEQ ID NO 54
<211> LENGTH: 206
<212> TYPE: PRT
<213> ORGANISM: Deschampsia antarctica

<400> SEQUENCE: 54

```
Leu Pro Arg Arg Gly Leu Ala Gly Pro Ile Thr Gly Ala Thr Leu Ala
 1               5                  10                  15
Gly Leu Thr Arg Leu Glu Ser Leu Asn Leu Ala Asn Asn Ser Leu Val
             20                  25                  30
```

Gly Thr Ile Pro Ser Trp Ile Gly Glu Leu Asp His Leu Cys Tyr Met
            35                  40                  45

Asp Leu Ser His Asn Ser Leu Asp Gly Glu Val Pro Lys Ser Leu Gln
 50                  55                  60

Ile Arg Leu Arg Ala Leu Thr Thr Thr Gly Arg Ser Leu Gly Met Val
 65                  70                  75                  80

Phe Ile Asn Met Pro Leu His Met Lys Arg Ser Arg Arg Thr Leu Gln
                85                  90                  95

Glu Gln Pro Asn Val Ile Thr Gly Thr Asn Asn Ser Val Arg Ser Gly
            100                 105                 110

Arg Asn Asn Val Val Ser Gly Asn Asp Asn Thr Val Ile Ser Gly Asn
            115                 120                 125

Asn Asn Val Val Ser Gly Ser His Asn Thr Val Thr Gly Ser Asp
            130                 135                 140

Asn Val Val Ser Gly Ser Asn His Val Val Ser Arg Thr Asn His Val
145                 150                 155                 160

Val Thr Asp Asn Asn Ala Val Thr Gly Asn His Asn Thr Val Ser
                165                 170                 175

Gly Ser His Asn Thr Val Ser Gly Ser Asn Val Val Ser Gly Ser
            180                 185                 190

Asn His Val Val Ser Gly Ser Asn Lys Val Val Thr Gly Gly
            195                 200                 205

<210> SEQ ID NO 55
<211> LENGTH: 1298
<212> TYPE: DNA
<213> ORGANISM: Lolium perenne

<400> SEQUENCE: 55
cccgggctgg taaaaggttt acgaaatagt tgttattaaa ctatatatgt tcatgtaact    60
atatttcaat ataattattt gtattacagc agaaaatcat tatttctatt actttgtatt   120
attattttgt tttgagtgtt gtaaaattgg gaattacaac tatactattt tcgtatggga   180
acaatttgtt aatttttgtg tctctctttc tcttcatagc tagctgacag cgagaacaaa   240
aaccaagatc taattgtgga agtagactag tagtcgacca cccatgcatg cttacataag   300
aaaacacacg cactataaga ttggatgcac cacccaagca ctataaaaag gatgcaccac   360
ctaagcaatt tttgccaaca gcgcgcactt gtttgcattc aaaagaaaa tcttacatag    420 ctgaaccaat ggagaaaagt tggttcttgc tccttttctt ggcgttcctc ctgccggcgg   480
cgagcgtggc ggtgtcatgc caccctgatg acctccttgc actgcgcggg ttcgccggta   540
atctcagcaa tgggggcgtg ctcctccatg ccaagtggcc cgacaaccct tgctgtagtt   600
gggaaggtgt gggatgcgac ggcggaagcg gccgtgtcac tacgttgtgg ctccctgggc   660
atggactcgc aggccacatc ccaacagcat ccttggctgg ccttgcacgg ctggagtcgc   720
tcaacctcgc caacaacaaa ctggtcggca caatcccatc ttggattggt gtgcttgacc   780
acctttgcta cttggatctc tcaaataatt cattggttgg tgagatacca aagaatttac   840
aaataaggct caggtgcctc aacatcgttg gtcgttcact gggtatggct tccactaaca   900
tgacattgca ggtgaagcat aaccaaatgg cactaagtgg gcaaccaaac acaataaccg   960
ggaccaataa ctatgtcaga tctggggtca caatgttgt ttctgggaac cacaacactg    1020
tcacatccgg gaacaacgat gttgtgtctg gaaaccacaa cactgtgtct ggaccaacc    1080 atgttgtaac tggtaacaac catgtcgtaa caaggaacca gaatactgta tctgggcgcc   1140

| | |
|---|---|
| atcataaagt atctggaggc cacaatactg tatctgggag ccacaatacc gtatctggaa | 1200 |
| gccacaacac agtatctggg agcaactgca tcgtacatgg gaacaacaaa gtcgtgacag | 1260 |
| gaggttaaca atctatagag aattgtttcc atattccc | 1298 |

<210> SEQ ID NO 56
<211> LENGTH: 1298
<212> TYPE: DNA
<213> ORGANISM: Lolium perenne

<400> SEQUENCE: 56

| | |
|---|---|
| cccgggctgg taaaaggttt acgaaatagt tgttattaaa ctatatatgt tcatgtaact | 60 |
| atatttcaat ataattattt gtattacagc agaaaatcat tatttctatt actttgtatt | 120 |
| attattttgt tttgagtgtt gtaaaattgg gaattacaac tatactattt tcgtatggga | 180 |
| acaatttgtt aattttttgtg tctctctttc tcttcatagc tagctgacag cgagaacaaa | 240 |
| aaccaagatc taattgtgga agtagactag tagtcgacca cccatgcatg cttacataag | 300 |
| aaaacacacg cactataaga ttggatgcac cacccaagca ctataaaaag gatgcaccac | 360 |
| ctaagcaatt tttgccaaca gcgcgcactt gtttgcattc aaaaagaaaa tcttacatag | 420 |
| ctgaaccaat ggagaaaagt tggttcttgc tccttttctt ggcgttcctc ctgccggcgg | 480 |
| cgagcgtggc ggtgtcatgc caccctgatg acctccttgc actgcgcggg ttcgccggta | 540 |
| atctcagcaa tggggcgtg ctcctccatg ccaagtggcc cgacaactct tgctgtagtt | 600 |
| gggaaggtgt gggatgcgtc ggcggaagcg gccgtgtcac tacgttgtgg ctccctggac | 660 |
| atggactcgc aggccacatc caacagcat ccttggctgg ccttgcacgg ctggagtcgc | 720 |
| tcaacctcgc cgacaacaaa ctggtcggca aatcccatc ttggattggt gtgcttggcc | 780 |
| acctttgcta cttggatctc tcaaataatt cattggttgg tgagatacca aagaatttac | 840 |
| aaataaggct caggtgcctc aacatcgttg gtcgttcact gggtatggct tccactaaca | 900 |
| cgacattgca ggtgaagcat aaccaaatag cactaagtgg gcaaccaaac acaataaccg | 960 |
| ggaccaataa ctatgtcaga tctggggtca acaatgttgt ttctgggaac cacaacactg | 1020 |
| tcacatccgg gaacaacaat gttgtgtctg gaaaccacaa cactgtgtct gggaccaacc | 1080 |
| atgttgtaac tggtaacaac catgtcgtaa caaggaacca gaatactgta tctgggagcc | 1140 |
| atcataaagt atctggaggc cacaatactg tatctgggag ccacaatacc gtatctggaa | 1200 |
| gccacaacac agtatctggg agcaaccaca tcgtacatgg gaacaacaaa gtcgtgacag | 1260 |
| gaggttaaca atctatagag aattgtttcc atattccc | 1298 |

<210> SEQ ID NO 57
<211> LENGTH: 568
<212> TYPE: DNA
<213> ORGANISM: Lolium perenne

<400> SEQUENCE: 57

| | |
|---|---|
| cttacatagc tgaaccaatg gagaaaagtt ggttcttgct ccttttcttg gcgttcctcc | 60 |
| tgccggcggc gagcgtggcg gtgtcatgcc accctgatga cctccttgca ctgcgcggt | 120 |
| tcgccggtaa tctcagcaat ggggcgtgc tcctccatgc caagtggccc gacaactctt | 180 |
| gctgtagttg ggaaggtgtg ggatgcgacg gcggaagcgg ccgtgtcact acgttgtggc | 240 |
| tccctgggca tggactcgca ggccacatcc aacagcatc cttggctggc cttgcacggc | 300 |
| tggagtcgct caacctcgcc aacaacaaac tggtcggcac aatcccatct tggattggtg | 360 |
| tgcttgacca ccctttgcta cttggatctct caaataattc attggttggt gagataccaa | 420 | agaatttaca aataaggctc aggtgcctca acatcgttgg tcgttcactg ggcatggctt    480 ccactaacat gacattgcag gtgaagcata accaaatagc actaagtggg caaccaaaca    540 caataaccgg gaccaataac tatgtcag                                       568

<210> SEQ ID NO 58
<211> LENGTH: 568
<212> TYPE: DNA
<213> ORGANISM: Lolium perenne

<400> SEQUENCE: 58
cttacatagc tgaaccaatg gagaaaagtt ggttcttgct ccttttcttg gcgttcctcc     60
tgccggcggc gagcgtggcg gtgtcatgcc accctgatga cctccttgca ctgcgcgggt   120
tcgccggtaa tctcagcaat gggggcgtgc tcctccatgc caagtggccc gacaactctt   180
gctgtagttg ggaaggtgtg ggatgcgacg gcggaagcgg ctgtgtcact acgttgtggc   240
tccctgggca tggactcgca ggccacatcc aacagcatc cttggctggc cttgcacggc     300
tggagtcgct caacctcgcc aacaacaaac tggtcggcac aatcccatct tggattggtg   360
tgcttgacca cctttgctac ttggatctct caaataattc attggttggt gagataccaa   420
agaatttaca aataaggctc aggtgcctca acatcgttgg tcgttcactg ggcatggctt   480
ccactaacat gacattgcag gtgaagcata accaaatagc actaagtggg caaccaaaca   540
caataaccgg gaccaataac tatgtcag                                       568

<210> SEQ ID NO 59
<211> LENGTH: 568
<212> TYPE: DNA
<213> ORGANISM: Lolium perenne

<400> SEQUENCE: 59
cttacatagc tgaaccaatg gagaaaagtt ggttcttgct ccttttcttg gcgttcctcc     60
tgccggcggc gagcgtggcg gtgtcatgcc accctgatga cctccttgca ctgcgcgggt   120
tcgccggtaa tctcagcaat gggggcgtgc tcctccatgc caagtggccc gacaactctt   180
gctgtagttg ggaaggtgtg ggatgcgacg gcggaagcgg ccgtgtcact acgttgtggc   240
tccctgggca tggactcgca ggccacatcc aacagcatc cttggctggc cttgcacggc     300
tggagtcgct caacctcgcc aacaacaaac tggtcggcac aatcccatct tggattggtg   360
tgcttgacca cctttgctac ttggatctct caaataattc attggttggt gagataccaa   420
agaatttaca aataaggctc aggtgcctca acatcgttgg tcgttcactg ggcatggctt   480
ccactaacat gacattgcag gtgaagcata accaaatagc actaagtggg caaccaaaca   540
caataaccgg gaccaataac tatgtcag                                       568

<210> SEQ ID NO 60
<211> LENGTH: 568
<212> TYPE: DNA
<213> ORGANISM: Lolium perenne

<400> SEQUENCE: 60
cttacatagc tgaaccaatg gagaaaagtt ggttcttgct ccttttcttg gcgttcctcc     60
tgccggcggc gagcgtggcg gtgtcatgcc accctgatga cctccttgca ctgcgcgggt   120
tcgccggtaa tctcagcaat gggggcgtgc tcctccatgc caagtggccc gacaactctt   180
gctgtagttg ggaaggtgtg ggatgcgacg gcggaagcgg ccgtgtcact acgttgtggc   240
tccctgggca tggactcgca ggccacatcc aacagcatc cttggctggc cttgcacggc     300

```
tggagtcgct caacctcgcc aacaacaaac tggtcggcac aatcccatct tggattggtg      360
tgcttgacca cctttgctac ttggatctct caaataattc attggttggt gagataccaa      420
ggaatttaca aataaggctc aggtgcctca acatcgttgg tcgttcactg ggcatggctt      480
ccactaacat gacattgcag gtgaagcata accaaatagc actaagtggg caaccaaaca      540
caataaccgg gaccaataac tatgtcag                                         568
```

<210> SEQ ID NO 61
<211> LENGTH: 554
<212> TYPE: DNA
<213> ORGANISM: Lolium perenne

<400> SEQUENCE: 61

```
cttacatagc tgaaccaatg gagaaaagtt ggttcttgct ccttttcttg gcgttcctcc       60
tgccggcggc gagcgtggcg gtgtcatgcc accctgatga cctccttgca ctgcgcgggt      120
tcgccggtaa tctcagcaat gggggcgtgc tcctccatgc caagtggccc gacaactctt      180
gctgtagttg ggaaggtgtg ggatgcgacg gcggaagcgg ccgtgtcact acgttgtggc      240
tccctgggca tggactcgca ggccacatcc aacagcatc cttggctggc cttgcacggc       300
tggagtcgct caacctcgcc aacaacaaac tggtcggcac aatcccatct tggattggtg      360
tgcttgacca cctttgctac ttggatctct caaataattc attggttggt gagataccaa      420
agaatttaca aataaggctc aggtgcctca acatcgttgg tcgttcactg ggcatggctt      480
ccactaacat gacattgcag gtgaagcata accaaatagc actaagtggg caaccaaaca      540
caataaccgg gacc                                                        554
```

<210> SEQ ID NO 62
<211> LENGTH: 568
<212> TYPE: DNA
<213> ORGANISM: Lolium perenne

<400> SEQUENCE: 62

```
cttacatagc tgaaccaatg gagaaaagtt ggttcttgct ccttttcttg gcgttcctcc       60
tgccggcggc gagcgtggcg gtgtcatgcc accctgatga cctccttgca ctgcgcgggt      120
tcgccggtaa tctcagcaat gggggcgtgc tcctccatgc caagtggccc gacaactctt      180
gctgtagttg ggaaggtgtg ggatgcgacg gcggaagcgg ccgtgtcact acgttgtggc      240
tccctgggca tggactcgca ggccacatcc aacagcatc cttggctggc cttgcacggc       300
tggagtcgct caacctcgcc aacaacaaac tggtcggcac aatcccatct tggattggtg      360
tgcttgacca cctttgctac ttggatctct caaataattc attggttggt gagataccaa      420
agaatttaca aataaggctc aggtgcctca acatcgttgg tcgttcactg ggcatggctt      480
ccactaacat gacattgcag gtgaagcata accaaatagc actaagtggg caaccaaaca      540
caataaccgg gaccaataac tatgtcag                                         568
```

<210> SEQ ID NO 63
<211> LENGTH: 569
<212> TYPE: DNA
<213> ORGANISM: Lolium perenne

<400> SEQUENCE: 63

```
cttacatagc tgaaccaatg gagaaaagtt ggttcttgct ccttttcttg gcgttcctcc       60
tgccggcggc gagcgtggcg gtgtcatgcc accctgatga cctccttgca ctgcgcgggt      120
tcgccggtaa tctcagcaat gggggcgtgc tcctccatgc caagtggccc gacaactctt      180
```

```
gctgtagttg ggaaggtgtg ggatgcgacg gcggaagcgg ccgtgtcact acgttgtggc    240
tccctgggca tggactcgca ggccacatcc aacagcatc cttggctggc cttgcacggc     300
tggagtcgct caacctcgcc aacaacaaac tggtcggcac aatcccatct tggattggtg    360
tgcttgacca cctttgctac ttggatctct caaataattc attggttggt gagataccaa    420
agaatttaca ataaggctc aggtgcctca acatcgttgg tcgttcactg ggcatggctt     480
ccactaacat gacattgcag gtgaagcata accaaatagc actaagtggg caaccaaaca    540
caataaccgg gaccaataac tatgtcaga                                      569
```

<210> SEQ ID NO 64
<211> LENGTH: 567
<212> TYPE: DNA
<213> ORGANISM: Lolium perenne

<400> SEQUENCE: 64

```
cttacatagc tgaaccaatg gagaaaagtt ggttcttgct ccttttcttg gcgttcctcc     60
tgccggcggc gagcgtggcg gtgtcatgcc accctgatga cctccttgca ctgcgcgggt    120
tcgccggtaa tctcagcaat gggggcgtgc tcctccatgc caagtggccc gacaactctt    180
gctgtagttg ggaaggtgtg ggatgcgacg gcggaagcgg ccgtgtcact acgttgtggc    240
tccctgggca tggactcgca ggccacatcc aacagcatc cttggctggc cttgcacggc     300
tggagtcgct caacctcgcc aacaacaaac tggtcggcac aatcccatct tggattggtg    360
tgcttgacca cctttgctac ttggatctct caaataattc attggttggt gagataccaa    420
agaatttaca ataaggctc aggtgcctca acatcgttgg tcgttcactg ggcatggctt     480
ccactaacat gacattgcag gtgaagcata accaaatagc actaagtggg caaccaaaca    540
caataaccgg gaccaataac tatgtca                                        567
```

<210> SEQ ID NO 65
<211> LENGTH: 566
<212> TYPE: DNA
<213> ORGANISM: Lolium perenne

<400> SEQUENCE: 65

```
cttacatagc tgaaccaatg gagaaaagtt ggttcttgct ccttttcttg gcgttcctcc     60
tgccggcggc gagcgtggcg gtgtcatgcc accctgatga cctccttgca ctgcgcgggt    120
tcgccggtaa tctcagcaat gggggcgtgc tcctccatgc caagtggccc gacaactctt    180
gctgtagttg ggaaggtgtg ggatgcgacg gcggaagcgg ccgtgtcact acgttgtggc    240
tccctgggca tggactcgca ggccacatcc aacagcatc cttggctggc cttgcacggc     300
tggagtcgct cagcctcgcc aacaacaaac tggtcggcac aatcccatct tggattggtg    360
tgcttgacca cctttgctac ttggatctct caaataattc attggttggt gagataccaa    420
agaatttaca ataaggctc aggtgcctca acatcgttgg tcgttcactg ggcatggctt     480
ccactaacat gacattgcag gtgaagcata accaaatagc actaagtggg caaccaaaca    540
caataaccgg gaccaataac tatgtc                                         566
```

<210> SEQ ID NO 66
<211> LENGTH: 568
<212> TYPE: DNA
<213> ORGANISM: Lolium perenne

<400> SEQUENCE: 66

```
cttacatagc tgaaccaatg gagaaaagtt ggttcttgct ccttttcttg gcgttcctcc      60
tgccggcggc gagcgtggcg gtgtcatgcc accctgatga cctccttgca ctgcgcgggt     120
tcgccggtaa tctcagcaat gggggcgtgc tcctccatgc caagtggccc gacaactctt     180
gctgtagttg ggaaggtgtg ggatgcgacg gcggaagcgg ccgtgtcact acgttgtggc     240
tccctgggca tggactcgca ggccacatcc aacagcatc cttggctggc cttgcacggc      300
tggagtcgct caacctcgcc aacaacaaac tggtcggcac aatcccatct tggattggtg     360
tgcttgacca ccttttgctac ttggatctct caaataattc attggttggt gagataccaa    420
agaatttaca aataaggctc aggtgcctca acatcgttgg tcgttcactg ggcatggctt     480
ccactaacat gacattgcag gtgaagcata accaaatagc actaagtggg caaccaaaca     540
caataaccgg gaccaataac tatgtcag                                        568
```

<210> SEQ ID NO 67
<211> LENGTH: 568
<212> TYPE: DNA
<213> ORGANISM: Lolium perenne

<400> SEQUENCE: 67

```
cttacatagc tgaaccaatg gagaaaagtt ggttcttgct ccttttcttg gcgttcctcc      60
tgccggcggc gagcgtggcg gtgtcatgcc accctgatga cctccttgca ctgcgcgggt     120
tcgccggtaa tctcagcaat gggggcgtgc tcctccatgc caagtggccc gacaactctt     180
gctgtagttg ggaaggtgtg ggatgcgacg gcggaagcgg ccgtgtcact acgttgtggc     240
tccctgggca tggactcgca ggccacatcc aacagcatc cttggctggc cttgcacggc      300
tggagtcgct caacctcgcc aacaacaaac tggtcggcac aatcccatct tggattggtg     360
tgcttgacca ccttttgctac ttggatctct caaataattc attggttggt gagataccaa    420
agaatttaca aataaggctc aggtgcctca acatcgttgg tcgttcactg ggcatggctt     480
ccactaacat gacattgcag gtgaagcata accaaatagc actaagtggg caaccaaaca     540
caataaccgg gaccaataac tatgtcag                                        568
```

<210> SEQ ID NO 68
<211> LENGTH: 568
<212> TYPE: DNA
<213> ORGANISM: Lolium perenne

<400> SEQUENCE: 68

```
cttacatagc tgaaccaatg gagaaaagtt ggttcttgct ccttttcttg gcgttcctcc      60
tgccggcggc gagcgtggcg gtgtcatgcc accctgatga cctccttgca ctgcgcgggt     120
tcgccggtaa tctcagcaat gggggcgtgc tcctccatgc caagtggccc gacaactctt     180
gctgtagttg ggaaggtgtg ggatgcgacg gcggaagcgg ccgtgtcact acgttgtggc     240
tccctgggca tggactcgca ggccacatcc aacagcatc cttggctggc cttgcacggc      300
tggagtcgct caacctcgcc aacaacaaac tggtcggcac aatcccatct tggattggtg     360
tgcttgacca ccttttgctac ttggatctct caaataattc attggttggt gagataccaa    420
agaatttaca aataaggctc aggtgcctca acatcgttgg tcgttcactg ggcatggctt     480
ccactaacat gacattgcag gtgaagcata accaaatagc actaagtggg caaccaaaca     540
caataaccgg gaccaataac tatgtcag                                        568
```

<210> SEQ ID NO 69
<211> LENGTH: 566
<212> TYPE: DNA
<213> ORGANISM: Lolium perenne

<400> SEQUENCE: 69

```
cttacatagc tgaaccaatg gagaaaagtt ggttcttgct ccttttcttg gcgttcctcc      60
tgccggcggc gagcgtggcg gtgtcatgcc accctgatga cctccttgca ctgcgcgggt     120
tcgccggtaa tctcagcaat ggggcgtgc tcctccatgc caagtggttc ggcaactctt     180
gctgtagttg ggaaggtgtg ggatgcgacg gcggaagcgg ccgtgtcact acgttgtggc     240
tccctgggca tggactcgca ggccacatcc aacagcatc cttggctggc cttgcacggc     300
tggagtcgct caacctcgcc aacaacaaac tggtcggcac aatcccatct tggattggtg     360
tgcttgacca cctttgctac ttggatctct caaataattc attggttggt gagataccaa     420
agaatttaca aataaggctc aggtgcctca acatcgttgg tcgttcactg ggcatggctt     480
ccactaacat gacattgcag gtgaagcata accaaatagc actaagtggg caaccaaaca     540
caataaccgg gaccaataac tatgtc                                          566
```

<210> SEQ ID NO 70
<211> LENGTH: 539
<212> TYPE: DNA
<213> ORGANISM: Lolium perenne

<400> SEQUENCE: 70

```
ggtgcctcaa catcgttggt cgttcactgg gcatggcttc cactaacatg acattgcagg      60
tgaagcataa ccaaatagca ctaagtgggc aaccaaacac aataaccggg accaataact     120
atgtcagatc tggggtcaac aatgttgttt ctgggaacca caacactgtc acatccggga     180
acaacaatgt tgtgtctgga aaccacaaca ccgtgtctgg gaccaaccat gttgtaactg     240
gtaacaacca tgtcgtaaca aggaaccaga atactgtatc tggagccat cataaagtat     300
ctggaggcca caatactgta tctgggagcc acaataccgt atctggaagc cacaacacag     360
tatctgggag caaccacatc gtacatggga acaacaaagt cgtgacagga ggttaacaat     420
ctatagagaa ttgtttccat attccctaac ggagttcacg tccttgtcca agctgggtgt     480
agctaaatat cacttggtgg ggccaatggc gttatgtaac ttcgtggata tagcatcac      539
```

<210> SEQ ID NO 71
<211> LENGTH: 539
<212> TYPE: DNA
<213> ORGANISM: Lolium perenne

<400> SEQUENCE: 71

```
ggtgcctcaa catcgttggt cgttcactgg gcatggcttc cactaacatg acattgcagg      60
tgaagcataa ccaaatagca ctaagtgggc aaccaaacac aataaccggg accaataact     120
atgtcagatc tggggtcaac aatgttgttt ctgggaacca caacactgtc acatccggga     180
acaacaatgt tgtgtctgga aaccacaaca ccgtgtctgg gaccaaccat gttgtaactg     240
gtaacaacca tgtcgtaaca aggaaccaga atactgtatc tggagccat cataaagtat     300
ctggaggcca caatactgta tctgggagcc acaataccgt atctggaagc cacaacacag     360
tatctgggag caaccacatc gtacatggga acaacaaagt cgtgacagga ggttaacaat     420
ctatagagaa ttgtttccat attccctaac ggagttcacg tccttgtcca agctgggtgt     480
agctaaatat cacttggtgg ggccaatggc gttatgtaac ttcgtggata tagcatcac      539
```

<210> SEQ ID NO 72
<211> LENGTH: 539
<212> TYPE: DNA
<213> ORGANISM: Lolium perenne

<400> SEQUENCE: 72

```
ggtgcctcaa catcgttggt cgttcactgg gcatggcttc cactaacatg acattgcagg      60
tgaagcataa ccaaatagca ctaagtgggc aaccaaacac aataaccggg accaataact     120
atgtcagatc tggggtcaac aatgttgttt ctgggaacca caacactgtc acatccggga     180
acaacaatgt tgtgtctgga aaccacaaca ccgtgtctgg gaccaaccat gttgtaactg     240
gtaacaacca tgtcgtaaca aggaaccaga atactgtatc tgggagccat cataaagtat     300
ctggaggcca caatactgta tctgggagcc acaataccgt atctggaagc cacaacacag     360
tatctgggag caaccacatc gtacatggga acaacaaagt cgtgacagga ggttaacaat     420
ctatagagaa ttgtttccat attccctaac ggagttcacg tccttgtcca agctgggtgt     480
agctaaatat cacttggtgg ggccaatggc gttatgtaac ttcgtggata tagcatcac     539
```

<210> SEQ ID NO 73
<211> LENGTH: 539
<212> TYPE: DNA
<213> ORGANISM: Lolium perenne

<400> SEQUENCE: 73

```
ggtgcctcaa catcgttggt cgttcactgg gcatggcttc cactaacatg acattgcagg      60
tgaagcataa ccaaatagca ctaagtgggc aaccaaacac aataaccggg accaataact     120
atgtcagatc tggggtcaac aatgttgttt ctgggaacca caacactgtc acatccggga     180
acaacaatgt tgtgtctgga aaccacaaca ccgtgtctgg gaccaaccat gttgtaactg     240
gtaacaacca tgtcgtaaca aggaaccaga atactgtatc tgggagccat cataaagtat     300
ctggaggcca caatactgta tctgggagcc acaataccgt atctggaagc cacaacacag     360
tatctgggag caaccacatc gtacatggga acaacaaagt cgtgacagga ggttaacaat     420
ctatagagaa ttgtttccat attccctaac ggagttcacg tccttgtcca agctgggtgt     480
agctaaatat cacttggtgg ggccaatggc gttatgtaac ttcgtggata tagcatcac     539
```

<210> SEQ ID NO 74
<211> LENGTH: 539
<212> TYPE: DNA
<213> ORGANISM: Lolium perenne

<400> SEQUENCE: 74

```
ggtgcctcaa catcgttggt cgttcactgg gcatggcttc cactaacatg acattgcagg      60
tgaagcataa ccaaatagca ctaagtgggc aaccaaacac aataaccggg accaataact     120
atgtcagatc tggggtcaac aatgttgttt ctgggaacca caacactgtc acatccggga     180
acaacaatgt tgtgtctgga aaccacaaca ccgtgtctgg gaccaaccat gttgtaactg     240
gtaacaacca tgtcgtaaca aggaaccaga atactgtatc tgggagccat cataaagtat     300
ctggaggcca caatactgta tctgggagcc acaataccgt atctggaagc cacaacacag     360
tatctgggag caaccacatc gtacatggga acaacaaagt cgtgacagga ggttaacaat     420
ctatagagaa ttgtttccat attccctaac ggagttcacg tccttgtcca agctgggtgt     480
agctaaatat cacttggtgg ggccaatggc gttatgtaac ttcgtggata tagcatcac     539
```

<210> SEQ ID NO 75
<211> LENGTH: 323
<212> TYPE: DNA
<213> ORGANISM: Lolium perenne

<400> SEQUENCE: 75

```
ggtgcctcaa catcgttggt cgttcactgg gcatggcttc cactaacatg acattgcagg    60
tgaagcataa ccaaatagca ctaagtgggc aaccaaacac aataaccggg accaataact   120
atgtcagatc tggggtcaac aatgttgttt ctgggaacca caacactgtc acatccggga   180
acaacaatgt tgtgtctgga aaccacaaca ccgtgtctgg gaccaaccat gttgtaactg   240
gtaacaacca tgtcgtaaca aggaaccaga atactgtatc tgggagccat cataaagtat   300
ctggaggcca caatactgta tct                                          323
```

<210> SEQ ID NO 76
<211> LENGTH: 539
<212> TYPE: DNA
<213> ORGANISM: Lolium perenne

<400> SEQUENCE: 76

```
ggtgcctcaa catcgttggt cgttcactgg gcatggcttc cactaacatg acattgcagg    60
tgaagcataa ccaaatagca ctaagtgggc aaccaaacac aataaccggg accaataact   120
atgtcagatc tggggtcaac aatgttgttt ctgggaacca caacactgtc acatccggga   180
acaacaatgt tgtgtctgga aaccacaaca ccgtgtctgg gaccaaccat gttgtaactg   240
gtaacaacca tgtcgtaaca aggaaccaga atactgtatc tgggagccat cataaagtat   300
ctggaggcca caatactgta tctgggagcc acaataccgt atctggaagc cacaacacag   360
tatctgggag caaccacatc gtacatggga acaacaaagt cgtgacagga ggttaacaat   420
ctatagagaa ttgttttccat attccctaac ggagttcacg tccttgtcca agctgggtgt   480
agctaaatat cacttggtgg ggccaatggc gttatgtaac ttcgtggata tagcatcac    539
```

<210> SEQ ID NO 77
<211> LENGTH: 539
<212> TYPE: DNA
<213> ORGANISM: Lolium perenne

<400> SEQUENCE: 77

```
ggtgcctcaa catcgttggt cgttcactgg gcatggcttc cactaacatg acattgcagg    60
tgaagcataa ccaaatagca ctaagtgggc aaccaaacac aataaccggg accaataact   120
atgtcagatc tggggtcaac aatgttgttt ctgggaacca caacactgtc acatccggga   180
acaacaatgt tgtgtctgga aaccacaaca ccgtgtctgg gaccaaccat gttgtaactg   240
gtaacaacca tgtcgtaaca aggaaccaga atactgtatc tgggagccat cataaagtat   300
ctggaggcca caatactgta tctgggagcc acaataccgt atctggaagc cacaacacag   360
tatctgggag caaccacatc gtacatggga acaacaaagt cgtgacagga ggttaacaat   420
ctatagagaa ttgttttccat attccctaac ggagttcacg tccttgtcca agctgggtgt   480
agctaaatat cacttggtgg ggccaatggc gttatgtaac ttcgtggata tagcatcac    539
```

<210> SEQ ID NO 78
<211> LENGTH: 482
<212> TYPE: DNA
<213> ORGANISM: Lolium perenne

<400> SEQUENCE: 78

```
ggtgcctcaa catcgttggt cgttcactgg gcatggcttc cactaacatg acattgcagg    60
tgaagcataa ccaaatagca ctaagtgggc aaccaaacac aataaccggg accaataact   120
atgtcagatc tggggtcaac aatgttgttt ctgggaacca caacactgtc acatccggga   180
acaacaatgt tgtgtctgga aaccacaaca ccgtgtctgg gaccaaccat gttgtaactg   240
gtaacaacca tgtcgtaaca aggaaccaga atactgtatc tgggagccat cataaagtat   300
ctggaggcca caatactgta tctgggagcc acaataccgt atctggaagc cacaacacag   360
tatctgggag caaccacatc gtacatggga acaacaaagt cgtgacagga ggttaacaat   420
ctatagagaa ttgtttccat attccctaac ggagttcacg tccttgtcca agctgggtgt   480
ag                                                                 482
```

<210> SEQ ID NO 79
<211> LENGTH: 539
<212> TYPE: DNA
<213> ORGANISM: Lolium perenne

<400> SEQUENCE: 79

```
ggtgcctcaa catcgttggt cgttcactgg gcatggcttc cactaacatg acattgcagg    60
tgaagcataa ccaaatagca ctaagtgggc aaccaaacac aataaccggg accaataact   120
atgtcagatc tggggtcaac aatgttgttt ctgggaacca caacactgtc acatccggga   180
acaacaatgt tgtgtctgga aaccacaaca ccgtgtctgg gaccaaccat gttgtaactg   240
gtaacaacca tgtcgtaaca aggaaccaga atactgtatc tgggagccat cataaagtat   300
ctggaggcca caatactgta tctgggagcc acaataccgt atctggaagc cacaacacag   360
tatctgggag caaccacatc gtacatggga acaacaaagt cgtgacagga ggttaacaat   420
ctatagagaa ttgtttccat attccctaac ggagttcacg tccttgtcca agctgggtgt   480
agctaaatat cacttggtgg ggccaatggc gttatgtaac ttcgtggata tagcatcac   539
```

<210> SEQ ID NO 80
<211> LENGTH: 539
<212> TYPE: DNA
<213> ORGANISM: Lolium perenne

<400> SEQUENCE: 80

```
ggtgcctcaa catcgttggt cgttcactag gcatggcttc cactaacatg acattgcagg    60
tgaagcataa ccaaatagca ctaagtgggc aaccaaacac aataaccggg accaataact   120
atgtcagatc tggggtcaac aatgttgttt ctgggaacca caacactgtc acatccggga   180
acaacaatgt tgtgtctgga aaccacaaca ccgtgtctgg gaccaaccat gttgtaactg   240
gtaacaacca tgtcgtaaca aggaaccaga atactgtatc tgggagccat cataaagtat   300
ctggaggcca caatactgta tctgggagcc acaataccgt atctggaagc cacaacacag   360
tatctgggag caaccacatc gtacatggga acaacaaagt cgtgacagga ggttaacaat   420
ctatagagaa ttgttaccat attccctaac ggagttcacg tccttgtcca agctgggtgt   480
agctaaatat cacttggtgg ggccaatggc gttatgtaac ttcgtggata tagcatcac   539
```

<210> SEQ ID NO 81
<211> LENGTH: 218
<212> TYPE: DNA
<213> ORGANISM: Lolium perenne

```
<400> SEQUENCE: 81
ggtgcctcaa catcgttggt cgttcactgg gcatggcttc cactaacatg acattgcagg      60
tgaagcataa ccaaatagca ctaagtgggc aaccaaacac aataaccggg accaataact     120
atgtcagatc tggggtcaac aatgttgttt ctgggaacca caacactgtc acatccggga     180
acaacaatgt tgtgtctgga aaccacaaca ccgtgtct                            218

<210> SEQ ID NO 82
<211> LENGTH: 539
<212> TYPE: DNA
<213> ORGANISM: Lolium perenne

<400> SEQUENCE: 82
ggtgcctcaa catcgttggt cgttcactgg gcatggcttc cactaacatg acattgcagg      60
tgaagcataa ccaaatagca ctaagtgggc aaccaaacac aataaccggg accaataact     120
atgtcagatc tggggtcaac aatgttgttt ctgggaacca caacactgtc acatccggga     180
acaacaatgt tgtgtctgga aaccacaaca ccgtgtctgg gaccaaccat gttgtaactg     240
gtaacaacca tgtcgtaaca aggaaccaga atactgtatc tgggagccat cataaagtat     300
ctggaggcca caatactgta tctgggagcc acaataccgt atctggaagc cacaacacag     360
tatctgggag caaccacatc gtacatggga acaacaaagt cgtgacagga ggttaacaat     420
ctatagagaa ttgtttccat attccctaac ggagttcacg tccttgtcca agctgggtgt     480
agctaaatat cacttggtgg ggccaatggc gttatgtaac ttcgtggata tagcatcac     539

<210> SEQ ID NO 83
<211> LENGTH: 539
<212> TYPE: DNA
<213> ORGANISM: Lolium perenne

<400> SEQUENCE: 83
ggtgcctcaa catcgttggt cgttcactgg gcatggcttc cactaacatg acattgcagg      60
tgaagcataa ccaaatagca ctaagtgggc aaccaaacac aataaccggg accaataact     120
atgtcagatc tggggtcaac aatgttgttt ctgggaacca caacactgtc acatccggga     180
acaacaatgt tgtgtctgga aaccacaaca ccgtgtctgg gaccaaccat gttgtaactg     240
gtaacaacca tgtcgtaaca aggaaccaga atactgtatc tgggagccat cataaagtat     300
ctggaggcca caatactgta tctgggagcc acaataccgt atctggaagc cacaacacag     360
tatctgggag caaccacatc gtacatggga acaacaaagt cgtgacagga ggttaacaat     420
ctatagagaa ttgtttccat attccctaac ggagttcacg tccttgtcca agctgggtgt     480
agctaaatat cacttggtgg ggccaatggc gttatgtaac ttcgtggata tagcatcac     539

<210> SEQ ID NO 84
<211> LENGTH: 539
<212> TYPE: DNA
<213> ORGANISM: Lolium perenne

<400> SEQUENCE: 84
ggtgcctcaa catcgttggt cgttcactgg gcatggcttc cactaacatg acattgcagg      60
tgaagcataa ccaaatagca ctaagtgggc aaccaaacac aataaccggg accaataact     120
atgtcagatc tggggtcaac aatgttgttt ctgggaacca caacactgtc acatccggga     180
acaacaatgt tgtgtctgga aaccacaaca ccgtgtctgg gaccaaccat gttgtaactg     240
gtaacaacca tgtcgtaaca aggaaccaga atactgtatc tgggagccat cataaagtat     300
```

```
ctggaggcca caatactgta tctgggagcc acaataccgt atctggaagc cacaacacag    360
tatctgggag caaccacatc gtacatggga acaacaaagt cgtgacagga ggttaacaat    420
ctatagagaa ttgtttccat attccctaac ggagttcacg tccttgtcca agctgggtgt    480
agctaaatat cacttggtgg ggccaatggc gttatgtaac ttcgtggata tagcatcac     539
```

<210> SEQ ID NO 85
<211> LENGTH: 539
<212> TYPE: DNA
<213> ORGANISM: Lolium perenne

<400> SEQUENCE: 85

```
ggtgcctcaa catcgttggt cgttcactgg gcatggcttc cactaacatg acattgcagg     60
tgaagcataa ccaaatagca ctaagtgggc aaccaaacac aataaccggg accaataact    120
atgtcagatc tggggtcaac aatgttgttt ctgggaacca caacactgtc acatccggga    180
acaacaatgt tgtgtctgga aaccacaaca ccgtgtctgg gaccaaccat gttgtaactg    240
gtaacaacca tgtcgtaaca aggaaccaga atactgtatc tgggagccat cataaagtat    300
ctggaggcca caatactgta tctgggagcc acaataccgt atctggaagc cacaacacag    360
tatctgggag caaccacatc gtacatggga acaacaaagt cgtgacagga ggttaacaat    420
ctatagagaa ttgtttccat attccctaac ggagttcacg tccttgtcca agctgggtgt    480
agctaaatat cacttggtgg ggccaatggc gttatgtaac ttcgtggata tagcatcac     539
```

<210> SEQ ID NO 86
<211> LENGTH: 524
<212> TYPE: DNA
<213> ORGANISM: Lolium perenne

<400> SEQUENCE: 86

```
ggtgcctcaa catcgttggt cgttcactgg gcatggcttc cactaacatg acattgcagg     60
tgaagcataa ccaaatagca ctaagtgggc aaccaaacac aataaccggg accaataact    120
atgtcagatc tggggtcaac aatgttgttt ctgggaacca caacactgtc acatccggga    180
acaacaatgt tgtgtctgga aaccacaaca ccgtgtctgg gaccaaccat gttgtaactg    240
gtaacaacca tgtcgtaaca aggaaccaga atactgtatc tgggagccat cataaagtat    300
ctggaggcca caatactgta tctgggagcc acaataccgt atctggaagc cacaacacag    360
tatctgggag caaccacatc gtacatggga acaacaaagt cgtgacagga ggttaacaat    420
ctatagagaa ttgtttccat attccctaac ggagttcacg tccttgtcca agctgggtgt    480
agctaaatat cacttggtgg ggccaatggc gttatgtaac ttcg                    524
```

<210> SEQ ID NO 87
<211> LENGTH: 539
<212> TYPE: DNA
<213> ORGANISM: Lolium perenne

<400> SEQUENCE: 87

```
ggtgcctcaa catcgttggt cgttcactgg gcatggcttc cactaacatg acattgcagg     60
tgaagcataa ccaaatagca ctaagtgggc aaccaaacac aataaccggg accaataact    120
atgtcagatc tggggtcaac aatgttgttt ctgggaacca caacactgtc acatccggga    180
acaacaatgt tgtgtctgga aaccacaaca ccgtgtctgg gaccaaccat gttgtaactg    240
gtaacaacca tgtcgtaaca aggaaccaga atactgtatc tgggagccat cataaagtat    300
ctggaggcca caatactgta tctgggagcc acaataccgt atctggaagc cacaacacag    360
```
tatctgggag caaccacatc gtacatggga acaacaaagt cgtgacagga ggttaacaat    420
ctatagagaa ttgtttccat attccctaac ggagttcacg tccttgtcca agctgggtgt    480
agctaaatat cacttggtgg ggccaatggc gttatgtaac ttcgtggata tagcatcac    539

<210> SEQ ID NO 88
<211> LENGTH: 539
<212> TYPE: DNA
<213> ORGANISM: Lolium perenne

<400> SEQUENCE: 88
ggtgcctcaa catcgttggt cgttcactgg gcatggcttc cactaacatg acattgcagg    60
tgaagcataa ccaaatagca ctaagtgggc aaccaaacac aataaccggg accaataact    120
atgtcagatc tggggtcaac aatgttgttt ctgggaacca caacactgtc acatccggga    180
acaacaatgt tgtgtctgga aaccacaaca ccgtgtctgg gaccaaccat gttgtaactg    240
gtaacaacca tgtcgtaaca aggaaccaga atactgtatc tgggagccat cataaagtat    300
ctggaggcca caatactgta tctgggagcc acaataccgt atctggaagc cacaacacag    360
tatctgggag caaccacatc gtacatggga acaacaaagt cgtgacagga ggttaacaat    420
ctatagagaa ttgtttccat attccctaac ggagttcacg tccttgtcca agctgggtgt    480
agctaaatat cacttggtgg ggccaatggc gttatgtaac ttcgtggata tagcatcac    539

<210> SEQ ID NO 89
<211> LENGTH: 539
<212> TYPE: DNA
<213> ORGANISM: Lolium perenne

<400> SEQUENCE: 89
ggtgcctcaa catcgttggt cgttcactgg gcatggcttc cactaacatg acattgcagg    60
tgaagcataa ccaaatagca ctaagtgggc aaccaaacac aataaccggg accaataact    120
atgtcagatc tggggtcaac aatgttgttt ctgggaacca caacactgtc acatccggga    180
acaacaatgt tgtgtctgga aaccacaaca ccgtgtctgg gaccaaccat gttgtaactg    240
gtaacaacca tgtcgtaaca aggaaccaga atactgtatc tgggagccat cataaagtat    300
ctggaggcca caatactgta tctgggagcc acaataccgt atctggaagc cacaacacag    360
tatctgggag caaccacatc gtacatggga acaacaaagt cgtgacagga ggttaacaat    420
ctatagagaa ttgtttccat attccctaac ggagttcacg tccttgtcca agctgggtgt    480
agctaaatat cacttggtgg ggccaatggc gttatgtaac ttcgtggata tagcatcac    539

<210> SEQ ID NO 90
<211> LENGTH: 539
<212> TYPE: DNA
<213> ORGANISM: Lolium perenne

<400> SEQUENCE: 90
ggtgcctcaa catcgttggt cgttcactgg gcatggcttc cactaacatg acattgcagg    60
tgaagcataa ccaaatagca ctaagtgggc aaccaaacac aataaccggg accaataact    120
atgtcagatc tggggtcaac aatgttgttt ctgggaacca caacactgtc acatccggga    180
acaacaatgt tgtgtctgga aaccacaaca ccgtgtctgg gaccaaccat gttgtaactg    240
gtaacaacca tgtcgtaaca aggaaccaga atactgtatc tgggagccat cataaagtat    300
ctggaggcca caatactgta tctgggagcc acaataccgt atctggaagc cacaacacag    360
tatctgggag caaccacatc gtacatggga acaacaaagt cgtgacagga ggttaacaat    420

```
ctatagagaa ttgtttccat attccctaac ggagttcacg tccttgtcca agctgggtgt    480
agctaaatat cacttggtgg ggccaatggc gttatgtaac ttcgtggata tagcatcac     539

<210> SEQ ID NO 91
<211> LENGTH: 539
<212> TYPE: DNA
<213> ORGANISM: Lolium perenne

<400> SEQUENCE: 91
ggtgcctcaa catcgttggt cgttcactgg gcatggcttc cactaacatg acattgcagg     60
tgaagcataa ccaaatagca ctaagtgggc aaccaaacac aataaccggg accaataact    120
atgtcagatc tggggtcaac aatgttgttt ctgggaacca caacactgtc acatccggga    180
acaacaatgt tgtgtctgga aaccacaaca ccgtgtctgg gaccaaccat gttgtaactg    240
gtaacaacca tgtcgtaaca aggaaccaga atactgtatc tgggagccat cataaagtat    300
ctggaggcca caatactgta tctgggagcc acaataccgt atctggaagc cacaacacag    360
tatctgggag caaccacatc gtacatggga acaacaaagt cgtgacagga ggttaacaat    420
ctatagagaa ttgtttccat attccctaac ggagttcacg tccttgtcca agctgggtgt    480
agctaaatat cacttggtgg ggccaatggc gttatgtaac ttcgtggata tagcatcac     539

<210> SEQ ID NO 92
<211> LENGTH: 539
<212> TYPE: DNA
<213> ORGANISM: Lolium perenne

<400> SEQUENCE: 92
ggtgcctcaa catcgttggt cgttcactgg gcatggcttc cactaacatg acattgcagg     60
tgaagcataa ccaaatagca ctaagtgggc aaccaaacac aataaccggg accaataact    120
atgtcagatc tggggtcaac aatgttgttt ctgggaacca caacactgtc acatccggga    180
acaacaatgt tgtgtctgga aaccacaaca ccgtgtctgg gaccaaccat gttgtaactg    240
gtaacaacca tgtcgtaaca aggaaccaga atactgtatc tgggagccat cataaagtat    300
ctggaggcca caatactgta tctgggagcc acaataccgt atctggaagc cacaacacag    360
tatctgggag caaccacatc gtacatggga acaacaaagt cgtgacagga ggttaacaat    420
ctatagagaa ttgtttccat attccctaac ggagttcacg tccttgtcca agctgggtgt    480
agctaaatat cacttggtgg ggccaatggc gttatgtaac ttcgtggata tagcatcac     539

<210> SEQ ID NO 93
<211> LENGTH: 539
<212> TYPE: DNA
<213> ORGANISM: Lolium perenne

<400> SEQUENCE: 93
ggtgcctcaa catcgttggt cgttcactgg gcatggctcc cactaacatg acattgcagg     60
tgaagcataa ccaaatagca ctaagtgggc aaccaaacac aataaccggg accaataact    120
atgtcagatc tggggtcaac aatgttgttt ctgggaacca caacactgtc acatccggga    180
acaacaatgt tgtgtctgga aaccacaaca ccgtgtctgg gaccaaccat gttgtaactg    240
gtaacaacca tgtcgtaaca aggaaccaga atactgtatc tgggagccat cataaagtat    300
ctggaggcca caatactgta tctgggagcc acaataccgt atctggaagc cacaacacag    360
tatctgggag caaccacatc gtacatggga acaacaaagt cgtgacagga ggttaacaat    420
```

```
ctatagagaa ttgtttccat attccctaac ggagttcacg tccttgtcca agctgggtgt        480
agctaaatat cacttggtgg ggccaatggc gttatgtaac ttcgtggata tagcatcac         539
```

<210> SEQ ID NO 94
<211> LENGTH: 537
<212> TYPE: DNA
<213> ORGANISM: Lolium perenne

<400> SEQUENCE: 94

```
tgcctcaaca tcgttggtcg ttcactgggc atggcttcca ctaacatgac attgcaggtg         60
aagcataacc aaatagcact aagtgggcaa ccaaacacaa taaccgggac caataactat        120
gtcagatctg gggtcaacaa tgttgtttct gggaaccaca acactgtcac atccgggaac        180
aacaatgttg tgtctggaaa ccacaacacc gtgtctggga ccaaccatgt tgtaactggt        240
aacaaccatg tcgtaacaag gaaccagaat actgtatctg ggagccatca taaagtatct        300
ggaggccaca atactgtatc tgggagccac aataccgtat ctggaagcca acacagta         360 tctgggagca accacatcgt acatgggaac aacaaagtcg tgacaggagg ttaacaatct        420
atagagaatt gtttccatat tccctaacgg agttcacgtc cttgtccaag ctgggtgtag        480
ctaaatatca cttggtgggg ccaatggcgt tatgtaactt cgtggatata gcatcac           537
```

<210> SEQ ID NO 95
<211> LENGTH: 536
<212> TYPE: DNA
<213> ORGANISM: Lolium perenne

<400> SEQUENCE: 95

```
gcctcaacat cgttggtcgt tcactgggca tggcttccac taacatgaca ttgcaggtga         60
agcataacca aatagcacta agtgggcaac caaacacaat aaccgggacc aataactatg        120
tcagatctgg ggtcaacaat gttgtttctg gaaccacaa cactgtcaca tccgggaaca         180
acaatgttgt gtctggaaac cacaacaccg tgtctgggac caaccatgtt gtaactggta        240
acaaccatgt cgtaacaagg aaccagaata ctgtatctgg agccatcat aaagtatctg         300 gaggccacaa tactgtatct gggagccaca ataccgtatc tggaagccac aacagtat         360 ctgggagcaa ccacatcgta catgggaaca acaaagtcgt gacaggaggt taacaatcta        420
tagagaattg tttccatatt ccctaacgga gttcacgtcc ttgtccaagc tgggtgtagc        480
taaatatcac ttggtggggc caatggcgtt atgtaacttc gtggatatag catcac            536
```

<210> SEQ ID NO 96
<211> LENGTH: 532
<212> TYPE: DNA
<213> ORGANISM: Lolium perenne

<400> SEQUENCE: 96

```
caacatcgtt ggtcgttcac tgggcatggc ttcactaac atgacattgc aggtgaagca         60
taaccaaata gcactaagtg ggcaaccaaa cacaataacc gggaccaata actatgtcag        120
atctggggtc aacaatgttg tttctgggaa ccacaacact gtcacatccg ggaacaacaa        180
tgttgtgtct ggaaaccaca acccgtgtc tgggaccaac catgttgtaa ctggtaacaa        240
ccatgtcgta acaaggaacc agaatactgt atctgggagc catcataaag tatctggagg        300
ccacaatact gtatctggga gccacaatac cgtatctgga agccacaaca cagtatctgg        360 agcaaccac atcgtacatg ggaacaacaa agtcgtgaca ggaggttaac aatctataga        420
```

```
gaattgtttc catattccct aacggagttc acgtccttgt ccaagctggg tgtagctaaa    480
tatcacttgg tggggccaat ggcgttatgt aacttcgtgg atatagcatc ac            532
```

<210> SEQ ID NO 97
<211> LENGTH: 532
<212> TYPE: DNA
<213> ORGANISM: Lolium perenne

<400> SEQUENCE: 97

```
caacatcgtt ggtcgttcac tgggcatggc ttccactaac atgacattgc aggtgaagca     60
taaccaaata gcactaagtg ggcaaccaaa cacaataacc gggaccaata actatgtcag    120
atctggggtc aacaatgttg tttctgggaa ccacaacact gtcacatccg ggaacaacaa    180
tgttgtgtct ggaaaccaca acaccgtgtc tgggaccaac catgttgtaa ctggtaacaa    240
ccatgtcgta acaaggaacc agaatactgt atctgggagc catcataaag tatctggagg    300
ccacaatact gtatctggga ccacaatac cgtatctgga agccacaaca cagtatctgg     360
gagcaaccac atcgtacatg ggaacaacaa agtcgtgaca ggaggttaac aatctataga    420
gaattgtttc catattccct aacggagttc acgtccttgt ccaagctggg tgtagctaaa    480
tatcacttgg tggggccaat ggcgttatgt aacttcgtgg atatagcatc ac            532
```

<210> SEQ ID NO 98
<211> LENGTH: 532
<212> TYPE: DNA
<213> ORGANISM: Lolium perenne

<400> SEQUENCE: 98

```
caacatcgtt ggtcgttcac tgggcatggc ttccactaac atgacattgc aggtgaagca     60
taaccaaata gcactaagtg ggcaaccaaa cacaataacc gggaccaata actatgtcag    120
atctggggtc aacaatgttg tttctgggaa ccacaacact gtcacatccg ggaacaacaa    180
tgttgtgtct ggaaaccaca acaccgtgtc tgggaccaac catgttgtaa ctggtaacaa    240
ccatgtcgta acaaggaacc agaatactgt atctgggagc catcataaag tatctggagg    300
ccacaatact gtatctggga ccacaatac cgtatctgga agccacaaca cagtatctgg     360
gagcaaccac atcgtacatg ggaacaacaa agtcgtgaca ggaggttaac aatctataga    420
gaattgtttc catattccct aacggagttc acgtccttgt ccaagctggg tgtagctaaa    480
tatcacttgg tggggccaat ggcgttatgt aacttcgtgg atatagcatc ac            532
```

<210> SEQ ID NO 99
<211> LENGTH: 526
<212> TYPE: DNA
<213> ORGANISM: Lolium perenne

<400> SEQUENCE: 99

```
cgttggtcgt tcactgggca tggcttccac taacatgaca ttgcaggtga agcataacca     60
aatagcacta agtgggcaac caaacacaat aaccgggacc aataactatg tcagatctgg    120
ggtcaacaat gttgtttctg gaaccacaa cactgtcaca tccgggaaca acaatgttgt     180
gtctggaaac cacaacaccg tgtctgggac caaccatgtt gtaactggta caaccatgt     240 cgtaacaagg aaccagaata ctgtatctgg gagccatcat aaagtatctg gaggccacaa    300
tactgtatct gggagccaca ataccgtatc tggaagccac aacacagtat ctgggagcaa    360
ccacatcgta catgggaaca caaagtcgt gacaggaggt taacaatcta tagagaattg     420
```

| | |
|---|---|
| tttccatatt ccctaacgga gttcacgtcc ttgtccaagc tgggtgtagc taaatatcac | 480 |
| ttggtggggc caatggcgtt atgtaacttc gtggatatag catcac | 526 |

<210> SEQ ID NO 100
<211> LENGTH: 399
<212> TYPE: DNA
<213> ORGANISM: Lolium perenne

<400> SEQUENCE: 100

| | |
|---|---|
| aatgttgttt ctgggaacca caacactgtc acatccggga caacaatgt tgtgtctgga | 60 |
| aaccacaaca ccgtgtctgg gaccaaccat gttgtaactg gtaacaacca tgtcgtaaca | 120 |
| aggaaccaga atactgtatc tgggagccat cataaagtat ctggaggcca caatactgta | 180 |
| tctgggagcc acaataccgt atctggaagc cacaacacag tatctgggag caaccacatc | 240 |
| gtacatggga caacaaagt cgtgacagga ggttaacaat ctatagagaa ttgtttccat | 300 |
| attccctaac ggagttcacg tccttgtcca agctgggtgt agctaaatat cacttggtgg | 360 |
| ggccaatggc gttatgtaac ttcgtggata tagcatcac | 399 |

<210> SEQ ID NO 101
<211> LENGTH: 1391
<212> TYPE: DNA
<213> ORGANISM: Lolium perenne

<400> SEQUENCE: 101

| | |
|---|---|
| cccgggctgg taaaaggttt acgaaatagt tgttattaaa ctatatatgt tcatgtaact | 60 |
| atatttcaat ataattattt gtattacagc agaaaatcat tatttctatt actttgtatt | 120 |
| attattttgt tttgagtgtt gtaaaattgg gaattacaac tatactattt tcgtatggga | 180 |
| acaatttgtt aattttgtg tctctctttc tcttcatagc tagctgacag cgagaacaaa | 240 |
| aaccaagatc taattgtgga agtagactag tagtcgacca cccatgcatg cttacataag | 300 |
| aaaacacacg cactataaga ttggatgcac cacccaagca ctataaaaag gatgcaccac | 360 |
| ctaagcaatt tttgccaaca gcgcgcactt gtttgcattc aaaagaaaa tcttacatag | 420 |
| ctgaaccaat ggagaaaagt tggttcttgc tcctttcctt ggcgttcctc ctgccggcgg | 480 |
| cgagcgtggc ggtgtcatgc caccctgatg acctccttgc actgcgcggg ttcgccggta | 540 |
| atctcagcaa tggggcgtg ctcctccatg ccaagtggcc cgacaactct tgctgtagtt | 600 |
| gggaaggtgt gggatgcgac ggcggaagcg gccgtgtcac tacgttgtgg ctccctgggc | 660 |
| atggactcgc aggccacatc ccaacagcat ccttggctgg ccttgcacgg ctggagtcgc | 720 |
| tcaacctcgc caacaacaaa ctggtcggca caatcccatc ttggattggt gtgcttgacc | 780 |
| acctttgcta cttggatctc tcaaataatt cattggttgg tgagatacca aagaatttac | 840 |
| aaataaggct caggtgcctc aacatcgttg gtcgttcact gggcatggct tccactaaca | 900 |
| tgacattgca ggtgaagcat aaccaaatag cactaagtgg gcaaccaaac acaataaccg | 960 |
| ggaccaataa ctatgtcaga tctggggtca acaatgttgt ttctgggaac cacaacactg | 1020 |
| tcacatccgg gaacaacaat gttgtgtctg gaaaccacaa caccgtgtct gggaccaacc | 1080 |
| atgttgtaac tggtaacaac catgtcgtaa caaggaacca gaatactgta tctgggagcc | 1140 |
| atcataaagt atctggaggc cacaatactg tatctgggag ccacaatacc gtatctggaa | 1200 |
| gccacaacac agtatctggg agcaaccaca tcgtacatgg gaacaacaaa gtcgtgacag | 1260 |
| gaggttaaca atctatagag aattgtttcc atattcccta acggagttca cgtccttgtc | 1320 |

```
caagctgggt gtagctaaat atcacttggt ggggccaatg gcgttatgta acttcgtgga      1380
tatagcatca c                                                          1391
```

<210> SEQ ID NO 102
<211> LENGTH: 279
<212> TYPE: PRT
<213> ORGANISM: Lolium perenne

<400> SEQUENCE: 102

```
Met Glu Lys Ser Trp Phe Leu Leu Phe Leu Ala Phe Leu Leu Pro
1               5                   10                  15

Ala Ala Ser Val Ala Val Ser Cys His Pro Asp Asp Leu Leu Ala Leu
            20                  25                  30

Arg Gly Phe Ala Gly Asn Leu Ser Asn Gly Gly Val Leu Leu His Ala
        35                  40                  45

Lys Trp Pro Asp Asn Ser Cys Cys Ser Trp Glu Gly Val Gly Cys Asp
    50                  55                  60

Gly Gly Ser Gly Arg Val Thr Thr Leu Trp Leu Pro Gly His Gly Leu
65              70                  75                  80

Ala Gly His Ile Pro Thr Ala Ser Leu Ala Gly Leu Ala Arg Leu Glu
            85                  90                  95

Ser Leu Asn Leu Ala Asn Asn Lys Leu Val Gly Thr Ile Pro Ser Trp
            100                 105                 110

Ile Gly Val Leu Asp His Leu Cys Tyr Leu Asp Leu Ser Asn Asn Ser
        115                 120                 125

Leu Val Gly Glu Ile Pro Lys Asn Leu Gln Ile Arg Leu Arg Cys Leu
    130                 135                 140

Asn Ile Val Gly Arg Ser Leu Gly Met Ala Ser Thr Asn Met Thr Leu
145                 150                 155                 160

Gln Val Lys His Asn Gln Ile Ala Leu Ser Gly Gln Pro Asn Thr Ile
                165                 170                 175

Thr Gly Thr Asn Asn Tyr Val Arg Ser Gly Val Asn Asn Val Val Ser
            180                 185                 190

Gly Asn His Asn Thr Val Thr Ser Gly Asn Asn Val Val Ser Gly
        195                 200                 205

Asn His Asn Thr Val Ser Gly Thr Asn His Val Val Thr Gly Asn Asn
    210                 215                 220

His Val Val Thr Arg Asn Gln Asn Thr Val Ser Gly Ser His His Lys
225                 230                 235                 240

Val Ser Gly Gly His Asn Thr Val Ser Gly Ser His Asn Thr Val Ser
                245                 250                 255

Gly Ser His Asn Thr Val Ser Gly Ser Asn His Ile Val His Gly Asn
            260                 265                 270

Asn Lys Val Val Thr Gly Gly
        275
```

<210> SEQ ID NO 103
<211> LENGTH: 568
<212> TYPE: DNA
<213> ORGANISM: Lolium perenne

<400> SEQUENCE: 103

```
cttacatagc tgaaccaatg gagaaaagtt ggttcttgct ccttttcttg acgttcctcc      60
tgccggcggc gagcgtggcg gtgtcgtgcc accctgatga cctccttgca ctgcgcgggt     120
```

| | |
|---|---|
| tcgccggtaa tctcagcaat gggggcgtcc tcctccatgc caagtggttc ggcaactctt | 180 |
| gctgtagttg ggaaggtgtg ggatgcgacg gcggaagcgg ccgtgtcact actttatggc | 240 |
| tccgtgggca tggactcgca ggccacatcc aacagcatc cttggctggc cttgcacggc | 300 |
| tggagtcgct caacctcgcc aacaacaaac tggtcggcac aatcccatca tggatgggtg | 360 |
| tgcttgacca ccttttgctac ttggatctct caaataattc attggttggt gagatacccca | 420 |
| agaatttaca gagaaggctc agtcgcccca acattattgg tcattcactg ggtacggctt | 480 |
| ccactaacat gccattgcag gtgaagcata accaaatagc actgagtggg caaccaaaca | 540 |
| caataaccgg gaccaataac tatgtcag | 568 |

<210> SEQ ID NO 104
<211> LENGTH: 568
<212> TYPE: DNA
<213> ORGANISM: Lolium perenne

<400> SEQUENCE: 104

| | |
|---|---|
| cttacatagc tgaaccaatg gagaaaagtt ggttcttgct ccttttcttg acgttcctcc | 60 |
| tgccggcggc gagcgtggcg gtgtcgtgcc accctgatga cctccttgca ctgcgcgggt | 120 |
| tcgccggtaa tctcagcaat gggggcgtcc tcctccatgc caagtggttc ggcaactctt | 180 |
| gctgtagttg ggaaggtgtg ggatgcgacg gcggaagcgg ccgtgtcact actttatggc | 240 |
| tccgtgggca tggactcgca ggccacatcc aacagcatc cttggctggc cttgcacggc | 300 |
| tggagtcgct caacctcgcc aacaacaaac tggtcggcac aatcccatca tggatgggtg | 360 |
| tgcttgacca ccttttgctac ttggatctct caaataattc attggttggt gagatacccca | 420 |
| agaatttaca gagaaggctc agttgcccca gcattattgg tcattcactg ggtacggctt | 480 |
| ccactaacat gccattgcag gtgaagcata accaaatagc actgagtggg caaccaaaca | 540 |
| caataaccgg gaccaataac tatgtcag | 568 |

<210> SEQ ID NO 105
<211> LENGTH: 568
<212> TYPE: DNA
<213> ORGANISM: Lolium perenne

<400> SEQUENCE: 105

| | |
|---|---|
| cttacatagc tgaaccaatg gagaaaagtt ggttcttgct ccttttcttg acgttcctcc | 60 |
| tgccggcggc gagcgtggcg gtgtcgtgcc accctgatga cctccttgca ctgcgcgggt | 120 |
| tcgccggtaa tctcagcaat gggggcgtcc tcctccatgc caagtggttc ggcaactctt | 180 |
| gctgtagttg ggaaggtgtg ggatgcgacg gcggaagcgg ccgtgtcact actttatggc | 240 |
| tccgtgggca tggactcgca ggccacatcc aacagcatc cttggctggc cttgcacggc | 300 |
| tggagtcgct caacctcgcc aacaacaaac tggtcggcac aatcccatca tggatgggtg | 360 |
| tgcttgacca ccttttgctac ttggatctct caaataattc attggttggt gagatacccca | 420 |
| agaatttaca gagaaggctc agttgcccca acattattgg tcattcactg ggtacggctt | 480 |
| ccactaacat gccattgcag gtgaagcata accaaatagc actgagtggg caaccaaaca | 540 |
| caataaccgg gaccaataac tatgtcag | 568 |

<210> SEQ ID NO 106
<211> LENGTH: 568
<212> TYPE: DNA
<213> ORGANISM: Lolium perenne

<400> SEQUENCE: 106

```
cttacatagc tgaaccaatg gaggaaagtt ggttcttgct cctttcttg gcgttcctcc    60
tgccggcggc gagcgtggcg gtggcgtgcc accctgatga cctccttgca ctgcgcgggt   120
tcgccggtaa tctcagcaat gggggcgtcc tcctccatgc caagtggtcc ggcaactctt   180
gctgtagttg ggaaggtgtg ggatgcgacg gcggaagcgg ccgtgtcact acgttgtggc   240
tccctgggca tggactcgca ggccacatcc aacagcatc cttggctggc cttgcacggc    300
tggagtcgct caacctcgcc aacaacaaac tggtcggcac aatcccatct ggattggtg    360
tgcttgacca cctttgctac ttggatctct caaataattc attggttggt gagatacccca   420
agaatttaca gagaaggctc agttgcccca acattgttgg tcattcactg ggtacggctt   480
ccactaacat gccattgcag gtgaagcata accaaatagc actgagtggg caaccaaaca   540
caataaccgg gaccaataac tatgtcag                                       568
```

<210> SEQ ID NO 107
<211> LENGTH: 568
<212> TYPE: DNA
<213> ORGANISM: Lolium perenne

<400> SEQUENCE: 107

```
cttacatagc tgaaccaatg gagaaaagtt ggttcttgct cctttcttg gcgttcctcc    60
tgccggcggc gagcgtggcg gtgtcgtgcc accctgatga cctccttgca ctgcgcgggt   120
tcgccggtaa tctcagcaat gggggcgtcc tcctccatgc caagtggttc ggcaactctt   180
gctgtagttg ggaaggtgtg ggatgcgacg gcggaagcgg ccgtgtcact actttatggc   240
ttcgtgggca tggactcgca ggccacatcc aacagcatc cttggctggc cttgcacggc    300
tggagtcgct caacctcgcc aacaacaaac tggtcggcac aatcccatca tggatgggtg   360
tgcttgacca cctttgctac ttggatctct caaataattc attggttggt gagatacccca   420
agaatttaca gagaaggctc agttgcccca acattgttgg tcattcactg ggtacggctt   480
ccactaacat gccattgcag gtgaagcata accaaatagc actgagtggg caaccaaaca   540
caataaccgg gaccaataac tatgtcag                                       568
```

<210> SEQ ID NO 108
<211> LENGTH: 568
<212> TYPE: DNA
<213> ORGANISM: Lolium perenne

<400> SEQUENCE: 108

```
cttacatagc tgaaccaatg gagaaaagtt ggttcttgct cctttcttg gcgttcctcc    60
tgccggcggc gagcgtggcg gtgtcgtgcc accctgatga cctccttgca ctgcgcgggt   120
tcgccggtaa tctcagcaat gggggcgtcc tcctccatgc caagtggttc ggcaactctt   180
gctgtagttg ggaaggtgtg ggatgcgacg gcggaagcgg ccgtgtcact actttatggc   240
ttcgtgggca tggactcgca ggccacatcc aacagcatc cttggctggc cttgcacggc    300
tggagtcgct caacctcgcc aacaacaaac tggtcggcac aatcccatca tggatgggtg   360
tgcttgacca cctttgctac ttggatctct caaataattc attggttggt gagatacccca   420
agaatttaca gagaaggctc agttgcccca acattgttgg tcattcactg ggtacggctt   480
ccactaacat gccattgcag gtgaagcata accaaatagc actgagtggg caaccaaaca   540
caataaccgg gaccaataac tatgtcag                                       568
```

<210> SEQ ID NO 109
<211> LENGTH: 568
<212> TYPE: DNA
<213> ORGANISM: Lolium perenne

<400> SEQUENCE: 109

| | | | | | |
|---|---|---|---|---|---|
| cttacatagc | tgaaccaatg | gagaaaagtt | ggttcttgct | cctttcttg | gcgttcctcc | 60 |
| tgccggcggc | gagcgtggcg | gtgtcgtgcc | accctgatga | cctccttgca | ctgcgcgggt | 120 |
| tcgccggtaa | tctcagcaat | ggggcgtcc | tcctccatgc | caagtggttc | ggcaactctt | 180 |
| gctgtagttg | ggaaggtgtg | ggatgcgacg | gcggaagcgg | ccgtgtcact | actttatggc | 240 |
| ttcgtgggca | tggactcgca | ggccacatcc | caacagcatc | cttggctggc | cttgcacggc | 300 |
| tggagtcgct | caacctcgcc | aacaacaaac | tggtcggcac | aatcccatca | tggatgggtg | 360 |
| tgcttgacca | cctttgctac | ttggatctct | caaataattc | attggttggt | gagatacca | 420 |
| agaatttaca | gagaaggctc | agttgcccca | acattgttgg | tcattcactg | ggtacggctt | 480 |
| ccactaacat | gccattgcag | gtgaagcata | accaaatagc | actgagtggg | caaccaaaca | 540 |
| caataaccgg | gaccaataac | tatgtcag | | | | 568 |

<210> SEQ ID NO 110
<211> LENGTH: 568
<212> TYPE: DNA
<213> ORGANISM: Lolium perenne

<400> SEQUENCE: 110

| | | | | | |
|---|---|---|---|---|---|
| cttacatagc | tgaaccaatg | gagaaaagtt | ggttcttgct | cctttcttg | gcgttcctcc | 60 |
| tgccggcggc | gagcgtggcg | gtgtcgtgcc | accctgatga | cctccttgca | ctgcgcgggt | 120 |
| tcgccggtaa | tctcagcaat | ggggcgtcc | tcctccatgc | caagtggttc | ggcaactctt | 180 |
| gctgtagttg | ggaaggtgtg | ggatgcgacg | gcggaagcgg | ccgtgtcact | actttatggc | 240 |
| ttcgtgggca | tggactcgca | ggccacatcc | caacagcatc | cttggctggc | cttgcacggc | 300 |
| tggagtcgct | caacctcgcc | aacaacaaac | tggtcggcac | aatcccatca | tggatgggtg | 360 |
| tgcttgacca | cctttgctac | ttggatctct | caaataattc | attggttggt | gagatacca | 420 |
| agaatttaca | gagaaggctc | agttgcccca | acattgttgg | tcattcactg | ggtacggctt | 480 |
| ccactaacat | gccattgcag | gtgaagcata | accaaatagc | actgagtggg | caaccaaaca | 540 |
| caataaccgg | gaccaataac | tatgtcag | | | | 568 |

<210> SEQ ID NO 111
<211> LENGTH: 570
<212> TYPE: DNA
<213> ORGANISM: Lolium perenne

<400> SEQUENCE: 111

| | | | | | |
|---|---|---|---|---|---|
| cttacatagc | tgaaccaatg | gagaaaagtt | ggttcttgct | cctttcttg | acgttcctcc | 60 |
| tgccggcggc | gagcgtggcg | gtgtcgtgcc | accctgatga | cctccttgca | ctgcgcgggt | 120 |
| tcgccggtaa | tctcagcaat | ggggcgtcc | tcctccatgc | caagtggttc | ggcaactctt | 180 |
| gctgtagttg | ggaaggtgtg | ggatgcgacg | gcggaagcgg | ccgtgtcact | actttatggc | 240 |
| tccgtgggca | tggactcgca | ggccacatcc | caacagcatc | cttggctggc | cttgcacggc | 300 |
| tggagtcgct | caacctcgcc | aacaacaaac | tggtcggcac | aatcccatca | tggatgggtg | 360 |
| tgcttgacca | cctttgctac | ttggatctct | caaataattc | attggttggt | gagatacca | 420 |
| agaatttaca | gagaaggctc | agttgcccca | acattattgg | tcattcactg | ggtacggctt | 480 |

```
ccactaacat gccattgcag gtgaagcata accaaatagc actgagtggg caaccaaaca    540
caataaccgg gaccaataac tatgtcagat                                    570

<210> SEQ ID NO 112
<211> LENGTH: 568
<212> TYPE: DNA
<213> ORGANISM: Lolium perenne

<400> SEQUENCE: 112
cttacatagc tgaaccaatg gagaaaagtt ggttcttgct cctttcttg acgttcctcc     60 tgccggcggc gagcgtggcg gtgtcgtgcc accctgatga cctccttgca ctgcgcgggt   120
tcgccggtaa tctcagcaat gggggcgtcc tcctccatgc caagtggttc ggcaactctt   180
gctgtagttg ggaaggtgtg ggatgcgacg gcggaagcgg ccgtgtcact actttatggc   240
tccgtgggca tggactcgca ggccacatcc caacagcatc cttggctggc cttgcacggc   300
tggagtcgct caacctcgcc aacaacaaac tggtcggcac aatcccatca tggatgggtg   360
tgcttgacca cctttgctac ttggatctct caaataattc attggttggt gagatacccca  420 agaatttaca gagaaggctc agttgcccca acattattgg tcattcactg ggtacggctt   480
ccactaacat gccattgcag gtgaagcata accaaatagc actgagtggg caaccaaaca   540
caataaccgg gaccaataac tatgtcag                                      568

<210> SEQ ID NO 113
<211> LENGTH: 569
<212> TYPE: DNA
<213> ORGANISM: Lolium perenne

<400> SEQUENCE: 113
cttacatagc tgaaccaatg gagaaaagtt ggttcttgct cctttcttg acgttcctcc     60 tgccggcggc gagcgtggcg gtgtcgtgcc accctgatga cctccttgca ctgcgcgggt   120
tcgccggtaa tctcagcaat gggggcgtcc tcctccatgc caagtggttc ggcaactctt   180
gctgtagttg ggaaggtgtg ggatgcgacg gcggaagcgg ccgtgtcact actttatggc   240
tccgtgggca tggactcgca ggccacatcc caacagcatc cttggctggc cttgcacggc   300
tggagtcgct caacctcgcc aacaacaaac tggtcggcac aatcccatca tggatgggtg   360
tgcttgacca cctttgctac ttggatctct caaataattc attggttggt gagatacccca  420 agaatttaca gagaaggctc agttgcccca acattattgg tcattcactg ggtacggctt   480
ccactaacat gccattgcag gtgaagcata accaaatagc actgagtggg caaccaaaca   540
caataaccgg gaccaataac tatgtcaga                                     569

<210> SEQ ID NO 114
<211> LENGTH: 552
<212> TYPE: DNA
<213> ORGANISM: Lolium perenne

<400> SEQUENCE: 114
aatggaggaa agttggttct tgctcctttt cttggcgttc ctcctgccgg cggcgagcgt     60
ggcggtggcg tgccaccctg atgacctcct tgcactgcgc gggttcgccg gtaatctcag   120 caatggggggc gtcctcctcc atgccaagtg gtccggcaac tcttgctgta gttgggaagg  180
tgtgggatgc gacggcggaa gcggccgtgt cactacgttg ggctccctg ggcatggact    240 cgcaggccac atcccaacag catccttggc tggccttgca cggctggagt cgctcaacct   300
cgccaacaac aaactggtcg gcacaatccc atcttggatt ggtgtgcttg accaccttg    360
```

```
ctacttggat ctctcaaata attcattggt tggtgagata cccaagaatt tacagagaag    420
gctcagttgc cccaacattg ttggtcattc actgggtacg gcttccacta acatgccatt    480
gcaggtgaag cataaccaaa tagcactgag tgggcaacca aacacaataa ccgggaccaa    540
taactatgtc ag                                                        552
```

<210> SEQ ID NO 115
<211> LENGTH: 536
<212> TYPE: DNA
<213> ORGANISM: Lolium perenne

<400> SEQUENCE: 115

```
ttcttgctcc ttttcttgac gttcctcctg ccggcggcga gcgtggcggt gtcgtgccac     60
cctgatgacc tccttgcact gcgcgggttc gccggtaatc tcagcaatgg gggcgtcctc    120
ctccatgcca gtggttcgg caactcttgc tgtagttggg aaggtgtggg atgcgacggc    180
ggaagcggcc gtgtcactac tttatggctc cgtgggcatg gactcgcagg ccacatccca    240
acagcatcct tggctggcct tgcacggctg gagtcgctca acctcgccaa caacaaactg    300
gtcggcacaa tcccatcatg gatgggtgtg cttgaccacc tttgctactt ggatctctca    360
aataattcat tggttggtga gatacccaag aatttacaga gaaggctcag ttgccccaac    420
attattggtc attcactggg tacggcttcc actaacatgc cattgcaggt gaagcataac    480
caaatagcac tgagtgggca accaaacaca ataaccggga ccaataacta tgtcag        536
```

<210> SEQ ID NO 116
<211> LENGTH: 488
<212> TYPE: DNA
<213> ORGANISM: Lolium perenne

<400> SEQUENCE: 116

```
cctgccggcg gcgagcgtgg cggtgtcgtg ccaccctgat gacctccttg cactgcgcgg     60
gttcgccggt aatctcagca atgggggcgt cctcctccat gccaagtggt tcggcaactc    120
ttgctgtagt tgggaaggtg tgggatgcga cggcggaagc ggccgtgtca ctactttatg    180
gcttcgtggg catggactcg caggccacat cccaacagca tccttggctg gccttgcacg    240
gctggagtcg ctcaacctcg ccaacaacaa actggtcggc acaatcccat catggatggg    300
tgtgcttgac cacctttgct acttggatct ctcaaataat tcattggttg gtgagatacc    360
caagaattta cagagaaggc tcagttgccc caacattgtt ggtcattcac tgggtacggc    420
ttccactaac atgccattgc aggtgaagca taaccaaata gcactgagtg ggcaaccaaa    480
cacaataa                                                             488
```

<210> SEQ ID NO 117
<211> LENGTH: 494
<212> TYPE: DNA
<213> ORGANISM: Lolium perenne

<400> SEQUENCE: 117

```
gtggcggtgt cgtgccaccc tgatgacctc cttgcactgc gcgggttcgc cggtaatctc     60
agcaatgggg gcgtcctcct ccatgccaag tggttcggca actcttgctg tagttgggaa    120
ggtgtgggat gcgacggcgg aagcggccgt gtcactactt tatggcttcg tgggcatgga    180
ctcgcaggcc acatcccaac agcatccttg gctggccttg cacggctgga gtcgctcaac    240
ctcgccaaca caaactggt cggcacaatc ccatcatgga tgggtgtgct tgaccacctt    300
tgctacttgg atctctcaaa taattcattg gttggtgaga tacccaagaa tttacagaga    360
```

```
aggctcagtt gccccaacat tgttggtcat tcactgggta cggcttccac taacatgcca    420
ttgcaggtga agcataacca aatagcactg agtgggcaac caaacacaat aaccgggacc    480
aataactatg tcag                                                      494
```

<210> SEQ ID NO 118
<211> LENGTH: 539
<212> TYPE: DNA
<213> ORGANISM: Lolium perenne

<400> SEQUENCE: 118

```
ggtgcctcaa catcgttggt cattcactgg gtacggcttc cactaacatg ccattgcagg     60
tgaagcataa ccaaatagca ctgagtgggc aaccaaacac aataaccggg accaataact    120
atgtcagatc tggggtcaac aatgttgttt ctgggaacca caacactgtc acatccggga    180
acaacaatgt tgtgtctggg aaccacaaca ccgtgtctgg gaccaaccat gttgtaactg    240
gtaacaacca tgtcgtaaca aggaaccaga ataccgtatc tgggagccat cataaagtat    300
ctggaggcca caatactgta tctggagcc acaataccgt atctggaagc cacaacacag    360
tatctgggag caaccacgtc gtacacggga caacaaagt cgtgacagga ggttaacaat    420 ctatagaaa ttgtttccat attccctaac ggagttcacg tccttgtcca agctgggtgt    480
agctaaatat cacttggtgg ggccaatggc gttatgtaac ttcgtggata tagcatcac    539
```

<210> SEQ ID NO 119
<211> LENGTH: 980
<212> TYPE: DNA
<213> ORGANISM: Lolium perenne

<400> SEQUENCE: 119

```
cttacatagc tgaaccaatg gagaaaagtt ggttcttgct ccttttcttg acgttcctcc     60
tgccggcggc gagcgtggcg gtgtcgtgcc accctgatga cctccttgca ctgcgcgggt    120
tcgccggtaa tctcagcaat gggggcgtcc tcctccatgc caagtggttc ggcaactctt    180
gctgtagttg ggaaggtgtg ggatgcgacg gcggaagcgg ccgtgtcact actttatggc    240
tccgtgggca tggactcgca ggccacatcc aacagcatc cttggctggc cttgcacggc    300
tggagtcgct caacctcgcc aacaacaaac tggtcggcac aatcccatca tggatgggtg    360
tgcttgacca ccttttgctac ttggatctct caaataattc attggttggt gagatacca    420 agaatttaca gagaaggctc agttgcccca acattgttgg tcattcactg ggtacggctt    480
ccactaacat gccattgcag gtgaagcata accaaatagc actgagtggg caaccaaaca    540
caataaccgg gaccaataac tatgtcagat ctggggtcaa caatgttgtt ctgggaacc    600 acaacactgt cacatccggg aacaacaatg ttgtgtctgg gaaccacaac accgtgtctg    660
ggaccaacca tgttgtaact ggtaacaacc atgtcgtaac aaggaaccag aataccgtat    720
ctggagccca tcataaagta tctggaggcc acaatactgt atctgggagc cacaataccg    780
tatctggaag ccacaacaca gtatctggga gcaaccacgt cgtacacggg aacaacaaag    840
tcgtgacagg aggttaacaa tctatagaga attgtttcca tattccctaa cggagttcac    900
gtccttgtcc aagctgggtg tagctaaata tcacttggtg gggccaatgg cgttatgtaa    960
cttcgtggat atagcatcac                                                980
```

<210> SEQ ID NO 120
<211> LENGTH: 279
<212> TYPE: PRT
<213> ORGANISM: Lolium perenne

<400> SEQUENCE: 120

```
Met Glu Lys Ser Trp Phe Leu Leu Phe Leu Thr Phe Leu Leu Pro
1               5                   10                  15
Ala Ala Ser Val Ala Val Ser Cys His Pro Asp Asp Leu Leu Ala Leu
            20                  25                  30
Arg Gly Phe Ala Gly Asn Leu Ser Asn Gly Gly Val Leu Leu His Ala
        35                  40                  45
Lys Trp Phe Gly Asn Ser Cys Cys Ser Trp Glu Gly Val Gly Cys Asp
    50                  55                  60
Gly Gly Ser Gly Arg Val Thr Thr Leu Trp Leu Arg Gly His Gly Leu
65                  70                  75                  80
Ala Gly His Ile Pro Thr Ala Ser Leu Ala Gly Leu Ala Arg Leu Glu
                85                  90                  95
Ser Leu Asn Leu Ala Asn Asn Lys Leu Val Gly Thr Ile Pro Ser Trp
            100                 105                 110
Met Gly Val Leu Asp His Leu Cys Tyr Leu Asp Leu Ser Asn Asn Ser
        115                 120                 125
Leu Val Gly Glu Ile Pro Lys Asn Leu Gln Arg Arg Leu Ser Cys Pro
    130                 135                 140
Asn Ile Val Gly His Ser Leu Gly Thr Ala Ser Thr Asn Met Pro Leu
145                 150                 155                 160
Gln Val Lys His Asn Gln Ile Ala Leu Ser Gly Gln Pro Asn Thr Ile
                165                 170                 175
Thr Gly Thr Asn Asn Tyr Val Arg Ser Gly Val Asn Asn Val Val Ser
            180                 185                 190
Gly Asn His Asn Thr Val Thr Ser Gly Asn Asn Val Val Ser Gly
        195                 200                 205
Asn His Asn Thr Val Ser Gly Thr Asn His Val Val Thr Gly Asn Asn
    210                 215                 220
His Val Val Thr Arg Asn Gln Asn Thr Val Ser Gly Ser His His Lys
225                 230                 235                 240
Val Ser Gly Gly His Asn Thr Val Ser Gly Ser His Asn Thr Val Ser
                245                 250                 255
Gly Ser His Asn Thr Val Ser Gly Ser Asn His Val Val His Gly Asn
            260                 265                 270
Asn Lys Val Val Thr Gly Gly
        275
```

<210> SEQ ID NO 121
<211> LENGTH: 472
<212> TYPE: DNA
<213> ORGANISM: Deschampsia antarctica

<400> SEQUENCE: 121

```
aatcgtcctt gcattaggcc ggtcacgatg tgtggtctag ccattccatg tcatccacat      60
catataggtt ggtgacgttt attttgaagt ctgcgtaata aaatcttcct aggatatttg     120
catggtatca ctcaattatt actctgagta ggcatgggtg acaagtacct ctccagcaca     180
gctccaatcc tacatgtggt agctgacaac aagcagcttg agtgcttgcc acccacgaat     240
tccagtcgac agaaaacacc aaaaaccaag cttgaattgg aggcagtttt gtgggccttg     300
tggtcacgga ctagtattag accacttgca atgcatgctt acaaacatac acgcacacta     360
taagtaagat gtaccaccca agcagttttt aacaacaacg cttgtgaatc acttccattc     420
caaaaaggtt tcttgccgaa tccatatata gcataccacg gctgaatcca tg             472
```

<210> SEQ ID NO 122
<211> LENGTH: 1404
<212> TYPE: DNA
<213> ORGANISM: Deschampsia antarctica

<400> SEQUENCE: 122

| | |
|---|---:|
| ccttgttcga ctccgtctca agggccttga acctcctcgc agactcctct tcgagggcct | 60 |
| ggagttttg ctctgagtcc ttggagcggc gcaaagcgtc atctctttcg gctacaaaat | 120 |
| aaagaatgtt acaagtgctt gcaagggaaa ttcatggaag gatcttaaag atagtgctat | 180 |
| acccggaagt cgagctcgct ctactagcag ggagccatga tcagcttcaa ccttcgcgaa | 240 |
| tctacgcgcc atgtccatta gctggcaaga aagaggctgc acagaaataa ttattcttag | 300 |
| tatcccgcgt tgccagaata ggctcggggg ctacattagg ataaaaaaga taagggtgcg | 360 |
| gaacttacgt tttctatgcg aggaggaggt gaaggtctgg gagtcgaagt tttctcctcc | 420 |
| cgcatgattg tcttctcagg tgaagacttc aaagcttcat catggtccac caacctccgc | 480 |
| gcttcatcag cggaagtggc tgtcgactcc atatcccttc tcggggtttt agctaagtca | 540 |
| tcttcccctt cggatctgtt gtttatattt gtatgtgtgg ttttattttt caaagctgat | 600 |
| acgatggttg ctaaatataa caggctacaa ataggatata ctttcctcta ctctcccgtc | 660 |
| tattaatctt catatgtatg tgtgcatgta tgatgtatca aagtagagca tgcatagggc | 720 |
| ttgtgcaccc cttggtagcc tcgatgacct tgaccttgtg ttgtttggta gcatcgaatc | 780 |
| gattgcgaga aaatagtaag tttctcaatc tgatcagcca gacaccgaac atattatttg | 840 |
| gtaaataatg acggcgattc acaattttc aataatcgtg tagaattagt tggcttaaca | 900 |
| aaagtcggca cattaggccg gtcacgatgt gtcgtctcat ccgagaaatt ccatgtcaac | 960 |
| cacatcgtct aggttcgtat cgtttatttt gacgtctgca taataagatc ttcctaggat | 1020 |
| attttgttcc tctgcgtgca ctggaactgt aggcgcgcgg tatcactcac ttgttactct | 1080 |
| gccaaggcat gggtgacaag tacctctcca gctcagttcc aaccctatat gcggtagctg | 1140 |
| acgaagggca gcttgagtcc atgccaccca cgaatttcag tcgacagaca acaccaaaaa | 1200 |
| ccaagtttga attgggaggc acctgtgggc cttgtggtca cggactagct agtactgaac | 1260 |
| cacttgcgac acatgcttac acacacacac acacacacta agtagcat gtaccaccca | 1320 |
| agtagttttt aacaacaaca cttgcgaatc acttgcattc caaaaaagtt cattcctgag | 1380 |
| ttgcatacca cagctgaatc catg | 1404 |

<210> SEQ ID NO 123
<211> LENGTH: 420
<212> TYPE: DNA
<213> ORGANISM: Lolium perenne

<400> SEQUENCE: 123

| | |
|---|---:|
| aaaaggttta cgaaatagtt gttattaaac tatatatgtt catgtaacta tatttcaata | 60 |
| taattatttg tattacagca gaaaatcatt atttctatta ctttgtatta ttattttgtt | 120 |
| ttgagtgttg taaattggg aattacaact atactatttt cgtatgggaa caatttgtta | 180 |
| attttgtgt ctctctttct cttcatagct agctgacagc gagaacaaaa accaagatct | 240 |
| aattgtggaa gtagactagt agtcgaccac ccatgcatgc ttacataaga aaacacacgc | 300 |
| actataagat tggatgcacc acccaagcac tataaaaagg atgcaccacc taagcaattt | 360 |
| ttgccaacag cgcgcacttg tttgcattca aaagaaaat cttacatagc tgaaccaatg | 420 |

```
<210> SEQ ID NO 124
<211> LENGTH: 118
<212> TYPE: PRT
<213> ORGANISM: Lolium perenne

<400> SEQUENCE: 124

Asp Glu Gln Pro Asn Thr Ile Ser Gly Ser Asn Asn Thr Val Arg Ser
1               5                   10                  15

Gly Ser Lys Asn Val Leu Ala Gly Asn Asp Asn Thr Val Ile Ser Gly
            20                  25                  30

Asp Asn Asn Ser Val Ser Gly Ser Asn Asn Thr Val Val Ser Gly Asn
        35                  40                  45

Asp Asn Thr Val Thr Gly Ser Asn His Val Val Ser Gly Thr Asn His
    50                  55                  60

Ile Val Thr Asp Asn Asn Asn Val Ser Gly Asn Asp Asn Val
65                  70                  75                  80

Ser Gly Ser Phe His Thr Val Ser Gly Gly His Asn Thr Val Ser Gly
                85                  90                  95

Ser Asn Asn Thr Val Ser Gly Ser Asn His Val Val Ser Gly Ser Asn
            100                 105                 110

Lys Val Val Thr Asp Ala
            115

<210> SEQ ID NO 125
<211> LENGTH: 285
<212> TYPE: PRT
<213> ORGANISM: Triticum aestivum

<400> SEQUENCE: 125

Met Ala Lys Cys Gly Leu Leu Leu Phe Leu Ala Phe Leu Leu Pro
1               5                   10                  15

Ala Ala Arg Ala Thr Ser Cys His Pro Asp Asp Leu Arg Ala Leu Arg
            20                  25                  30

Gly Phe Ala Gly Asn Leu Ser Gly Gly Ala Ala Leu Leu Arg Ala Ala
        35                  40                  45

Trp Ser Gly Ala Ser Cys Cys Val Trp Glu Gly Val Asn Cys Asp Gly
    50                  55                  60

Thr Ser Gly Arg Val Thr Ala Leu Arg Leu Pro Gly His Gly Leu Val
65                  70                  75                  80

Gly Leu Ile Pro Gly Ala Ser Leu Ala Gly Leu Ala Arg Leu Glu Glu
                85                  90                  95

Leu Asn Leu Ala Asn Asn Lys Leu Val Gly Thr Ile Pro Ser Trp Ile
            100                 105                 110

Gly Glu Leu Asp His Leu Cys Tyr Leu Asp Leu Ser Asp Asn Ser Leu
            115                 120                 125

Val Gly Glu Val Pro Lys Ser Leu Ile Arg Leu Lys Gly Leu Val Ile
        130                 135                 140

Ala Gly His Ser Leu Gly Met Val Phe Thr Asn Met Pro Leu Tyr Val
145                 150                 155                 160

Lys Arg Asn Arg Arg Thr Leu Asp Glu Gln Pro Asn Thr Ile Ser Gly
                165                 170                 175

Ser Asn Asn Thr Val Arg Ser Gly Ser Thr Asn Val Val Ser Gly Asn
            180                 185                 190

Asp Asn Thr Val Ile Ser Gly Asn Asn Asn Val Ala Gly Ser Asn
        195                 200                 205
```

```
Asn Thr Val Ile Thr Gly Asn Asp Asn Thr Val Thr Gly Ser Asn His
    210                 215                 220
Val Val Ser Gly Asp Lys His Ile Val Thr Asp Asn Asn Ala Val
225                 230                 235                 240
Ser Gly Asn Asp Asn Val Ser Gly Ser Phe His Thr Val Ser Gly
                245                 250                 255
Ser His Asn Thr Val Ser Gly Thr Asn Asn Thr Val Ser Gly Ser Asn
        260                 265                 270
His Val Val Ser Gly Ser Asn Lys Val Val Gly Asp Glu
    275                 280                 285

<210> SEQ ID NO 126
<211> LENGTH: 430
<212> TYPE: PRT
<213> ORGANISM: Hordeum vulgare

<400> SEQUENCE: 126

Met Ala Arg Cys Trp Leu Leu Leu Leu Cys Ala Phe Leu Trp Pro
1                5                  10                  15
Ala Val Ser Ala Thr Pro Cys His His His Asp Leu His Ala Leu Arg
            20                  25                  30
Gly Phe Ala Glu Glu Leu Gly Gly Gly Ala Leu Leu Arg Thr Ala
            35                  40                  45
Trp Ser Gly Ala Ser Cys Cys Asp Trp Glu Gly Val Gly Cys Asp Gly
    50                  55                  60
Ala Thr Gly Arg Val Thr Ala Leu Arg Leu Pro Gly His Gly Leu Ala
65                  70                  75                  80
Gly Pro Ile Pro Gly Ala Ser Leu Ala Gly Leu Val Trp Leu Glu Glu
                85                  90                  95
Leu Phe Leu Gly Ser Asn Ser Phe Val Gly Val Leu Pro Asp Glu Leu
            100                 105                 110
Phe Gly Leu Ala Arg Leu Arg Lys Leu Ser Leu Ala Ser Asn Glu Leu
            115                 120                 125
Thr Gly Glu Leu Ser Pro Arg Leu Gly Glu Leu Thr Arg Leu Thr Ser
    130                 135                 140
Leu Asp Leu Ser Asp Asn Arg Phe Ser Gly Arg Leu Pro Asp Val Phe
145                 150                 155                 160
Asp Asp Leu Thr Ser Leu Glu His Leu Ala Ala His Ser Asn Asp Phe
                165                 170                 175
Ser Gly Phe Leu Pro Pro Ser Leu Ala Ser Leu Ser Ser Leu Arg Glu
            180                 185                 190
Leu Asn Leu Arg Asn Asn Ser Met Ser Gly Pro Ile Ala Arg Val Ser
    195                 200                 205
Phe Ser Gly Met Pro Phe Leu Ser Ser Val Asp Phe Ser Thr Asn His
    210                 215                 220
Leu Thr Gly Trp Leu Pro Thr Ser Leu Ala Ala Cys Gly Glu Leu Arg
225                 230                 235                 240
Ser Leu Asn Leu Ala Asn Asn Thr Leu Val Gly Asn Ile Pro Ser Trp
                245                 250                 255
Met Gly Glu Phe Asp Arg Leu Trp Tyr Leu Asp Leu Ser Asn Asn Ser
            260                 265                 270
Phe Val Gly Glu Val Pro Arg Ser Leu Ile Arg Leu Met Asp Leu Thr
            275                 280                 285
Thr Val Gly Thr Ser Pro Gly Ile Ala Leu Ser Asn Leu Pro Leu Tyr
    290                 295                 300
```

Val Asn His Asn Arg Arg Thr Leu Asp Glu Gln Pro Asn Thr Ile Thr
305                 310                 315                 320

Gly Thr Asn Asn Thr Val Arg Ser Gly Arg Asn Asn Thr Met Ser Gly
            325                 330                 335

Asn Asp Asn Thr Val Met Ser Gly Asp Asn Asn Ala Val Ser Gly Ser
            340                 345                 350

Phe Asn Thr Leu Val Cys Gly Asp Asn Asn Val Leu Thr Gly Asp His
            355                 360                 365

His Val Val Ser Gly Ser Asn His Ile Val Thr Asn Ser Tyr Asn Lys
370                 375                 380

Val Ser Gly Cys Thr Asn Asn Val Ser Gly Ser Asn His Thr Val Ser
385                 390                 395                 400

Gly Ser Asn Asn Thr Val Ser Gly Ser Ser Asn Thr Val Ser Gly Ser
            405                 410                 415

Asn His Ile Val Ser Gly Ser Asn Lys Ile Val Thr Gly Gly
            420                 425                 430

<210> SEQ ID NO 127
<211> LENGTH: 1010
<212> TYPE: PRT
<213> ORGANISM: Oryza sativa

<400> SEQUENCE: 127

Met Ala Arg Arg Ala Pro Leu Arg Cys Leu Phe Leu Ser Leu Val Ala
1               5                   10                  15

Leu Phe Ala Leu Leu Pro Phe Pro Ala Ala Ala Pro Cys His
            20                  25                  30

Pro Glu Asp Leu Leu Ala Leu Arg Ala Phe Ala Gly Asn Leu Ser Ala
            35                  40                  45

Gly Gly Gly Gly Ala Gly Leu Arg Ala Ala Trp Ser Gly Asp Ala Cys
50                  55                  60

Cys Ala Trp Asp Gly Val Ala Cys Asp Ala Ala Arg Val Thr Ala
65                  70                  75                  80

Leu Arg Leu Pro Gly Arg Gly Leu Glu Gly Pro Ile Pro Pro Ser Leu
            85                  90                  95

Ala Ala Leu Ala Arg Leu Gln Asp Leu Asp Leu Ser His Asn Ala Leu
            100                 105                 110

Thr Gly Gly Ile Ser Ala Leu Leu Ala Ala Val Ser Leu Arg Thr Ala
            115                 120                 125

Asn Leu Ser Ser Asn Leu Leu Asn Asp Thr Leu Leu Asp Leu Ala Ala
130                 135                 140

Leu Pro His Leu Ser Ala Phe Asn Ala Ser Asn Asn Ser Leu Ser Gly
145                 150                 155                 160

Ala Leu Ala Pro Asp Leu Cys Ala Gly Ala Pro Ala Leu Arg Val Leu
            165                 170                 175

Asp Leu Ser Ala Asn Leu Leu Ala Gly Thr Leu Ser Pro Ser Pro Ser
            180                 185                 190

Pro Pro Pro Cys Ala Ala Thr Leu Gln Glu Leu Tyr Leu Ala Ser Asn
            195                 200                 205

Ser Phe His Gly Ala Leu Pro Pro Thr Leu Phe Gly Leu Ala Ala Leu
            210                 215                 220

Gln Lys Leu Ser Leu Ala Ser Asn Gly Leu Thr Gly Gln Val Ser Ser
225                 230                 235                 240

Arg Leu Arg Gly Leu Thr Asn Leu Thr Ser Leu Asp Leu Ser Val Asn
            245                 250                 255

```
-continued

Arg Phe Thr Gly His Leu Pro Asp Val Phe Ala Asp Leu Thr Ser Leu
                260                 265                 270

Gln His Leu Thr Ala His Ser Asn Gly Phe Ser Gly Leu Leu Pro Arg
            275                 280                 285

Ser Leu Ser Ser Leu Ser Ser Leu Arg Asp Leu Asn Leu Arg Asn Asn
290                 295                 300

Ser Phe Ser Gly Pro Ile Ala Arg Val Asn Phe Ser Ser Met Pro Phe
305                 310                 315                 320

Leu Val Ser Ile Asp Leu Ala Thr Asn His Leu Asn Gly Ser Leu Pro
                325                 330                 335

Leu Ser Leu Ala Asp Cys Gly Asp Leu Lys Ser Leu Ser Ile Ala Lys
            340                 345                 350

Asn Ser Leu Thr Gly Gln Leu Pro Glu Glu Tyr Gly Arg Leu Gly Ser
                355                 360                 365

Leu Ser Val Leu Ser Leu Ser Asn Asn Thr Met Arg Asn Ile Ser Gly
            370                 375                 380

Ala Leu Thr Val Leu Arg Ala Cys Lys Asn Leu Thr Thr Leu Ile Leu
385                 390                 395                 400

Thr Lys Asn Phe Val Gly Glu Asp Leu Pro Asp Asp Gly Ile Ala Gly
                405                 410                 415

Phe Asp Asn Leu Glu Val Leu Ala Leu Gly Asp Cys Ala Leu Arg Gly
            420                 425                 430

Arg Val Pro Glu Trp Leu His Gln Cys Lys Arg Leu Glu Val Leu Asp
                435                 440                 445

Leu Ser Trp Asn Gln Leu Val Gly Thr Ile Pro Glu Trp Ile Gly Gln
            450                 455                 460

Leu Asp Asn Leu Thr Tyr Leu Asp Leu Ser Asn Asn Ser Leu Val Gly
465                 470                 475                 480

Glu Ile Pro Lys Ser Leu Thr Gln Leu Lys Ser Leu Val Thr Ala Arg
                485                 490                 495

Arg Ser Pro Gly Met Ala Phe Thr Asn Met Pro Leu Tyr Val Lys His
            500                 505                 510

Asn Lys Ser Thr Ser Gly Arg Gln Tyr Asn Gln Leu Ser Asn Phe Pro
            515                 520                 525

Pro Ser Leu Phe Leu Asn Asp Asn Gly Leu Asn Gly Thr Ile Trp Pro
530                 535                 540

Glu Phe Gly Asn Leu Lys Glu Leu His Val Leu Asp Leu Ser Asn Asn
545                 550                 555                 560

Ala Ile Ser Gly Ser Ile Pro Asp Val Leu Ser Arg Met Glu Asn Leu
                565                 570                 575

Glu Val Leu Asp Leu Ser Ser Asn Asn Leu Ser Gly Ser Ile Pro Ser
            580                 585                 590

Ser Leu Thr Asp Leu Thr Phe Leu Ser Lys Phe Ser Val Ala His Asn
            595                 600                 605

His Leu Val Gly Pro Ile Pro Asn Gly Gly Gln Phe Phe Thr Phe Ser
610                 615                 620

Asn Ser Ser Phe Glu Gly Asn Pro Gly Leu Cys Arg Ser Ser Ser Cys
625                 630                 635                 640

Asp Gln Asn Gln Pro Gly Glu Thr Pro Thr Asp Asn Asp Ile Gln Arg
                645                 650                 655

Ser Gly Arg Asn Arg Lys Asn Lys Ile Leu Gly Val Ala Ile Cys Ile
            660                 665                 670
```

```
Gly Leu Val Leu Val Leu Ala Val Ile Leu Val Asn Ile Ser
            675                 680                 685
Lys Arg Glu Val Ser Ile Ile Asp Asp Glu Glu Ile Asn Gly Ser Cys
690                 695                 700
His Asp Ser Tyr Asp Tyr Trp Lys Pro Val Leu Phe Phe Gln Asp Ser
705                 710                 715                 720
Ala Lys Glu Leu Thr Val Ser Asp Leu Ile Lys Ser Thr Asn Asn Phe
                725                 730                 735
Asp Gln Ala Asn Ile Ile Gly Cys Gly Phe Gly Leu Val Tyr Lys
            740                 745                 750
Ala Tyr Leu Pro Asp Gly Thr Lys Ala Ala Val Lys Arg Leu Ser Gly
            755                 760                 765
Asp Cys Gly Gln Met Glu Arg Glu Phe Arg Ala Glu Val Glu Ala Leu
            770                 775                 780
Ser Gln Ala Gln His Lys Asn Leu Val Ser Leu Arg Gly Tyr Cys Arg
785                 790                 795                 800
Tyr Gly Asn Asp Arg Leu Leu Ile Tyr Ser Tyr Met Glu Asn Asn Ser
                805                 810                 815
Leu Asp Tyr Trp Leu His Glu Arg Ser Asp Gly Gly Tyr Met Leu Lys
            820                 825                 830
Trp Glu Ser Arg Leu Lys Ile Ala Gln Gly Ser Ala Arg Gly Leu Ala
            835                 840                 845
Tyr Leu His Lys Asp Cys Glu Pro Asn Ile Ile His Arg Asp Val Lys
            850                 855                 860
Ser Ser Asn Ile Leu Leu Asn Glu Asn Phe Glu Ala His Leu Ala Asp
865                 870                 875                 880
Phe Gly Leu Ala Arg Leu Ile Gln Pro Tyr Asp Thr His Val Thr Thr
                885                 890                 895
Asp Leu Val Gly Thr Leu Gly Tyr Ile Pro Pro Glu Tyr Ser Gln Ser
            900                 905                 910
Val Ile Ala Thr Pro Lys Gly Asp Val Tyr Ser Phe Gly Val Val Leu
            915                 920                 925
Leu Glu Leu Leu Thr Gly Arg Arg Pro Met Asp Val Ser Lys Ala Lys
930                 935                 940
Gly Ser Arg Asp Leu Val Ser Tyr Val Leu Gln Met Lys Ser Glu Lys
945                 950                 955                 960
Lys Glu Glu Gln Ile Phe Asp Thr Leu Ile Trp Ser Lys Thr His Glu
                965                 970                 975
Lys Gln Leu Phe Ser Val Leu Glu Ala Ala Cys Arg Cys Ile Ser Thr
            980                 985                 990
Asp Pro Arg Gln Arg Pro Ser Ile Glu Gln Val Val Ala Trp Leu Asp
            995                 1000                1005
Ser Val
    1010

<210> SEQ ID NO 128
<211> LENGTH: 24
<212> TYPE: PRT
<213> ORGANISM: Deschampsia antarctica
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
```

```
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 128

Leu Xaa Leu Xaa Xaa Asn Xaa Leu Thr Gly Xaa Ile Pro Xaa Xaa Leu
 1               5                  10                  15

Gly Xaa Leu Xaa Xaa Leu Xaa Xaa
             20

<210> SEQ ID NO 129
<211> LENGTH: 24
<212> TYPE: PRT
<213> ORGANISM: Lolium perenne
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 129

Leu Xaa Leu Xaa Xaa Asn Xaa Leu Thr Gly Xaa Ile Pro Xaa Xaa Leu
 1               5                  10                  15

Gly Xaa Leu Xaa Xaa Leu Xaa Xaa
             20
```

<210> SEQ ID NO 130
<211> LENGTH: 26
<212> TYPE: DNA
<213> ORGANISM: Artificial
<220> FEATURE:
<223> OTHER INFORMATION: Synthetic primer

<400> SEQUENCE: 130
gacatcgcga ttggtcccac caagtg                                          26

<210> SEQ ID NO 131
<211> LENGTH: 24
<212> TYPE: DNA
<213> ORGANISM: Artificial
<220> FEATURE:
<223> OTHER INFORMATION: Synthetic primer

<400> SEQUENCE: 131
gcatcctgca cggacatatc atta                                            24

<210> SEQ ID NO 132
<211> LENGTH: 28
<212> TYPE: DNA
<213> ORGANISM: Artificial
<220> FEATURE:
<223> OTHER INFORMATION: Synthetic primer

<400> SEQUENCE: 132
gttacataag acgattggcc ccaccaag                                        28

<210> SEQ ID NO 133
<211> LENGTH: 27
<212> TYPE: DNA
<213> ORGANISM: Artificial
<220> FEATURE:
<223> OTHER INFORMATION: Synthetic primer

<400> SEQUENCE: 133
caatccactc actgatcatt aaccacc                                         27

<210> SEQ ID NO 134
<211> LENGTH: 24
<212> TYPE: DNA
<213> ORGANISM: Artificial
<220> FEATURE:
<223> OTHER INFORMATION: Synthetic primer

<400> SEQUENCE: 134
gatgctatat ccacgaagtt acat                                            24

<210> SEQ ID NO 135
<211> LENGTH: 18
<212> TYPE: DNA
<213> ORGANISM: Artificial
<220> FEATURE:
<223> OTHER INFORMATION: Synthetic primer

<400> SEQUENCE: 135
attggcccca ccaagtga                                                   18

<210> SEQ ID NO 136
<211> LENGTH: 26
<212> TYPE: DNA
<213> ORGANISM: Artificial
<220> FEATURE:
<223> OTHER INFORMATION: Synthetic primer

<400> SEQUENCE: 136
aagcagtggt aacaacgcag agtggg        26

<210> SEQ ID NO 137
<211> LENGTH: 33
<212> TYPE: DNA
<213> ORGANISM: Artificial
<220> FEATURE:
<223> OTHER INFORMATION: Synthetic primer

<400> SEQUENCE: 137
cagcttggat ccatggcgaa ctgctgtctg cta        33

<210> SEQ ID NO 138
<211> LENGTH: 33
<212> TYPE: DNA
<213> ORGANISM: Artificial
<220> FEATURE:
<223> OTHER INFORMATION: Synthetic primer

<400> SEQUENCE: 138
actcacaagc ttaacctcct gtcacgactt tgt        33

<210> SEQ ID NO 139
<211> LENGTH: 33
<212> TYPE: DNA
<213> ORGANISM: Artificial
<220> FEATURE:
<223> OTHER INFORMATION: Synthetic primer

<400> SEQUENCE: 139
aggagaggat ccatggcgcg taccaaacag acc        33

<210> SEQ ID NO 140
<211> LENGTH: 33
<212> TYPE: DNA
<213> ORGANISM: Artificial
<220> FEATURE:
<223> OTHER INFORMATION: Synthetic primer

<400> SEQUENCE: 140
taattgaagc ttttaggcgc gttcgccacg gat        33

<210> SEQ ID NO 141
<211> LENGTH: 8
<212> TYPE: PRT
<213> ORGANISM: Deschampsia antarctica
<220> FEATURE:
<221> NAME/KEY: VARIANT
<222> LOCATION: (1)..(1)
<223> OTHER INFORMATION: Ser may be replaced with any of Gln, Thr, Arg,
    Asn, Asp, Cys, Leu, Lys, or His
<220> FEATURE:
<221> NAME/KEY: VARIANT
<222> LOCATION: (2)..(2)
<223> OTHER INFORMATION: Asn may be replaced with any of Pro, Lys, His,
    Asp, Phe, Tyr or Arg
<220> FEATURE:
<221> NAME/KEY: VARIANT
<222> LOCATION: (3)..(3)
<223> OTHER INFORMATION: Asn may be replaced with any of Lys, His, Asp
    or Gln
<220> FEATURE:
<221> NAME/KEY: VARIANT
<222> LOCATION: (4)..(4)
<223> OTHER INFORMATION: Thr may be replaced with any of Ser or Asn

```
<220> FEATURE:
<221> NAME/KEY: VARIANT
<222> LOCATION: (5)..(5)
<223> OTHER INFORMATION: Val may be replaced with any of Arg, Lys, Ala,
      Asn, Ile, Leu or Asp
<220> FEATURE:
<221> NAME/KEY: VARIANT
<222> LOCATION: (6)..(6)
<223> OTHER INFORMATION: Val may be replaced with any of Ile, Arg, or
      Leu
<220> FEATURE:
<221> NAME/KEY: VARIANT
<222> LOCATION: (7)..(7)
<223> OTHER INFORMATION: Ser may be replaced with any of Ile, Phe, Ala,
      Thr, Arg, Pro, Gln or Asp
<220> FEATURE:
<221> NAME/KEY: VARIANT
<222> LOCATION: (8)..(8)
<223> OTHER INFORMATION: Gly may be replaced with any of Asp or Arg

<400> SEQUENCE: 141

Ser Asn Asn Thr Val Val Ser Gly
1               5

<210> SEQ ID NO 142
<211> LENGTH: 279
<212> TYPE: PRT
<213> ORGANISM: Lolium multiflorum

<400> SEQUENCE: 142

Met Glu Lys Ser Trp Phe Leu Leu Leu Phe Leu Ala Phe Leu Leu Pro
1               5                   10                  15

Ala Ala Ser Val Ala Val Ser Cys His Pro Asp Asp Leu Leu Ala Leu
            20                  25                  30

Arg Arg Phe Ala Gly Asn Leu Ser Asn Gly Gly Val Leu Leu His Ala
        35                  40                  45

Lys Trp Ser Gly Asn Ser Cys Cys Ser Trp Glu Gly Val Gly Cys Asp
    50                  55                  60

Gly Gly Ser Gly Arg Val Thr Thr Leu Trp Leu Pro Gly His Gly Leu
65                  70                  75                  80

Ala Gly His Ile Pro Thr Ala Ser Leu Ala Gly Leu Ala Arg Leu Glu
                85                  90                  95

Ser Leu Asn Leu Ala Asn Asn Lys Leu Val Gly Thr Ile Pro Ser Trp
            100                 105                 110

Ile Gly Glu Leu Asp His Leu Cys Tyr Leu Asp Leu Ser Asn Asn Ser
        115                 120                 125

Leu Val Gly Glu Ile Pro Lys Asn Leu Gln Arg Arg Leu Ser Cys Pro
    130                 135                 140

Asn Ile Val Gly His Ser Leu Gly Thr Ala Ser Thr Asn Met Pro Leu
145                 150                 155                 160

Gln Val Lys His Asn Gln Ile Ala Leu Ser Gly Gln Pro Asn Thr Ile
                165                 170                 175

Thr Gly Thr Asn Asn Tyr Val Arg Ser Gly Ile Asn Asn Val Val Ser
            180                 185                 190

Gly Asn His Asn Thr Val Thr Ser Gly Asn Asn Val Val Ser Gly
        195                 200                 205

Asn His Asn Thr Val Ser Gly Thr Asn His Val Val Thr Gly Asn Asn
    210                 215                 220

His Val Val Thr Arg Asn Gln Asn Thr Val Ser Gly Ser His His Lys
225                 230                 235                 240
```

```
Val Ser Gly Gly His Asn Thr Val Ser Gly Ser His Asn Thr Val Ser
                245                 250                 255

Gly Ser His Asn Thr Val Ser Gly Ser Asn His Val Val His Gly Asn
            260                 265                 270

Asn Lys Val Val Thr Gly Gly
        275

<210> SEQ ID NO 143
<211> LENGTH: 24
<212> TYPE: PRT
<213> ORGANISM: Deschampsia antarctica
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 143

Leu Xaa Leu Xaa Xaa Asn Xaa Leu Ser Gly Xaa Ile Pro Xaa Xaa Leu
1               5                   10                  15

Gly Xaa Leu Xaa Xaa Leu Xaa Xaa
            20

<210> SEQ ID NO 144
<211> LENGTH: 24
<212> TYPE: PRT
<213> ORGANISM: Lolium perenne
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
```

```
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 144

Leu Xaa Leu Xaa Xaa Asn Xaa Leu Ser Gly Xaa Ile Pro Xaa Xaa Leu
1               5                   10                  15

Gly Xaa Leu Xaa Xaa Leu Xaa Xaa
            20

<210> SEQ ID NO 145
<211> LENGTH: 10
<212> TYPE: PRT
<213> ORGANISM: Deschampsia antarctica
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 145

Cys Cys Xaa Trp Glu Gly Val Xaa Cys Asp
1               5                   10
```

ICE RECRYSTALLISATION INHIBITION PROTEIN OR ANTIFREEZE PROTEINS FROM *DESCHAMPSIA* SPECIES OF GRASS

The present invention relates to nucleic acids or nucleic acid fragments encoding amino acid sequences for polypeptides involved in tolerance to freezing and/or low temperature stress in plants. More particularly, the present invention relates to nucleic acids or nucleic acid fragments encoding amino acid sequences for ice recrystallisation inhibition proteins (IRIPs) in plants, and the use thereof for the modification of plant response to freezing and/or low temperature stress. Even more particularly, the present invention relates to polypeptides involved in tolerance to freezing and/or low temperature stress in *Deschampsia* and *Lolium* species.

Plants have evolved a range of physiological and biochemical responses to freezing and low temperature stress. As a consequence of poikilothermy many plant species are tolerant of temperature extremes, including exposure to sub-zero temperatures. Subzero temperatures negatively impact on plant cells in many ways. As temperatures drop below freezing ice crystal formation initially takes place extracellularly, in the apoplasm. This leads to an elevation of infracellular solute concentration as water is lost by osmosis to the extracellular ice, resulting in severe dehydration. Desiccation, whereby as much as 90% of intracellular water can be lost at −10° C., induces multiple forms of membrane damage. Furthermore, extracellular ice obstructs gas and solute exchange, and growing ice crystals cause plasmolysis.

Plants and other organisms that are exposed to subzero temperatures have evolved varied mechanisms to confer tolerance to freezing stress including deployment of variant isozymes, synthesis of osmoprotectants and compatible solutes, and modification of membrane lipid composition. A particular characteristic of tolerance to freezing, and to temperature stresses in general, is the phenomenon of acquired tolerance. For freezing stress this is termed cold acclimation, whereby a transition to low, non-freezing temperature can confer tolerance of subsequent exposure to otherwise lethal subzero temperatures.

A common response of plant and other species with tolerance to subzero temperatures and freezing is the expression of anti-freeze proteins (AFPs). AFPs have an affinity for ice, by virtue of structural complementarity, thereby inhibiting its growth. Adsorbtion of AFPs onto ice surfaces has two distinct effects: thermal hysteresis (TH) and recrystallisation inhibition (RI). TH results from a noncolligative freezing point depression as ice front growth becomes restricted to sterically unfavourable spaces between AFPs. This broadens the gap between the melting and freezing points of ice, and this range is the measure of TH. AFPs mediate the effect of RI by interfering with the migration of ice boundaries which normally thermodynamically favour the creation of large, ice crystals at the expense of smaller ones. Thus RI activity limits the growth of large ice crystals that have the potential to puncture cell walls and membranes and cause plasmolysis. RI activity has been identified in extracts from a limited number of plant species, and the nucleotide sequence of one ice recrystallisation inhibition protein (IRIP) conferring such activity has been reported from *Lolium perenne*.

Antarctic hair grass *Deschampsia antarctica* is one of only two angiosperms to have overcome the geographical and environmental impediments to colonising the Antarctic continent. It grows in favourable locations along the western coast of the Antarctic Peninsula. *D. antarctica* is an overwintering species with a short growing season that at Palmer Station (64°47'S), is typically November to March. In respect of low temperature stress, on Leonie Island in northern Marguerite Bay (67°36'S) towards the southern limit of distribution of *D. antarctica*, air temperatures below −30° C. have been recorded during the austral winter. During the growing season, when plants are most vulnerable to freezing stress, episodes of temperatures down to −15° C. can occur early in the growing season. *D. antarctica* has a well developed cold-acclimation response, and significant cellular damage only occurs in plants exposed to temperatures substantially below those at which they freeze.

Despite *D. antarctica*'s well developed freezing tolerance no biochemical or physiological mechanisms have been identified that can coherently account for this capacity.

There is a need for materials useful in modifying the tolerance to freezing and low temperature stress in a wide range of plants, and for methods for their use.

It is an object of the present invention to overcome, or at least alleviate, one or more of the difficulties or deficiencies associated with the prior art.

In one aspect, the present invention provides substantially purified or isolated nucleic acids or nucleic acid fragments encoding IRIPs from a *Deschampsia* species, preferably Antarctic hair-grass, *Deschampsia antarctica*, or functionally active fragments or variants thereof.

In a preferred embodiment of this aspect of the invention, the substantially purified or isolated nucleic acid or nucleic acid fragment includes a nucleotide sequence selected from the group consisting of (a) sequences shown in FIGS. 8A-8H, 9A, 9B, 11, 12, 14A-14D, 15A, 15B, 17A-17C, 18A, 18B, 20A-20C, 21, 23A-23C, and 24 hereto; (b) complements of the sequences recited in (a); (c) sequences antisense to the sequences recited in (a) and (b); (d) functionally active fragments and variants of the sequences recited in (a), (b) and (c); and (e) RNA sequences corresponding to the sequences recited in (a), (b), (c) and (d).

In another aspect, the present invention provides substantially purified or isolated nucleic acids or nucleic acid fragments encoding IRIPs from a ryegrass (*Lolium*) or fescue (*Festuca*) species. These species may be of any suitable type, including Italian or annual ryegrass, perennial ryegrass, tall fescue, meadow fescue and red fescue. Preferably the species is a ryegrass, more preferably perennial ryegrass (*L. perenne*).

In a preferred embodiment of this aspect of the invention, the substantially purified or isolated nucleic acid or nucleic acid fragment includes a nucleotide sequence selected from the group consisting of (a) sequences shown in FIGS. 26A-26X, 27A, 27B, 29A-29F, 30A, and 30B hereto; (b) complements of the sequences recited in (a); (c) sequences antisense to the sequences recited in (a) and (b); (d) functionally active fragments and variants of the sequences recited in (a), (b) and (c); and (e) RNA sequences corresponding to the sequences recited in (a), (b), (c) and (d).

The present invention provides substantially purified or isolated nucleic acids or nucleic acid fragments encoding amino acid sequences for a class of polypeptides which are related to IRIP or functionally active fragments or variants thereof. Such proteins are referred to herein as IRIP-like. The genes which encode these polypeptides are expressed in a similar manner to IRIP. The invention also encompasses functionally active fragments and variants of nucleic acids encoding such polypeptides.

The individual or simultaneous enhancement or otherwise manipulation of IRIP or like gene activities in plants may enhance or otherwise alter the freezing and/or low temperature tolerance of plants.

The modification of plant freezing and/or low temperature tolerance based on the individual or simultaneous enhancement or otherwise manipulation of IRIP or like gene activities in plants has significant consequences for a range of applications in plant production and plant protection. For example, it has applications in increasing the range and productivity of plants.

Methods for the modification of plant freezing and/or low temperature tolerance may facilitate the production of, for example, plants with enhanced tolerance of freezing and/or low temperature stress.

Nucleic acids according to the invention may be full-length genes or part thereof, and are also referred to as "nucleic acid fragments" and "nucleotide sequences" in this specification.

The nucleic acid or nucleic acid fragment may be of any suitable type and includes DNA (such as cDNA or genomic DNA) and RNA (such as mRNA) that is single- or double-stranded, optionally containing synthetic, non-natural or altered nucleotide bases, and combinations thereof.

Such nucleic acid fragments could be assembled to form a consensus contig.

In a further aspect of the present invention there is provided a substantially purified or isolated regulatory element from a *Deschampsia* species, preferably *Deschampsia antarctica*, said regulatory element being capable of modifying plant response to freezing and/or low temperature stress.

More preferably the regulatory element includes a nucleotide sequence selected from the groups consisting of (a) sequences shown in FIGS. 32 and 33 hereto; (b) complements of the sequences recited in (a); and (c) functionally active fragments and variants of the sequences recited in (a) and (b).

In a further aspect of the present invention there is provided a substantially purified or isolated regulatory element from a *Lolium* or *Festuca* species, preferably *Lolium perenne*, said regulatory element being capable of modifying plant response to freezing and/or low temperature stress.

More preferably the regulatory element includes a nucleotide sequence selected from the group consisting of (a) sequence shown in FIG. 34 hereto; (b) complement of the sequence recited in (a) and (c) functionally active fragments and variants of the sequences recited in (a) and (b).

Preferably the regulatory element is a promoter.

Preferably the regulatory element is isolated from an IRIP nucleic acid or nucleic acid fragment.

As used herein, the term IRIP-like relates to polypeptides that are produced in the plant in substantially the same organs and at substantially the same developmental stages as IRIP.

The term "isolated" means that the material is removed from its original environment (eg. the natural environment if it is naturally occurring). For example, a naturally occurring nucleic acid or polypeptide present in a living plant is not isolated, but the same nucleic acid or polypeptide separated from some or all of the coexisting materials in the natural system, is isolated. Such nucleic acids could be part of a vector and/or such nucleic acids could be part of a composition, and still be isolated in that such a vector or composition is not part of its natural environment.

As used herein, the term "consensus contig" refers to a nucleotide sequence that is assembled from two or more constituent nucleotide sequences that share common or overlapping regions of sequence homology. For example, the nucleotide sequence of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

The term "purified" means that the nucleic acid or polypeptide is substantially free of other nucleic acids or polypeptides.

By "functionally active" in respect of a nucleic acid it is meant that the fragment or variant (such as an analogue, derivative or mutant) is capable of modifying the tolerance of freezing and/or low temperature stress in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, more preferably at least approximately 90% identity, most preferably at least approximately 95% identity. Such functionally active variants and fragments include, for example, those having nucleic acid changes which result in conservative amino acid substitutions of one or more residues in the corresponding amino acid sequence. Preferably the fragment has a size of at least 30 nucleotides, more preferably at least 45 nucleotides, most preferably at least 60 nucleotides.

By "functionally active" in respect of a polypeptide is meant that the fragment or variant has one or more of the biological properties of an IRIP or IRIP-like protein. Additions, deletions, substitutions and derivatizations of one or more of the amino acids are contemplated so long as the modifications do not result in loss of functional activity of the fragment or variant. Preferably the functionally active fragment or variant has at least approximately 60% identity to the relevant part of the above mentioned sequence, more preferably at least approximately 80% identity, most preferably at least approximately 90% identity. Such functionally active variants and fragments include, for example, those having conservative amino acid substitutions of one or more residues in the corresponding amino acid sequence. Preferably the fragment has a size of at least 10 amino acids, more preferably at least 15 amino acids, most preferably at least 20 amino acids.

The term "construct" as used herein refers to an artificially assembled or isolated nucleic acid molecule which includes the gene of interest. In general a construct may include the gene or genes of interest, a marker gene which in some cases can also be the gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

The term "vector" as used herein encompasses both cloning and expression vectors. Vectors are often recombinant molecules containing nucleic acid molecules from several sources.

By "operatively linked" is meant that said regulatory element is capable of causing expression of said nucleic acid or nucleic acid fragment in a plant cell and said terminator is capable of terminating expression of said nucleic acid or nucleic acid fragment in a plant cell. Preferably, said regulatory element is upstream of said nucleic acid or nucleic acid fragment and said terminator is downstream of said nucleic acid or nucleic acid fragment.

By "an effective amount" it is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the relevant disclosure of which is incorporated herein by reference.

It will also be understood that the term "comprises" (or its grammatical variants) as used in this specification is equivalent to the term "includes" and should not be taken as excluding the presence of other elements or features.

Genes encoding other IRIP or IRIP-like proteins for modifying the tolerance of plants to freezing and/or low temperature stress, either as cDNAs or genomic DNAs, may be isolated directly by using all or a portion of the nucleic acids or nucleic acid fragments of the present invention as hybridisation probes to screen libraries from the desired plant employing the methodology well known to those skilled in the art. Specific oligonucleotide probes based upon the nucleic acid sequences of the present invention may be designed and synthesized by methods known in the art. Moreover, the entire sequences may be used directly to synthesize DNA probes by methods known to the skilled artisan, such as random primer DNA labelling, nick translation, or end-labelling techniques, or RNA probes using available in vitro transcription systems. In addition, specific primers may be designed and used to amplify a part or all of the sequences of the present invention. The resulting amplification products may be labelled directly during amplification reactions or labelled after amplification reactions, and used as probes to isolate full length cDNA or genomic fragments under conditions of appropriate stringency.

In addition, short segments of the nucleic acids or nucleic acid fragments of the present invention may be used in protocols to amplify longer nucleic acid fragments encoding homologous genes from DNA or RNA. For example, polymerase chain reaction may be performed on a library of cloned nucleic acid fragments wherein the sequence of one primer is derived from the nucleic acid sequences of the present invention, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, those skilled in the art can follow the RACE protocol [Frohman et al. (1988) Proc. Natl. Acad Sci. USA 85:8998, the entire disclosure of which is incorporated herein by reference] to generate cDNAs by using PCR to amplify copies of the region between a single point in the transcript and the 3' or 5' end. Using commercially available 3' RACE and 5' RACE systems (BRL), specific 3' or 5' cDNA fragments may be isolated [Ohara et al. (1989; Proc. Natl. Acad Sci USA 86:5673; Loh et al. (1989) Science 243:217, the entire disclosures of which are incorporated herein by reference]. Products generated by the 3' and 5' RACE procedures may be combined to generate full-length cDNAs.

In a further aspect of the present invention there is provided a substantially purified or isolated IRIP or IRIP-like polypeptide from a *Deschampsia* species, preferably from Antarctic hair-grass, *Deschampsia antarctica*; and functionally active fragments and variants thereof.

In a preferred embodiment of this aspect of the invention, the substantially purified or isolated polypeptide includes an amino acid sequence selected from the group consisting of sequences shown in FIGS. 10, 13, 16, 19, 22 and 25 hereto; and functionally active fragments and variants thereof.

In a still further aspect of the present invention there is provided a substantially purified or isolated IRIP or IRIP-like polypeptide from a ryegrass (*Lolium*) or fescue (*Festuca*) species; and functionally active fragments and variants thereof.

The ryegrass (*Lolium*) or fescue (*Festuca*) species may be of any suitable type, including Italian or annual ryegrass, perennial ryegrass, tall fescue, meadow fescue and red fescue. Preferably the species is a ryegrass, more preferably perennial ryegrass (*L. perenne*).

In a preferred embodiment of this aspect of the invention, the substantially purified or isolated polypeptide includes an amino acid sequence selected from the group consisting of sequences shown in FIGS. 28 and 31 hereto; and functionally active fragments and variants thereof.

The Applicant has found that the polypeptides of the present invention include relatively few leucine rich repeat (LRR) motifs.

Preferably said LLR motifs from a *Deschampsia* species include the consensus sequence:

(SEQ ID NO. 128)
LxLxxNxLTGxIPxxLGxLxxLxx or the consensus sequence:

(SEQ ID NO. 143)
LxLxxNxLSGxIPxxLGxLxxLxx

Preferably said LRR motifs from a *Lolium* or *Festuca* species include the consensus sequence:

(SEQ ID NO. 129)
LxLxxNxLTGxIPxxLGxLxxLxx or the consensus sequence:

(SEQ ID NO. 144)
LxLxxNxLSGxIPxxLGxLxxLxx

Applicant has found that polypeptides of the present invention including relatively few LRR motifs, preferably 3 or fewer LRR motifs, more preferably 1 or fewer LRR motifs, may be more efficient at modifying tolerance of freezing and/or low temperature stress in a plant than nucleic acids or nucleic acid fragments having relatively more LRR motifs, for example approximately 9 or more LRR motifs. Similarly, the nucleic acids or nucleic acid fragments encoding such polypeptides may be more efficient at modifying tolerance of freezing and/or low temperature stress in a plant.

In a further embodiment of this aspect of the invention, there is provided a polypeptide recombinantly produced from a nucleic acid or nucleic acid fragment according to the present invention. Techniques for recombinantly producing polypeptides are known to those skilled in the art.

Availability of the nucleotide sequences of the present invention and deduced amino acid sequences facilitates immunological screening of cDNA expression libraries. Synthetic peptides representing portions of the instant amino acid sequences may be synthesized. These peptides may be used to immunise animals to produce polyclonal or monoclonal antibodies with specificity for peptides and/or proteins comprising the amino acid sequences. These antibodies may be then used to screen cDNA expression libraries to isolate full-length cDNA clones of interest.

A genotype is the genetic constitution of an individual or group. Variations in genotype are essential in commercial breeding programs, in determining parentage, in diagnostics and fingerprinting, and the like. Genotypes can be readily described in terms of genetic markers. A genetic marker identifies a specific region or locus in the genome. The more genetic markers, the finer defined is the genotype. A genetic marker becomes particularly useful when it is allelic between organisms because it then may serve to unambiguously identify an individual. Furthermore, a genetic marker becomes particularly useful when it is based on nucleic acid sequence information that can unambiguously establish a genotype of an individual and when the function encoded by such nucleic acid is known and is associated with a specific trait. Such nucleic acids and/or nucleotide sequence information including single nucleotide polymorphisms (SNP's), variations in single nucleotides between allelic forms of such nucleotide sequence, can be used as perfect markers or candidate genes for the given trait.

Applicants have identified a number of SNPs of the nucleic acids or nucleic acid fragments of the present invention. These are indicated (marked with grey on the black background) in the figures that show multiple alignments of nucleotide sequences of nucleic acid fragments contributing to consensus contig sequences. See for example, FIGS. 8A-8H, 11, 14A-14D, 17A-17C, 20A-20C, 23A-23C, 26A-26X and 29A-29F hereto.

Accordingly, in a further aspect of the present invention, there is provided a substantially purified or isolated nucleic acid or nucleic acid fragment including a single nucleotide polymorphism (SNP) from a nucleic acid fragment shown in FIGS. 8A-8H, 9A, 9B, 11, 12, 14A-14D, 15A, 15B, 17A-17C, 18A, 18B, 20A-20C, 21, 23A-23C, 24, 26A-26X, 27A, 27B, 29A-29F, 30A, and 30B hereto, or complements or sequences antisense thereto.

In a still further aspect of the present invention there is provided a method of isolating a nucleic acid or nucleic acid fragment of the present invention including a single nucleotide polymorphism (SNP), said method including sequencing nucleic acid fragments from a nucleic acid library.

The nucleic acid library may be of any suitable type and is preferably a cDNA library.

The nucleic acid fragments may be isolated from recombinant plasmids or may be amplified, for example using polymerase chain reaction.

The sequencing may be performed by techniques known to those skilled in the art.

In a still further aspect of the present invention, there is provided use of nucleic acids or nucleic acid fragments of the present invention including SNP's, and/or nucleotide sequence information thereof, as molecular genetic markers.

In a still further aspect of the present invention there is provided use of a nucleic acid or nucleic acid fragment according to the present invention, and/or nucleotide sequence information thereof, as a molecular genetic marker.

More particularly, nucleic acids or nucleic acid fragments according to the present invention and/or nucleotide sequence information thereof may be used as a molecular genetic marker for quantitative trait loci (QTL) tagging, QTL mapping, DNA fingerprinting and in marker assisted selection, particularly in grasses and cereals. Even more particularly, nucleic acids or nucleic acid fragments according to the present invention and/or nucleotide sequence information thereof may be used as molecular genetic markers in grass and cereal improvement, e.g. tagging QTLs for tolerance to freezing and/or low temperature stress. Even more particularly, sequence information revealing SNPs in allelic variants of the nucleic acids or nucleic acid fragments of the present invention and/or nucleotide sequence information thereof may be used as molecular genetic markers for QTL tagging and mapping and in marker assisted selection, particularly in grasses and cereals.

In a still further aspect of the present invention there is provided a construct including a nucleic acid or nucleic acid fragment according to the present invention. The construct may be a vector.

In a preferred embodiment of this aspect of the invention, the vector may include a regulatory element such as a promoter, a nucleic acid or nucleic acid fragment according to the present invention and a terminator; said regulatory element, nucleic acid or nucleic acid fragment and terminator being operatively linked.

In a further preferred embodiment of this aspect of the invention, the vector may include a regulatory element according to the present invention, a further nucleic acid molecule and a terminator; said regulatory element, further nucleic acid molecule and terminator being operatively linked.

In a still further preferred embodiment of this aspect of the invention, the vector may include a regulatory element according to the present invention, a nucleic acid or nucleic acid fragment according to the present invention and a terminator, said regulatory element, nucleic acid or nucleic acid fragment and terminator being operatively linked.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, or integrative or viable in the plant cell.

The regulatory element and terminator may be of any suitable type and may be endogenous to the target plant cell or may be exogenous, provided that they are functional in the target plant cell.

In another embodiment, the construct or vector may include more than one nucleic acid. The nucleic acids within the same construct or vector may have identical or differing sequences. In one preferred embodiment, the construct or vector has at least two nucleic acids encoding functionally similar enzymes. In a particularly preferred embodiment, each further nucleic acid molecule has one or more upstream regulatory elements and one or more downstream terminators, although expression of more than one further nucleic acid molecule from an upstream regulatory element or termination of more than one further nucleic acid molecule from a downstream terminator(s) is not precluded.

Preferably the regulatory element is a promoter. A variety of promoters which may be employed in the constructs and vectors of the present invention are well known to those skilled in the art. Factors influencing the choice of promoter include the desired tissue specificity of the vector, and whether constitutive or inducible expression is desired and the nature of the plant cell to be transformed (eg. monocotyledon or dicotyledon). Particularly suitable promoters include but are not limited to the constitutive Cauliflower Mosaic Virus 35S (CaMV 35S) promoter and derivatives thereof, the maize Ubiquitin promoter, the rice Actin promoter, and the tissue-specific *Arabidopsis* small subunit (ASSU) promoter. Alternatively, the regulatory element may be a regulatory element according to the present invention.

A variety of terminators which may be employed in the vectors and constructs of the present invention are also well known to those skilled in the art. The terminator may be from the same gene as the promoter sequence or a different gene. Particularly suitable terminators are polyadenylation signals, such as the CaMV 35S polyA and other terminators from the nopaline synthase (nos), the octopine synthase (ocs) and the rbcS genes.

The further nucleic acid molecule may be a sequence, for example a gene or fragment thereof, or sequence antisense thereto, which is capable of modifying plant response to freezing and/or low temperature stress. It may be a nucleic acid or nucleic acid fragment according to the present invention, but is not limited thereto.

The vector, in addition to the regulatory element, the nucleic acid or nucleic acid fragment of the present invention and the terminator, may include further elements necessary for expression of the nucleic acid or nucleic acid fragment, in different combinations, for example vector backbone, origin of replication (ori), multiple cloning sites, recognition sites for recombination events, spacer sequences, enhancers, introns (such as the maize Ubiquitin (Ubi) intron), antibiotic resistance genes and other selectable marker genes [such as the neomycin phosphotransferase (npt2) gene, the hygromycin phosphotransferase (hph) gene, the phosphinothricin acetyltransferase (bar or pat) gene and the gentamycin acetyl transferase (aaacCI) gene], and reporter genes (such as beta-glucuronidase (GUS) gene (gusA) and green fluorescent protein (gfp)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the construct or vector in transformed cells may be determined by other techniques well known in the art, such as PCR (polymerase chain reaction), Southern blot hybridisation analysis, histochemical GUS assays, visual examination including microscopic examination of fluorescence emitted by gfp, northern and Western blot hybridisation analyses.

Those skilled in the art will appreciate that the various components of the construct or vector are operatively linked, so as to result in expression of said nucleic acid or nucleic acid fragment. Techniques for operatively linking the components of the vector of the present invention are well known to those skilled in the art. Such techniques include the use of linkers, such as synthetic linkers, for example including one or more restriction enzyme sites.

The constructs and vectors of the present invention may be incorporated into a variety of plants, including monocotyledons (such as grasses from the genera *Deschampsia, Lolium, Festuca, Paspalum, Pennisetum, Panicum* and other forage and turf grasses, corn, oat, sugarcane, wheat and barley), dicotyledons (such as *Arabidopsis*, tobacco, white clover, red clover, subterranean clover, alfalfa, *eucalyptus*, potato, sugarbeet, canola, soybean, chickpea) and gymnosperms.

Techniques for incorporating the constructs and vectors of the present invention into plant cells (for example by transduction, transfection or transformation) are well known to those skilled in the art. Such techniques include *Agrobacterium*-mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Cells incorporating the constructs and vectors of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, a construct or vector of the present invention.

The plant cell, plant, plant seed or other plant part may be from any suitable species, including monocotyledons, dicotyledons and gymnosperms.

The present invention also provides a plant, plant seed or other plant part, or a plant extract, derived from a plant cell of the present invention.

The present invention also provides a plant, plant seed or other plant part, or a plant extract, derived from a plant of the present invention.

In a further aspect of the present invention there is provided a method of modifying tolerance of freezing and/or low temperature stress in a plant, said method including introducing into said plant an effective amount of a nucleic acid or nucleic acid fragment, construct and/or a vector according to the present invention.

Using the methods and materials of the present invention, the tolerance of freezing and/or low temperature stress in a plant may be increased or decreased or otherwise modified. For example, the tolerance of freezing and/or low temperature stress may be increased or otherwise altered. They may be increased, for example, by incorporating additional copies of a sense nucleic acid or nucleic acid fragment of the present invention. They may be decreased, for example, by incorporating an antisense nucleic acid or nucleic acid fragment of the present invention.

In a further aspect of the present invention there is provided a preparation for transforming a plant comprising at least one nucleic acid according to the present invention. The preparation may contain vectors or other constructs to facilitate administration to and/or transformation of the plant with the nucleic acid.

The present invention will now be more fully described with reference to the accompanying Examples and drawings. It should be understood, however, that the description following is illustrative only and should not be taken in any way as a restriction on the generality of the invention described above.

In the Figures:

FIG. 1. RI assay on total extracts of leaves from non-acclimated (grown at 22° C.) and cold acclimated (5° C.) *D. antarctica*. A, Initial ice crystal structure following snap freezing. B, Ice crystal structure after 16 h incubation at −3° C. Capillary B contains extraction buffer; capillaries 1-7: 1000, 250, 62.5, 15.6, 3.91, 0.977 and 0.244 µg mL$^{-1}$ respectively of total leaf protein. Extracts were either untreated or subject to incubation at 95° C. for 5 min as indicated. Endpoint of RI activity defined as the lowest protein concentration (µg mL$^{-1}$) at which ice crystal structure in B remains unchanged from that in A.

Figures 1, 2A:
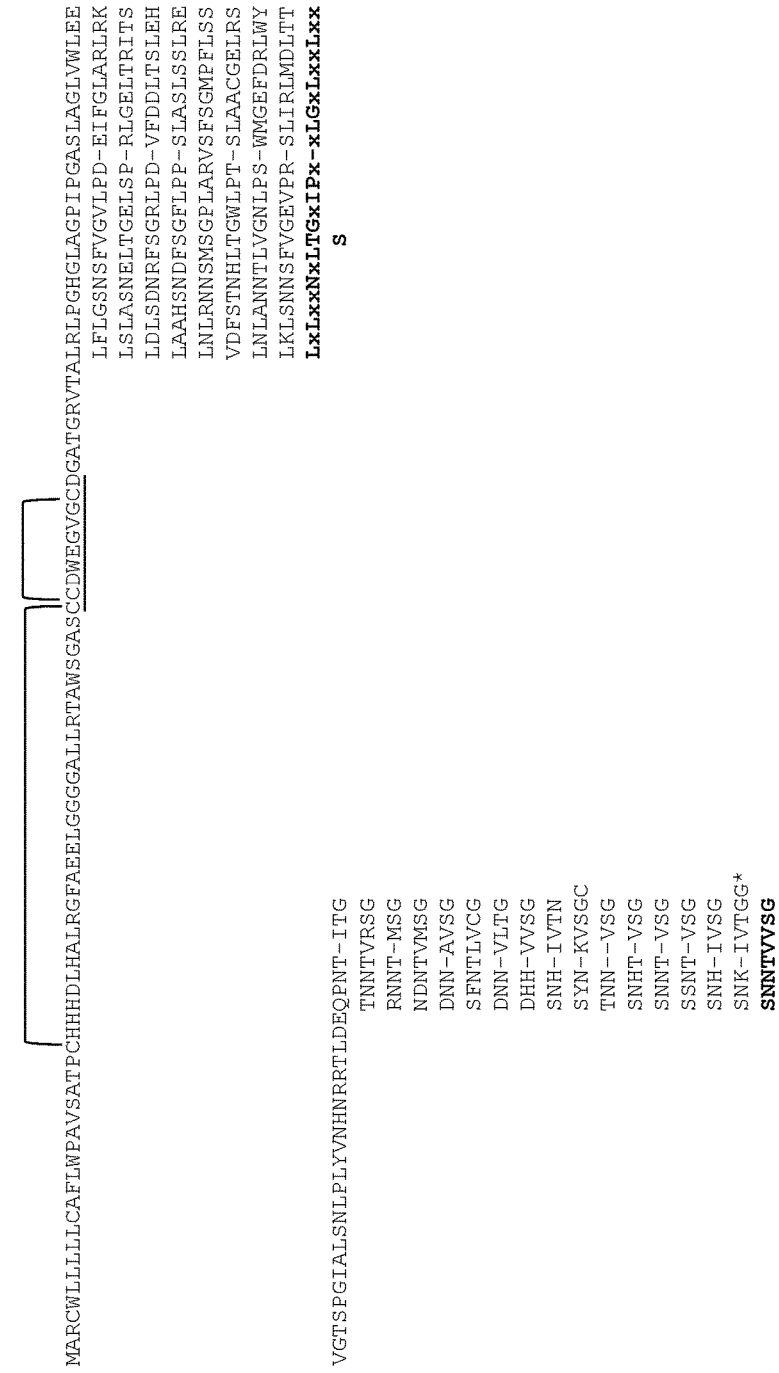
Figures 2, 2B:
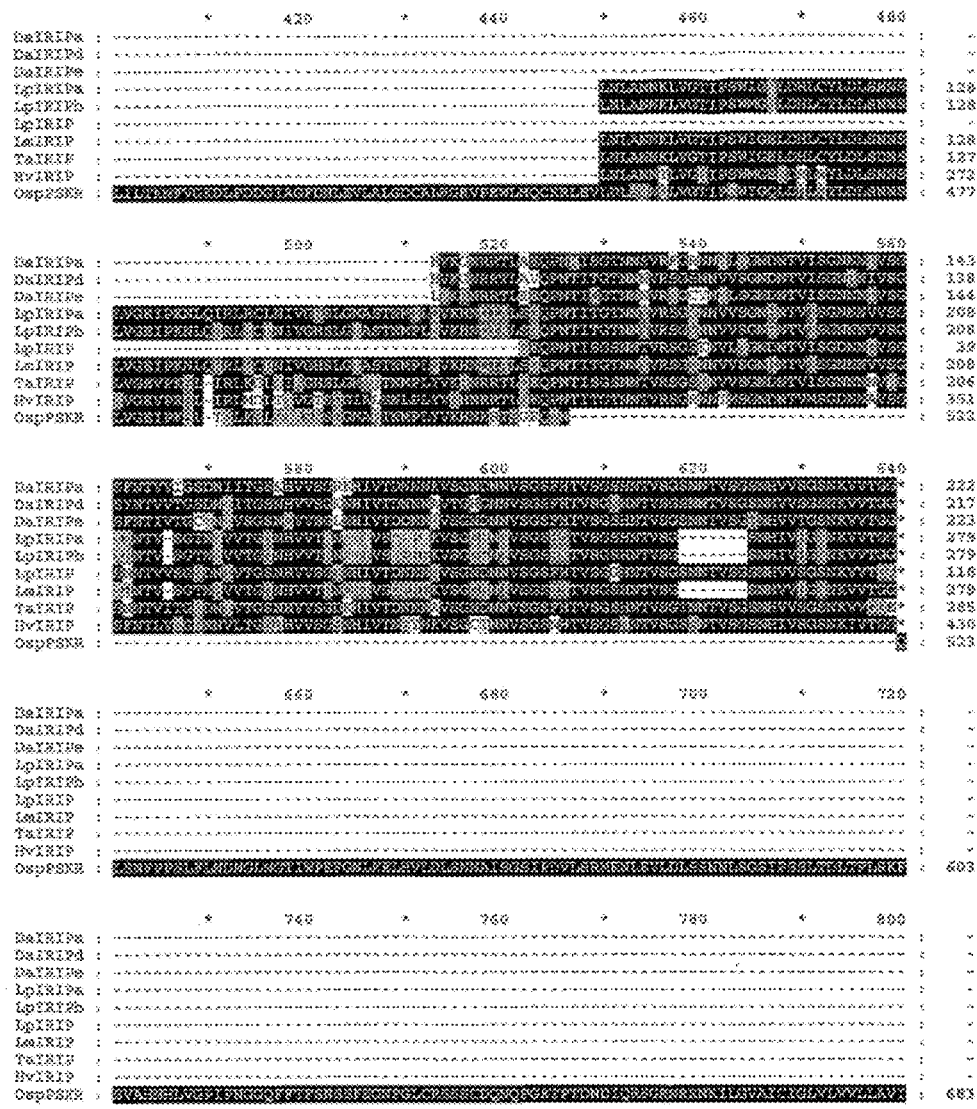
Figure 2C:
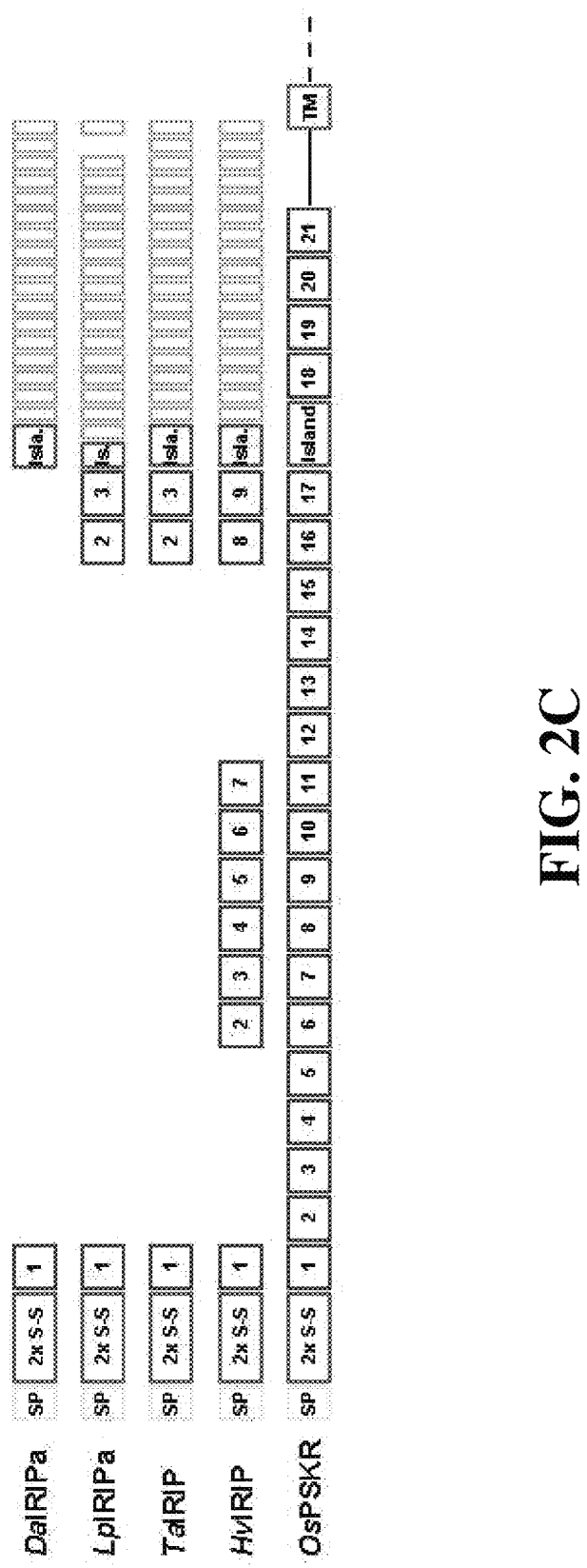
Figure 2D:
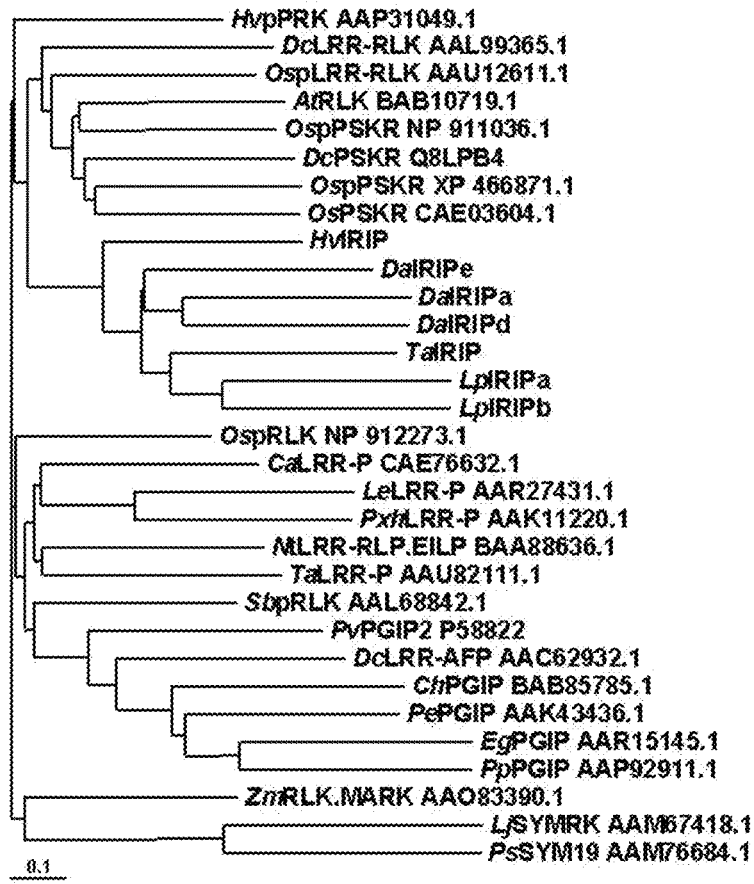

FIGS. 2A-1, 2A-2, 2B-1, 2B-2, 2B-3, 2C, 2D. FIG. 2A-1 and FIG. 2A-2: Repeat structures of representative IRIP orthologues HvIRIP (FIG. 2A-1; SEQ ID NO. 126) and DaIRIPd (FIG. 2A-2; SEQ ID NO. 31). Four cysteine residues conserved in LRR proteins, and predicted to form two disulphide bridges are shown, connected by lines to show predicted bridges. A highly conserved 9 amino acid motif including 3 of these cysteine residues is underlined. Consensus sequences for plant LRRs (SEQ ID NOs. 128 and 143) (Kobe and Kajava (2001) *Curr Opin Struct Biol* 11:725), and the IRIP repeat (SEQ ID NO. 141) are shown in bold below the tandem repeat alignments, and identical residues are apparent. FIG. 2B-1; FIG. 2B-2; FIG. 2B-3: Sequence alignment of IRIP orthologues and a putative PSKR orthologue from *Oryza sativa*. Sequences include LpIRIP (Sidebottom, et al. (2000 *Nature* 406:256)) (SEQ ID NO. 124), predicted IRIP orthologue TaIRIP derived from assembly of *T. aestivum* sequences in the NCBI EST database (SEQ ID NO. 125), predicted HvIRIP derived from assembly of *H. vulgare* sequences in the NCBI EST database (SEQ ID NO. 126), predicted LmIRIP derived from assembly of *L. multiflorum* sequences in the NCBI EST database (SEQ ID NO. 142), and OsPSKR a putative PSKR orthologue from *Oryza sativa* (NP_911036) (SEQ ID NO. 127). Sequences of the present invention are DaIRIPa (SEQ ID NO. 17), DaIRIPd (SEQ ID NO. 31) DaIRIPe.7 (SEQ ID NO. 38), LpIRIPa (SEQ ID NO. 102) and LpIRIPb (SEQ ID NO. 120). Identical and conserved residues are apparent from the alignments. Four invariantly conserved cysteine residues are also apparent. FIG. 2C: Schematic of domain organisation in IRIP orthologues and OsPSKR. SP: signal peptide; 2× S-S; domain predicted to form 2 disulphide bridges; LRRs numbered; Island/Isla/Is.: island domain; IRIP repeats unlabelled; TM: transmembrane domain. FIG. 2D: Phylogenetic tree of IRIP orthologues and LRR proteins. Branch lengths are proportional to the number of amino acid substitutions per site (indicated by scale bar). LRR proteins include accession number as suffix.

FIG. 3. Structural modelling of IRIPs. Panel A, Theoretical structure of DaIRIPa aligned along the prism face of ice (parallel to the a-axis). Panel B, Theoretical structure of LpIRIPa aligned along the prism face of ice (parallel to the a-axis). Cysteine residues at positions 120 and 143 have been modelled to participate in an additional disulphide bond, relative to DaIRIPa. Panel C, Ribbon backbone diagram of DaIRIPa highlighting the amino acid residue composition of the two putative ice binding surfaces, side "A" and side "B". Panel D, Cross-sectional view of ribbon backbone of 2 β-roll loops of DaIRIPa showing positions of amino acid residue side chains.

Figure 4:
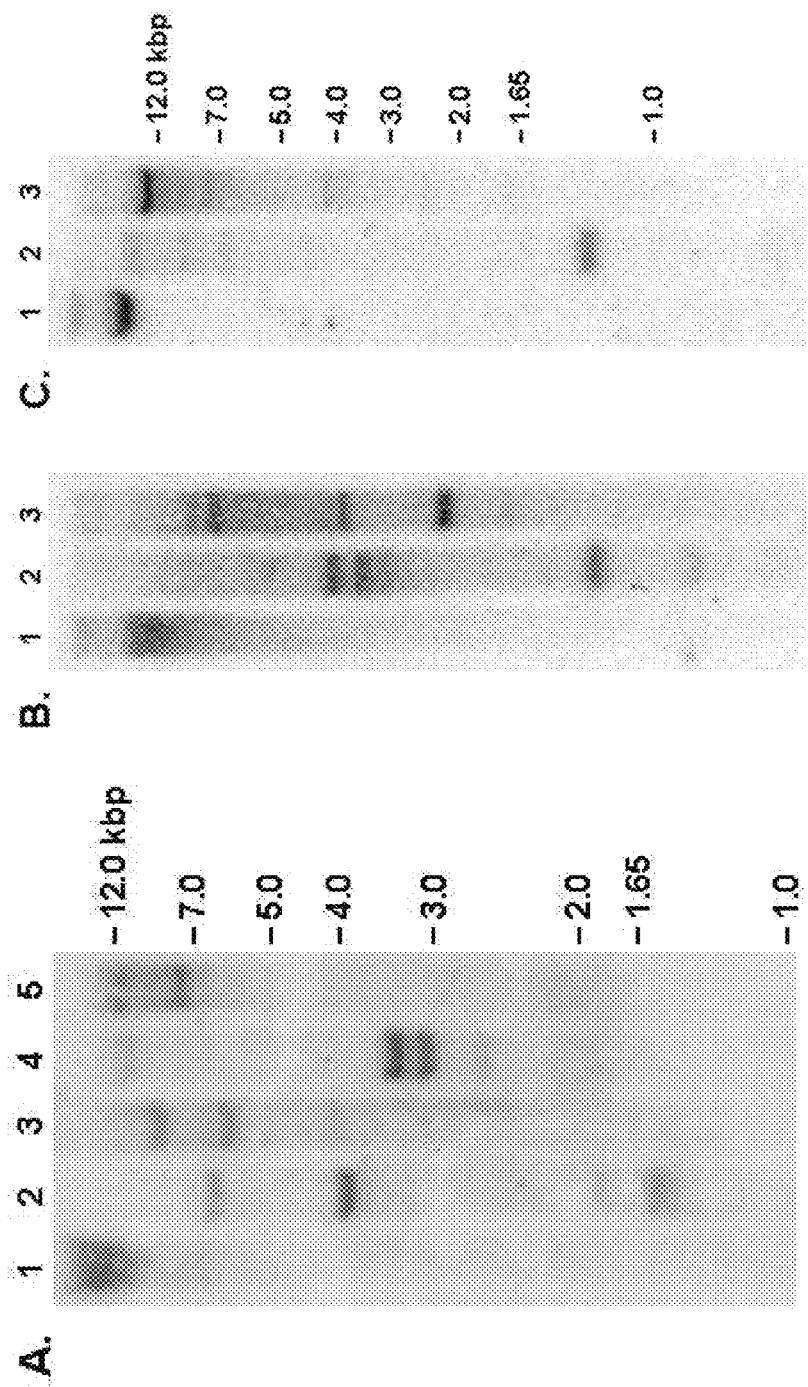

FIG. 4. Genomic organisation of IRIP genes. A, *D. antarctica* genomic Southern probed with DaIRIPe. B, *L. perenne* polygenic genomic Southern probed with LpIRIPa. C, *L. perenne* isogenic genomic Southern probed with LpIRIPa. 1: Undigested; 2: SphI; 3: KpnI; 4: HindIII; 5: BamHI.

Figure 5:
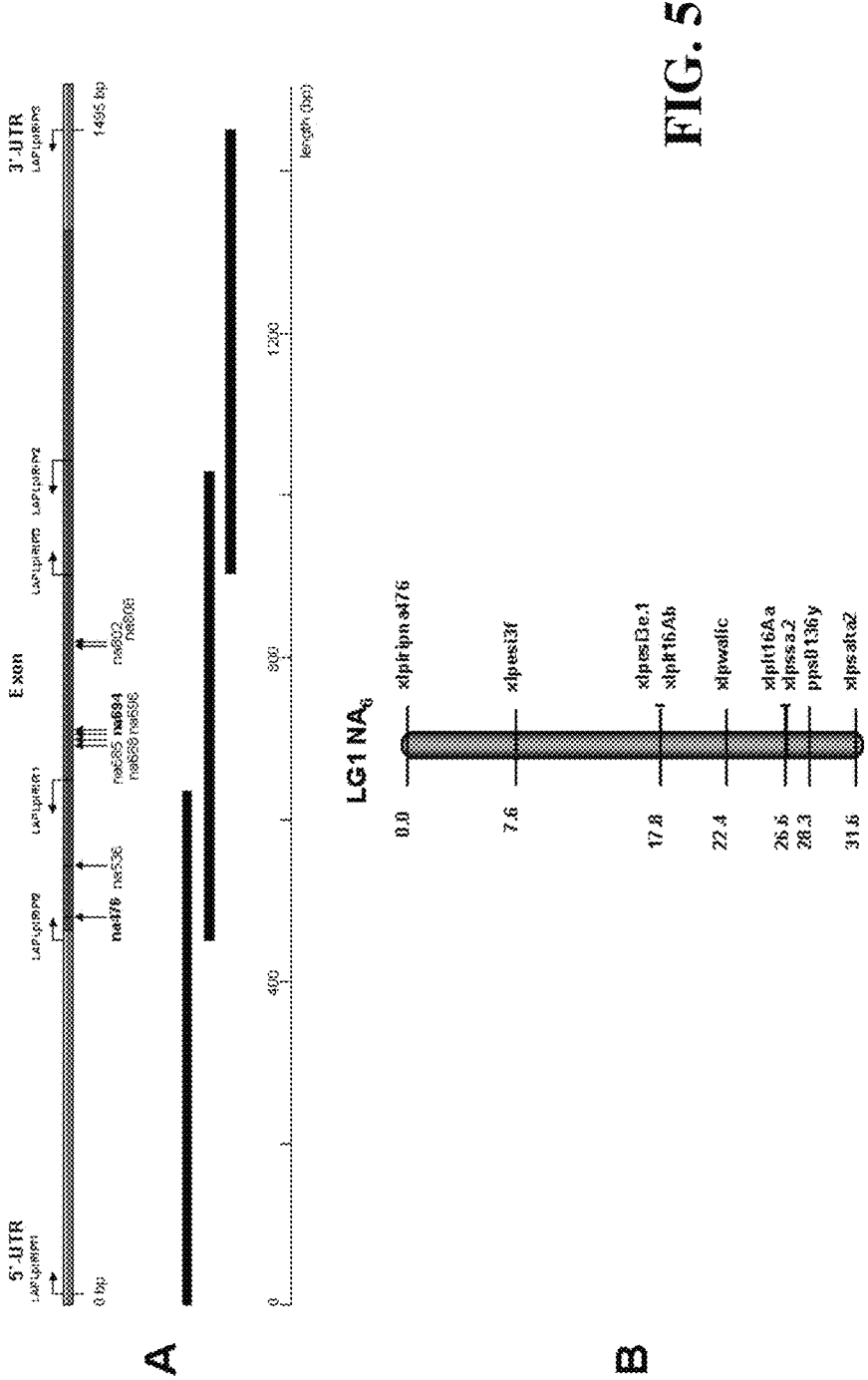

FIG. 5. SNP-based genetic mapping. A, Distribution of locus-specific amplification primers, genomic amplicons and putative SNP loci across the components of the LpIRIPa transcriptional unit. LpIRIP SNPs are indicated using the nomenclature na (number), indicating that the SNP was identified between NA$_6$ parental haplotypes, and the relevant base pair coordinate. SNPs derived from single gene copies that segregate in the F$_1$ progeny are shown in bold, while SNPs that potentially discriminate between paralogous gene copies are shown in normal text. B, Genetic map order in the upper part of the LG1 of the NA$_6$ parental genetic map, showing the LpIRIPNA476-detected SNP locus.

Figure 6:
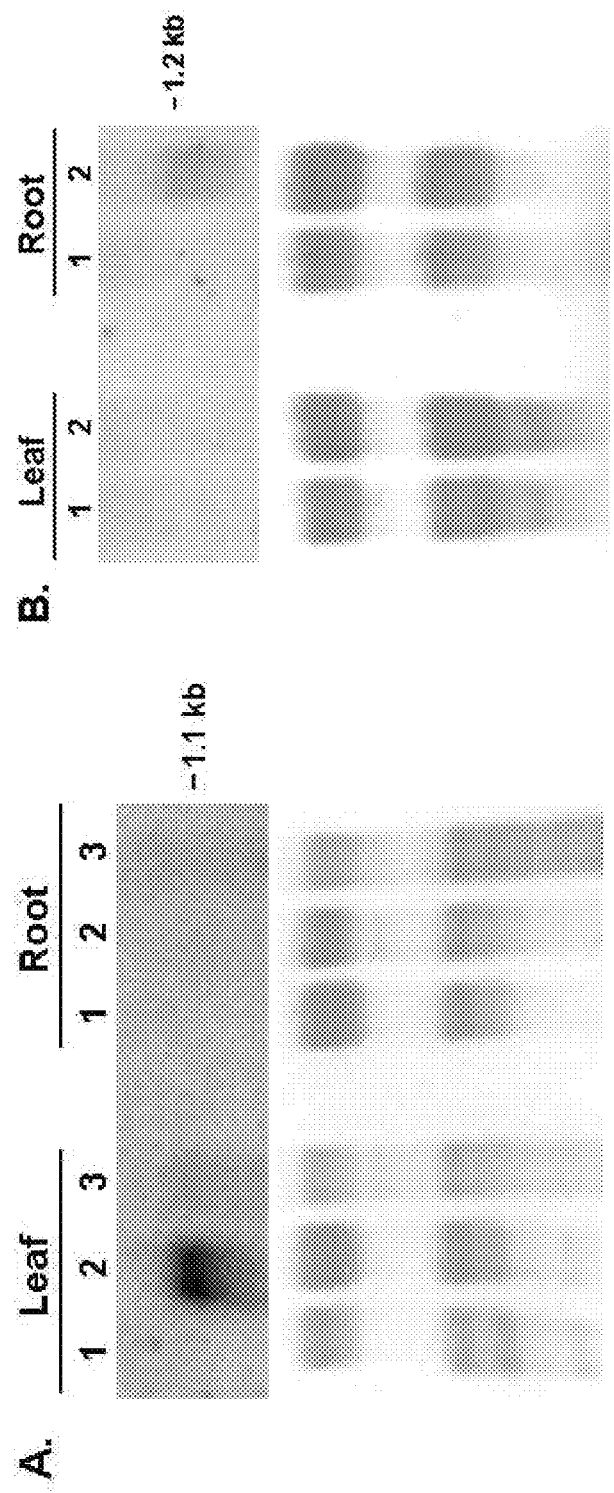

FIG. 6. Analysis of IRIP gene expression in response to temperature. A, Northern blot of RNA from *D. antarctica* leaves and roots grown at 22, 4, and −16° C., probed with DaIRIPe. B, Northern blot of RNA from *L. perenne* leaves and roots grown at 22 and 4° C., probed with LpIRIPa.

Figure 7:
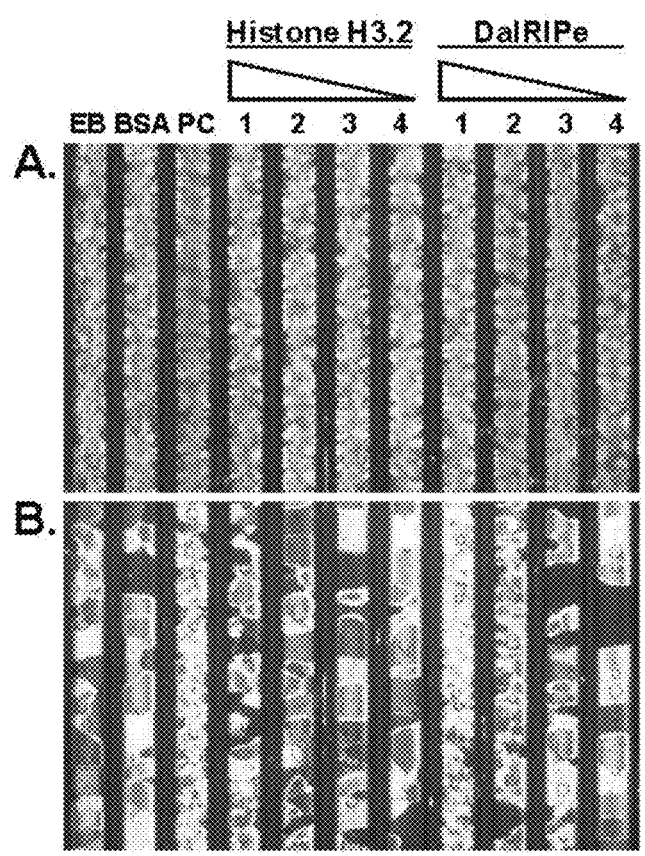

FIG. 7. RI assay on total extracts of *E. coli* expressing a putative orthologue of histone H3.2 and DaIRIPe. A, Initial ice crystal structure following snap freezing. B, Ice crystal structure after 16 h incubation at −3° C. Capillary EB contains extraction buffer; capillary BSA 1000 µg mL$^{-1}$ bovine serum albumin; capillary PC cold acclimated *D. antarctica* leaf extract as positive control; capillaries 1-4: 400, 100, 25 and 6.25 µg mL$^{-1}$ respectively of total extracts of *E. coli*.

Figure 8A:
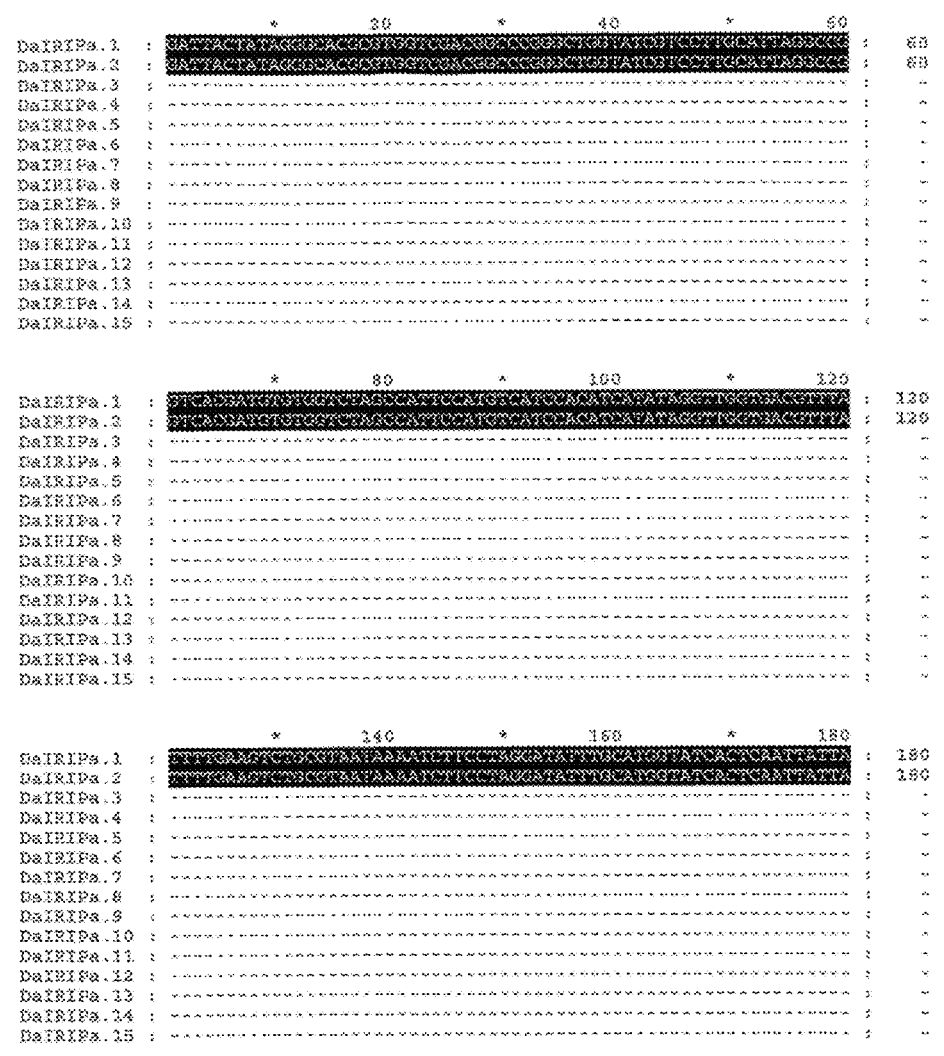
Figure 8B:
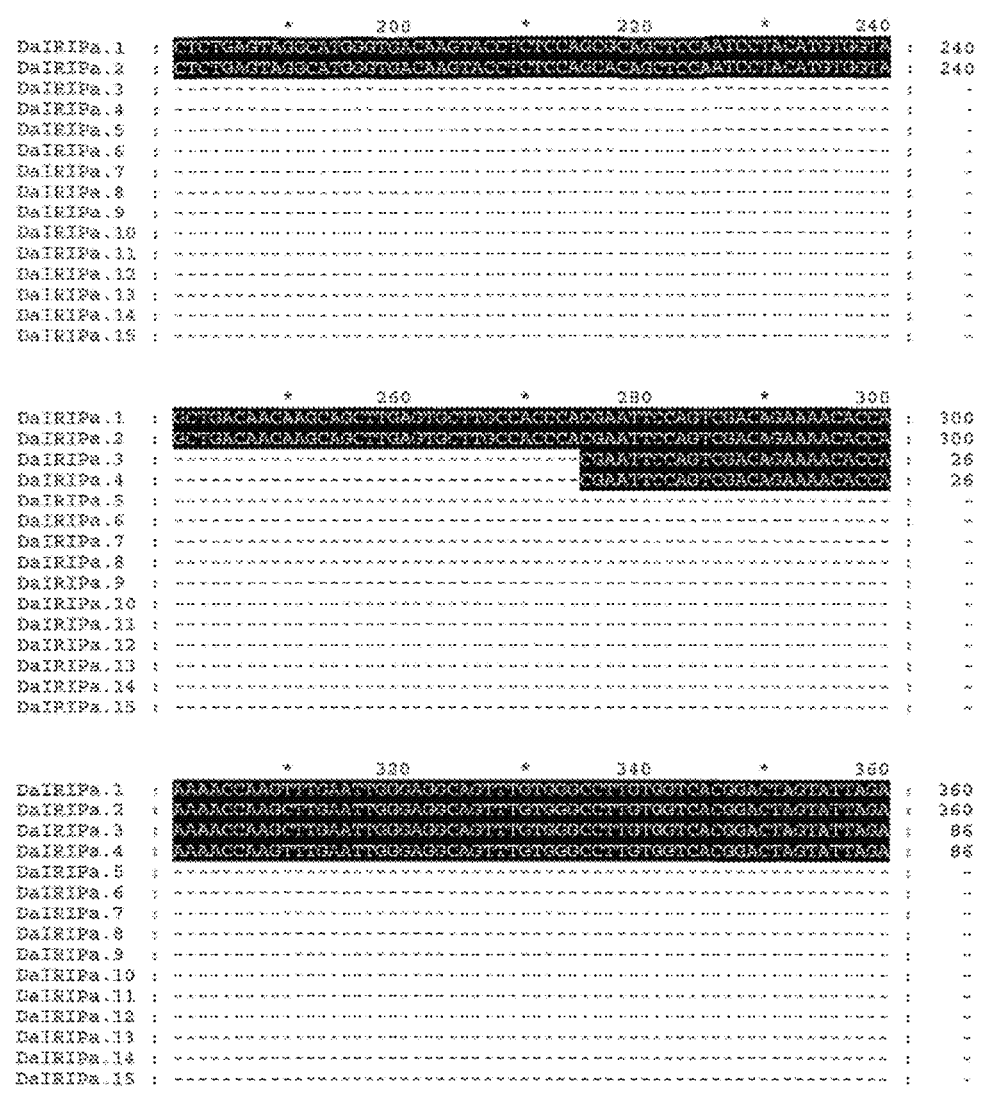
Figure 8C:
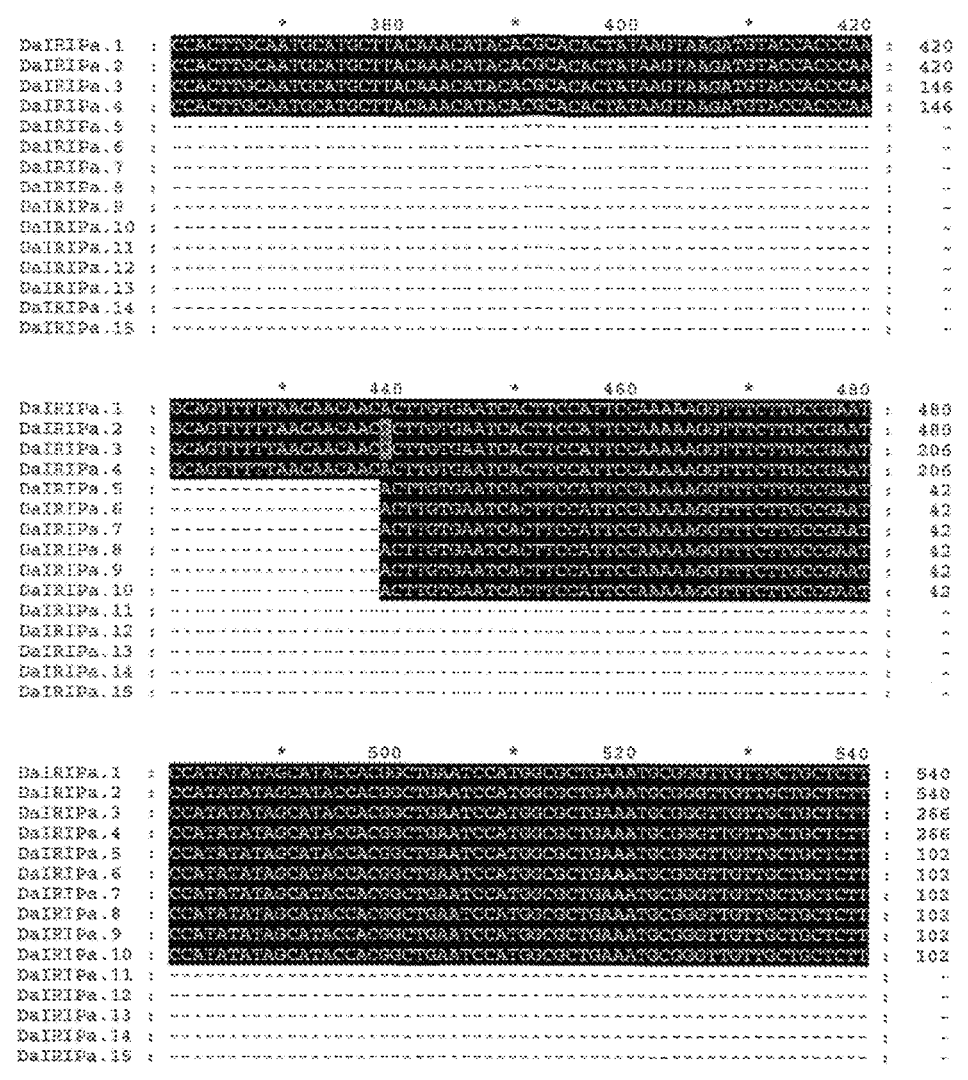
Figure 8D:
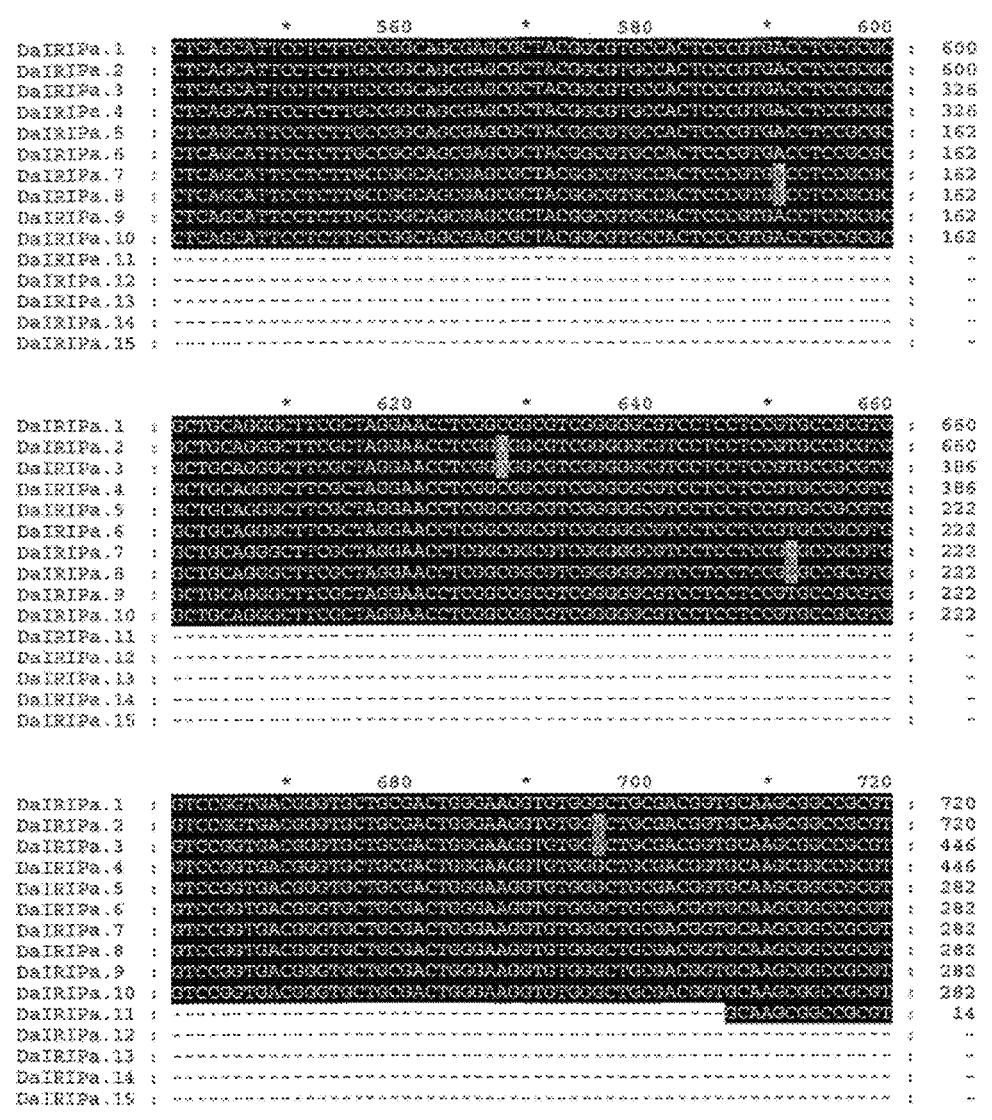
Figure 8E:
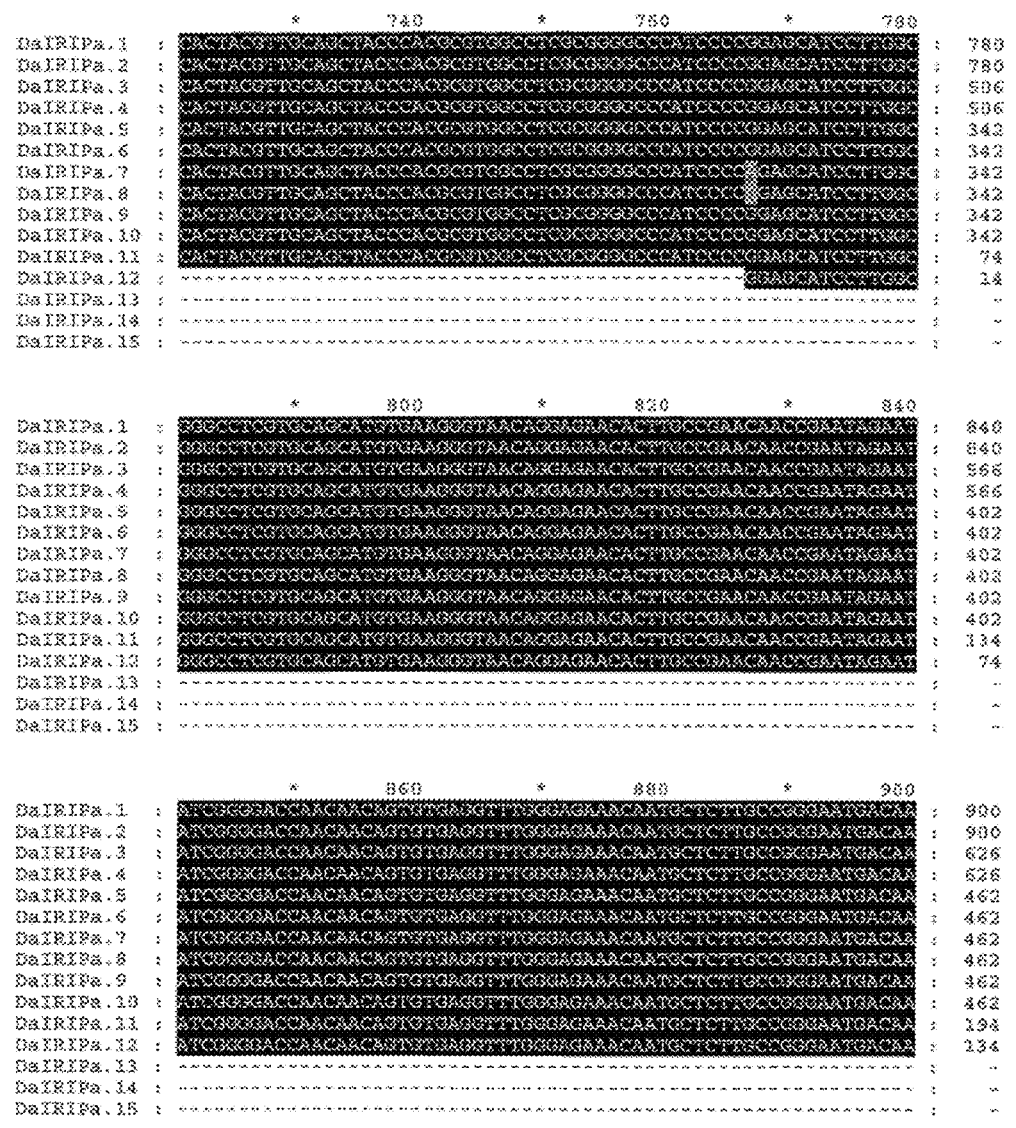
Figure 8F:
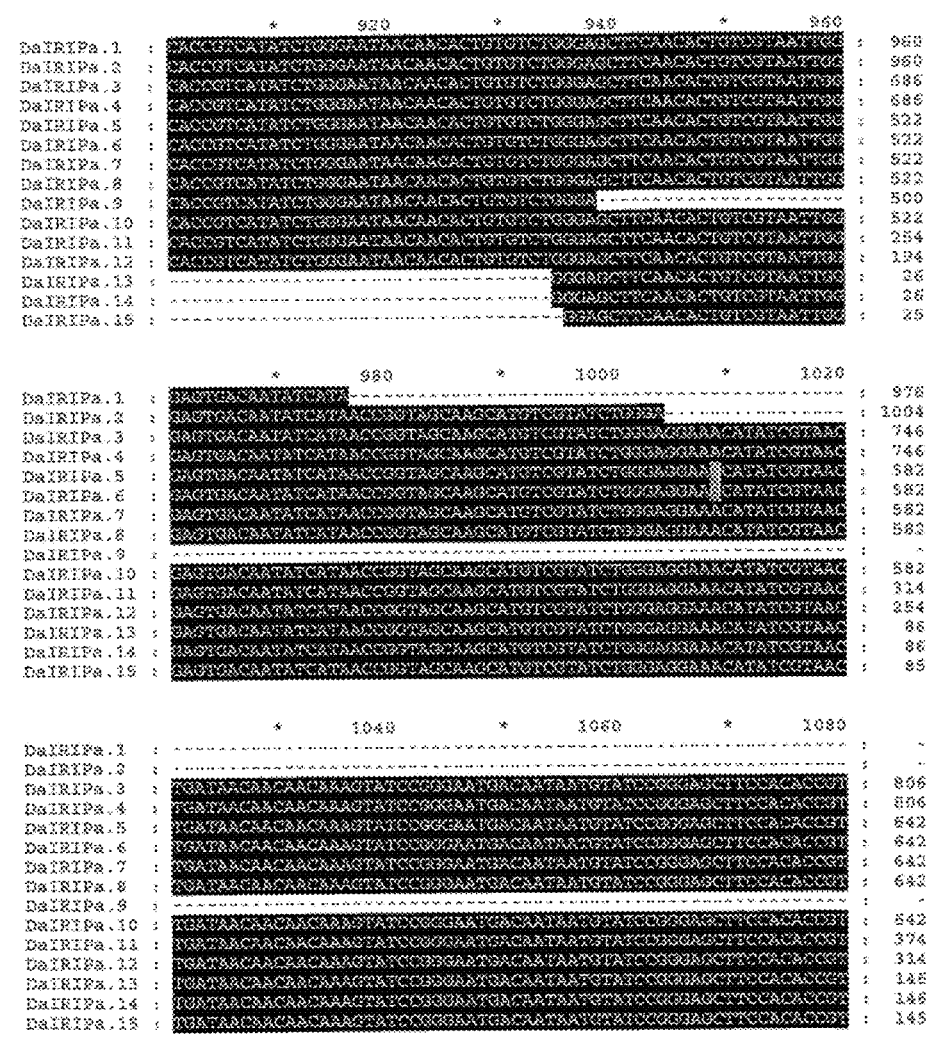
Figure 8G:
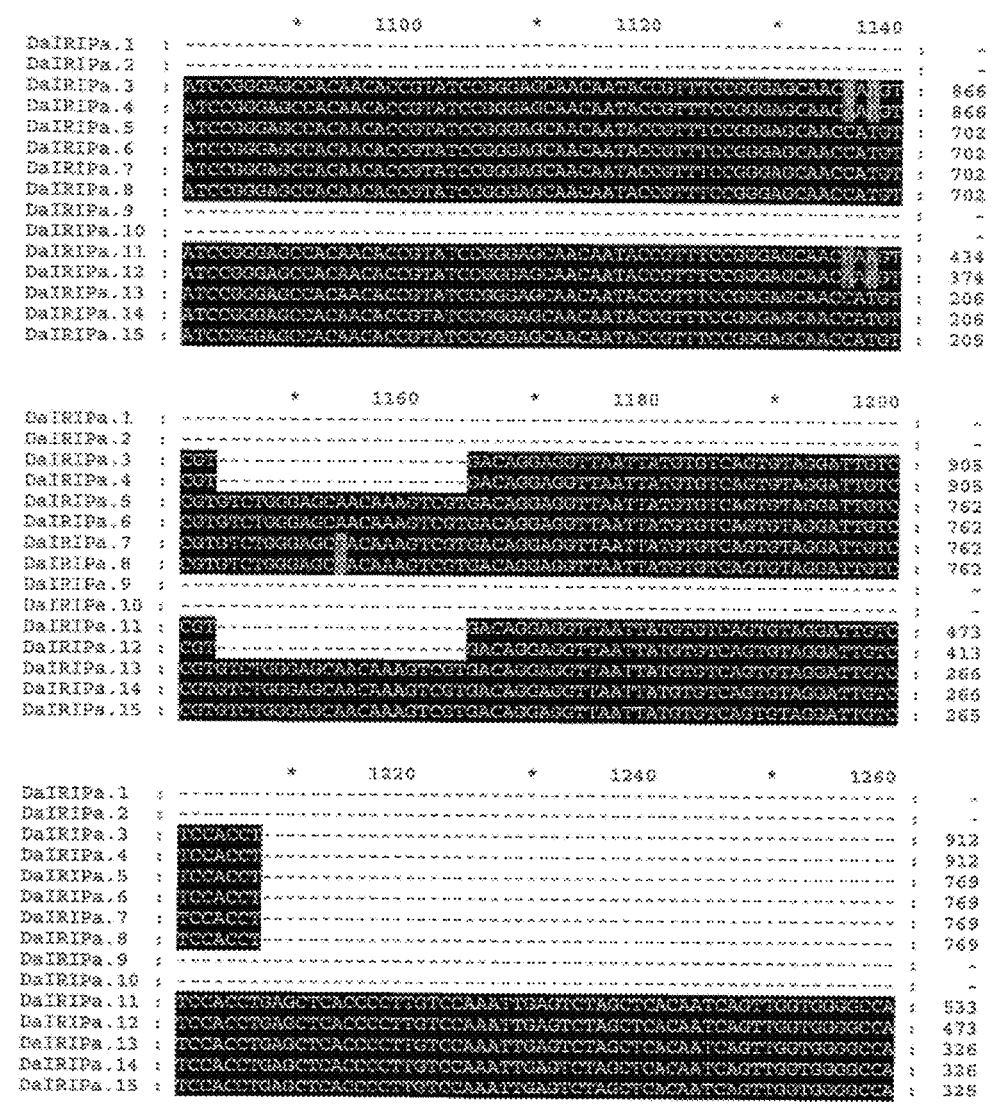
Figure 8H:
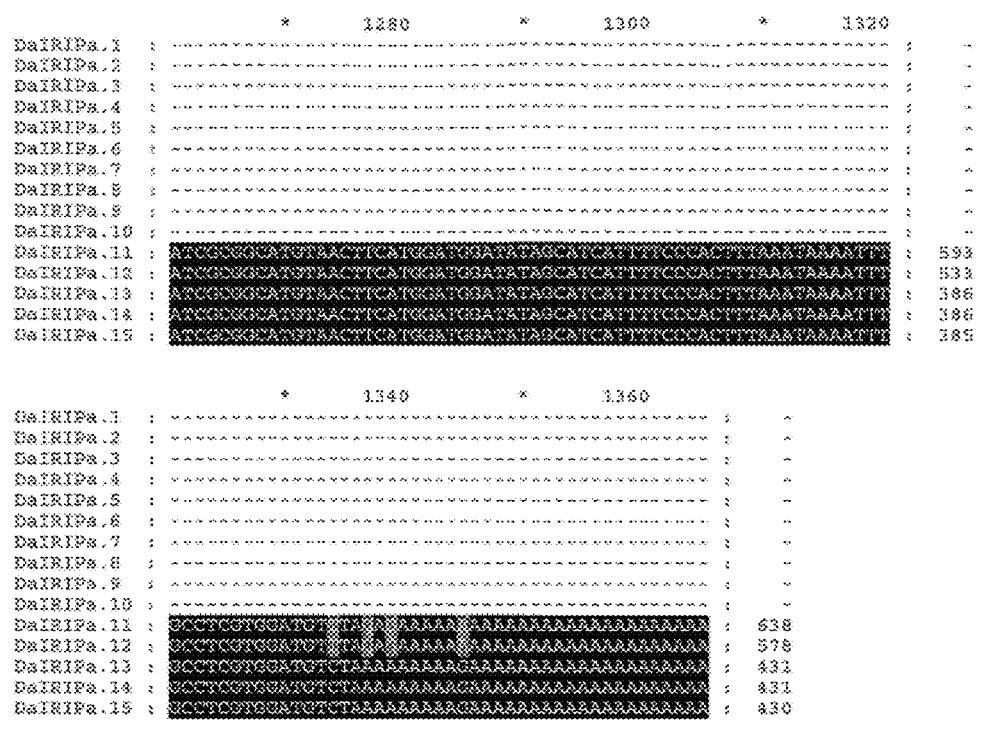

FIG. 8A to FIG. 8H. Nucleotide sequences of the nucleic acid fragments contributing to the consensus contig sequence DaIRIPa (SEQ ID NOs. 1-15)

FIG. 9A to FIG. 9B. Consensus nucleotide sequence of DaIRIPa (SEQ ID NO. 16)

FIG. 10. Deduced amino acid sequence of DaIRIPa (SEQ ID NO. 17)

FIG. 11. Nucleotide sequences of the nucleic acid fragments contributing to the consensus contig sequence DaIRIPb (SEQ ID NOs. 18-20)

FIG. 12. Consensus nucleotide sequence of DaIRIPb (SEQ ID NO. 21)

FIG. 13. Deduced amino acid sequence of DaIRIPb (SEQ ID NO. 22)

FIG. 14A to FIG. 14D. Nucleotide sequences of the nucleic acid fragments contributing to the consensus contig sequence DaIRIPd (SEQ ID NOs. 23-29)

FIG. 15A to FIG. 15B. Consensus nucleotide sequence of DaIRIPd (SEQ ID NO. 30)

FIG. 16. Deduced amino acid sequence of DaIRIPd (SEQ ID NO. 31)

FIG. 17A to FIG. 17C Nucleotide sequences of the nucleic acid fragments contributing to the consensus contig sequence DaIRIPe7 (SEQ ID NOs. 32-36)

FIG. 18A to FIG. 18B. Consensus nucleotide sequence of DaIRIPe7 (SEQ ID NO. 37)

FIG. 19. Deduced amino acid sequence of DaIRIPe7 (SEQ ID NO. 38)

FIG. 20A to FIG. 20C. Nucleotide sequences of the nucleic acid fragments contributing to the consensus contig sequence DaIRIPe8 (SEQ ID NOs. 39-44)

FIG. 21. Nucleotide sequence of DaIRIPe8 (SEQ ID NO. 45)

FIG. 22. Deduced amino acid sequence of DaIRIPe8 (SEQ ID NO. 46)

FIG. 23A to FIG. 23C. Nucleotide sequences of the nucleic acid fragments contributing to the consensus contig sequence DaIRIPf (SEQ ID NOs. 47-52)

FIG. 24. Consensus nucleotide sequence of DaIRIPf (SEQ ID NO. 53)

FIG. 25. Deduced amino acid sequence of DaIRPf (SEQ ID NO. 54)

FIG. 26A to FIG. 26X. Nucleotide sequences of the nucleic acid fragments contributing to the consensus contig sequence LpIRIPa (SEQ ID NOs. 55-100)

FIG. 27A to FIG. 27B. Consensus nucleotide sequence of LpIRIPa (SEQ ID NO. 101)

FIG. 28. Deduced amino acid sequence of LpIRIPa (SEQ ID NO. 102)

FIG. 29A to FIG. 29F. Nucleotide sequences of the nucleic acid fragments contributing to the consensus contig sequence LpIRIPb (SEQ ID NOs. 103-118)

FIG. 30A to FIG. 30B. Consensus nucleotide sequence of LpIRIPb (SEQ ID NO. 119)

FIG. 31. Deduced amino acid sequence of LpIRIPb (SEQ ID NO. 120)

FIG. 32. Nucleotide sequence of promoter region of DaIRIPa extending to the initiating ATG (underlined) (SEQ ID NO. 121)

FIG. 33. Nucleotide sequence of promoter region of DaIRIPd extending to the initiating ATG (underlined) (SEQ ID NO. 122)

FIG. 34. Nucleotide sequence of promoter region of LpIRIPa extending to the initiating ATG (underlined) (SEQ ID NO. 123)

Figure 35:
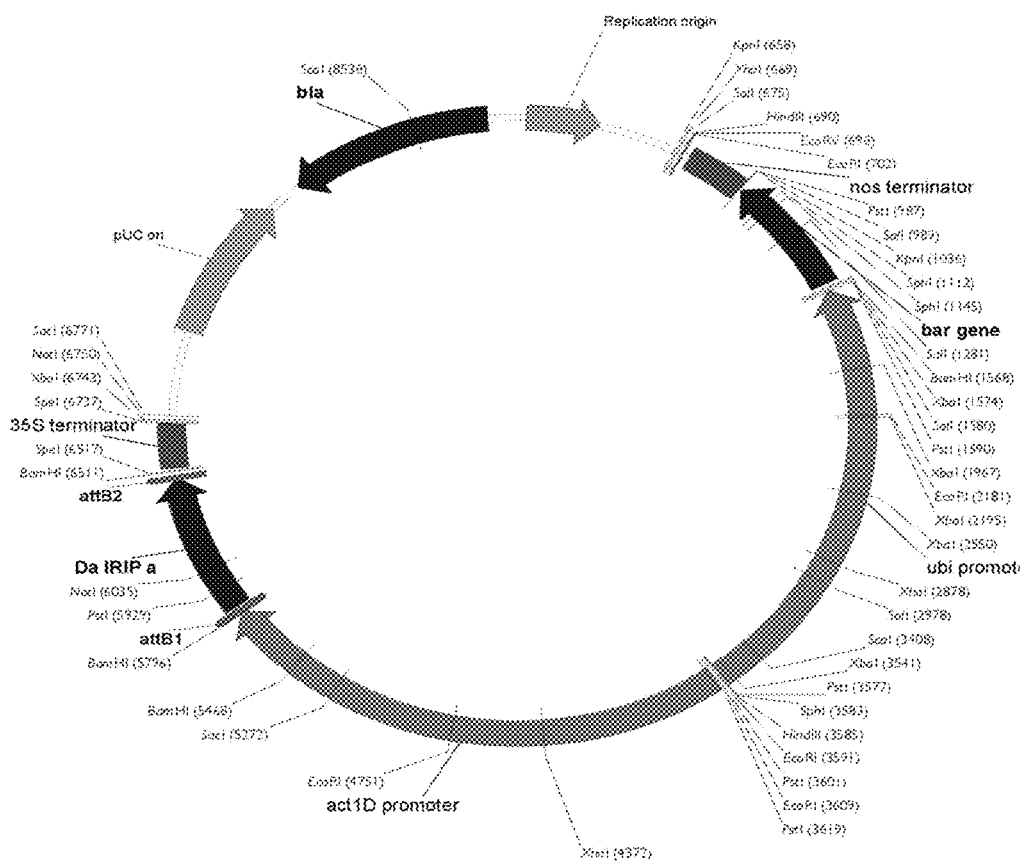

FIG. 35. Plasmid map of vector used for DaIRIPa gain of function biolistic transformation of wheat.

Figure 36:
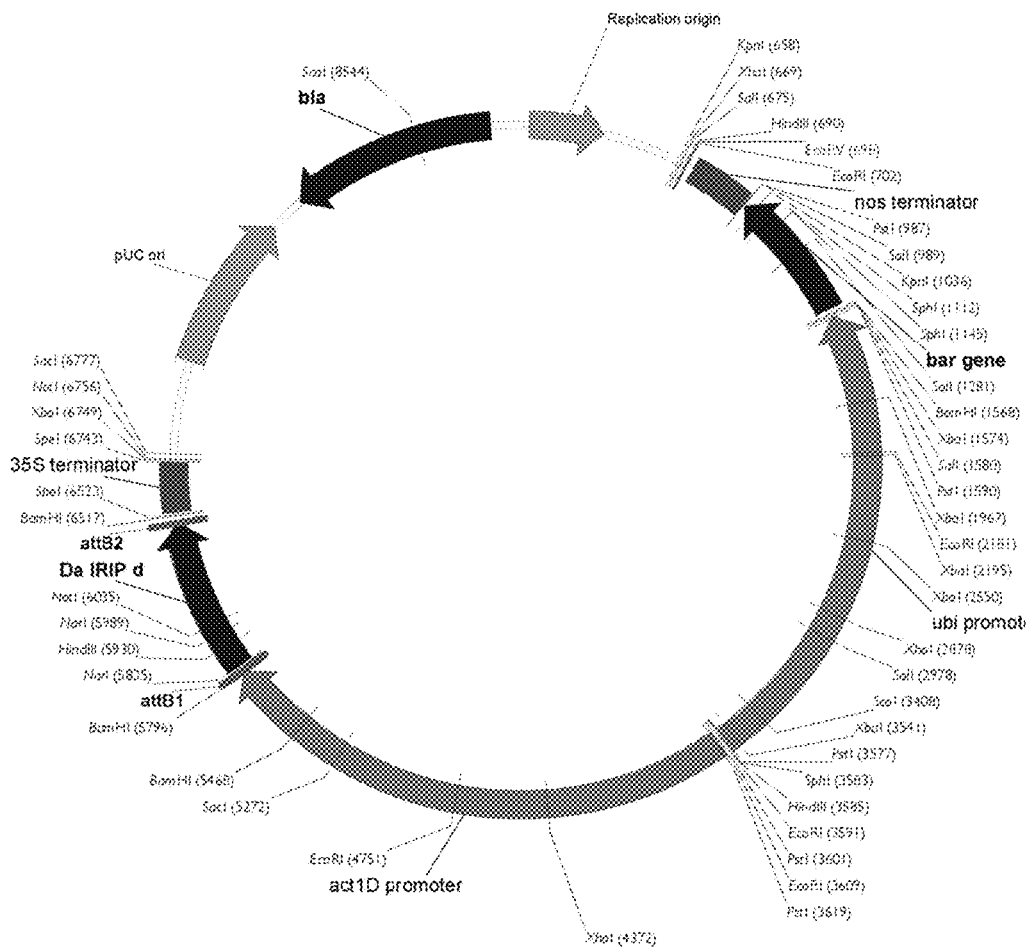

FIG. 36. Plasmid map of vector used for DaIRIPd gain of function biolistic transformation of wheat.

Figure 37:
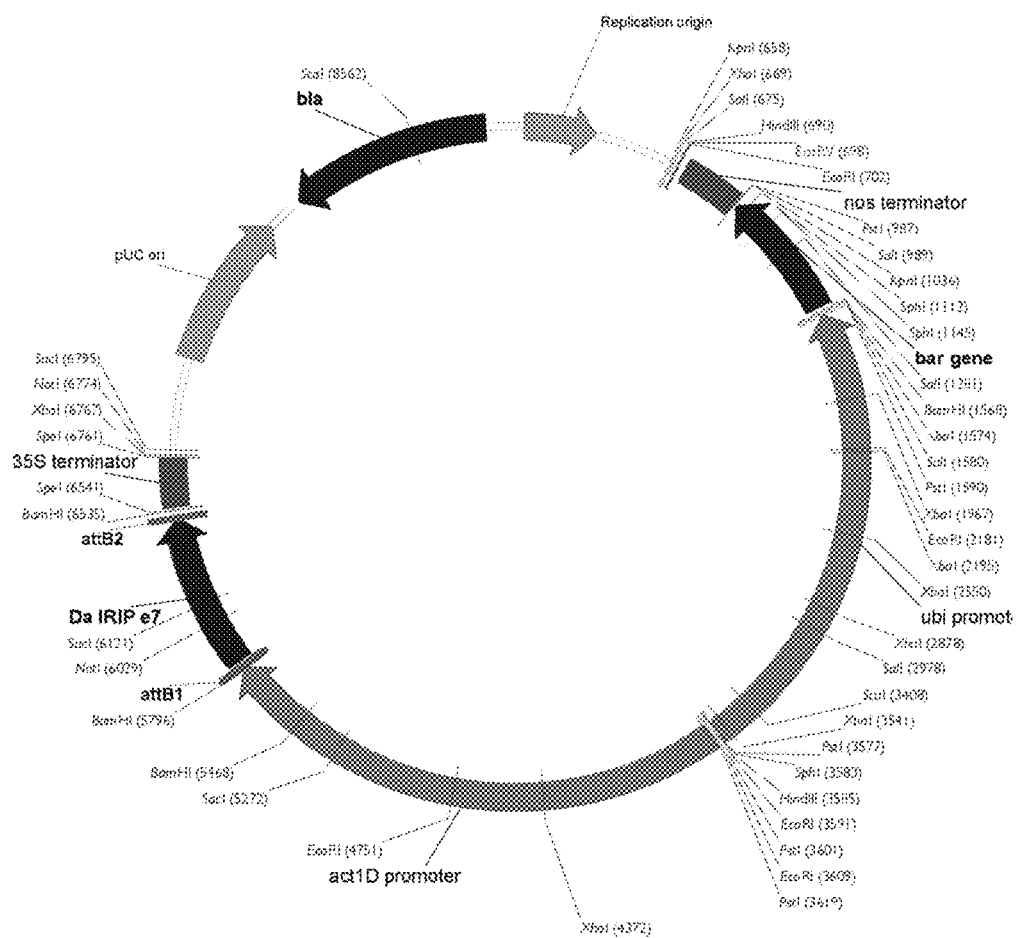

FIG. 37. Plasmid map of vector used for DaIRIPe7 gain of function biolistic transformation of wheat.

Figure 38:
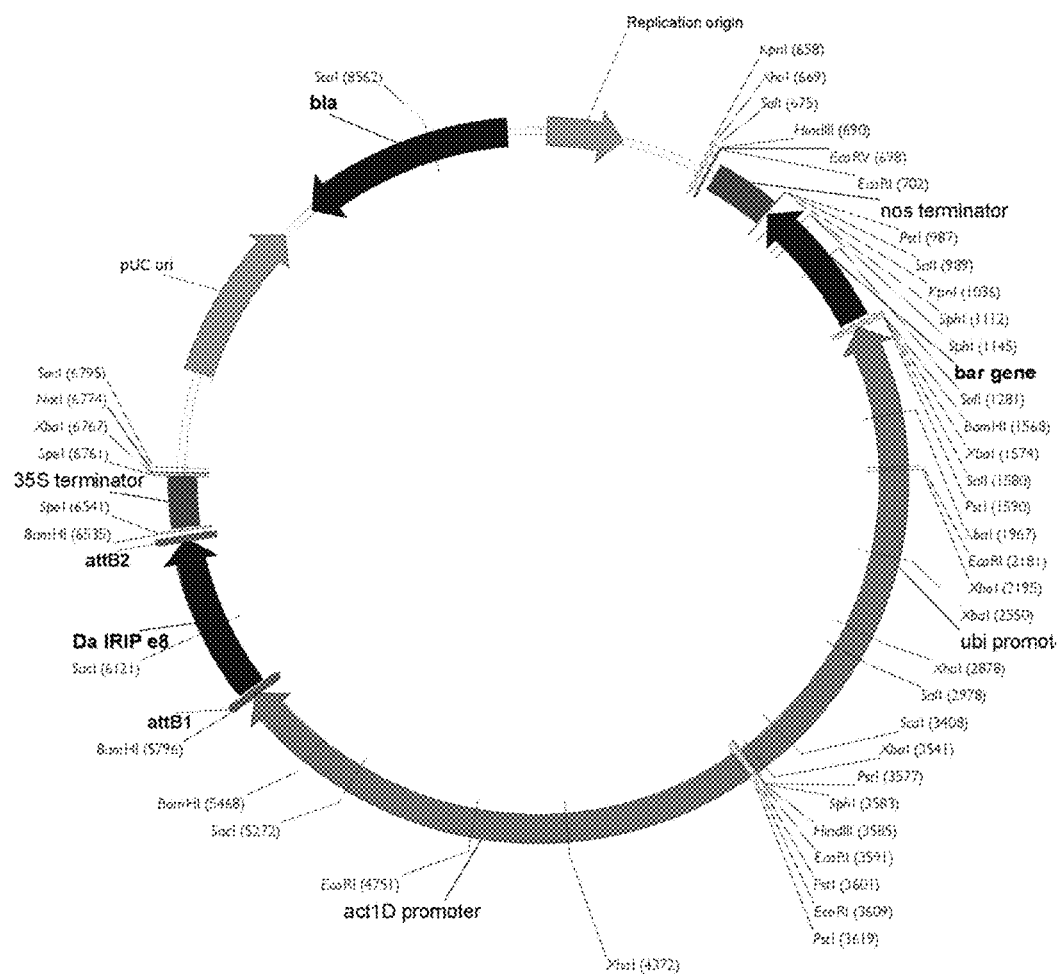

FIG. 38. Plasmid map of vector used for DaIRIPe8 gain of function biolistic transformation of wheat.

Figure 39:
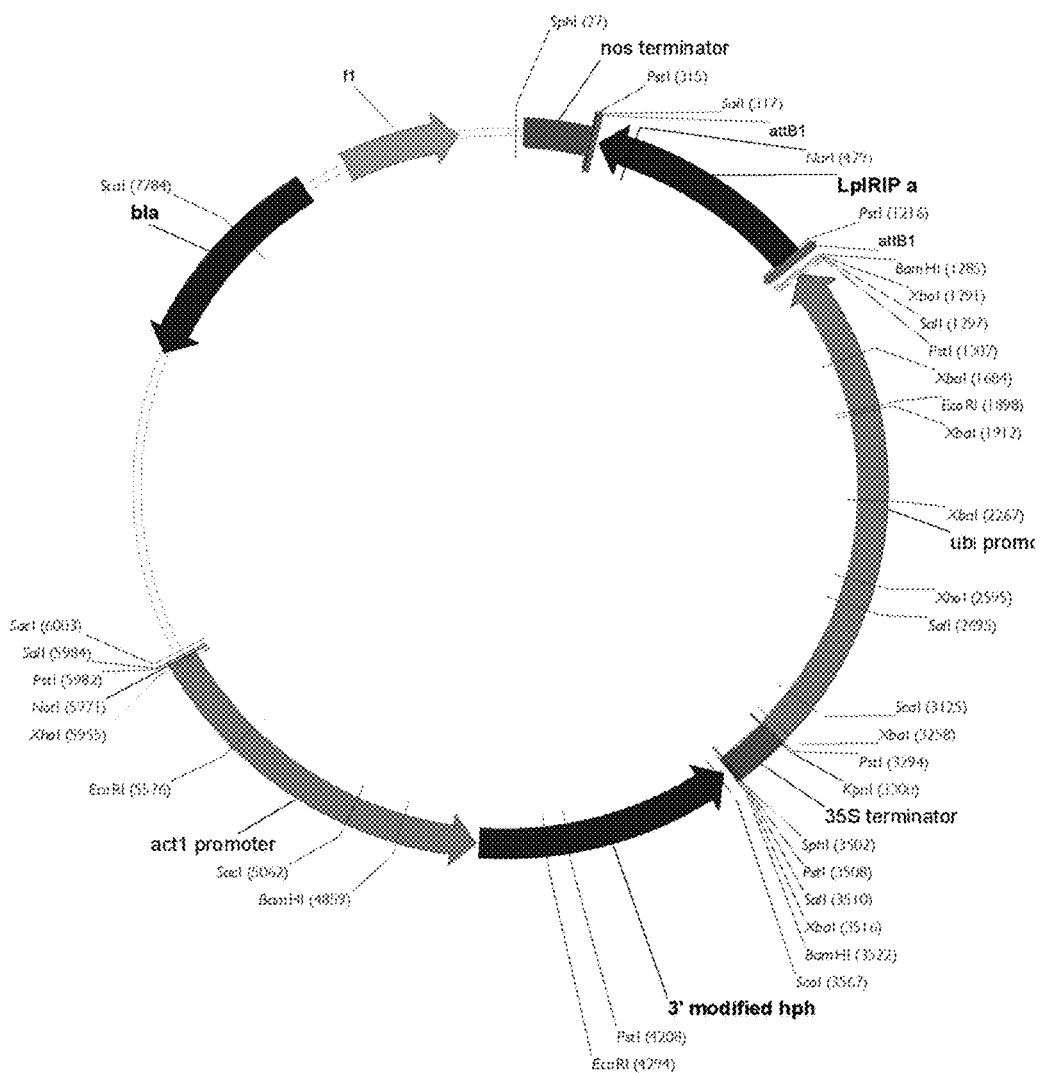

FIG. 39. Plasmid map of vector used for LpIRIPa gain of function biolistic transformation of ryegrass.

Figure 40:
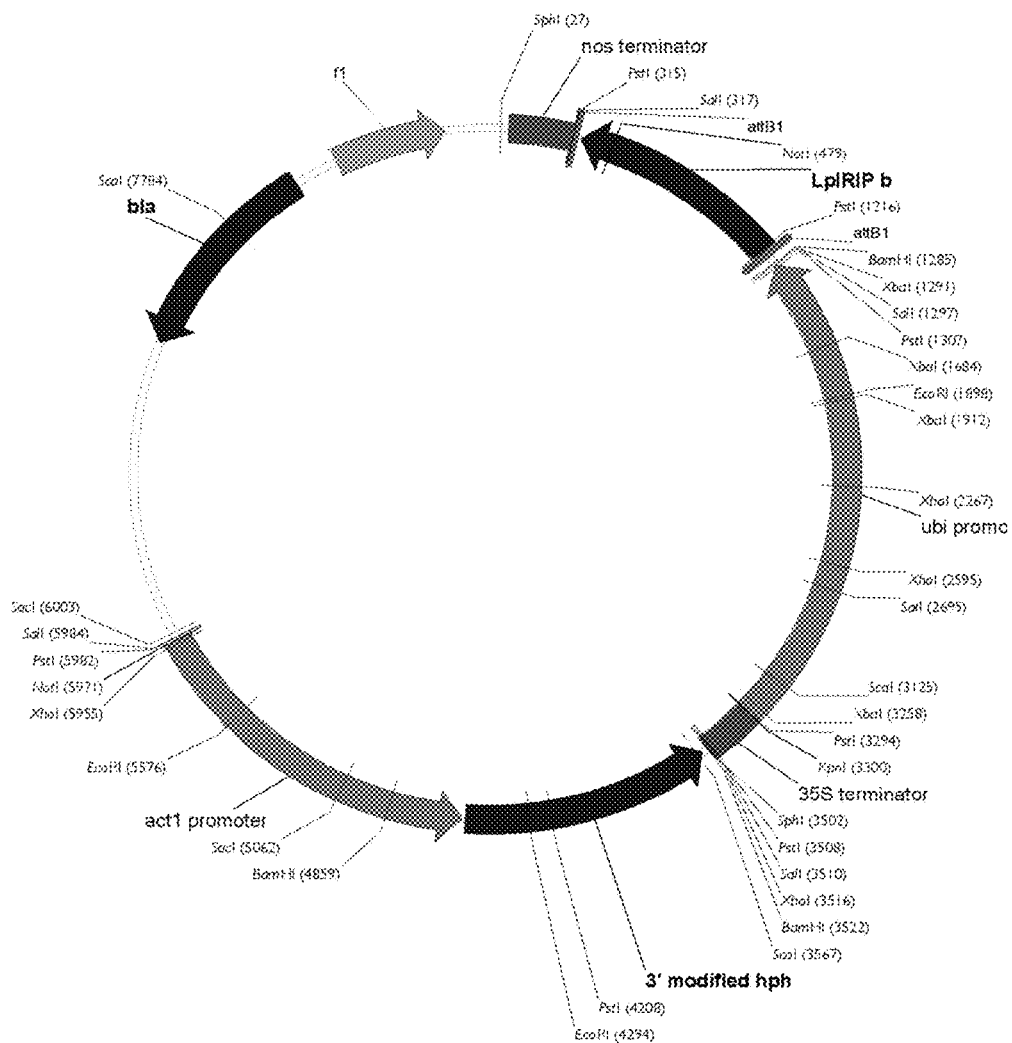

FIG. 40. Plasmid map of vector used for LpIRIPb gain of function biolistic transformation of ryegrass.

Figure 41:
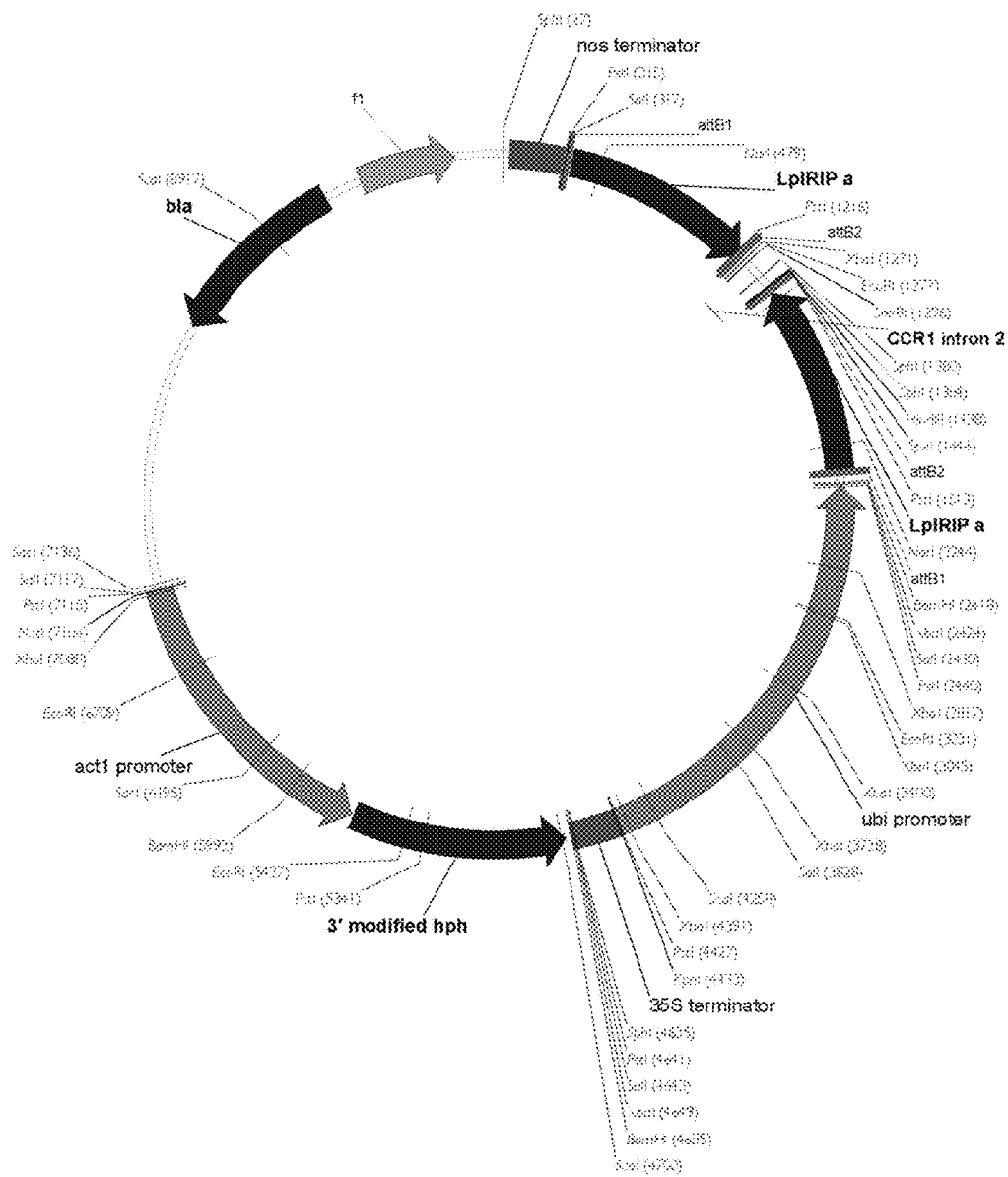

FIG. 41. Plasmid map of vector used for LpIRIPa loss of function biolistic transformation of ryegrass.

Figure 42:
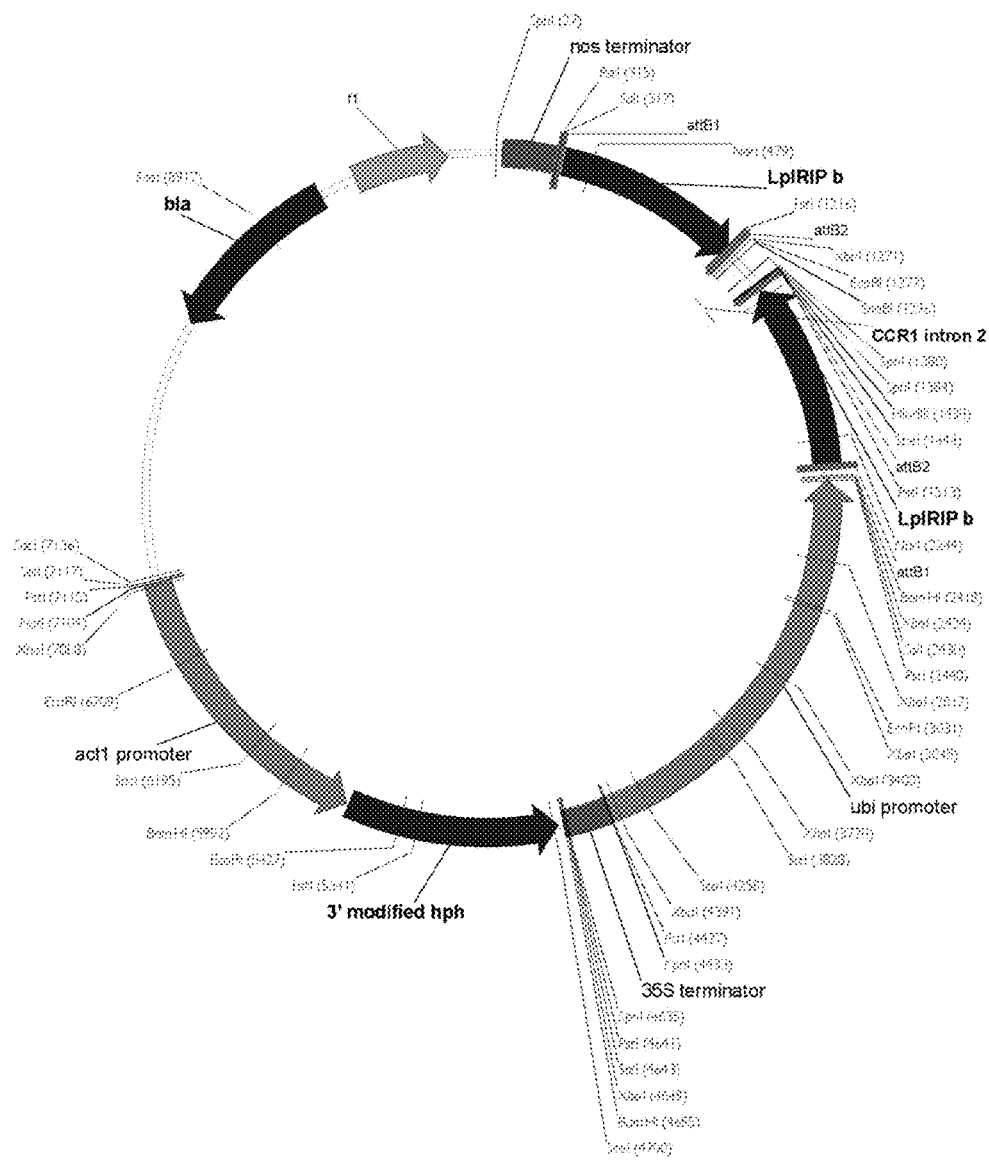

FIG. 42. Plasmid map of vector used for LpIRIPb loss of function biolistic transformation of ryegrass.

Figure 43:
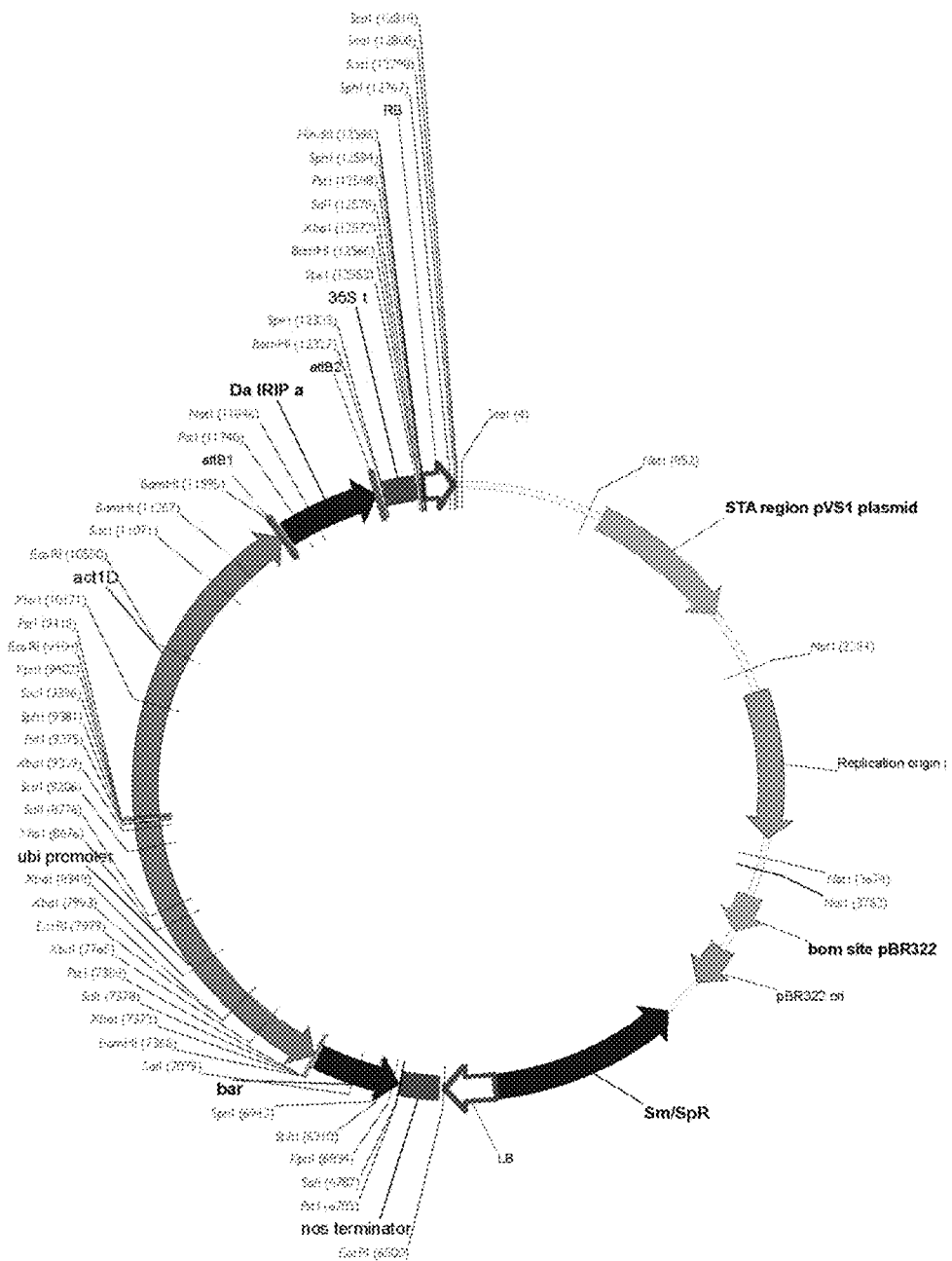

FIG. 43. Plasmid map of vector used for DaIRIPa gain of function *Agrobacterium* mediated transformation of wheat and barley.

Figure 44:
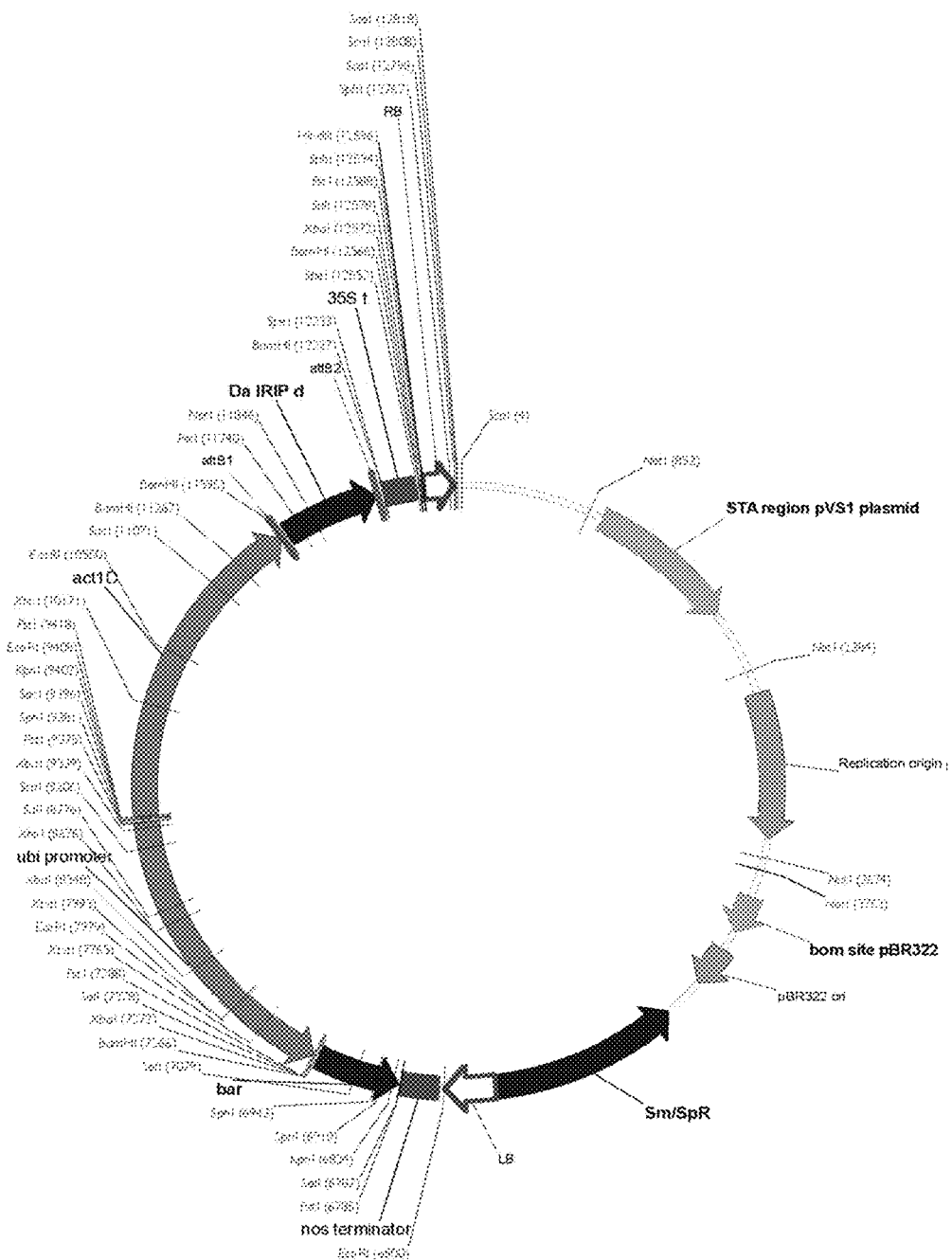

FIG. 44. Plasmid map of vector used for DaIRIPd gain of function *Agrobacterium* mediated transformation of wheat and barley.

Figure 45:
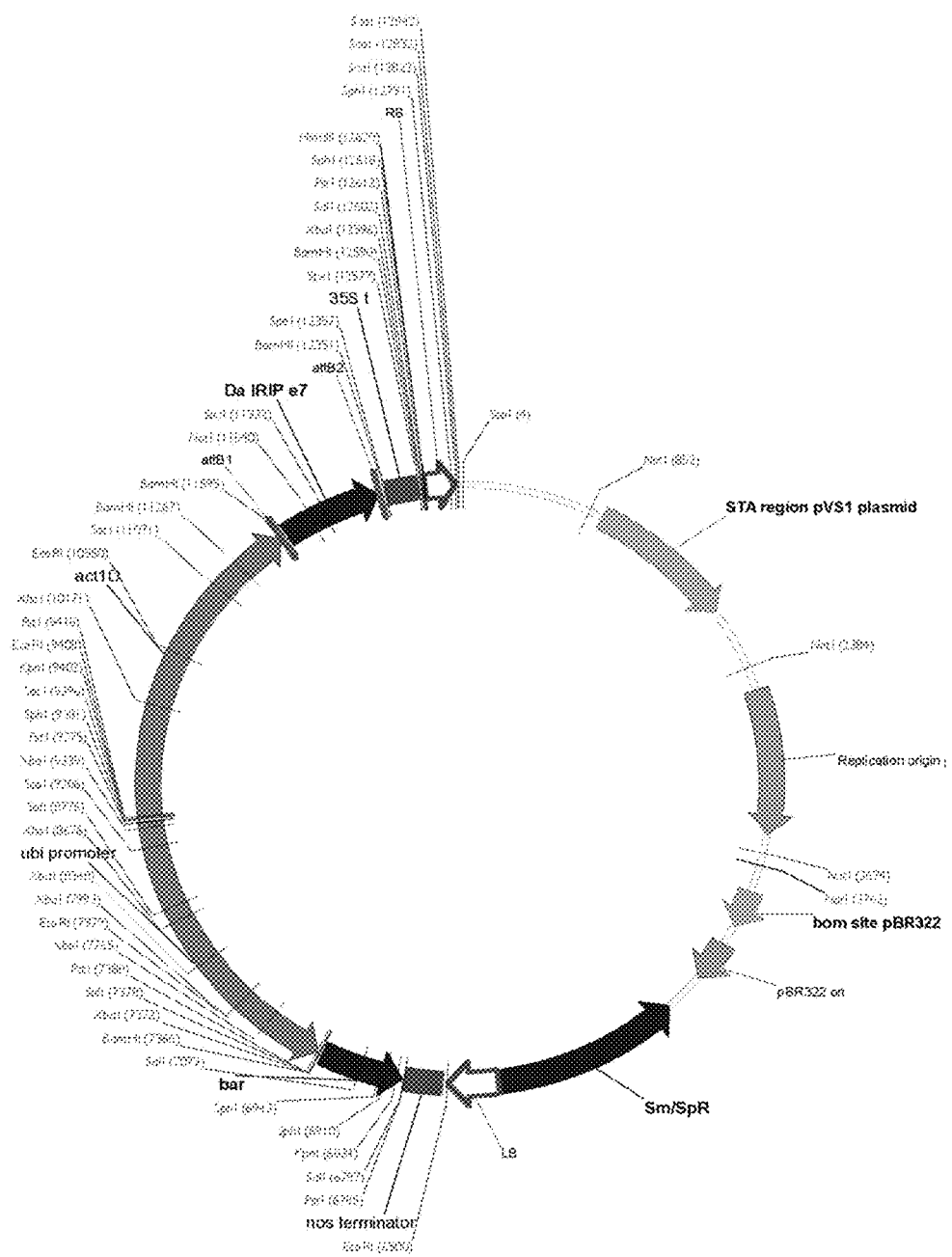

FIG. 45. Plasmid map of vector used for DaIRIPe7 gain of function *Agrobacterium* mediated transformation of wheat and barley.

Figure 46:
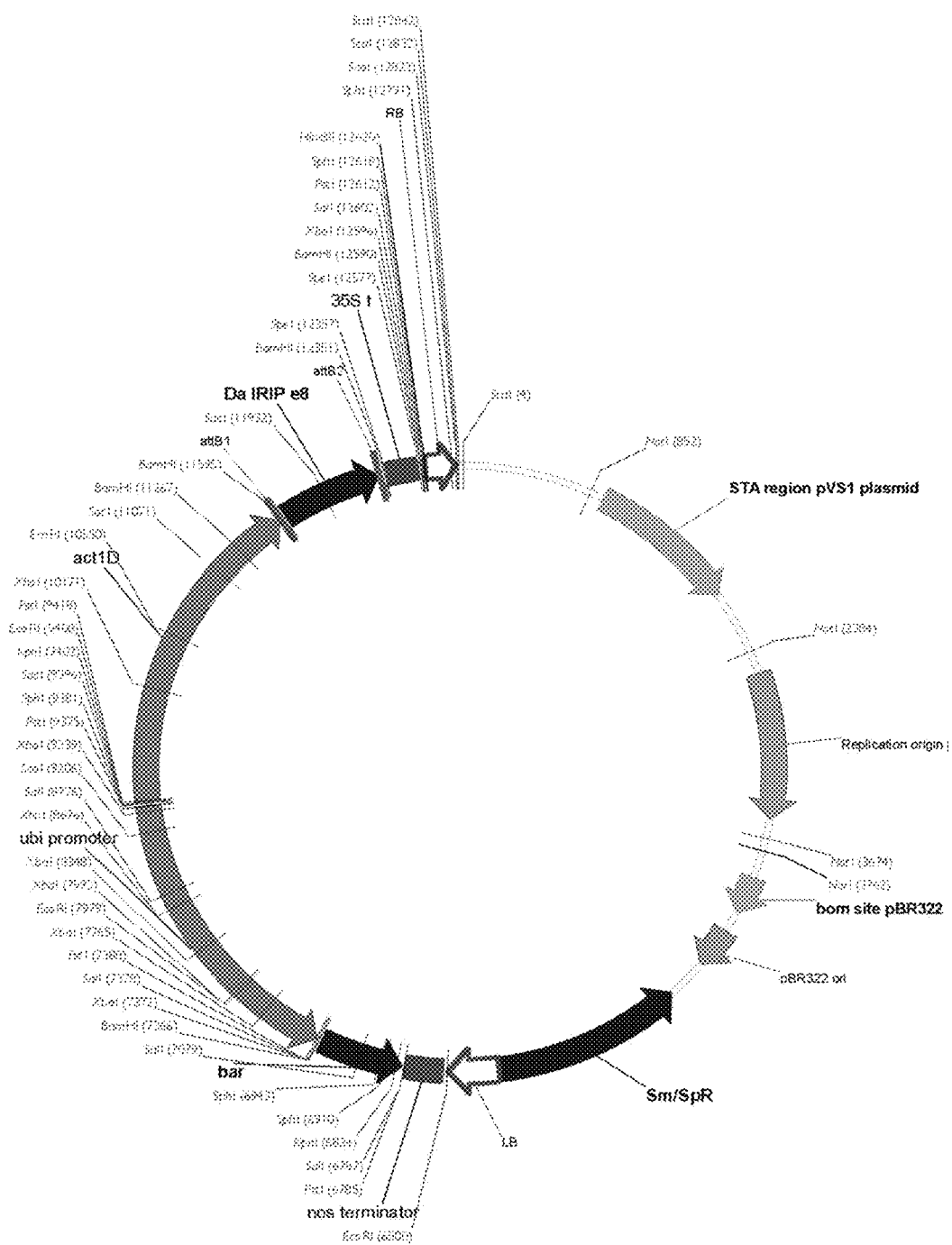

FIG. 46. Plasmid map of vector used for DaIRIPe8 gain of function *Agrobacterium* mediated transformation of wheat and barley.

Figure 47:
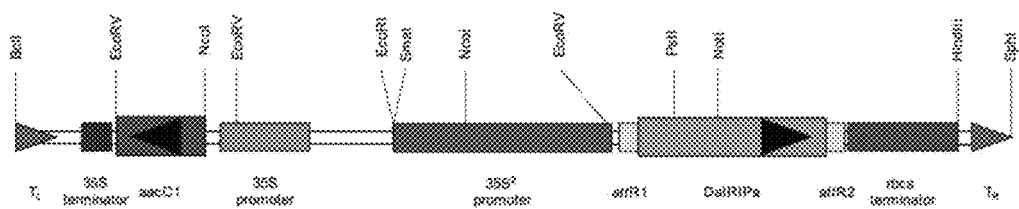

FIG. 47. Plasmid map of vector used for DaIRIPa gain of function *Agrobacterium* mediated transformation of *Arabidopsis*.

Figure 48:
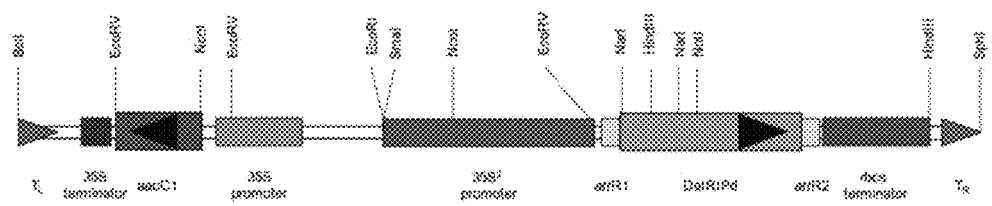

FIG. 48. Plasmid map of vector used for DaIRIPd gain of function *Agrobacterium* mediated transformation of *Arabidopsis*.

Figure 49:
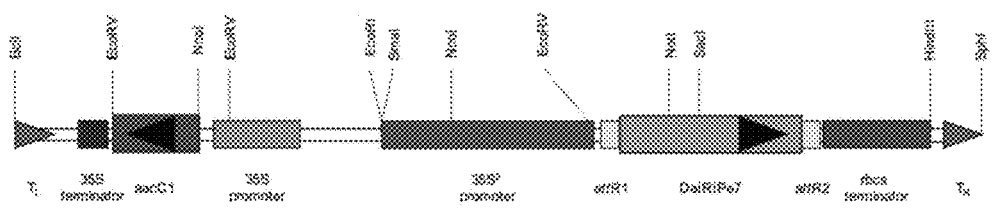

FIG. 49. Plasmid map of vector used for DaIRIPe7 gain of function *Agrobacterium* mediated transformation of *Arabidopsis*.

Figure 50:
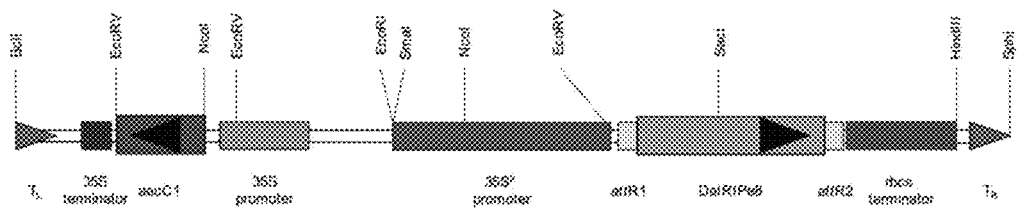

FIG. 50. Plasmid map of vector used for DaIRIPe8 gain of function *Agrobacterium* mediated transformation of *Arabidopsis*.

Figure 51:
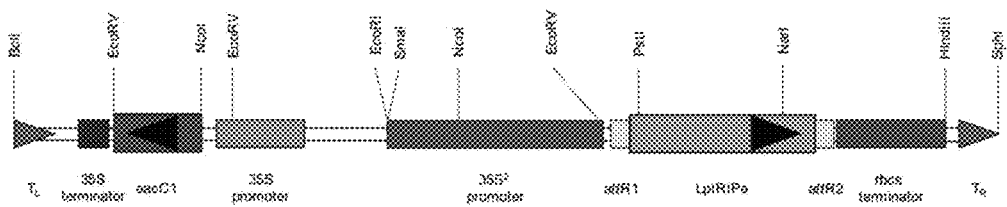

FIG. 51. Plasmid map of vector used for LpIRIPa gain of function *Agrobacterium* mediated transformation of *Arabidopsis*.

Figure 52:
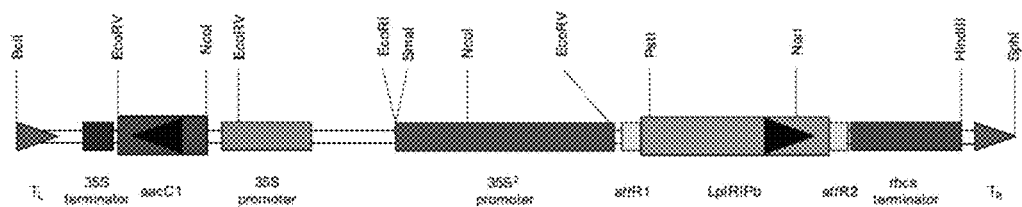

FIG. 52. Plasmid map of vector used for LpIRIPb gain of function *Agrobacterium* mediated transformation of *Arabidopsis*.

Figure 53:
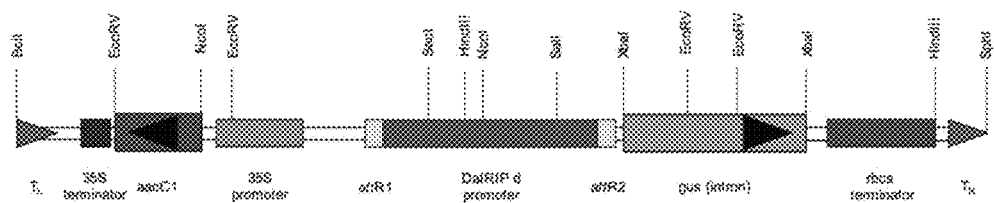

FIG. 53. Plasmid map of vector used for DaIRIPd promoter::GUS reporter gene *Agrobacterium* mediated transformation of *Arabidopsis*.

EXAMPLE 1

Materials and Methods

Plant Propagation, Stress Treatments, Extraction of RI Activity, DNA and RNA

*D. antarctica* material was collected in the vicinity of Jubany station on King George Island (62° 14'S 58° 40'W). Plants were germinated from seeds in the soil seed bank and thereafter were propagated vegetatively. *Lolium perenne* plants were of cultivar Impact. Doubled haploid *L. perenne* plants were isolate DH297 of cultivar Verna.

Individual plants were grown in soil at the indicated temperatures under a 16/8 h light/dark regime and photosynthetic photon flux intensity of 400 μmol $m^{-2}$ $s^{-1}$ in Enconair (Winnipeg, Canada) GC-20 plant growth chambers. Plants were cold acclimated by growth at 5° C. for 2 weeks. Plants were divided into aerial and subterranean parts and snap frozen in liquid N2.

Total cellular extracts were prepared after (Doucet et al (2000) *Cryobiology* 40:218) by grinding plant material under liquid N2 and resuspending the powder in 2 mL $g^{-1}$ of freshly prepared extraction buffer (50 mM Tris pH 7.4, 20 mM ascorbate, 10 mM EDTA). The extract was filtered through miracloth (Calbiochem, La Jolla, USA). Apoplastic extracts were based on the method of Chun et al (1998) *Euphytica* 102:219. Leaf material was vacuum infiltrated in extraction buffer for 30 min, excess liquid removed from the leaves, and extracts collected by centrifugation at 800 g for 30 min. All extracts were aliquoted, frozen in liquid N2, and stored at −80° C.

RNA and DNA were extracted using RNeasy and DNeasy Plant Mini kits (QIAGEN, Germany) respectively.

Ice Recrystallisation Inhibition (RI) Assays

Extracts were thawed and insoluble material pelleted by centrifugation at 16,060 g for 5 min. Supernatants were collected and for total cellular extracts protein content quantified using the Bio-Rad protein assay (Bio-Rad, Mississauga, ON, Canada), according to the manufacturer's instructions. Unless otherwise stated all extracts were incubated at 95° C. for 5 min. The supernatants from both heat treated and untreated extracts were collected following centrifugation at 16,060 g for 2 min. Serial 2 or 4-fold dilutions into extraction buffer were prepared.

The capillary method for the RI assay was modified from that of Tomczak et al (2003) Biochem. Biophys. Res. Commun. 311:1041. Briefly, extracts were loaded into 10 μl glass capillaries (Drummond Scientific, Broomall, Pa., USA), heat sealed and arrayed on a glass slide secured with adhesive tape. Extraction buffer, and BSA (Bio-Rad, Mississauga, ON, Canada) dissolved in extraction buffer to a final concentration of 1000 μg $mL^{-1}$ were included as negative controls. The capillary array was snap-frozen in an ethanol/dry ice bath and immersed in a reservoir of motor vehicle coolant diluted to a final concentration of 10% monoethylene glycol, atop a jacketed stage through which the same solution at −3° C. was circulated using a refrigerated water bath (PolyScience Model 910, Niles, Ill., USA).

Samples were scored after overnight (~16 h) incubation at −3° C. The endpoint of RI activity in total leaf extracts is defined as the lowest protein concentration (μg mL$^{-1}$) at which ice crystal structure following incubation at −3° C. for 16 h, remained unchanged from that initially induced by snap freezing. For apoplastic extracts, because of the low yields of protein from non-acclimated plants, the endpoint of RI activity was expressed as the equivalent wet weight of starting plant material per volume of extract.

Digital images were captured with a Leica DFC 300 F camera mounted on a Leica MZFL III stereoscopic zoom microscope using Leica FireCam software (Leica, Heerbrugg, Switzerland). Polarising light filters mounted perpendicularly on the microscope objective lens and beneath the stage enhanced visualisation of ice crystal morphology.

Preparation of cDNA Libraries, Isolation and Sequencing of cDNAs Coding for IRIPs from Antarctic Hair-Grass, *Deschampsia antarctica*.

cDNA libraries representing mRNAs from various organs and tissues from Antarctic hair-grass, *Deschampsia antarctica* were prepared. The characteristics of the libraries are described below (Table 1).

TABLE 1 cDNA libraries from Antarctic hair-grass, *Deschampsia antarctica*.

| Library | Organ/Tissue |
|---|---|
| 05Da | Aerial parts grown at 4° C. |
| 08Da | Roots grown at −15° C. |
| 09Da | Roots transferred from −15° C. to 25° C. for 24 h |
| 10Da | Aerial parts transferred from −15° C. to 25° C. for 24 h |
| 11Da | Aerial parts grown at −15° C. |
| 12Da | Roots grown at −15° C. |
| 15Da | Roots grown at 4° C. |
| 16Da | Aerial parts grown at 4° C. |
| 17Da | Roots transferred from 25° C. to 0° C. for 48 h |
| 18Da | Aerial parts transferred from −15° C. to 0° C. for 48 h |
| 19Da | Aerial parts transferred from 25° C. to 0° C. for 48 h, then to −15° C. for 48 h |
| 20Da | Aerial parts grown at −15° C. |
| 21Da | Aerial parts grown at 4° C. |
| 22Da | Roots grown at −15° C. |
| 23Da | Roots grown at 4° C. |

The cDNA libraries may be prepared by any of many methods available. For example, total RNA may be isolated using the Trizol method (Gibco-BRL, USA) or the RNeasy Plant Mini kit (Qiagen, Germany), following the manufacturers' instructions. cDNAs may be generated using the SMART PCR cDNA synthesis kit (Clontech, USA), cDNAs may be amplified by long distance polymerase chain reaction using the Advantage 2 PCR Enzyme system (Clontech, USA), cDNAs may be cleaned using the GeneClean spin column (Bio 101, USA), tailed and size fractionated, according to the protocol provided by Clontech. The cDNAs may be introduced into the pGEM-T Easy Vector system 1 (Promega, USA) according to the protocol provided by Promega. The cDNAs in the pGEM-T Easy plasmid vector are transfected into *Escherichia coli Epicurian coli* XL10-Gold ultra competent cells (Stratagene, USA) according to the protocol provided by Stratagene.

Alternatively, the cDNAs may be introduced into plasmid vectors for first preparing the cDNA libraries in Uni-ZAP XR vectors according to the manufacturer's protocol (Stratagene Cloning Systems, La Jolla, Calif., USA). The Uni-ZAP XR libraries are converted into plasmid libraries according to the protocol provided by Stratagene. Upon conversion, cDNA inserts will be contained in the plasmid vector pBluescript. In addition, the cDNAs may be introduced directly into precut pBluescript II SK(+) vectors (Stratagene) using T4 DNA ligase (New England Biolabs), followed by transfection into *E. coli* DH10B cells according to the manufacturer's protocol (GIBCO BRL Products).

cDNA clones encoding putative IRIP orthologues from *D. antarctica* came from 5 libraries derived from either shoots or roots grown at 4° C. or −15° C., and from shoots transferred from −15° C. to 25° C. for 24 hours. One of these variants (DaIRIPe) was isolated from both root and shoot libraries, whilst the other four forms were derived from shoot libraries only.

Molecular Cloning of Genomic Sequences

All but one of *D. antarctica* cDNAs encoding IRIP orthologues (DaIRIPa), encoded N-terminally truncated hypothetical IRIP forms. Therefore full length genomic sequences where isolated using the GenomeWalker kit (BD Biosciences, Palo Alto, USA) and nested gene specific primers. The 3' UTR primers for DaIRIPd were:

```
                                      (SEQ ID NO. 130)
    5' GACATCGCGATTGGTCCCACCAAGTG 3',
    and
                                      (SEQ ID NO. 131)
    5' GCATCCTGCACGGACATATCATTA 3';
``` and DaIRIPe:

```
                                      (SEQ ID NO. 132)
    5' GTTACATAAGACGATTGGCCCCACCAAG 3',
    and
                                      (SEQ ID NO. 133)
    5' CAATCCACTCACTGATCATTAACCACC 3'.
```

For the isolation of LpIRIPa nested primers

```
                                      (SEQ ID NO. 134)
    5' GATGCTATATCCACGAAGTTACAT 3',
    and
                                      (SEQ ID NO. 135)
    5' ATTGGCCCCACCAAGTGA 3'
``` complementary to conserved regions within the 3' UTR of the *D. antarctica* IRIP forms were employed. LpIRIPa was also obtained from the *L. perenne* North African$_6$×Aurora$_6$ genetic mapping population (see below). PCR products were purified using QIAquick gel extraction kit (QIAGEN, Germany) and molecularly cloned into pGEM-T Easy as above.

DNA Template Preparation, Sequencing and Analysis

Templates for sequencing of cDNA and genomic clones plasmid DNA was purified using a QIAprep spin miniprep kit (QIAGEN, Germany). Sequencing reactions primed with a modified SMART primer (5' AAGCAGTGG-TAACAACGCAGAGTGGG 3') (SEQ ID NO. 136), M13F or M13R primers were performed either using BigDye Terminators or ET Terminators, and the reaction products resolved on an ABI Prism 3700, or 3730xI DNA Analyser (PE Biosystems, Foster City, USA), or a MegaBACE 4000 (Amersham Biosciences, UK) respectively. Sequence files were used as queries for BLASTX, BLASTN and TBLASTN (Altschul et al 1987 Nucleic Acids Res. 25:3389) searches of the SWISS-PROT, GenBank Main and GenBank EST databases respectively. BLASTX searches of the NCBI database of GenBank+EMBL+DDBJ sequences from EST divisions with full length IRIP gene sequences reveal the presence of many IRIP gene related sequences in grasses including *Lolium multiflorum* (Italian rye grass), *Leymus chinensis, Puccinellia tenuiflora*, and from in-house EST data *Agrostis tenuis*. We have also identified in the NCBI EST database orthologous sequences in the cereals *Hordeum vulgare* (barley), *S. cereale* (winter rye), and *Triticum monococcum, T. turgidum* and *T. aestivum* (diploid, tetraploid and hexaploid forms of wheat), frequently associated with cDNA libraries derived from cold-stressed or vernalised material. We are not yet aware of any species of the Pooideae without IRIP orthologues. EST sequences were also assembled to derive representative IRIP orthologues. Sequence assembly was performed using Sequencher (Gene Codes, Ann Arbor, Mich., USA). Potential signal sequences were identified by analysis with SignalP (www.cbs.dtu.dk/services/SignalP/). Subcellular localisation was predicted using TMHMM (www.cbs.dtu.dk/services/TMHMM/) and PSORT (psort.nibb.ac.ip). Phylogenetic analysis was performed using Vector NTI (Invitrogen, Carlsbad, Calif., USA) using the Align X algorithm with default parameters.

Structural Modelling

Homology modelling was performed using Schrödinger molecular modelling software (version macromodel 8.6, Portland, Oreg., USA) using the Prime homology modelling module. A homology model of the DaIRIPa and LpIRIPa proteins was build using the N terminus of the crystal structure of *Phaseolus vulgaris* polygalacturonase-inhibiting protein (PGIP) (pdb entry: 10GQ) and a right-handed version of a theoretical *Lolium perenne* AFP model (Kuiper et al (2001) *Biophys. J.* 81:3560) as templates. The model was geometrically optimised with distance constraints holding optimal hydrogen bond distances between beta sheet regions for 10,000 iterations using an OPLS2001 forcefield and Generalised Born (GB) solvation. This was followed by an additional 5000 iterations minimisation without constraints applied. Images were generated using Swiss Pdb Viewer and Pov-Ray3.5.

Southern and Northern Analysis

For Southerns 10 μg of DNA was digested with restriction enzymes, separated on a 1% agarose TAE gel and stained with ethidium bromide before transfer to Hybond-N membrane (Amersham Biosciences). For Northerns 10 μg of RNA was separated on a 1% agarose formaldehyde gel, transferred to Hybond-N membrane (Amersham Biosciences) and stained with methylene blue. Isolated fragments of DaIRIPe7 and LpIRIPa were radio-labelled with $\alpha$-$^{32}$P-dCTP using the Rediprime II Random Prime Labelling System (Amersham Biosciences) and purified with MicroSpin™ S-400 HR Columns (Amersham Biosciences) according to the manufacturer's instructions. The blotted membranes were hybridised with radio-labelled probe as described by Maniatis et al, Molecular Cloning: A Laboratory Manual, Cold Spring Harbor Laboratory, Cold Spring Harbor. Hybridisation patterns were visualised and quantified on a Typhoon 8600 Variable Mode Imager (Amersham Biosciences) according to the manufacturers instructions.

SNP-Based Genetic Mapping

The perennial ryegrass population used for SNP discovery and genetic mapping was an Fi progeny set derived from a reciprocal pair-cross between the heterozygous parental genotypes North African$_6$ (NA$_6$) and Aurora$_6$ (AU$_6$) (Faville et al. *Theor Appl Genet*, in press).

The procedure for targeted in vitro SNP discovery in perennial ryegrass was described by Forster et al. (2004) Molecular marker-based genetic analysis of pasture and turf grasses, in: Molecular Breeding of Forage and Turf, Hopkins et al (eds) Kluwer Academic Press pp 197-239. The partial cDNA sequence of the IRIP reported from *L. perenne* (Sidebottom et al (2000) *Nature* 406:256), along with the sequence of LpIRIPa, were assembled into a single contig and locus amplification primers (LAPs) were designed to generate 3 amplicons located at various positions within the gene unit (FIG. 5A), to cover the 5'-untranslated region (UTR), single exon and 3'-UTR regions. Genomic amplicons were generated using standard PCR conditions from each parental genotype of the F$_1$(NA$_6$×AU$_6$) population. PCR fragments were cloned using the TOPO TA system (Invifrogen K4575-40) and DNA sequences were derived through cycle-sequencing. Sequences were assembled in contigs using the Sequencher ver. 4.1.4 application (Gene Codes) and putative SNPs were identified. A total of 1072 bp from the 1495 bp gene length was represented by high quality sequence. In all 26 SNPs were identified following alignment of sequences from the parental genotypes, at an average incidence of 1 per 40 bp, which is higher than the global frequency of 1 per 60 bp observed through resequencing of 87 genes and c. 76 kb of perennial ryegrass genomic DNA (N.O.I. Cogan, unpublished data). This high SNP frequency, along with the observation of more than two haplotype structures in the NA$_6$ parent, suggests that paralogous DNA sequences may have been clustered, due to cross-amplification between gene copies. Polymorphic SNP loci were validated using the single nucleotide primer extension (SNuPe) assay system followed by capillary electrophoresis on the MegaBACE1000 platform (Amersham Biosciences).

Genotypic variation for the SNP locus LpIRIPNA476 was determined using a sub-set (96) genotypes of the F$_1$(NA$_6$×AU$_6$) population. The corresponding genomic locus was integrated within the framework of the existing genetic map as previously described (Faville et al, *Theor Appl Genet*. in press). Comparative genomics analysis of IRIP genes was performed using the wEST SQL database in the GrainGenes resource (wheat.pw.usda.gov/wEST/). The nucleotide sequences were used for BLASTN and TBLASTX analysis in the GrainGenes BLAST page with the search restricted to ESTs that have been assigned to wheat deletion bins Qi et al (2003) *Functional and Integrative Genomics* 3:39) The highest matching ESTs were then used to detect the relevant deletion bins using the Mapped Loci query function in wEST SQL.

Genetic map information for the LpIRIPb gene was obtained from the second generation perennial ryegrass genetic mapping population derived from a pair-cross between the genotypes North African$_6$ (NA$_6$) and Aurora$_6$ (AU$_6$). LpIRIPa specific locus amplification primers (LAPs) were employed to generate 3 genomic amplicons (FIG. 5A) from each parental genotype. Sequence assembly and analysis revealed 2 distinct LpIRIP paralogues LpIRIP a and b, and a total of 26 SNPs. An assayed SNP locus in LpIRIPa showing an AB×BB segregation structure produced only AB-type F$_1$ progeny (data not shown), which is diagnostic of multiple gene structure. A total of 8 SNP loci in LpIRIPb showed structures consistent with a single gene copy, but of these 6 showed AA×BB patterns, and could not be genetically mapped in the F$_1$(NA$_6$×AU$_6$) sib-ship. Of the two loci revealing polymorphism within the NA$_6$ parental genotype (LpIRIPNA476 and LpIRIPNA694) (FIG. 5A), LpIRIPNA476 was used to genotype the mapping population. The corresponding genomic locus was located on NA$_6$ LG1 in the terminal location c. 7 cM from locus xLpesi3f (FIG. 5B).

Expression Profiling: RT-PCR Expression in *E. coli*

The sequence encoding DaIRIPe and a putative orthologue of histone H3.2 was PCR adapted with the primer pairs 5' CAGCTTGGATCCATGGCGAACTGCTGTCTGCTA 3' (SEQ ID NO. 137) and 5' ACTCACAAGCTTAACCTCCTGTCACGACTTTGT 3' (SEQ ID NO. 138); and 5' AGGAGAGGATCCATGGCGCGTACCAAACAGACC 3' (SEQ ID NO. 139) and

5' TAATTGAAGCTTTTAGGCGCGTTCGCCACGGAT 3' (SEQ ID NO. 140)

respectively. They were molecularly cloned into BamHI and HindUI restricted pQE-30 (QIAGEN, Germany) and transformed into M15[pREP4]. To induce expression a culture was grown in the presence of ampicillin and kanamycin to mid-log phase, where upon IPTG to 1 mM was added and incubation continued for a further 4 h. Cells were harvested, resuspended in 1 ml extraction buffer and lysed by sonication. The lysate was incubated at 95° C. for 10 min., spun at 16,060 g for 5 min, the supernatant aliquoted, frozen in liquid N2, and stored at −80° C.

EXAMPLE 2

Results

RI Activity in *D. antarctica* and *L. perenne* is Induced by Cold Acclimation and Present in the Apoplasm RI assays reveal that *D. antarctica* has activity, induced by cold acclimation, to inhibit further growth of ice crystals following freezing. Given that total leaf extracts from plants grown at 22° C. containing 1000 μg mL$^{-1}$ of protein possess no RI activity (FIG. 1) transfer of plants to 5° C. for 2 weeks induces RI activity by greater than 64 fold. Furthermore this activity is unaffected by incubation at 95° C. for 5 min (FIG. 1). RI activity is also induced more than 8 fold in the roots of *D. antarctica* in response to cold acclimation (Table 2). Similarly RI activity in *L. perenne* is below the threshold of detection in the leaves and roots of non-acclimated plants but is induced in excess of 16 and 4 fold respectively following cold acclimation (Table 2).

TABLE 2

RI activity[a] in leaves and roots of non-acclimated (grown at 22° C.) and cold acclimated (5° C.) *D. antarctica* and *L. perenne*.

|  | Leaves | | Roots | |
| --- | --- | --- | --- | --- |
|  | 22° C. | 5° C. | 22° C. | 5° C. |
| *D. antarctica* | ND[b] | 15.6 | ND[b] | 100 |
| *L. perenne* | ND[b] | 62.5 | ND[b] | 200 |

[a]Expressed as lowest concentration of total protein extract (μg mL$^{-1}$) at which activity retained.
[b]No activity detectable at 1000 and 800 μg mL$^{-1}$ for leaves and roots respectively.

Moreover RI activity is present in the extracellular spaces of *D. antarctica* and *L. perenne*. Leaf apoplastic extracts from plants of both species grown at 22° C. possess no RI activity whilst activity is induced in response to acclimation at least 73 fold in *D. antarctica* and 1.7 fold in *L. perenne* (Table 3). These correspond to apoplastic protein concentrations, in cold acclimated plants, of 0.31 and 14 μg mL$^{-1}$ respectively.

TABLE 3

RI activity[a] in apoplastic extracts of leaves from non-acclimated (grown at 22° C.) and cold acclimated (5° C.) *D. antarctica* and *L. perenne*.

|  | 22° C. | 5° C. |
| --- | --- | --- |
| *D. antarctica* | ND[b] | 89.1 |
| *L. perenne* | ND[b] | 3.830 |

[a]Expressed as the lowest equivalent wet weight of starting plant material per volume of extract (mg mL$^{-1}$) at which activity retained.
[b]No activity detectable at 6,550 and 6,590 mg mL$^{-1}$ for *D. antarctica* and *L. perenne* respectively.

Therefore activity to inhibit the consolidation of ice crystals by recrystallisation is induced in response to cold acclimation in both leaves and roots of *D. antarctica*, and to a significantly lesser extent in *L. perenne*. Moreover a significant proportion of this RI activity, particularly in *D. antarctica*, is localised to apoplastic spaces.

IRIP Orthologues from *D. antarctica* are Predicted to be Secreted Proteins and Contain Two Types of Repeat Motif.

Full length clones of the putative IRIP orthologues DaIRIPa, and DaIRIPd, e7 and e8 were obtained from *D. antarctica* cDNA and genomic resources respectively. Two genomic clones encoding putative IRIP paralogues LpIRIP a and b were also obtained from *L. perenne*. In addition many IRIP related sequences have been identified in EST collections from other cereals and grasses. The repeat structures of the longest IRIP orthologue, HvIRIP from *Hordeum vulgare* (barley), and the shortest, DaIRIPd, are shown in FIGS. 2A-1, 2A-2. In all predicted IRIP orthologues (FIGS. 2B-1, 2B-2, 2B-3, and 2C), the C-terminal approximate 120 residues consist entirely of 16 tandem repeats of a degenerate 7-8 amino acid residue motif (the "IRIP repeat") (FIGS. 2A-1, 2A-2). The consensus sequence for the IRIP repeat is SNNTWSG (SEQ ID NO. 141), with the glycine residue being most conserved (91.9% identity) across all forms. A multiple sequence alignment (FIGS. 2B-1, 2B-2, 2B-3) indicates that relative to IRIP forms in other species IRIPs from *L. perenne* lack the 14th IRIP repeat but have an additional highly degenerate repeat immediately N-terminal to the usual start position of the IRIP domain (FIGS. 2B-1, 2B-2, 2B-2, and 2C).

Database sequence similarity searches with IRIP sequences reveal that the region N-terminal to the IRIP domain is related to proteins with leucine rich repeat (LRR) motifs. Most closely related is a putative *Oryza sativa* orthologue of a phytohormone receptor, the phytosulfokine receptor (PSKR) (NP_911036). Regions of significant sequence similarity with IRIPs extend in a discontinuous fashion through the first 17 LRRs of the putative PSKR orthologue and approximately 22 residues into a 36 amino acid residue "island" domain (Li and Chory (1997) *Cell* 90:929), where similarity ceases with the advent of the IRIP domain (FIG. 2B, C). With reference to the organisation of LRRs in the *O. sativa* PSKR orthologue IRIPs lack between 8 and 16 of the 17 LRRs (FIG. 2B, C).

Phylogenetic analysis on the sequences of IRIP orthologues outside of the IRIP domain, together with representative LRR containing proteins reveal that IRIPs fall into a highly robust and distinct clade (FIG. 2D). The sister group to the IRIP clade includes PSKR orthologues and contains LRR receptor-like kinases (LRR-RLKs) of both monocot and dicot origin (FIG. 2D). The most distant clade in this analysis includes polygalacturonase-inhibiting protein (PGIP) orthologues, and a LRR containing AFP from *D. carota* (FIG. 2D).

Immediately N-terminal to the LRRs in the predicted IRIPs is a highly conserved 10 amino acid residue motif CCXWEGVXCD (SEQ ID NO. 145) containing 3 invariant cysteine residues (FIGS. 2A-1, 2A-2, 2B-1, 2B-2, and 2B-3). An additional invariant cysteine residue occurs a further 31-32 residues proximal to the N-terminus (FIGS. 2A-1, 2A-2, 2B-1, 2B-2, and 2B-3). The corresponding cysteine residues have been shown to form 2 conformationally critical disulphide bridges in the structural determination of the LRR-RLK PGIP of Phaseolus vulgaris (Di Matteo et al (2003) Proc. Natl. Acad Sci. USA 100:10124). It is surmised based on their conservation in all IRIP forms that the orthologous residues also participate in structurally important disulphide bonds.

At the N-terminus of all IRIP orthologues is a 20 or 21 amino acid residue region predicted to function as a signal peptide, with a cleavage site between conserved alanine, and threonine or valine residues (FIGS. 2B-1, 2B-2, and 2B-3). Consistent with this the mature versions of all full length IRIP forms are predicted to be extracellularly localised. Thus it is likely that IRIPs, are predominantly apoplastic.

Structural Modelling of IRIPs Predict Conformations that are Lattice Matched to Ice Surfaces Three-dimensional structures of DaIRIPa and LpIRIPa (FIG. 3) were constructed by comparative homology modelling. The structural model of DaIRIPa has three main regions, the double disulphide bonded N-terminal domain, one LRR loop and the IRIP domain (FIG. 3 (panel A)). LpIRIPa is similar to the DaIRIPe in overall structure except for its three LRRs, and additional predicted disulphide bond (FIG. 3 (panel B)).

The extended β-roll structure of the IRIP domain is predicted to form two surfaces complementary to the prism face of ice, on alternate sides of the domain. Adjacent parallel β-loops are spaced approximately 4.5 Å apart (FIG. 3 (panels A, B)), whilst threonine and other solvent-accessible residues are arrayed in two ranks on the β-strand faces, spaced 2 residues, or approximately 7.4 Å apart (FIG. 3 (panel C)). This almost exactly matches the prism ice surface that has repeating structures 4.5 Å parallel to the a-axis, and 7.35 Å parallel to the c-axis of ice. The putative ice-binding surfaces are stabilised by valine residues that allow tight regular hydrophobic packing of the central core of the β-roll region, and by asparagine residues that participate in hydrogen bonds between adjacent β-strands (FIG. 3 (panel D)). The highly conserved glycine residues in the IRIP repeat are structurally important as they form the turns between the upper and lower β-strand faces of the ice-binding β-roll.

Although the conformation of the LRR regions of the DaIRIPa and LpIRIPa models recapitulate the right-handed β-roll of the IRIP repeat they do not engender a flat β-sheet roll. On one side of the β-roll adjacent parallel β-loops are spaced approximately 4.5 Å apart, but on the other, adjacently α-helical strands cannot pack as closely (FIG. 3 (panels A, B)). Therefore with each iteration of the LRR the β-roll structure becomes increasingly curved, displaying a concave β-sheet region. As a consequence relative to DaIRIPa the predicted LpIRIPa structure with three LRRs appears to display a less than optimal surface lattice match to the ice prism face (FIG. 3 (panel B)).

Genomic Organisation of IRIP Related Sequences in D. antarctica and L. perenne

Consistent with the multiple IRIP gene variants isolated from them, the genomes of D. antarctica and L. perenne both appear to harbour multiple IRIP-related sequences. Up to 5 hybridising bands are detected by interrogation of a Southern blot of D. antarctica genomic DNA with DaIRIPe (FIG. 4 (part A)). The occurrence of as few as 2 hybridising bands (tracks 3 and 5, FIG. 4 (part A)), is evidence that IRIP related sequences may be physically linked on 2 genomic fragments totaling 20 kbp. At least 4 LpIRIPa sequence related restriction fragments are detected in a sample genome from a heterogeneous breeding population of L. perenne (FIG. 4 (part B)). The isogenic genomic DNA from a doubled haploid plant, however, exhibits only one strongly hybridising band, with a background of less intense bands (FIG. 4 (part C)).

SNP-Based Genetic Mapping of LpIRIPb

The genetic map position of LpIRIPb was determined using single nucleotide polymorphism (SNP). Genetic map information for the LpIRIPb gene was obtained from the second generation perennial ryegrass genetic mapping population derived from a pair-cross between the genotypes North African$_6$ (NA$_6$) and Aurora$_6$ (AU$_6$). A total of 8 SNP loci in LpIRIPb (FIG. 5 (part A)) showed structures consistent with a single gene copy, but of these 6 showed AA×BB patterns, and could not be genetically mapped in the F$_1$(NA$_6$×AU$_6$) sib-ship. Of the two loci revealing polymorphism within the NA$_6$ parental genotype (LpIRIPNA476 and LpIRIPNA694) (FIG. 5A), LpIRIPNA476 was used to genotype the mapping population. The corresponding genomic locus was located on NA$_6$ LG1 in the terminal location c. 7 cM from locus xLpesi3f (FIG. 5 (part B)).

The DNA sequence from LpIRIPb was used to detect putatively orthologous wheat ESTs that had been assigned to the wheat deletion map (Endo and Gill (1996) Journal of Heredity 87:95; Qi et al (2003) Functional and Integrative Genomics 3:39). The three highest matching ESTs based on TBLASTX analysis were all assigned to deletion bins on chromosomes 4AL, 5BL and 5DL (BE48991: E=7×10$^{-71}$; BF200590: E=5×10$^{-58}$; BG314423: E=2×10$^{-41}$). The next lowest matching wheat EST (BG607348: E=2×10$^{-40}$) detected a deletion bin on chromosome 1BL, as well as 5BL.

Expression Analysis of LpIRIPs and DaIRIPs

The modulation of steady state levels of IRIP gene transcripts in response to temperature in D. antarctica and L. perenne, were investigated. A Northern blot comprising RNA samples extracted from the roots and leaves of D. antarctica plants grown at 22° C., 4° C. and −16° C. probed with full length DaIRIPe7 detects appreciable levels of transcript only in leaves of cold-acclimated plants (FIG. 6 (part A)). Quantitative analysis reveal that transfer of plants to 4° C. for 2 weeks increases steady state IRIP mRNA levels approximately 47 fold relative to those grown at 22° C. By contrast LpIRIPa transcript levels in L perenne are below the threshold level of detection in leaves, but elevated approximately 4 fold in the roots of cold-acclimated plants relative to those grown at 22° C. (FIG. 6 (part B)). Thus steady state levels of IRIP transcripts are greatly elaborated in leaves of D. antarctica in response to cold-acclimation, but only moderately so in the roots of L. perenne.

Heterologously Expressed DaIRIPe7 Possesses RI Activity

Extract from E. coli expressing DaIRIPe was assayed for RI activity. Whilst extracts from cells expressing a putative D. antarctica orthologue of histone H3.2 at a concentration of 400 μg mL$^{-1}$ of protein possess no RI activity, those expressing DaIRIPe7 retain activity down to 100 μg mL$^{-1}$ (FIG. 7). Therefore activity to inhibit further growth of ice crystals following freezing is specifically conferred by DaIRIPe7 and can account, in some part, for this activity in planta.

EXAMPLE 3

Discussion

A physiological and functional genomics study in *D. antarctica* has resulted in the identification and characterisation of a gene family encoding IRIPs, the actions of which can account for its tolerance of freezing. *D. antarctica* has activity induced by cold acclimation, and present in the apoplasm, to inhibit ice recrystallisation thereby minimising the catastrophic plasmolytic consequences of uncontrolled ice crystal growth. This capacity is correlated with the expression of IRIP genes, and the primary structure, conformation, localisation, and most significantly, the activity of their products.

IRIP Genes Encode Proteins with Two Types of Potential Ice Binding Domains

We have isolated and characterised putative full length IRIP genes from both *D. antarctica* and *L. perenne*. The form reported previously from *L. perenne* (Sidebottom et al (2000) *Nature* 406:256), isolated as a protein associated with RI activity, lacked an N-terminal methionine, and was comprised solely of 16 IRIP repeats. The IRIP forms reported here, unlike any other known AFPs, include 2 ice binding domains, the IRIP and LRR domains. Ten LRRs are also the predominant feature of an unrelated (FIG. 2D) ice recrystallisation inhibiting AFP from *D. carota* (Worrall et al. (1998) *Science* 282:115; Meyer et al. (1999) *FEBS Lett.* 447:171).

Although the LRR domain has the potential to function in ice binding, in the various IRIP forms described here, there is a wide range of variation in its relative contribution to the overall primary structure. Thus whilst all IRIPs contain 16 IRIP repeats, LRRs are present from as many as 9 iterations in the *H. vulgare* form HvIRIP to as few as one in the *D. antarctica* forms, and in the extreme case of DaIRIPd the residues with similarity to the LRR number only 17 of the usual complement of 24 or 25 residues (FIG. 2A, B, C).

Despite the apparent plasticity in the number of LRRs, and even their dispensability, other features commonly found in LRR proteins, including the region predicted to participate in 2 disulphide bridges, and the probable signal sequence are invariant in IRIPs, suggesting that they are important for structure/function and/or localisation.

What is Evolutionary Origin of IRIP Genes?

All plant (and animal) AFPs characterised to date appear to have arisen relatively recently in evolutionary terms by the co-option of existing protein structures (Logson and Doolittle (1997) *Proc Natl Acad Sci USA.* 94:3485). This is also true of the IRIPs characterised in this study. Outside the IRIP domain itself IRIPs are structurally related to LRR-RLKs, having greatest affinity with orthologues of PSKR, a receptor for the plant hormone phytosulfokine. PSKR first isolated and characterised in *Daucus carota* (carrot) consists of an extracellular domain containing 21 LRRs, a single pass transmembrane domain, and a cytoplasmic serine-threonine kinase domain (Matsubayashi et al. (2002) *Science.* 296: 1470). Phytosulfokine is a secreted 5 residue sulfated peptide with a key role in cellular de-differentiation and redifferentiation (Matsubayashi and Sakagami (1996) *Proc Natl Acad Sci USA.* 93:7623). It is difficult to conceive the mechanistic connection between hormonal regulation of cell fate determination and antifreeze activity. A more likely scenario is that a PSKR related protein was co-opted as an AFP, either because of intrinsic structural complementarity to ice crystals, but more credibly as a vehicle to target the "hitch hiking" IRIP domain to the cellular compartment where RI activity is critical, the apoplast. It is possible to envisage an evolutionary scenario whereby a PSKR-like LRR-RLK protein has acquired a novel domain, the IRIP repeat domain, in the process losing its transmembrane and infracellular kinase domains, thereby becoming an untethered apoplastic protein with a novel function. Moreover PSKR-like genes might have been predisposed for such a role because of their expression in organ primordia, cells of which are particularly vulnerable to freezing induced damage. Like the IRIPs, the majority of known plant AFPs are derived from secreted proteins, many being orthologues of pathogenesis-related proteins (Griffith and Yaish (2004) *Trends Plant Sci.* 9:399), and one, the AFP from *D. carota* (Worrall et al. (1998) *Science* 282:115; Meyer et al. (1999) *FEBS Lett.* 447:171) also being related to LRR-RLKs.

IRIPs exhibit plasticity in the number and arrangement of LRRs, more so when compared to their presumed nearest relatives the PSKRs. Thus, there are 17 LRRs in *D. carota* PSKR and its presumed homologue in *O. sativa,* 9 in HvIRIP, 3 in the *L. perenne* and *T. aestivum* IRIP versions, and one, or part of one, in the *D. antarctica* forms (FIG. 2B, C). Such evolutionary plasticity in number and arrangement of LRRs has been noted in analyses of LRR-RLKs (see for example Dixon et al. (1998) *Plant Cell.* 10:1915)). All the LRRs in extant IRIP forms have high levels of identity and conservation with LRRs in the PSKRs, with no evidence for the addition of any other sequences, LRR or otherwise. Therefore in respect of the principle of maximum parsimony it is most likely that the evolution of IRIPs has resulted from the progressive loss of LRRs rather than their acquisition or rearrangement.

Because of their evolutionarily recent co-option as AFPs all known plant AFPs exhibit in their sequences clear affinities to particular classes of protein. Although this is true for the PSKR affinities of the LRR related N-terminal part of the IRIPs, the other potential ice binding motif in IRIPs, the IRIP repeat, exhibits no sequence similarity to any reported nucleotide or amino acid sequences. For this reason its origin is unknown. Because of its length, the shortest repeat known in an AFP, the IRIP repeat could conceivably be derived from a simple repetitive element of as few as 21 nucleotides in length, such as those found in intergenic DNA. However to date BLASTN searches have failed to identify any closely related genomic sequences.

Genes encoding IRIP orthologues appear to be monophyletic in origin and confined to the sub-family Pooideae. No sequences related to the IRIP domain have been found in sequence similarity searches of any dicots including *Arabidopsis thaliana*, in the genome of *O. sativa*, or the extensive EST resources derived from *Zea mays* or *Sorghum bicolor*. Furthermore the IRIP clade (FIG. 3 (panel B)) is highly distinct and deeply rooted supporting the notion that IRIPs arose once early in the evolutionary history of the Pooideae and have subsequently diverged in both copy number and structure. On this basis IRIP genes are predicted to have arisen sometime after the divergence of the Pooideae and Panicoideae 60 mya, but before that of the Triticodae and Poodae 35 mya (Huang et al, (2002) *Plant Mol Biol.* 48:805).

Structural Modelling Predicts that IRIP Repeat has Greater Affinity for Ice than LRR We have used comparative homology modelling to devise a theoretical 3-D structure for full length IRIPs. A truncated version of LpIRIP modelled previously (Kuiper et al (2001) *Biophys. J.* 81:3560) did not include the LRR domain, nor the twin disulphide bond-forming N-terminal domain. The structural model demonstrates that both the IRIP and LRR domains can contribute to a common, structurally complementary ice-binding domain.

The predominant ice-binding region is predicted to be the IRIP domain, which presents two ice-binding faces, on either side of the β-roll domain. The putative ice binding surfaces however are not as regular as the stereotypical threonine-X-threonine motifs in beta-roll configurations observed in two unrelated insect AFPs with high TH activity (Graether et al (2000) *Nature.* 406:325; Liou et al, (2000) *Nature.* 406:322). The *D. antarctica* and *L. perenne* IRIPs exhibit only 30 to 40% threonine at the analogous positions. This is likely due to the differences in the primary function of the proteins. Insect AFPs must provide appreciable TH activity as most insects are not freeze-tolerant. The regularity of the threonine residues on the presenting ice binding surfaces has been implicated in their high TH activity, TH activity having been shown to rapidly decrease with increasing mutational substitution of residues in the ice binding surface (Marshall et al (2002) *FEBS Lett.* 529:261). By contrast since *D. antarctica* is freeze tolerant the primary purpose of AFPs in this organism would be to provide RI activity, to avoid the plasmolytic consequences of continued ice crystal growth in already frozen tissue.

In fact, IRIPs may have evolved to have low TH activity as high activity may prove detrimental during the inevitable seasonal freezing of these plants. If a plant were to deploy an IRIP with a relatively high TH activity, the apoplastic fluid of the plant would remain liquid until the temperature dropped below the lower end of the TH gap.

Freezing would then occur much more rapidly than if initiated close to the freezing equilibrium point, and would do so with the spicular dendritic growth observed with other AFPs, potentially doing much mechanical damage to cells.

The LRR domains of full-length IRIPs are also predicted to contribute to ice binding surfaces but not with the inherent structural complementary to the prism face of ice of the IRIP domain. Whilst solved crystal structures of LRRs in proteins form parallel β-sheets on one side of a β-roll, the other side is made up of adjacently packed α-helical strands (Di Matteo et al (2003) *Proc. Natl. Acad Sci. USA* 100: 10124). As the α-helical regions cannot pack as closely as the β-sheet regions the β roll structure will curve, displaying a concave β-sheet region, proportional to the numbers of LRRs. Extended curved β-sheet surfaces of LRR regions do not present an optimal surface lattice match to ice, although the AFP from *D. carota* consists predominantly of 10 LRRs.

Indeed globular type III fish AFP also does not have an obvious regular ice binding surface and yet displays reasonable TH and RI activity (Baardsnes and Davies, (2002) *Biochim Biophys Acta.* 1601:49).

Genetic Mapping of LpIRIP and Relationship to Syntenic Cold Tolerance and Vernalisation QTLs In order to determine the location of IRIP genes in the genome of *L. perenne* and their proximity to endogenous or syntenic cold tolerance and vernalisation quantitative trait loci (QTLs) LpIRIPb was genetically mapped using single nucleotide polymorphism (SNP).

The analysis of SNP variation in LpIRIP gene(s) revealed a high level of variation, even compared to average values observed over a large sample of perennial ryegrass. This observation, along with the excess of recovered haplotype structures, is strongly suggestive of multiple gene structure. Although Southern hybridisation analysis indicated a relatively simple genome organisation (FIG. 5), a number of minor bands were observed, which may correspond to paralogues of the LpIRIPa gene. The segregating Lp/R/ PNA476 SNP locus may identify such a paralogous sequence, based on the results of comparative genetics and genomics analysis. Macrosynteny based on heterologous RFLP markers has demonstrated a broad correspondence between each of the perennial ryegrass linkage groups and each of the homoeologous groups of wheat (Jones et al. (2002) *Theoretical and Applied Genetics* 105: 577). On this basis, the SNP locus location on perennial ryegrass LG1 should correspond to a region of conserved synteny with the wheat homoeologous 1S chromosomes. However, comparative genomics has identified wheat sequences assigned to the group 4L and 5L chromosomes, which are related through evolutionary translocations (Devos et al, (1995) *Theoretical and Applied Genetics* 91:282). The location of LpIRIP ortholoci on Triticeae group 5 chromosomes is also consistent with the detection of QTLs for winter hardiness and frost tolerance on these chromosomes in wheat (Sutka (1994) *Euphytica* 77:277; Galiba et al, (1995). *Theoretical and Applied Genetics* 90:1174; Galiba et al, (1997) *Theoretical and Applied Genetics* 95:265; Toth et al. (2003) *Theor Appl Genet.* 107:509) and barley (Pan et al. (1994) *Theoretical and Applied Genetics* 89: 900; Francia et al. (2004) *Theoretical and Applied Genetics* 108: 670; Reinheimer et al, (2004) *Theoretical and Applied Genetics* 109: 1267), in the same region as the vernalisation response genes that control heading date. Based on conserved synteny, this would predict a location in perennial ryegrass on the upper part of LG4 (Yamada et al. (2004) *Crop Science* 44: 925). The detection of wheat IRIP paralogues on chromosome 1BL, however, indicates the complexity of this gene family in wheat, and suggests that paralogous sequences may be located on other LGs in perennial ryegrass as well. In this interpretation, the non-segregating SNPs may identify variation between LG1 and LG4-located paralogues. In order to test this hypothesis, it would be necessary to identify polymorphic SNPs for the second gene copy in other germplasm. Another possibility is that the LG1-located xLpiripna476 locus identifies a non-syntenic region. The ends of each LG in perennial ryegrass were enriched for non-syntenic markers, as previously shown for other Poaceae species (Jones et al (2002) *Theoretical and Applied Genetics* 105:577). The closest marker to xLpiripna476 is an EST-RFLP marker, xLpesi3f (Faville et al, *Theor Appl Genet*, in press), which preferentially detected wheat ESTs allocated to deletion bins on chromosome 4A. Finally, it is to be understood that various alterations, modifications and/or additions may be made without departing from the spirit of the present invention as outlined herein.

Documents cited in this specification are for reference purposes only and their inclusion is not acknowledgment that they form part of the common general knowledge in the relevant art.

What is claimed:

1. A method of increasing tolerance of freezing and/or decreasing low temperature stress in a plant, said method including:
   introducing into said plant a nucleic acid construct that includes a substantially purified or isolated nucleic acid sequence encoding a protein from a *Deschampsia* species wherein the nucleic acid sequence encoding the protein is SEQ ID NO: 37; and
   expressing the nucleic acid sequence encoding the protein,
   thereby increasing tolerance of freezing and/or decreasing low temperature stress in the plant.

2. The method of claim 1, wherein the introducing the nucleic acid construct into the plant and the expressing the nucleic acid sequence results in an increased tolerance of freezing in the plant.

3. The method of claim 1, wherein the introducing the nucleic acid construct into the plant and the expressing the nucleic acid sequence results in an decrease of low temperature stress in the plant.

* * * * *